(12) United States Patent
Tomizuka et al.

(10) Patent No.: US 6,632,976 B1
(45) Date of Patent: Oct. 14, 2003

(54) CHIMERIC MICE THAT ARE PRODUCED BY MICROCELL MEDIATED CHROMOSOME TRANSFER AND THAT RETAIN A HUMAN ANTIBODY GENE

(75) Inventors: Kazuma Tomizuka, Kanagawa (JP); Hitoshi Yoshida, Kanagawa (JP); Kazunori Hanaoka, Kanagawa (JP); Mitsuo Oshimura, Tottori (JP); Isao Ishida, Kanagawa (JP)

(73) Assignee: Kirin Beer Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/033,936

(22) Filed: Mar. 2, 1998

Related U.S. Application Data

(63) Continuation-in-part of application No. PCT/JP96/02427, filed on Aug. 29, 1996.

(30) Foreign Application Priority Data

Aug. 29, 1995 (JP) .............................................. 7-242340
Feb. 15, 1996 (JP) .............................................. 8-027940
Feb. 28, 1997 (JP) .............................................. 9-062309

(51) Int. Cl.$^7$ ........................ A01K 67/027; C12P 21/04; C12N 15/87
(52) U.S. Cl. ................................ 800/18; 800/5; 800/6; 800/25; 435/70.1; 435/70.2; 435/70.21; 435/455; 435/463
(58) Field of Search .............................. 800/21, 22, 25, 800/13, 4, 5, 6, 18; 435/455, 463, 70.1, 70.2, 70.21

(56) References Cited

U.S. PATENT DOCUMENTS

| | | | | |
|---|---|---|---|---|
| 5,288,625 A | * | 2/1994 | Hadlaczky | 435/172.2 |
| 5,695,967 A | | 12/1997 | Van Bokkelen et al. | 435/91.1 |
| 5,712,134 A | | 1/1998 | Hadlaczky | 435/465 |
| 5,721,367 A | | 2/1998 | Kay et al. | 800/18 |
| 5,776,773 A | | 7/1998 | Bruggemann | 435/325 |
| 5,891,691 A | | 4/1999 | Hadlaczky | 435/465 |
| 6,133,503 A | * | 10/2000 | Scheffler | 800/21 |

FOREIGN PATENT DOCUMENTS

| | | |
|---|---|---|
| CA | 2040178 A1 | 10/1991 |
| WO | 93/05165 | 3/1993 |
| WO | 94/00569 | 1/1994 |
| WO | 94/02602 | 2/1994 |
| WO | 95/32297 | 11/1995 |
| WO | 96/14436 | 5/1996 |
| WO | 96/33735 | 10/1996 |
| WO | 96/40965 | 12/1996 |

OTHER PUBLICATIONS

Green et al. Antigen–specific Human Monoclonal Antibodies from Mice Engineered with Human Ig Heavy and Light Chain YACs. Nature Genetics, vol. 7, pp. 13–21 (full article).*

Green et al., Nature Genetics, vol. 7, pp. 13–21. (Abstract), May 1994.*

Moreadith et al., J. Mol. Med., vol. 75, pp. 208–216, 1997.*

Mullins et al., J. Clin. Invest., vol. 98, pp. S37–S40, 1996.*

Hammer et al., J. Anim. Sci., vol. 63, pp. 269–278, 1986.*

Wall, Theriogenology, vol. 45, pp. 57–68, 1996.*

Ted K. Choi et al., "Transgenic Mice Containing A Human Heavy Chain Immunoglobulin Gene Fragment Cloned In A Yeast Artificial Chromosome," *Nature Genetics*, vol. 4, pp. 117–123, Jun. 1993.

Paul J. Saxon et al., "Introduction Of Human Chromosome 11 Via Microcell Transfer Controls Tumorigenic Expression of HeLa cells," *The EMBO Journal*, vol. 5, No. 13, pp. 3461–3466, 1986.

Minoru Koi et al., "Construction of Mouse A9 Clones Containing a Single Human Chromosome Tagged With Neomycin–Resistance Gene via Microcell Fusion" *Jpn. J. Cancer Res.*, vol. 80, pp. 413–418, May 1989.

Jean McGowan–Jordan et al., "Suppression of Tumorigenicity in Human Teratocarcinoma Cell Line PA–1 By Introduction of Chromosome 4," *Cancer Research*, vol. 54, pp. 2568–2572, May 15, 1994.

Kazuma Tomizuka et al., "Functional Expression and Germline Transmission Of A Human Chromosome Fragment in Chimaeric Mice," *Nature Genetics*, vol. 16, pp. 133–143, Jun. 1997.

Ning, et al., "Isolation of monochromosomal hybrids following fusion of human diploid fibroblast–derived microcells with mouse A9 cells", *Cytogenetics and Cell Genetics*, 60(1):79–80 (1992).

Langston, et al., "Preparation and Properties of Microcell Hybrids", *Methods in Moleuclar Genetics*, 1(A):115–133 (1993).

Jakobovits, et al., "Germ–line transmission and expression of a human–derived yeast artificial chromosome", *Nature*, 362(6417):255–258 (1993).

K. Tomizuka et al., "Creation of mice producing human antibodies by using chromosome vectors," *Abridged Translation of The Tissue Culture Engineering*, 1998, pp. 14–16, vol. 24, translation of relevant portions provided.

(List continued on next page.)

*Primary Examiner*—Deborah Crouch
(74) *Attorney, Agent, or Firm*—Foley & Lardner

(57) ABSTRACT

A chimeric, non-human animal can be produced by a method that entails providing a microcell that contains one or more foreign chromosomes or fragment(s) thereof and then fusing the microcell with a pluripotent cell, thereby introducing the foreign chromosome(s) or fragment(s) into the latter. The pluripotent cell thus obtained can be used to generate a chimeric, non-human animal, the cells, tissues, and/or progeny of which can be the source of a product, such as an antibody, that is associated with one or more genes on the foreign chromosome(s) or fragment(s).

54 Claims, 45 Drawing Sheets

OTHER PUBLICATIONS

Y. Kuroiwa et al., "Manipulation of human minichromosomes to carry greater than mega–sized chromosome inserts," *Nature Biotechnology*, 2000, pp. 1086–1090, vol. 18.

F. Benham et al., "Differentiation in vitro of human–mouse teratocarcinoma hybrids," *Molecular and Cellular Biology*, 1983, pp. 2259–2270, vol. 3, No. 12, American Society for Microbiology.

P. Goodfellow et al., "Introduction of a human X–6 translocation chromosome into a mouse teratocarcinoma: Investigation of HLA–A, B, C expression," *Developmental Biology*, 1982, pp. 1190–1194, vol. 79, Proc. Natl. Acad. Sci., USA.

K. Illmensee et al., "Chimeric mice derived from human–mouse hybrid cells," *Genetics*, 1978, pp. 1914–1918, vol. 75, No. 4, Proc. Natl. Acad. Sci., USA.

K. Illmensee et al., "Xenogeneic gene expression in chimeric mice derived from rat–mouse hybrid cells," *Genetics*, 1979, pp. 897–883, vol. 76, No. 2, Proc. Natl. Acad. Sci., USA.

M. Mendez et al., "Analysis of the structural integrity of YACs comprising human immunoglobin genes in yeast and in embryonic stem cells," *Genomics*, 1995, pp. 294–307, vol. 26, Academic Press.

N. Davies et al., "Creation of mice expressing human antibody light chains by introduction of a yeast artificial chromosome containing the core region of the human immunoglobin k locus," *Boi/Technology*, 1993, pp. 911–914, vol. 11.

E. Heard et al., "Creation of a deletion series of mouse YACs covering a 500 kb region around Xist," *Nucleic Acids Research*, 18994, pp. 1–11, vol. 22, No. 10, Oxford University Press.

T. Noguchi et al., "Chimeras of EC cells with normal embryos," *Teratoma of mouse, Rikogaku–sha*, pp. 5-2-5-34, English translation provided.

M. Bruggemann et al., PNAS 86:6709–6713, 1989, title: A repertoire of monoclonal antibodies with human heavy chains from transgenic mice.

R.L. Gardner et al., Int. J. Dev. Biol. 41:235–243, 1997, title: Reflections on the biology of embryonic stem (ES) cells.

K.H.S. Campbell et al., Nature 380:64–66, 1996, title: Sheep cloned by nuclear transfer from a cultured cell line.

K. Tomizuka et al., PNAS 97:722–727, 2000, title: Double trans–chromosomic mice: Maintenance of two individual human chromosome fragments Containing Ig heavy and κ loci and expression of fully human antibodies.

A.E. Schnieke et al., Science 278:2130–2133, 1997, title: Human Factor IX Transgenic Sheep Produced by Transfer of Nuclei from Transfected Fetal Fibroblasts.

J. Richa et al., Science 245:175–177, 1989, title: Introduction of Human DNA into Mouse Eggs by Injection of Dissected Chromosome Fragments.

W.M. Strauss et al., EMBO J. 11:417–422, 1992, title: Molecular complementation of a collagen mutation in mammalian cells using yeast artificial chromosomes.

V. Pachnis et al., PNAS 87:5109–5113, 1990, title: Transfer of a yeast artificial chromosome carrying human DNA from *Saccharomyces cerevisiae* into mammalian cells.

Mendez et al., "Functional transplant of megabase human immunoglobulin loci recapitulates human antibody response in mice," *Nature Genetics*, 15:146–156 (1997).

Smith et al., "Construction of a Panel of Transgenic Mice Containing a Contiguous 2–Mb Set of YAC/P1 Clones from Human Chromosome 21q22.2," *Genomics* 27:425–434(1995) ©Academic Press, Inc.

Zou et al., "Dominant expression of a 1.3 Mb human Igκ locus replacing mouse light chain production," *The FASEB Journal*, 10:1227–1232 (1996) ©FASEB.

* cited by examiner

FIG. 1 pLoxP-PGKPuro PLASMID DNA

MOUSE ANTIBODY LIGHT-CHAIN k TARGETING VECTOR, PROBE FOR USE IN
THE SOUTHERN BLOT ANALYSIS OF GENOMIC DNA FROM TRANSFORMANT TT2F CELLS,
AND DNA FRAGMENT TO BE DETECTED IN HOMOLOGOUS RECOMBINANTS

RETENTION OF SC20 FRAGMENT IN MICE

|  | BRAIN | | SPLEEN | | LIVER | | BONE MARROW | | TESTIS | | | | | |
|---|---|---|---|---|---|---|---|---|---|---|---|---|---|---|
|  | | | | | | | | | 1ST MEIOSIS | | 2ND MEIOSIS | | SPERM | |
|  | + | - | + | - | + | - | + | - | + | - | + | - | + | - |
| 16-5 (F1) | 30 (100%) | 0 | 11 (21%) | 42 | 30 (97%) | 1 | 1 (3%) | 30 | 15 (100%) | 0 | 15 (94%) | 1 | 11 (32%) | 23 |
| 17-8 (F1) | 30 (100%) | 0 | 12 (30%) | 28 | 30 (100%) | 0 | 21 (43%) | 28 | 16 (100%) | 0 | 9 (53%) | 7 | 14 (34%) | 27 |
| 17-23 (F1) | 41 (95%) | 2 | 7 (17%) | 34 | 31 (97%) | 1 | 5 (17%) | 25 | 15 (100%) | 0 | 13 (81%) | 3 | 13 (52%) | 12 |

FIG. 39

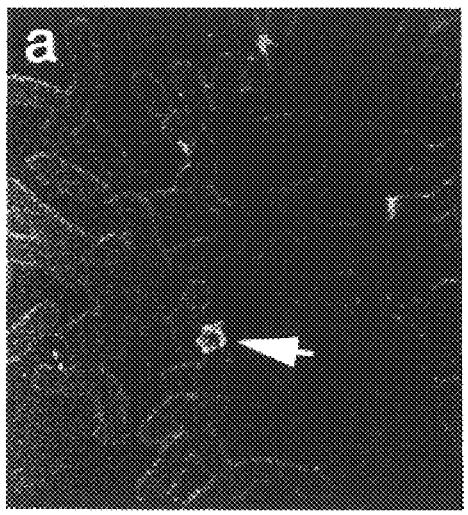
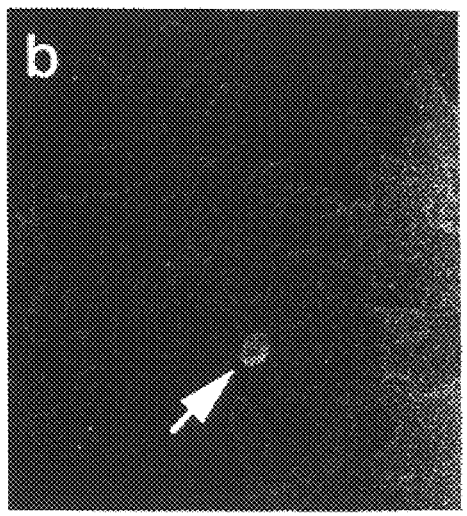
FIG. 41(a) CLONE #28
FIG. 41(b) CONTROL

ESTABLISHMENT OF COMPLETE HUMAN ANTIBODY-PRODUCING MOUSE STRAINS BY MATING

| | HK23 | HK28 | HK29 |
|---|---|---|---|
| ANTIBODY HEAVY-CHAIN KNOCKOUT | HOMO | WILD-TYPE OR HETERO | WILD-TYPE OR HETERO |
| ANTIBODY LIGHT-CHAIN KNOCKOUT | HETERO | WILD-TYPE | HETERO |
| W23 FRAGMENT | + | + | + |
| SC20 FRAGMENT | + | + | + |
| HUMAN μ CHAIN IN SERUM (mg/l) | 100 | 5.9 | 14 |
| HUMAN κ CHAIN IN SERUM (mg/l) | 8.6 | 8.4 | 25 |
| HUMAN μ/κ CHAINS IN SERUM (mg/l) | 18 | 0.13 | BELOW DETECTION LIMIT |

\* SINCE "ANTIBODY HEAVY-CHAIN KNOCKOUT" IS JUDGED BY THE PRESENCE OR ABSENCE OF THE EXPRESSION OF MOUSE μ CHAIN, IT IS IMPOSSIBLE TO DISCRIMINATE HETERO FROM WILD-TYPE.

\*\* "ANTIBODY LIGHT-CHAIN KNOCKOUT" IS JUDGED BY SOUTHERN BLOT ANALYSIS.

FIG. 42

SEQUENCE LISTING

```
<160> NUMBER OF SEQ ID NOS: 74

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 1
tggaaggtgg ataacgccct                                              20

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer
```

```
<400> SEQUENCE: 2
tcattctcct ccaacattag ca                                          22

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 3
gcaatcggtc tgccggaaga                                             20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 4
ttggatcact ttggacccag                                             20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 5
ctctcctgca gggccagtca                                             20

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 6
tgctgatggt gagagtgaac tc                                          22

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
agtcagggca ttagcagtgc                                             20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
gctgctgatg gtgagagtga                                             20

<210> SEQ ID NO 9
<211> LENGTH: 20
```

```
<212> TYPE: DNA
<213> ORGANISM: Artificial Sequence
<220> FEATURE:
<223> OTHER INFORMATION: Description of Artificial Sequence: Primer

<400> SEQUENCE: 9
tggtggctga aagctaagaa                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
ccagaagaat ggtgtcatta                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
tccaggttct gcagagcaag                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
tgtagttgga ggccatgtcc                                               20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
ccccacccat gatccagtac                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gccctcagaa gacgaagcag                                               20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 15
```
gagagttgca gaagggtga ct                                      22

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 16
ggagaccacc aaaccctcca aa                                     22

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
ggctatgggg acctgggctg                                        20

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 18
cagagacaca ggcacgtaga ag                                     22

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
ttaagggtca cccagagact                                        20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
tgtagttgga ggccatgtcc                                        20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
caaaaagtcc aaccctatca                                        20

<210> SEQ ID NO 22
<211> LENGTH: 20
<212> TYPE: DNA
<213> ORGANISM: Artificial Sequence

```
<220> FEATURE:
<223> OTHER INFORMATION: Description of Artificial Sequence: Primer

<400> SEQUENCE: 22
gccctcagaa gacgaagcag                                              20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
tcgttcctgt cgaggatgaa                                              20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
tcactccgaa gctgcctttc                                              20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 25
atgtacagga tgcaactcct g                                            21

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
tcatctgtaa atccagcagt                                              20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
gatcccatcg cagctaccgc                                              20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 28
ttcgccgagt agtcgcacgg                                              20
```

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 29
gatgaactag tccaggtgag tt                                          22

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 30
ccttttggct tctactcctt ca                                          22

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 31
atagagggta cccactctgg                                             20

<210> SEQ ID NO 32
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 32
aaccaggtag gttgatatgg                                             20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 33
aagttcctgt gatgtcaagc                                             20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 34
tcatgagcag attaaacccg                                             20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 35
tgtgaaggag gaccaggtgt                                           20

<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 36
tgtaggggtt gacagtgaca                                           20

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 37
ctgagagatg cctctggtgc                                           20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 38
ggcggttagt ggggtcttca                                           20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 39
ggtgtcgtgg aactcaggcg                                           20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 40
ctggtgcagg acggtgagga                                           20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 41
gcatcctgac cgtgtccgaa                                           20

<210> SEQ ID NO 42

```
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 42
gggtcagtag caggtgccag                                            20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 43
agtgagataa gcagtggatg                                            20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 44
gttgtgctac tcccatcact                                            20

<210> SEQ ID NO 45
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 45
ttgtatttcc aggagaaagt g                                          21

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 46
ggagacgagg gggaaaaggg                                            20

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 47
atggactgga cctggaggrt cytctkc                                    27

<210> SEQ ID NO 48
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 48
```
atggagyttg ggctgasctg gstttyt                                      27

<210> SEQ ID NO 49
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 49
atgrammwac tktgkwbcwy sctyctg                                      27

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 50
cagaggcagt tccagatttc                                              20

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 51
tgggatagaa gttattcagc                                              20

<210> SEQ ID NO 52
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 52
atggacatgr rrdycchvgy kcasctt                                      27

<210> SEQ ID NO 53
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 53
ccaagcttca ggagaaagtg atggagtc                                     28

<210> SEQ ID NO 54
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 54
ccaagcttag gcagccaacg gccacgct                                     28

<210> SEQ ID NO 55
<211> LENGTH: 28
<212> TYPE: DNA

```
<213> ORGANISM: Artificial Sequence
<220> FEATURE:
<223> OTHER INFORMATION: Description of Artificial Sequence: Primer

<400> SEQUENCE: 55
ccaagcttca gaggcagttc cagatttc                                          28

<210> SEQ ID NO 56
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 56
gggaattcgg gtagaagtca ctgatcag                                          28

<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 57
gggaattcgg gtagaagtca cttatgag                                          28

<210> SEQ ID NO 58
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 58
gggaattcgg gtagaagtca cttacgag                                          28

<210> SEQ ID NO 59
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 59
accttcatcg tcctcttcct cctgagcctc ttctacagca ccaccgtcac cctgttcaag       60

<210> SEQ ID NO 60
<211> LENGTH: 60
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 60
tgatgctgca ccaactgtat ccatcttccc accatccagt gagcagttaa catctggagg       60

<210> SEQ ID NO 61
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 61
```

```
ctggggtgag ccggatgttt tg                                    22
```

<210> SEQ ID NO 62
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 62

```
ccaacccagc tcagcccagt tc                                    22
```

<210> SEQ ID NO 63
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 63

```
aattcccgcg ggtcgacgga tccctcgagg gtacca                     36
```

<210> SEQ ID NO 64
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 64

```
gggcgcccag ctgcctaggg agctcccatg gttcga                     36
```

<210> SEQ ID NO 65
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 65

```
tcgaactagt aggagaagtg aacttgagga ggc                        33
```

<210> SEQ ID NO 66
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 66

```
tcgaactagt gattcagtga tgctgtgcag g                          31
```

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 67

```
gagagttgca gaagggtga ct                                     22
```

<210> SEQ ID NO 68

<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 68
ggagaccacc aaaccctcca aa                                          22

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 69
gagctgcaag aactcttcct cacg                                        24

<210> SEQ ID NO 70
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 70
atgactctaa ggcaggaaca tctgtacc                                    28

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 71
ctgcgtgtgt aatcgtgtcc                                             20

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 72
tctgctgtga gtgaacctgc                                             20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 73
aggaggcacc ttggataagc                                             20

<210> SEQ ID NO 74
<211> LENGTH: 22
<212> TYPE: DNA
<213> ORGANISM: Artificial Sequence
<220> FEATURE:

-continued

<223> OTHER INFORMATION: Description of Artificial Sequence: Primer

<400> SEQUENCE: 74
tcactctgac ccacgataca gc                                      22

CHIMERIC MICE THAT ARE PRODUCED BY MICROCELL MEDIATED CHROMOSOME TRANSFER AND THAT RETAIN A HUMAN ANTIBODY GENE

CROSS-REFERENCES TO RELATED APPLICATIONS

This is a continuation-in-part application of International Application No. PCT/JP96/02427 with an international filing date of Aug. 29, 1996.

BACKGROUND OF THE INVENTION

The present invention relates to chimeric non-human animals, a method for producing the same and a method for using the same. The present invention allows chimeric non-human animals to retain a foreign giant DNA fragment(s) of at least 1 Mb and to express the gene(s) on such a fragment(s), which was impossible heretofore. Hence, the following becomes possible by using the method.

Production of animals which retain and express a full length of a gene encoding a biologically active substance, for example, a full length of human antibody gene. The biologically active substance, for example, a human-type antibody is useful as a pharmaceutical product.

Analysis of functions of human giant genes (e.g., histocompatibility antigen, dystrophin, etc.) in animals.

Production of model animals with human dominant hereditary disease and a disease due to chromosomal aberration.

The present invention relates to pluripotent cells in which endogenous genes are disrupted, use of the same, and a method for producing chimeric non-human animals and use of the animals. If a foreign chromosome or a fragment thereof containing a gene encoding a gene product identical with or homologous to the gene product encoded by the disrupted endogenous gene is transferred into the pluripotent cell of the present invention as a recipient cell so that a desired functional cell or a desired chimeric non-human animal is produced from the cell, the transferred gene can be expressed efficiently without differentiation of the pluripotent cell into a germ cell. Even if a germ cell of the non-human animal is affected or the pluripotent cell cannot be differentiated into a germ cell by the disruption of the endogenous gene or the introduction of a foreign gene, a functional cell, or a chimeric non-human animal, a tissue or a cell of the animal can retain and express a foreign giant DNA fragment in excess of the heretofore unattainable 1 Mb (a million bases) in conditions of a deficiency in the endogenous gene and a decrease in the production of an endogenous gene product by producing the desired functional cell or non-human animal from the pluripotent cell.

Techniques of expressing foreign genes in animals, that is, techniques of producing transgenic animals are used not only for obtaining information on the gene's functions in living bodies but also for identifying DNA sequences that regulate the expression of the genes (e.g., Magram et al., Nature, 315:338, 1985), for developing model animals with human diseases (Yamamura et al., "Manual of model mice with diseases" published by Nakayama Shoten, 1994), for breeding farm animals (e.g., Muller et al., Experientia, 47:923, 1991) and for producing useful substances with these animals (e.g., Velander et al., P.N.A.S., 89:12003, 1992). Mice have been used the most frequently as hosts for gene transfer. Since mice have been studied in detail as experimental animals and the embryor manipulating techniques for mice have been established, they are the most appropriate kind of mammals for gene transfer.

Two methods are known for transferring foreign genes into mice. One is by injecting DNA into a pronucleus of a fertilized egg (Gordon et al., P.N.A.S., 77:7380, 1980). The other is by transferring DNA into a pluripotent embryonic stem cell (hereinafter referred to as "ES cell") to produce a chimeric mouse (Takahashi et al., Development, 102:259, 1988). In the latter method, the transferred gene is retained only in ES cell-contributing cells and tissues of chimeric mice whereas it is retained in all cells and tissues of progenies obtained via ES cell-derived germ cells. These techniques have been used to produce a large number of transgenic mice up to now.

However, there had been a limit of the size of DNA capable of being transferred and this restricts the application range of these techniques. The limit depends on the size of DNA which can be cloned. One of the largest DNA fragments which have ever been transferred is a DNA fragment of about 670 kb cloned into a yeast artificial chromosome (YAC) (Jakobovits et al., Nature, 362:255, 1993). Recently, introduction of YAC containing an about 1 Mb DNA fragment containing about 80 percent of variable regions and portions of constant regions ($C\mu$, $C\delta$ and $C\gamma$) of a human antibody heavy-chain was reported (Mendes et al., Nature Genetics, 15:146, 1997). These experiments were carried out by fusing a YAC-retaining yeast cell with a mouse ES cell. Although it is believed that foreign DNA of up to about 2 Mb can be cloned on YAC (Den Dunnen et al., Hum. Mol. Genet., 1:19, 1992), the recombination between homologous DNA sequences occurs frequently in budding yeast cells and therefore, in some cases, a human DNA fragment containing a large number of repeated sequences is difficult to retain in a complete form. In fact, certain recombinations occur in 20–40% of the clones of YAC libraries containing human genomic DNA (Green et al., Genomics, 11:584, 1991).

In another method that was attempted, a metaphase chromosome from a cultured human cell was dissected under observation with a microscope and the fragment (presumably having a length of at least 10 Mb) was injected into a mouse fertilized egg (Richa et al., Science, 245:175, 1989). In the resulting mice, a human specific DNA sequence (Alu sequence) was detected but the expression of human gene was not confirmed. In addition, the procedure used in this method to prepare chromosomes causes unavoidable fragmentation of DNA into small fragments due to the use of acetic acid and methanol in fixing the chromosome on slide glass and the possibility that the injected DNA exists as an intact sequence is small.

In any event, no case has been reported to date that demonstrates successful transfer and expression in mice of uninterrupted foreign DNA fragments having a length of at least 1 Mb.

Useful and interesting human genes which are desirably transferred into mice, such as genes for antibody (Cook et al., Nature Genetics, 7: 162, 1994), for T cell receptor (Hood et al., Cold Spring Harbor Symposia on Quantitative Biology, Vol. LVIII, 339, 1993), for histocompatibility antigen (Carrol et al., P.N.A.S, 84:8535, 1987), for dystrophin (Den Dunnen et al., supra). are known to be such that their coding regions have sizes of at least 1 Mb. Since human-type antibodies are important as pharmaceutical products, the production of mice which retain and express full lengths of genes for human immunoglobulin heavy chains (~1.5 Mb, Cook et al., supra), and light chain κ (~3 Mb, Zachau, Gene, 135:167, 1993), and light chain λ (~1.5 Mb, Frippiat et al., Hum. Mol. Genet., 4:983, 1995) is desired but this is impossible to achieve by the state-of-the-art technology (Nikkei Biotec, Jul., 5, 1993).

Many of the causative genes for human dominant hereditary disease and chromosomal aberration which causes congenital deformity (Down's syndrome, etc.) have not been cloned and only the information on the approximate location of the genes on chromosome is available. For example, when a gene of interest is found to be located on a specific G band, which is made visible by subjecting a metaphase chromosome to Giemsa staining, the G band has usually a size of at least several Mb to 10 Mb. In order to transfer these abnormal phenotypes into mice, it is necessary to transfer chromosomal fragments of at least several Mb that surround the causative genes, but this is also impossible with the presently available techniques.

Hence, it is desired to develop a technique by which a foreign DNA longer than the heretofore critical 1 Mb can be transferred into a mouse and expressed in it.

DNA longer than 1 Mb can be transferred into cultured animal cells by the techniques available today. Such transfer is carried out predominantly by using a chromosome as a mediator. In the case of human, chromosomes have sizes of about 50–300 Mb. Some methods for chromosome transfer into cells have been reported (e.g., McBride et al., P.N.A.S., 70:1258, 1973). Among them, microcell fusion (Koi et al., Jpn. J. Cancer Res., 80:413, 1989) is the best method for selective transfer of a desired chromosome. The microcell is a structural body in which one to several chromosomes are encapsulated with a nuclear membrane and a plasma membrane. A few chromosomes (in many cases, one chromosome) can be transferred by inducing a microcell with an agent that inhibits the formation of spindle in a specific kind of cell, separating the microcell and fusing it with a recipient cell. The resulting libraries of monochromosomal hybrid cells containing only one human chromosome have been used for mapping known genes and specifying the chromosomes on which unknown tumor-suppressor genes and cellular senescence genes exist (e.g., Saxon et al., EMBO J., 5:3461, 1986). In addition, it is possible to fragment a chromosome by irradiating a microcell with γ-rays and to transfer part of the fragments (Koi et al., Science, 260:361, 1993). As described above, microcell fusion is considered to be an appropriate method for transferring DNA larger than 1 Mb into a cultured animal cell.

The expectation that a mouse could be generated from a cultured cell turned to a real fact when the ES cell which has stable pluripotency was discovered (Evans et al., Nature, 292:154, 1981). Foreign genes, various mutations and mutations by targeted gene recombination could be introduced into the ES cell, making it possible to perform a wide variety of genetic modifications in mice (e.g., Mansour et al., Nature, 336:348, 1988). The ES cell can be used to produce a mouse having a disrupted target gene by gene targeting techniques. The mouse is mated with a transgenic mouse having a gene of interest to produce a mouse that expresses the gene of interest efficiently. For example, a mouse having a disrupted endogenous antibody gene can be mated with a mouse having a human antibody gene transferred to produce a mouse that expresses the human antibody efficiently. A normal diploid cell has alleles. A transgenic mouse having one allele of an mouse antibody heavy-chain gene disrupted expresses an increased level of human antibody in its serum. A mouse having both alleles of mouse antibody heavy-chain gene disrupted expresses a further remarkably increased level of human antibody (S. D. Wagner et al., Genomics, 35:405–414, 1996).

Some researchers have developed a technique in which one allele of a target gene is disrupted, and then the concentration of a selective drug is increased, thereby deleting both alleles of the target gene (double knock-out). However, this technique holds the possibility of a decrease in the ability of the target gene-deficient cell to differentiate into a germ cell because the target gene-deficient cell obtained by the high-concentration-selective-culture method is cultured in vivo for a long period and because the drug-selection pressure is severe (Takatsu•Taki, Experimental Medicine, supplement, Biomanual UP Series Basic Techniques for Immunological Study, Yodo-sha, 1995). In another case, if two kinds of selective drugs are used for double knocking-out, for example, if a neomycin-resistant cell is subjected to a double knock-out treatment with hygrbmycin, the double drug-resistant ES cell is rarely differentiated to produce a mutant mouse (Watanabe et al., Tissue Culture 21, 42–45, 1995). ES cells may lose their differentiation and growth capabilities under certain culture conditions. When a gene targeting procedure is performed twice, ES cells do not lose the ability to differentiate into germ cells of a chimeric mouse but the second homologous recombination frequency is extremely low (Katsuki et al., Experimental Medicine, Vol. 11, No. 20, special number, 1993). Hence, when a target gene-deficient homozygote is produced, particularly when at least two target genes are targeted, a mouse deficient in each target gene is produced and then the produced mice are mated with each other to produce a homozygote mouse deficient in at least two genes (N. Longberg et al., Nature, 368:856–859, 1994). If genes to be disrupted exist close to each other and if a mouse deficient in at least two genes cannot be obtained by mating, heterozygote mice deficient in the two target genes are produced from ES cells and they are mated to produce homo deficient mice (J. H. van Ree et al., Hum Mol Genet 4:1403–1409, 1995).

An attempt to differentiate a pluripotent ES cell into a functional cell in vitro has been made (T. Nakano et al., Science, 265:1098–1101, 1994, A. J. Potocnik et al., The EMBO Journal, 13:5274–5283, 1994). The cultivation system used in this attempt, for example, a system in which the differentiation into a mature B cell can be induced is expected to be used in the identification of unknown growth and differentiation factors which will work in development and differentiation processes of B cells.

As long as the transfer of giant DNA is concerned, it has been believed that the size of the aforementioned foreign DNA fragment which can be cloned into a YAC vector is the upper limit. The prior art technology of chromosome transfer for introducing a longer DNA into cultured cells has never been applied to gene transfer into mice and this has been believed to be difficult to accomplish (Muramatsu et al., "Transgenic Biology", published by Kodansha Scientific, p.143-, 1989).

The reasons are as follows.

The transfer of a human chromosome into a mouse ES cell of a normal karyotype as a recipient cell would be a kind of transfer of chromosomal aberration. Up to now, it has been believed that genetic aberration at chromosomal levels which is large enough to be recognizable with microscopes is generally fatal to the embryogeny in mice (Gropp et al., J. Exp. Zool., 228:253, 1983 and Shinichi Aizawa, "Biotechnology Manual Series 8, Gene Targeting", published by Yodosha, 1995).

Available human chromosomes are usually derived from finitely proliferative normal fibroblasts or differentiated somatic cells such as cancer cells and the like. It was believed that if a chromosome derived from such a somatic cell was transferred into an undifferentiated ES cell, the transferred chromosome might cause differentiation of the ES cell orbits senescence (Muller et al., Nature, 311:438, 1984; Sugawara, Science, 247:707, 1990).

Only few studies have been reported as to whether a somatic cell-derived chromosome introduced into an early embryo can function in the process of embryonic development as normally as a germ cell-derived chromosome to ensure the expression of a specific gene in various kinds of tissues and cells. One of the big differences between the two chromosomes is assumed to concern methylation of the chromosomal DNA. The methylation is changed according to differentiation of cells and its important role in the expression of tissue-specific genes has been suggested (Ceder, Cell, 53:3, 1988). For example, it has been reported that if a methylated DNA substrate is introduced into a B cell, the methylated DNA is maintained after replication and suppresses a site-directed recombination reaction which is essential to the activation of an antibody gene (Hsieh et al., EMBO J., 11:315, 1992). In addition, it was reported that higher levels of de novo methylation occurred in established cell lines than in vivo (Antequera et al., Cell, 62:503, 1990). On the basis of the studies reported, it could not be easily expected that an antibody gene in a human fibroblast or a human-mouse hybrid cell which was likely to be methylated at a high level would be normally expressed in a mouse B cell.

It should be noted that there are two related reports of Illmensee et al. (P.N.A.S., 75:1914, 1978; P.N.A.S., 76:879, 1979). One report is about the production of chimeric mice from fused cells obtained by fusing a human sarcoma cell with a mouse EC cell and the other is about the production of chimeric mice from fused cells obtained by fusing a rat liver cancer cell with a mouse EC cell. Many questions about the results of the experiments in these two reports were pointed out and thus these reports are considered unreliable (Noguchi et al., "Mouse Teratoma", published by Rikogakusha, Section 5, 1987). Although it has been desired to perform a follow-up as early as possible, as of today when 17 years have passed since the publication of these reports, successful reproduction of these experiments has not been reported. Hence, it is believed that foreign chromosomes cannot be retained and the genes on the chromosomes cannot be expressed in mice by the method described in these reports.

Under these circumstances, it has been believed to be difficult to transfer a giant DNA such as a chromosomal fragment and express it in an animal such as mouse. Actually, no study has been made about this problem since the Illmensee's reports.

Therefore, an object of the present invention is to provide chimeric non-human animals which retain foreign chromosomes or fragments thereof and express genes on the chromosomes or fragments, and their progenies, and a method for producing the same.

It is also an object of the present invention to provide pluripotent cells containing foreign chromosomes or fragments thereof and a method for producing the pluripotent cells.

Another object of the present invention is to provide tissues and cells derived from the chimeric non-human animals and their progenies.

A further object of the present invention is to provide hybridomas prepared by fusing the cells derived from the chimeric non-human animals and their progenies with myeloma cells.

A still further object of the present invention is to provide a method for producing a biologically active substance that is an expression product of the gene on a foreign chromosome or a fragment thereof by using the chimeric non-human animals or their progenies, or their tissues or cells.

It is also an object of the present invention to provide pluripotent cells which can be used as recipient cells into which a foreign chromosome(s) or a fragment(s) thereof is transfered in the production of chimeric non-human animals retaining the foreign chromosome(s) or fragment(s) thereof and expressing a gene(s) on the foreign chromosome(s) or fragment(s) thereof.

A further object of the present invention is to provide a method for using the pluripotent cells.

SUMMARY OF THE INVENTION

As a result of the various studies conducted to achieve the above objects, the inventors succeeded in transferring chromosomes or fragments thereof derived from human normal fibroblast cells into mouse ES cells and obtaining clones which were capable of stable retention of the chromosomes or fragments. Moreover, they produced from these ES clones those chimeric mice which retained human chromosomes in normal tissues and which expressed several human genes including human antibody heavy-chain genes. It has become possible to make that animals retain and express giant DNA fragments by the series of these techniques, although this has been impossible by conventional techniques. Moreover, the inventors succeeded in obtaining embryonic stem cells having both of antibody heavy-chain and light-chain genes knocked out.

The subject matter of the present invention is as follows:
1. A method for producing a chimeric non-human animal, which comprises preparing a microcell containing a foreign chromosome(s) or a fragment(s) thereof and transferring the foreign chromosome(s) or fragment(s) into a pluripotent cell by fusion with the microcell.
2. A method for producing a pluripotent cell containing a foreign chromosome(s) or a fragment(s) thereof, which comprises preparing a microcell containing a foreign chromosome(s) or a fragment(s) thereof and transferring the foreign chromosome(s) or fragment(s) thereof into a pluripotent cell by fusion with the microcell.

In the method of item 1 or 2, the foreign chromosome(s) or fragment(s) thereof may be larger than 670 kb, further, at least 1 Mb (one million base pairs). The foreign chromosome or fragment thereof may contain a region encoding an antibody. The microcell containing a foreign chromosome(s) or a fragment(s) thereof may be induced from a hybrid cell prepared by the fusion of a cell from which the foreign chromosome(s) or fragment(s) thereof is(are) derived, with a cell having a high ability to form a microcell. The microcell containing a foreign chromosome(s) or a fragments) thereof may be induced from a cell prepared by a further fusion of the microcell induced from the hybrid cell with a cell having a high ability to form a microcell. The cell from which the foreign chromosome(s) or fragment(s) thereof is(are) derived may be a human normal diploid cell. The cell having a high ability to form a microcell may be a mouse A9 cell. The pluripotent cell can be selected from embryonal carcinoma cells, embryonic stem cells, embryonic germ cells and mutants thereof. It is preferred that the foreign chromosome or fragment thereof contains a gene of interest and that the pluripotent cell has a disrupted gene identical with or homologous to said gene of interest on the foreign chromosome or fragment thereof. It is also preferred that the foreign chromosome or fragment thereof contains at least two genes of interest and that the pluripotent cell has disrupted genes identical with or homologous to said genes of interest on the foreign chromosome or fragment thereof. In the pluripotent cell, one or both alleles of a gene identical with or homologous to the gene of interest on the foreign chromosome or fragment thereof may be disrupted. The gene of interest may be an antibody gene. The antibody gene may be one or more sets of antibody heavy-chain and light-chain genes. In the method of item 1 or 2, it is preferred that the foreign chromosome or fragment thereof contains a gene of interest and that the foreign chromosome or fragment thereof is transferred into a pluripotent cell having a disrupted gene identical with or homologous to the gene of interest and then, a chimera is produced from the pluripotent cell by using an embryo of a non-human animal in a strain deficient in an endogenous gene identical with or homologous to the gene of interest. The non-human animal in a strain deficient in an endogenous gene identical with or homologous to the gene of interest can be produced by homologous recombination in gene targeting. Preferably, the chimeric non-human animal retains the foreign chromosome(s) or fragment(s) thereof, expresses the gene(s) on the foreign chromosome(s) or fragment(s) thereof, and can transmit the foreign chromosome(s) or fragment(s) thereof to its progeny. The chimeric non-human animal is preferably a mammal, more preferably a mouse.

3. A pluripotent cell containing a foreign chromosome(s) or a fragment(s) thereof.

In the pluripotent cell, the foreign chromosome(s) or fragment(s) thereof may be larger than 670 kb. In the cell of item 3, the foreign chromosome or fragment thereof may contain a gene of interest and the pluripotent cell has a disrupted gene identical with or homologous to the gene of interest on the foreign chromosome or a fragment thereof. The foreign chromosome or fragment thereof may contain at least two genes of interest and the pluripotent cell has disrupted genes identical with or homologous to the genes of interest on the foreign chromosome or a fragment thereof. In the pluripotent cell, one or both alleles of a gene identical with or homologous to the gene of interest may be disrupted. The foreign chromosome or fragment thereof may contain an antibody gene. The antibody gene may be one or more sets of antibody heavy-chain and light-chain genes. The pluripotent cell can be selected from embryonal carcinoma cells, embryonic stem cells, embryonic germ cells and mutants thereof.

4. A chimeric non-human animal retaining a foreign chromosome(s) or a fragment(s) thereof and expressing a gene(s) on the foreign chromosome(s) or fragment(s) thereof, or its progeny retaining the foreign chromosome(s) or fragment(s) thereof and expressing the gene(s) on the foreign chromosome(s) or fragment(s) thereof.

In the chimeric non-human animal or its progeny, the foreign chromosome(s) or fragment(s) thereof may be larger than 670 kb. The foreign chromosome or fragment thereof may contain a gene of interest and the animal may have a disrupted gene identical with or homologous to the gene of interest. The foreign chromosome or fragment thereof may contain at least two genes of interest and the animal may have disrupted genes identical with or homologous to said genes of interest. In the chimeric non-human animal or its progeny, one or both alleles of a gene identical with or homologous to the gene of interest may be disrupted. The gene of interest may be an antibody gene. The antibody gene may be one or more sets of antibody heavy-chain and light-chain genes.

5. A non-human animal which can be produced by mating the chimeric non-human animals or their progenies of item 4, said non-human animal retaining the foreign chromosome(s) or fragment(s) thereof and expressing the gene(s) on the foreign chromosome(s) or fragment(s) thereof, or its progeny retaining the foreign chromosome(s) or fragment(s) thereof and expressing the gene(s) on the foreign chromosome(s) or fragment(s) thereof:.

6. A non-human animal retaining the foreign chromosome(s) or fragment(s) thereof and expressing a gene(s) on the foreign chromosome(s) or fragment(s) thereof, which can be produced by mating the chimeric non-human animal or its progeny of item 4, or the non-human animal or its progeny of item 5, with a non-human animal in a strain deficient in said gene(s) or a gene homologous thereto, or its progeny retaining the foreign chromosome(s) or fragment(s) thereof and expressing the gene(s) on the foreign chromosomes) or fragment(s) thereof.

7. A tissue from the chimeric non-human animal or its progeny of item 4 or from the non-human animal or its progeny of item 5 or from the non-human animal or its progeny of item 6.

8. A cell from the chimeric non-human: animal or its progeny of item 4 or from the non-human animal or its progeny of item 5 or from the non-human animal or its progeny of item 6.

The cell may be a B cell, a primary culture cell derived from an animal tissue or a cell fused with an established cell.

9. A hybridoma prepared by the fusion of the B cell with a myeloma cell.

10. A method for producing a biologically active substance, which comprises expressing the gene(s) oh the foreign chromosome(s) or fragment(s) thereof in the chimeric non-human animal or its progeny of item 4, the non-human animal or its progeny of item 5 or the non-human animal or its progeny of item 6, or a tissue or a cell thereof, and recovering the biologically active substance as an expression product.

In the method, the cell of the chimeric non-human animal may be a B cell. The B cell may be immortalized by fusion with a myeloma cell. The chimeric non-human animal cell may be fused with a primary culture cell derived from an animal tissue or fused with an established cell line. The biologically active substance may be an antibody. The antibody is preferably an antibody of a mammal, more preferably a human antibody.

11. A biologically active substance which can be produced by the method of item 10.

12. A non-human animal retaining at least one human antibody gene larger than 670 kb and expressing the, gene.

The non-human animal of item 12 preferably retains at least one human antibody gene of at least 1 Mb and expresses the gene. The human antibody gene may be a human heavy-chain gene, a human light-chain κ gene, a human light-chain λ gene, or a combination thereof. The non-human animal of item 12 may be deficient in a non-human animal antibody gene identical with or homologous to the human antibody gene. The deficiency of non-human animal antibody gene may be caused by disrupting the non-human animal antibody gene by homologous recombination.

13. A hybridoma prepared by the fusion of a spleen cell of the non-human animal of item 12 with a myeloma cell.

14. An antibody produced by the hybridoma of item 13.

15. A non-human animal expressing at least one class or subclass of human antibody.

The non-human animal of item 15 may be deficient in an endogenous antibody gene identical with or homologous to the expressed human antibody gene. The class or subclass of human antibody may be IgM, IgG, IgE, IgA, IgD or a subclass, or a combination thereof.

16. A non-human animal retaining a foreign DNA(s) larger than 670 kb and expressing a gene(s) on the foreign DNA(s).

The non-human animal of item 16 may be deficient in an endogenous gene identical with or homologous to the expressed gene on the foreign DNA. The non-human animal of item 16 may retain a foreign DNA(s) of at least 1 Mb and express the gene(s) on the foreign DNA(s). The non-human animal may be deficient in an endogenous gene identical with or homologous to the expressed gene on the foreign DNA.

17. A method for producing a transgenic non-human animal, which comprises preparing a microcell containing a foreign chromosome(s) or a fragment(s) thereof, transferring the foreign chromosome(s) or fragment(s) into a cultured cell derived from a blastcyst by fusion with the microcell and transplanting the nucleus of the cultured cell into an enucleated unfertilized egg.

18. A pluripotent cell in which at least two endogenous genes are disrupted.

In the cell of item 18, each of the endogenous genes may be disrupted in one or both alleles. The disrupted endogenous genes may be antibody genes. The disrupted antibody genes may be antibody heavy-chain and light-chain genes. The pluripotent cell can be selected from embryonal carcinoma cells, embryonic stem cells, embryonic germ cells and mutants thereof.

19. A method of producing the cell of item 18 by at least two homologous recombinations.

The method of item 19 may comprise the steps of:
disrupting one allele of the endogenous gene in the pluripotent cell by homologous recombination using a drug-resistant marker gene;
culturing the pluripotent cell in the presence of the drug to select drug-resistant cells; and
screening the selected drug-resistant cells to yield a cell in which both alleles of the endogenous gene have been disrupted.

In the method of item 19, one allele of the endogenous gene in the pluripotent cell may be disrupted by homologous recombination using a drug-resistant marker gene and the other allele of the endogenous gene may be disrupted by another homologous recombination using a drug-resistant marker gene. The same drug-resistant marker gene may be used in the two homologous recombinations. Alternatively, different drug-resistant marker genes may be used in the two homologous recombinations.

Furthermore, the present invention provides a method of using the pluripotent cell as a recipient cell into which a foreign gene(s) or a fragment(s) thereof, or a foreign chromosome(s) or a fragment(s) thereof are to be transferred. The foreign gene(s) or fragment(s) thereof may be incorporated in a vector such as a plasmid, a cosmid, YAC or the like. Alternatively, the foreign chromosome(s) or fragment(s) thereof may be contained in a microcell. The foreign chromosome(s) or fragment(s) thereof is preferably, but not limited to, one that contains a gene(s) identical with or homologous to the endogenous gene(s) disrupted in the pluripotent cell. The term "homologous gene" means herein a gene encoding the same kind of protein or a protein having a similar property in the same or different species of a given organism.

Moreover, the present invention provides a method of using the pluripotent cell for producing a chimeric non-human animal.

The present invention also provides a method of producing a pluripotent cell containing a foreign chromosome(s) or a fragment(s) thereof, which comprises the steps of:
preparing a microcell containing the foreign chromosome(s) or fragments) thereof; and
fusing the microcell with said pluripotent cell having at least two endogenous genes disrupted, whereby said foreign chromosome(s) or fragment(s) thereof is transferred into said pluripotent cell.

The present invention further provides a method of producing a chimeric non-human animal, which comprises the steps of:
preparing a microcell containing a foreign chromosomes) or a fragment(s) thereof; and
fusing the microcell with said pluripotent cell having at least two endogenous genes disrupted, whereby said foreign chromosome(s) or fragment(s) thereof is transferred into said pluripotent cell.

In the aforementioned two methods, the foreign chromosome(s) or fragment(s) thereof may have a length(s) of at least 1 Mb (100 million base pairs). The foreign chromosome(s) or a fragment(s) thereof may contain a region encoding an antibody. The microcell containing the foreign chromosome(s) or fragment(s) thereof may be induced from a hybrid cell prepared by the fusion of a cell containing the foreign chromosome(s) or fragment(s) thereof, with a cell having a high ability to form a microcell. The microcell containing the foreign chromosome(s) or fragment(s) thereof may be induced from a cell prepared by a further fusion of the microcell induced from the hybrid cell, with a cell having a high ability to form a microcell. The cell containing the foreign chromosome(s) or fragment(s) thereof may be a human normal diploid cell. The cell having a high ability to form a microcell may be a mouse A9 cell. In the methods of producing a chimeric non-human animal, a foreign chromosome(s) or a fragment(s) thereof containing gene(s) identical with or homologous to the endogenous gene(s) disrupted in the pluripotent cell may be transferred into the pluripotent cell having the disrupted at least two endogenous genes and then, a chimera of the cell with an embryo of a non-human animal in a strain deficient in a gene(s) identical with or homologous to said endogenous gene(s) may be prepared. The chimeric non-human animal deficient in a gene identical with or homologous to the endogenous gene disrupted in said pluripotent cell may be produced by homologous recombination in gene targeting. The chimeric non-human animal may be such that it retains the foreign chromosome(s) or fragment(s) thereof, expresses a gene(s) on the foreign chromosome(s) or fragment(s) thereof, and can transmit the foreign chromosome(s) or fragment(s) thereof to its progeny. The chimeric non-human animal may be a mammal, preferably a mouse.

The present invention also provides a pluripotent cell containing a foreign chromosome(s) or a fragment(s) thereof, which is obtainable by a method of producing a chimeric non-human animal, which method comprises the steps of:
preparing a microcell containing the foreign chromosome(s) or fragment(s) thereof; and
fusing the microcell with said pluripotent cell having at least two endogenous genes disrupted, whereby said foreign chromosome(s) or fragment(s) thereof is transferred into said pluripotent cell. The present invention further provides a method of using the cell for producing a chimeric non-human animal.

The present invention also provides a chimeric non-human animal retaining a foreign chromosome(s) or a fragment(s) thereof and expressing the gene(s) on the foreign chromosome(s) or fragment(s) thereof, which is obtainable by one of the aforementioned methods of producing a chimeric non-human animal, or its progeny. The present invention also provides a non-human animal retaining a foreign chromosome(s) or a fragment(s) thereof and expressing the gene(s) on the foreign chromosome(s) or fragment(s) thereof which is obtainable by mating between the chimeric non-human animals or its progenies, or its progeny. The present invention further provides a tissue from the aforementioned chimeric non-human animal or its progeny, or the aforementioned non-human animal or its progeny. The present invention still more provides a cell from the aforementioned chimeric non-human animal or its progeny, or the aforementioned non-human animal or its progeny. The cell may be a B cell.

The present invention also provides a hybridoma prepared by the fusion of the cell from the aforementioned chimeric non-human animal or its progeny, or the aforementioned non-human animal or its progeny with a myeloma cell.

The present invention provides a non-human animal or its progeny retaining a foreign chromosome(s) or a fragment(s) thereof and expressing a gene(s) on the foreign chromosome(s) or fragment(s) thereof, which is obtainable by mating said chimeric non-human animal or its progeny or said non-human animal or its progeny retaining the foreign chromosome(s) or fragment(s) thereof and expressing the gene(s) on the foreign chromosome(s) or fragment(s) thereof, with a non-human animal in a stain deficient in a gene(s) identical with or homologous to said gene(s).

Furthermore, the present invention provides a method of producing a biologically active substance, which comprises expressing a gene(s) on a foreign chromosome(s) or a fragment in the chimeric non-human animal or its progeny, or the non-human animal or its progeny, or a tissue or a cell thereof and recovering the biologically active substance as the expression product. The cell of the chimeric non-human animal or its progeny, or the non-human animal or its progeny may be a B cell. The B cell may be immortalized by fusion with a myeloma cell. The biologically active substance may be an antibody. The antibody may be an antibody of mammal, preferably a human antibody.

Moreover, the present invention provides a method of producing a biologically active substance, which comprises expressing a gene(s) on a foreign chromosome(s) or a fragment in a offspring or a tissue and a cell thereof, wherein the offspring is produced by mating the chimeric non-human animal or its progeny, or the non-human animal or its progeny retaining the foreign chromosome(s) or fragment(s) thereof with a non-human animal in a strain deficient in a gene identical with or homologous to said genes, and expressing the gene(s) on the foreign chromosome(s) or fragment(s) thereof, and recovering the biologically active substance as the expression product.

The present invention also provides a vector containing a foreign chromosomal gene(s) for use in gene transfer into a non-human animal and a non-human animal cell. The foreign chromosome(s) is preferably one from human, more preferably a human chromosome #14 fragment. The non-human animal is preferably a mouse.

The term "allele" is used herein.

The term "homologous gene" means herein a gene encoding the same kind of protein or a protein having a similar property in the same or different species of a given organism.

According to the present invention, a chimeric non-human animal retaining a foreign chromosome(s): or a fragment(s) thereof and expressing the gene(s) on the chromosome(s) or fragment(s) is provided. The chimeric non-human animal of the present invention can be used to produce biologically active substances.

According to the present invention, a pluripotent cell retaining a foreign chromosome(s) or a fragment(s) thereof and expressing a gene(s) on the chromosome(s) or fragment(s) thereof is provided. The pluripotent cell can be used for treatment of hereditary diseases, for example, by bone marrow transplantation.

According to the present invention, a pluripotent cell having at least two endogenous genes disrupted is provided. The cell of the present invention can be used as a recipient cell for transferring a foreign chromosome(s) or a fragment(s) thereof containing a gene identical with or homologous to the disrupted endogenous genes to produce a functional cell or a chimeric non-human animal retaining the foreign chromosome(s) or fragment(s) thereof and expressing the gene(s) on the chromosome(s) or fragment(s). A biologically active substance(s) can be produced as a gene product(s) by expressing the gene(s) on the chromosome(s) or fragment(s) thereof in the chimeric non-human animal or its progeny, or a tissue or a cell thereof.

BRIEF DESCRIPTION OF THE DRAWINGS

FIG. 1 shows the results of PCR analysis of an A9 cell retaining human chromosome #2 (fragment).

FIG. 39 shows the results of analysis for stability of human chromosome #14 fragments in a mouse.

FIG. 41 shows the results of FISH analysis of an A9 cell retaining fragmented human chromosome #22.

FIG. 42 shows the results of complete human antibody-producing mouse strains established by mating.

BEST MODE FOR CARRYING OUT THE INVENTION

Figure 2:
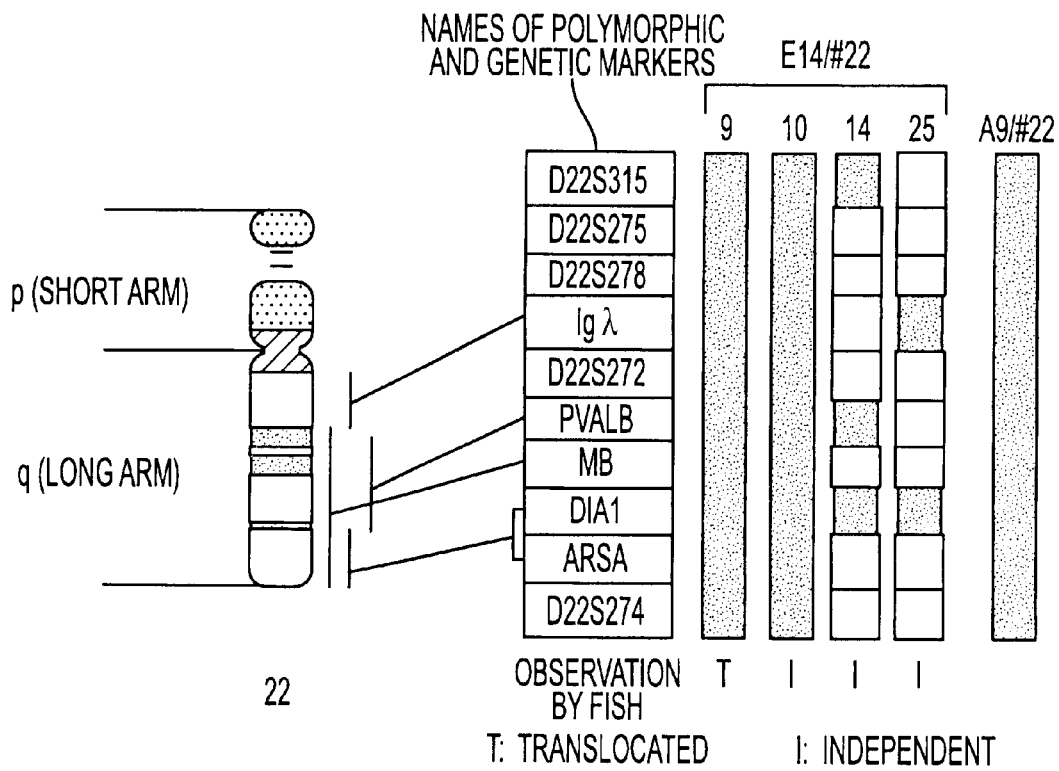
FIG. 2 shows that human chromosome #22 (fragment) is retained in an E14 drug resistant cell (PCR analysis).

The present invention will now be described in detail.

A non-human animal that retains a human chromosome(s) or a fragment(s) thereof and which expresses the gene on the chromosome(s) or fragment(s) thereof can be produced by (1) preparing a chromosome donor cell which retains a labeled human chromosome or a fragment thereof;

(2) transferring the human chromosome or fragment thereof into a non-human animal pluripotent cell by microcell fusion;

(3) producing a chimeric non-human animal from the cell; and (4) confirming that the human chromosome is retained in the chimeric non-human animal and that a human gene is expressed.

In this procedure, a mouse is used as a non-human animal that retains a human chromosome or a fragment thereof and which expresses the gene on the chromosome or fragment thereof (the mouse is hereinafter referred to as a "human chromosome transferred mouse").

The term "human chromosome" means a naturally occurring complex which consists of nucleic acids and proteins that are derived from human cells. There are 46 normal human chromosomes of 23 kinds (24 kinds in male), each of which contains DNAs of about 50–300 Mb in size. In the present invention, the human chromosome includes not only partial fragments which can be stably replicated and segregated as independent chromosomes but also fragments that are translocated on mouse chromosomes and which are retained stably. The size of the DNA is usually at least 1 Mb and in some-cases, it is smaller than 1 Mb. The feature of the present invention resides in that a mouse can retain and express the foreign gene on a foreign chromosome as a mediator without treatments such as cloning in an *E. coli* or yeast cell, or extraction of the DNA from a cell.

The term "human chromosome transferred mouse" means a mouse retaining a human chromosome(s) or a fragment(s) thereof in all or part of its normal somatic cells. The mouse expresses the gene(s) on a human chromosome(s) or a fragment(s) thereof in all or part of its normal somatic cells.

(1) Preparation of a Chromosome Donor Cell Which Retains a Labeled Human Chromosome or a Fragment Thereof A desired chromosome donor cell 1) retains a human chromosome(s) labeled with a marker also available for selection of recipient cells; 2) does not contain other human chromosomes; and 3) has a higher ability to form a microcell.

Any human-derived cell lines, cancer cells and primary culture cells can be used as materials for providing human chromosomes. Among them, normal fibroblast cells are suitable because they have a low possibility of abnormality such as deletion and amplification of chromosomes and can be readily cultured.

As for 1), human cells can be transformed with vectors that express genes for markers such as drug-resistance (e.g., G418-, puromycin-, hygromycin- or blasticidin-resistance). Promoters operating efficiently not only in human cells but also in recipient cells such as mouse ES cells are desirably used to regulate the expression of the marker used. For this purpose, herpes simplex virus thymidine kinase promoter linked with SV 40 enhancer (Katoh et al., Cell Struct. Funct., 12:575, 1987), mouse PGK-1 promoter (Soriano et al., Cell, 64:693, 1991) and the like can be used. A library of human cell transformants in which the introduced marker genes have been inserted into 46 human chromosomes of 23 kinds at random can be prepared by transformation through electroporation (Ishida et al., "Cell Technology Experiment Manual", published by Kodansha, 1992) and the like and subsequent selection of transformants.

As for 3), since many human normal cells have a very low ability to form microcells, the whole cell of the transformant may be fused with a cell having a high ability to form microcells such as mouse A9 cell (Oshimura, M., Environ. Health Perspect., 93:57, 1991) so as to provide the transformed cell with an ability to form microcells. It is known that in mouse-human hybrid cells, human chromosomes selectively disappear. The fused cell selected by the marker can retain stably the marked human chromosome.

In order to meet the condition of 2), it is desired to obtain a microcell from the fused cell and fuse it again with a mouse A9 cell. In this case, too, most of the cells selected by the marker will meet the three conditions 1), 2) and 3) above. The marked human chromosomes can be identified in the finally obtained mouse-human monochromosomal hybrid cells by PCR (Polymerase Chain Reaction, Saiki et al., Science, 239:487, 1988), Southern blot analysis (Ausubel et al., Current protocols in molecular biology, John Wiley & Sons, Inc., 1994), FISH analysis (Fluorescence In Situ Hybridization, Lawrence et al., Cell, 52: 51, 1988) and the like. If the transfer of a specified chromosome is desired, the above procedures are applied to each of many human cell transformant clones to select a clone in which a chromosome of interest is marked. Alternatively, the above procedures are applied to a mixture of human cell transformant clones and the identification of human chromosomes is carried out on a large number of the resulting mouse-human monochromosome hybrid cells.

In addition, a marker gene can be inserted into a desired site by homologous recombination of a specific DNA sequence on the chromosome which is to be transferred (Thomas et al., Cell, 51:503, 1987).

A microcell prepared from the mouse-human hybrid cell may be irradiated with γ-rays such that the marked human chromosome is fragmented and transferred into a mouse A9 cell. Even if the microcell is not irradiated with γ-rays, a partially fragmented human chromosome may be transferred at a certain frequency. In these cases, the resulting microcell fused clones retain partial fragments of the marked human chromosomes. These clones can be used when it is desired to transfer the partial fragments into recipient cells.

Human chromosomes to be introduced into ES cells may be modified by deletion, translocation, substitution and the like. Specific procedures for these modifications are as follows:

1) In each of the steps of preparing the aforementioned mouse-human hybrid cell, inducing a microcell from the mouse-human hybrid cell, further fusing the microcell with a mouse A9 cell, inducing a microcell from the further fused cell and fusing the latter microcell with a mouse ES cell, deletion and/or translocation of human chromosomes may occasionally occur. Cells retaining such mutated chromosomes are selected under the microscopic observation of chromosomes or by use of PCR, Southern analysis, or the like. A clone retaining a desired mutant chromosome can be selected from a mouse A9 library retaining various human chomosomes. A clone retaining a desired mutant chromosome can be selected from A9 or ES cell fused with a microcell induced from a mouse A9 cell retaining a certain human chromosome. The frequency of fragmentation of-chromosomes can be raised by γ-ray irradiation (Koi et al., Science, 260:361, 1993).

2) A targeting vector retaining a loxp sequence that is recognized by Cre enzyme is constructed. A clone into which a loxp sequence has been inserted at a desired site on a chromosome is obtained by homologous recombination in a cell retaining a human chromosome. Subsequently, Cre enzyme is expressed in the cell of:the clone to select a mutant having chromosomal deletion and/or translocation caused by site-specific recombination. See WO97/49804 and Smith et al., Nature Genetics, 9:376, 195. As a host into which a targeting vector is to be introduced, a cell allowing for high-frequency homologous recombination such as DT40 cell (Dieken et al., Nature Genetics, 12:174, 1996) may also be used.

3) A targeting vector retaining a human telomere sequence is constructed and the telomere sequence is inserted in the cell at a desired site on a chromosome by homologous recombination in a cell retaining a human chromosome. After a clone into which the telomere sequence has been inserted is obtained, a mutant having deletion caused by the telomere truncation is obtained. See Itzhaki et al., Nature Genet., 2, 283–287, 1992 and Brown et al., P. N. A. S., 93:7125, 1996. As a host into which a targeting vector is to be introduced, a cell allowing for high-frequency homologous recombination such as DT40 cell (Dieken et al., supra) may also be used. Telomere truncation of human chromosomes in DT40 cell is first disclosed in the present invention. Brown (supra) discloses that a vector was inserted into a repeat sequence on a chromosome. However, no specific site can be targeted. Itzhaki et al. discloses that tumor cells, i.e., 12000 cells of cell line HT1080 into which a telomere sequence was introduced were analyzed and 8 homologous recombinants were obtained. They found that out of the 8 cells, only one caused deletion by insertion of the telomere sequence. For some kinds of cells, results were reported that no mutant having truncation was obtained by insertion of a telomere sequence into some kinds of cells (Barnett et al., Nucleic Acids Res., 21:27, 1993). In spite of this report, the inventors believed that it was necessary to increase the absolute number of homologous recombinants in order to obtain mutants having truncation and made an attempt to perform telomere truncation using a DT40 cell as a host. As a result, it was surprisingly found that truncation occurred in all of the 8 homologous recombinants obtained.

As mentioned above, a gene that should not be expressed in a human chromosome-transferred mouse can be removed by modification of a introduced chromosome. If the size of a chromosome to be transferred is shortened by fragmentations, the chromosome fragment to be transferred can be transmitted;to progenies of the chromosome-transferred mice. In addition, using chromosome translocation and substitution techniques, genes derived from a plurality of chromosomes can be expressed on the same chromosome fragment and portions of a plurality of genes on the chromosome fragments can be replaced with different genes. In other words, foreign chromosome fragments can be used as vectors for transferring genes into individual mice and their cells.

(2) Transfer of the Human Chromosome or Fragment Thereof into a Mouse Pluripotent Cell It has been reported to date that an embyonic carcinoma cell (EC cell, Hanaoka et al., Differentiation, 48:83, 1991), an embyonic stem cell (ES cell, Evans, Nature, 292:154, 1981) or an embyonic germ cell (EG cell, Matsui et al., Cell, 70:841, 1992) that are derived from various strains of mice contribute to the normal somatic cells in mice, or are capable of the production of chimeric mice, by injection into or coculturing with a mouse early embryo. ES and EG cells have a very high ability in this respect and in many cases, they also contribute to germ cells thereby making it possible to produce progenies derived from the cells. EC cells can be obtained predominantly from teratocarcinoma; ES cells from the inner cell masses of blastocysts; and EG cells from primordial germ cells appearing at the early stage of embryogeny. These cell lines and their mutants, and any undifferentiated cells that are capable of differentiation into all or part of the normal somatic cells in mice can be used as recipient cells for the transfer of human chromosomes in the present invention. In these recipient cells, for the purpose of achieving advantageous expression of a human gene to be introduced, a gene or genes such as a mouse gene homologous to the human gene can be disrupted in a chimeric mouse or a chimeric-mouse derived tissue or cell by using homologous recombination in gene targeting (Joyner et al., Gene Targeting, 1993, IRL PRESS) or other techniques.

The microcells prepared from the human chromosome donor cells or the microcells irradiated with γ-rays can be used as materials for the transfer of human chromosomes into the recipient cells. The human chromosome can be transferred into the recipient cell through fusion of the recipient cell with the microcell by the method described in motoyuki Shimizu, "Cell Technology Handbook", published by Yodosha, 1992. The microcell donor cells retain markers by which human chromosomes or fragments thereof can be selected in the recipient cells. The clone containing a gene, a chromosome or a fragment of interest can be selected by PCR, Southern blot analysis, FISH method or the like in the same manner as in (1), thus all kinds of human chromosomes or fragments thereof can be transferred. Moreover, if several chromosomes or fragments thereof which contain different selection markers are transferred sequentially, a recipient cell retaining these chromosomes or fragments at the same time can be obtained. In addition, clones having an increased number of the transferred chromosome can be selected from the clones into which the human chromosome has been transferred. Such selection can be accomplished by increasing the concentration of a selection drug to be added to a culture medium.

In order to determine whether the recipient cell selected by the marker (e.g., G418 resistance) on the human chromosome retains the whole or part of the chromosome retained by the donor cell, the following confirmative techniques may be employed: Southern blot analysis using the genomic DNA extracted from the selected recipient cell, with a human specific repeated sequence (L1, Alu, etc.: Korenberg et al., Cell, 53:391, 1988) or a human gene used as a probe; and chromosome analysis such as PCR method using a human gene specific primer or FISH method using a human chromosome specific probe (Lichter et al., Human Genetics, 80:224, 1988).

(3) Production of a Chimeric Mouse from the Human Chromosome Transferred ES Cell The method described in Shinichi Aizawa, "Biotechnology Manual Series 8, Gene Targeting", published by Yodosha, 1995 may be used to produce chimeric mice from the ES cell clone obtained in (2). In selecting factors for efficient production of chimeric mice, such as the developmental stage of the host embryo and its strain, it is desired to employ the conditions already reviewed for the respective ES cell clones. For example, 8 cell stage embryos derived from Balb/c (albino, CREA JAPAN, INC.) or ICR (albino, CREA JAPAN, INC.) are desirably used for CBAxC57BL/6 F1-derived TT2 cell (agouti, Yagi et al., Analytical Biochemistry, 214:70, 1993).

(4) Confirmation of the Retention of the Human Chromosome in the Chimeric Mice and the Expression of a Human Gene The contribution of the ES cells in mice produced from the embryos into which ES cells were injected can be roughly judged by the color of their coat. However, it should be noted that the total absence of contribution to the coat color does not always lead to the conclusion that there is no contribution to other tissues. The detailed information on the retention of the human chromosome in various tissues of the chimeric mice can be obtained by Southern blot analysis using the genomic DNA extracted from various tissues, by PCR or the like.

The expression of the gene on the transferred human chromosome can be confirmed by the following methods. The expression of mRNA transcribed from the human chromosome can be detected by RT-PCR method or northern blotting (Ausubel et al., supra) using RNAs derived from various tissues (Kawasaki et al., P.N.A.S., 85:5698, 1988). The expression at the protein level can be detected by enzyme immunoassay using an anti-human protein antibody that is rendered minimal in its ability to enter into a cross reaction with mouse homologous proteins (ELISA, Toyama and Ando, "Monoclonal Antibody Experiment Manual", published by Kodansha Scientific, 1987; Ishikawa, "Enzyme immunoassay with Superhigh Sensitivity", published by Gakkai Shuppan Center, 1993), western blotting (Ausuel et al., supra), isozyme analysis utilizing the difference in electrophoretic mobility (Koi et al., Jpn. J. Cancer Res., 80:413, 1989) or the like. The retention of the human chromosome in the chimeric mice and the expression of the gene on the human chromosome can be confirmed by the appearance of the cells expressing a drug resistance marker gene in primary culture cells derived from the chimeric mice.

For example, human IgM, IgG, IgA and the like in sera of the chimeric mice which are produced from ES cells retaining human chromosome #14 on which a gene for human immunoglobulin heavy chain exists can be detected by enzyme immunoassay using an anti-human Ig antibody that is rendered minimal in its ability to enter into cross reaction with mouse antibody. Hybridomas capable of producing a human immonoglobulin heavy chain can be obtained by ELISA screening of hybridomas prepared by immunizing the chimeric mouse with a human-derived antigen (e.g., HSA) and fusing the spleen cells of the immunized mice with mouse myeloma cells (Toyama and Ando, "Monoclonal Antibody Experiment Manual", published by Kodansha Scientific, 1987).

The method for producing a chimeric non-human animal of the present invention has been explained above with reference to the case of a mouse retaining a human chromosome(s) or a fragment(s) thereof and expressing the gene(s) on the chromosome(s) or fragments). In the present invention, chromosomes or fragments thereof to be transferred into chimeric non-human animals are not limited to those derived from humans but include any foreign chromosomes and fragments thereof. The term "foreign chromosome" means a chromosome which is transferred into a pluripotent cell and, subsequently, the gene on which (or a fragment thereof) is expressed in a chimeric non-human animal. The organism species from which the foreign chromosome is derived is not particularly limited. Other kinds of chimeric animals such as chimeric rat and pig can be produced by the method of the present invention. ES cells or ES-like cells derived from animals other than mouse were established with rat (Iannaccone et al., Dev. Biol., 163, 288-, 1994), pig (Wheeler et al., Reprod. Fertil. Dev., 6, 563-, 1994) and bovine (Sims et al., Proc. Natl. Acad. Sci. USA, 91, 6143–6147, 1994) and attempts have been made on cyprinodont, chicken and the like ("Transgenic Animal", Protein·Nucleic Acid·Enzyme, October, 1995, Special Issue, published by Kyoritsu Shuppan). It is known that sheep is developed normally from an unfertilized egg transplanted with the nucleus from ES-like cell (ED cell) or epithelial-like cell obtained by subcultivation of the ES-like cell through at least 10 generations (Campbell et al., Nature, 380, 64-, 1996). These ES cells and ES-like cells can be used as recipient cells in the transfer of foreign chromosomes to produce chimeric non-human animals retaining the foreign chromosomes or fragments thereof and expressing the genes on the chromosomes or fragments thereof in the same manner as in the case of mouse.

In the present invention, pluripotent cells into which a foreign chromosome(s) or a fragment(s) thereof are transferred are not limited to the ES cells, EC cells and EG cells mentioned above. For example, it is possible to transfer a foreign chromosome(s) or a fragment(s) thereof into bone marrow stem cells. If these bone marrow stem cells are transplanted into a living organism, hereditary diseases, etc. may be treated.

If an ES cell retaining a foreign chromosome(s) or a fragment(s) thereof is differentiated to a germ cell in the chimeric non-human animal, reproduced progenies will, retain the transferred chromosome(s) or fragment(s) thereof and express the gene(s) on the chromosome(s) or fragment(s) thereof.

The chimeric non-human animals or their progenies can be used to express the gene on the foreign chromosome or fragment thereof and to recover the expression product, thereby producing a biologically active substance. More specifically, the chimeric non-human animals or their progenies can be bred under the conditions for expressing the gene on the foreign chromosome or fragment thereof to recover the expression product from the blood, ascites and the like of the animals. Alternatively, the tissues or cells of the chimeric non-human animal, or immortalized cells derived therefrom (e.g., hybridomas immortalized by fusion with myeloma cells) can be cultured under the conditions for expressing the gene on the foreign chromosome or fragment thereof and the expression product is thereafter recovered from the culture. Furthermore, a foreign chromosome(s) or a fragment(s) thereof which was extracted from tissues or cells of these chimeric non-human animals or their progenies, or from immortalized cells derived therefrom; the DNA which is a component of said foreign chromosome(s) or fragment(s) thereof; or cDNA derived from the foreign chromosome(s) or fragment(s) thereof retained in tissues or cells of the chimeric non-human animals or their progenies, or in immortalized cells derived therefrom may be used to transform animal cells or insect cells (e.g., CHO cells, BHK cells, hepatoma cells, myeloma cells, SF9 cells) and the transformed cells may be cultured under the conditions for expressing the gene on the foreign chromosome(s) or fragment(s) thereof to recover the expression product (e.g., an antibody protein specific to a particular antigen) from the culture. The expression product can be collected by known techniques such as centrifugation and purified by known techniques such as ammonium sulfate fractionation, partition chromatography, gel filtration chromatography, adsorption chromatography, preparative thin-layer chromatography and the like. The biologically active substance includes any kinds of substances encoded on foreign chromosomes, for example, antibodies, particularly human antibodies. For example, the human antibody gene on the foreign chromosome can be cloned from spleen cells of the chimeric non-human animal or immortalized cells such as hybridomas derived therefrom and transferred into Chinese hamster ovary cells (CHO), myeloma cells or the like to produce a human antibody (Lynette et al., Biotechnology, 10:1121-, 1992; Bebbington et al., Biotechnology, 10:169-, 1992).

The chimeric mice or their progenies that retain human chromosomes #2, 14 and/or 22 (or fragments thereof) which can be produced by the method of the present invention can retain the greater part of the functional sequences of respective genes for human antibody heavy chain on chromosome #14, light chains on chromosome #2 and light chain λ on chromosome #22. Hence, they can produce a wide repertory of antibodies which are more similar to human antibody repertory, compared with known transgenic mice into which parts of human antibody gene have been transferred by using yeast artificial chromosomes and the like (Green et al., Nature Genetics, 7, 13-, 1994; Lonberg et al., Nature, 368, 856-, 1994). Also, the chimeric mice and their progenies retaining two human chromosomes (or fragments) of #2+#14, #22+#14 or other combination and the mice and their progenies retaining three human chromosomes (or fragments) of #2+#14+#22 or other combination which are obtainable by mating said chimeric mice and their progenies retaining two human chromosomes (or fragments), as produced by the method of the invention, can produce complete human antibodies both heavy- and light-chains of which are derived from human. These mice can recognize human-derived antigens as foreign substances to cause an immunoreaction with the antigens, thereby producing antigen-specific human antibodies. These properties can be utilized to produce human monoclonal and polyclonal antibodies for therapeutic treatments (Green et al, supra; Longberg et al., supra). On the other hand, in order to obtain a human antibody having high affinity for a particular antigen more efficiently, it is desirable to produce a mouse which produces a human antibody but not a mouse antibody (Green et al., supra; Lonberg et al., supra). In the present invention, this is achieved typically by the following Method A or B using known techniques.

Method A: a method using a mouse antibody-deficient ES cell and a mouse antibody-deficient host embryo for chimera production.

Method B: a method in which a progeny retaining a human chromosome is obtained from a human chromosome-transferred chimeric mouse, followed by mating said progeny with a mouse in a strain deficient in a mouse antibody gene.

A typical example for each of Methods A and B will be described below specifically.

Specific Procedures for Method A

1. One allele of a mouse antibody heavy-chain gene present in two copies in a mouse ES cell is disrupted by homologous recombination in gene targeting (Joyner et al., "Gene Targeting", published by IRL PRESS, 1993). A marker gene, such as a G 418 resistance gene, sandwiched with two copies of a sequence which can be removed later by site-specific recombination [for example, loxp sequence (see recombination with Cre recombinase in Sauer et al., supra; and see also the use of FLP recombinase-FRT sequence in O'Gorman, Science, 251;1351-, 1991)] is inserted at the site where the targeted gene is disrupted.

2. The resultant drug-resistant mouse ES cells in which one allele of an antibody heavy-chain gene was disrupted is cultured in the presence of the drug at a high concentration. Then, those clones which became high concentration drug-resistant are selected. By screening these clones, clones in which both antibody heavy-chain genes were disrupted can be obtained (Shinichi Aizawa, supra).

Alternatively, the other allele of a target gene in the drug-resistant mouse ES cell in which one allele of the antibody heavy-chain gene has been disrupted is also disrupted by homologous recombination. The same procedure may be repeated using a marker gene other than the precedingly inserted marker gene. For example, homologous recombination is performed using a G418-resistance gene, followed by another homologous recombination using a puromycin-resistance gene to obtain clones in which both alleles of the antibody heavy-chain gene have been disrupted. When the same marker as the precedingly inserted marker is used, an enzyme gene that can cause site-specific recombination between recombinant sequences inserted at the both ends of the drug-resistance gene of item 1 is transiently introduced. Subsequently, drug-sensitive clones are selected that are free of the drug-resistance gene that has been inserted in the target gene. Then, a marker gene is inserted again by homologous recombination in gene targeting to obtain clones in which both alleles of the target gene have been disrupted (Seishi Takatsu et al., Experimental Medicine, supplement, Basic Techniques for Immunological Study, p. 255-, 1995, Yodosha).

3. An enzyme gene (e.g., a Cre recombinase gene (Sauer et al., supra)) which causes a site-specific recombination between the recombination sequences inserted at both the ends of the drug-resistance gene in step 1 above is transiently transferred into the mouse ES cells from step 2 above in which both antibody heavy-chain genes were disrupted. Then, drug-sensitive clones are selected in which the drug-resistance genes inserted at the sites of both heavy-chain genes were deleted as a result of recombination between the loxP sequences [Seiji Takatsu et al., "Experimental Medicine (extra number): Basic Technologies in Immunological Researches", p. 2515-, published by Yodosha, 1995].

4. The same procedures in steps 1–3 above are repeated for the mouse antibody light-chain κ gene to finally obtain drug-sensitive clones which are completely deficient in antibody heavy-chain and light-chain κ.

5. Human chromosome #14 (fragment) containing a human antibody heavy-chain gene and marked with a drug-resistance gene (e.g., G418 resistance gene) is transferred into the clone from step 4 above (antibody heavy-chain and light-chain κ -deficient mouse ES cell) by microcell fusion.

6. Human chromosome #2 (fragment) or #22 (fragment) or both containing a human antibody light-chain gene(s) and marked with a drug-resistance gene different from the one used in step 5 above (e.g., puromycin resistance gene) are transferred into the clone obtained in step 5 above by microcell fusion.

7. Chimeric mice are produced from the ES cells obtained in step 6 above by using embryos obtained from a mouse in a strain having no ability to produce its own antibody (e.g., RAG-2 knockout mouse, Shinkai et al., Cell, 68:855-, 1992; membrane-type μ chain knockout mouse, Kitamura et al., Nature, 350:423-, 1991) as host embryos.

8. Most of the functional B lymphocytes in the resultant chimeric mice are derived from the ES cells [Seiji Takatsu et al., "Experimental Medicine (extra number): Basic Technologies in Immunological Researches", p. 234-, published by Yodosha, 1995]. Since those B lymphocytes are deficient in mouse heavy-chain and light-chain κ, they produce human antibodies alone mainly as a result of the expression of the functional human antibody genes on the transferred chromosomes.

Specific Procedures for Method B

1. Chimeric mice retaining a human chromosome or a fragment thereof containing human antibody heavy-chain, light-chain κ or light-chain λ are used to produce a progeny which stably retains the human chromosome or fragment thereof and which can transmit it to the next generation.

2. A mouse in a strain which is homozygous regarding the deficiency in mouse antibody heavy-chain and light-chain κ and which retains human chromosomes containing human antibody heavy-chain (#14)+light-chain κ (#2), heavy-chain (#14)+light-chain λ (#22) or heavy-chain (#14)+light-chain κ (#2)+light-chain λ (#22) is obtained by mating the mouse in a strain expressing human antibody heavy-chain or light-chain from step 1 above or a mouse in a strain expressing both human antibody heavy and light-chains obtained by mating the mice from step 1, with a mouse in a strain deficient in its own antibody genes (e.g., the membrane-type μ chain knockout mouse mentioned above; light-chain κ knockout mouse, Chen et al., EMBO J., 3:821-, 1993). Since mice in the resultant strain are deficient in:mouse antibody heavy-chain and light-chain κ genes, they produce human antibodies alone mainly as a result of the expression of the functional human antibody genes on the transferred chromosomes.

Both Method A and Method B may be used not only to yield human antibodies but also to yield products of any genes located on a foreign chromosome efficiently.

The present invention will now be explained in greater detail with reference to the following examples, which do not limit the scope of the present invention.

EXAMPLE 1

Production of Chromosome Donor Cell Retaining Human Chromosome (Fragment) Labeled with G418 Resistance Plasmid pSTneoB containing a G418 resistance gene (Katoh et al., Cell Struct. Funct., 12:575, 1987; Japanese Collection of Research Biologicals (JCRB), Deposit Number: VE 039) was linearized with restriction enzyme SalI (TAKARA SHUZO CO., LTD.) and introduced into human normal fibroblast cell HFL-1 (obtained from RIKEN Cell Bank, RCB0251). The HFL-1 cells were treated with trypsin and suspended in Dulbecco's phosphate-buffered saline (PBS) at a concentration of $5\times10^6$ cells/ml, followed by electroporation using a Gene Pulser (Bio-Rad Laboratories, Inc.) in the presence of 10 μg of DNA (Ishida et al., "Cell Technology Experiment Procedure Manual", published by Kodansha, 1992). A voltage of 1000 V was applied at a capacitance of 25 μF with an Electroporation Cell of 14 mm in length (165–2088, Bio-Rad Laboratories, Inc.) at room temperature. The electroporated cells were inoculated into an Eagle's F12 medium (hereinafter referred to as "F12") supplemented with 15% fetal bovine serum (FBS) in 3–6 tissue culture plastic plates (Corning) of 100 mmφ. After one day, the medium was replaced with a F12 supplemented with 15% FBS and containing 200 μg/ml of G418 (GENENTICIN, Sigma). The colonies formed after 2–3 weeks were collected in 52 groups each consisting of about 100 colonies. The colonies of each group were inoculated again into a plate of 100 mmφ and cultured.

Mouse A9 cells (Oshimura, Environ. Health Perspect., 93:57, 1991; JCRB 0211) were cultured in Dulbecco's modified Eagle's medium (hereinafter referred to as "DMEM") supplemented with 10% FBS in plates of 100 mmφ. The G418 resistant HFL-1 cells of 52 groups were cultured in F12 supplemented with 15% FBS and 200 μg/ml of G418 in plates of 100 mmφ. The mouse A9 cells and HFL-1 cells were treated with trypsin and one fourth to one half of both cells were mixed. The mixed cells were inoculated into a plate of 100 mmφ and cultured in a mixture of equal amounts of DMEM containing 10% FBS and F12 containing 15% FBS for a period ranging from a half day to one day. Cell fusion was carried out in accordance with the method described in Shimizu et al., "Cell Technology Handbook", published by Yodosha, p.127-, 1992. The cell surface was washed twice with DMEM and then treated sequentially with 2 ml of a PEG (1:1.4) solution for 1 minute and with 2 ml of PEG (1:3) for 1 minute. After the PEG solution was sucked up, and the cells were washed three times with a serum-free DMEM, followed by cultivation in DMEM supplemented with 10% FBS for 1 day. The cells were dispersed by treatment with trypsin and suspended in a double selective medium (10% FBS supplemented DMEM) containing ouabain ($1\times10^{-5}$ M, Sigma) and G418 (800 μg/ml), followed by inoculation in 3 plates of 100 mmφ. After about 3 weeks cultivation, the colonies formed were treated with trypsin to disperse the cells, which were cultured in a selective medium (10% FBS supplemented DMEM) containing G418 (800 μg/ml).

The cells were dispersed by treatment with trypsin and two groups of the cells were collected, followed by cultivation in 6 centrifuge flasks (Coaster, 3025) of 25 cm² until the cell density reached 70–80% confluence. The medium was replaced with a medium (20% FBS supplemented DMEM) containing Colcemid (0.05 μg/ml, Demecolcine, Wako Pure Chemicals Co., Ltd) and the cells were cultured for 2 days to form microcells. After the culture medium was removed, a cytochalasin B (10 μg/ml, Sigma) solution preliminarily warmed at 37° C. was filled in the 25 cm² centrifuge flask, which were inserted into an acryl centrifuge container, followed by centrifugation at 34° C. at 8,000 rpm for 1 hour. The microcells were suspended in a serum-free medium and purified by passage through a filter. To the mouse A9 cells cultured to 80% confluence in the flask of 25 cm², the purified micorcells were added and the two kinds of cells were fused with a PEG solution. The fused cells were cultured in a G418 containing selective medium and colonies formed were isolated. Human chromosomes #2, 4, 14 and 22 retained in the respective clones were identified by the methods described in (1)–(3) below. All other experimental conditions such as operating procedures and reagents were in accordance with Shimizu et al., "Cell Technology Handbook", published by Yodosha, p127-.

(1) PCR Analysis

The isolated cells were cultured and genomic DNA was extracted from the cells with a Puregene DNA Isolation kit (Gentra System Co.). PCR was performed using the genomic DNA as a template with human chromosome specific primers to select the clones retaining human chromosome #2, 4, 14 or 22. The PCR amplification was conducted with about 0.1 μg of the genomic DNA as a template, using a thermal cycler (GeneAmp 9600, Perkin-Elmer Corp.) in accordance with the method described in Innis et al., "PCR Experiment Manual", published by HBJ Publication Office, 1991. Taq polymerase was purchased from Perkin-Elmer Corp. and the reaction was performed in a cycle of 94° C., 5 minutes and 35 cycles of denaturing at 94° C., 15 seconds, annealing at 54–57° C., 15 seconds (variable with the primers) and extension at 72° C., 20 seconds. The gene on each chromosome (O'Brien, Genetic Maps, 6th edition, Book 5, Cold Spring Harbor Laboratory Press, 1993) and polymorphic markers (Polymorphic STS Primer Pair, BIOS Laboratories, Inc.; Weissenbach et al., Nature 359:794, 1992; Walter et al., Nature Genetics, 7:22, 1994) were used as primers. The primers for the genes were prepared on the basis of nucleotide sequences obtained from data bases such as GenBank, EMBL and the like. The names of the polymorphic primers and the sequences of the primers for the genes will be shown for the respective chromosomes in the following examples (#2, Example 1; #4, Example 6, #14, Example 9; #22, Example 2). The following genetic markers and polymorphic makers (Polymorphic STS Primer Pairs: D2S207, D2S177, D2S156 and D2S159, BIOS Laboratories, Inc.) were used to identify chromosome #2.

Cκ (immunoglobulin kappa constant):
5'-TGGAAGGTGGATAACGCCCT (SEQ ID NO:1),
5'-TCATTCTCCTCCAACATTAGCA (SEQ ID NO:2)

FABP1 (fatty acid binding protein-1 liver):
5'-GCAATCGGTCTGCCGGAAGA (SEQ ID NO:3),
5'-TTGGATCACTTTGGACCCAG (SEQ ID NO:4 )

Vk3-2 (immunoglobulin kappa variable):
5'-CTCTCCTGCAGGGCCAGTCA (SEQ ID NO:5),
5'-TGCTGATGGTGAGAGTGAACTC (SEQ ID NO:6)

Vk1-2 (immunoglobulin kappa variable):
5'-AGTCAGGGCATTAGCAGTGC (SEQ ID NO:7),
5'-GCTGCTGATGGTGAGAGTGA (SEQ ID NO:8)

(2) Fluorescence in Situ Hybridization (FISH)

FISH analysis was conducted with probes specific to human chromosomes #2, 4, 14 and 22 (CHROMOSOME PAINTING SYSTEM, Cambio Ltd.) in accordance with the method described in Matsubara et al., "FISH Experiment Protocol", published by Shujunsha, 1994.

Figure 1:
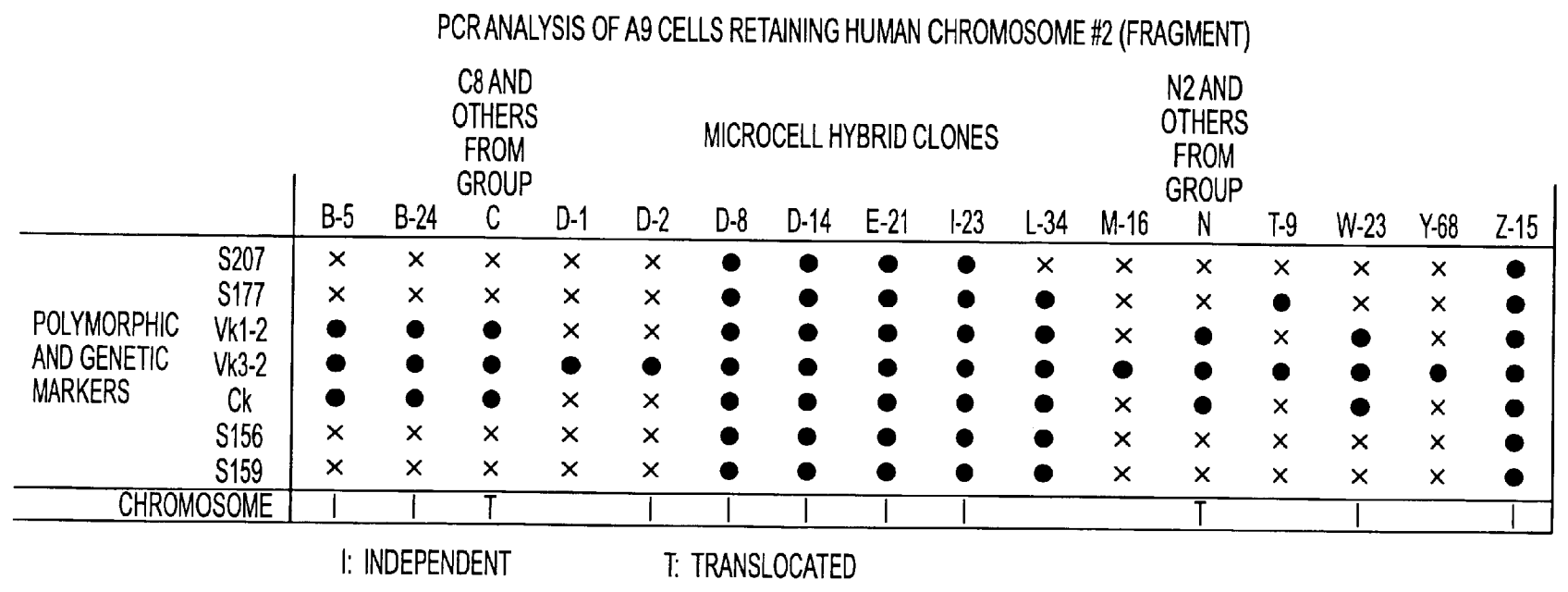

For example, at least one clone retaining chromosome #2 was obtained in 10 groups out of 26 groups (745 clones). Among them, only 5 clones were positive to all the used primers specific to chromosome #2. FISH analysis was conducted with these clones. FISH analysis was conducted with probes specific to human chromosomes #2 (CHROMOSOME PAINTING SYSTEM, Cambio Ltd.) in accordance with the method described in Matsubara et al., "FISH Experiment Protocol", published by Shujunsha, 1994. In the cells positive to all the primers, an intact form of human chromosome #2 was observed. In some of the clones positive to part of the primers, an independent chromosome smaller than human chromosome #2 was observed or a cell having a chromosome in a form fusing with chromosomes other than human chromosome #2 was observed (FIG. 1). In FIG. 1, the names of the clones are shown in the horizontal line and the primers used in the PCR are shown in the left longitudinal line. ● shows positive clones and × shows negative clones. The forms of human chromosome #2 observed by FISH are shown in the bottom line. No description means no performance of experiment.

A9 cells retaining human chromosomes #4, 14 and 22 were obtained by the same procedure.

EXAMPLE 2

Transfer of Human Chromosome #22 into Mouse ES Cells by Microcell Fusion

The mouse A9 cell clones retaining human chromosome #22 (hereinafter referred to as "A9/#22") from Example 1 were used as chromosome donor cells. Mouse ES cell line E14 (obtained from Martin L. Hooper; Hooper et al., Nature, 3;26:292, 1987) was used as a chromosome recipient cell. E14 cells were cultured in accordance with the method described in Aizawa Shinichi, "Biomanual Series 8, Gene Targeting", published by Yodosha, 1995 and G418 resistant STO cell line (obtained from Prof. Kondo Hisato, Osaka University) treated with mitomycin C (Sigma) was used as a feeder cell. In the first step, microcells were prepared from about $10^8$ cells of A9/#22 in accordance with the method reported by Shimizu et al. "Cell Technology Handbook", published by Yodosha, 1992. The total amount of the resulting microcells were suspended in 5 ml of DMEM. About $10^7$ cells of E14 were dispersed with trypsin and washed three times with DMEM and suspended in 5 ml of DMEM. The cells were then mixed with the microcells and the mixture was centrifuged at 1,250 rpm for 10 minutes to remove the supernatant. The precipitate was dispersed by tapping and 0.5 ml of a PEG solution (1:1.4) [5 g of PEG 1000 (Wako Pure Chemicals Co., Ltd.) and 1 ml of DMSO (Sigma) as dissolved in 6 ml of DMEM] was added. The mixture was left to stand at room temperature for 1 minute and 30 seconds and 10 ml of DMEM was added slowly. Immediately thereafter, the resulting mixture was centrifuged at 1,250 rpm for 10 minutes to remove the supernatant. The precipitate was suspended in 30 ml of a medium for ES cells and inoculated into 3 tissue culture plastic plates (Corning) of 100 mm in diameter into which feeder cells were inoculated. After 24 hours, the medium was replaced with a medium supplemented with 300 μg/ml of G418 (GENETICIN, Sigma) and medium replacements were thereafter conducted daily. Drug resistant colonies appeared in 1 week to 10 days. The frequency of appearance was 0–5 per $10^7$ of E14 cells. The colonies were picked up and grown. The cells were suspended in a storage medium (a medium for ES cells+10% DMSO (Sigma)) at a concentration of $5 \times 10^6$ cells per ml and stored frozen at −80° C. At the same time, genomic DNA was prepared from $10^6$–$10^7$ cells of each drug resistant clone with a Puregene DNA Isolation Kit (Gentra System Co.).

Human chromosome #22 was fragmented by irradiating the microcells with γ rays (Koi et al., Science, 260:361, 1993). The microcells obtained from about $10^8$ cells of A9/#22 were suspended in 5 ml of DMEM and irradiated with γ rays of 60 Gy on ice with a Gammacell 40 (Canadian Atomic Energy Public Corporation) at 1.2 Gy/min for 50 minutes. The fusion of γ ray-irradiated microcells and the selection of drug resistant clones were conducted by the same procedure as in the case of the unirradiated microcells. As a result, the frequency of the appearance of the drug resistant clones was 1–7 per $10^7$ of E14 cells. The drug resistant clones were stored frozen and DNA was prepared from the clones by the same procedure as in the case of the unirradiated microcells.

The retention of the transferred chromosomes in the unirradiated microcell-transferred drug resistant clones E14/#22-9 and E14/#22-10, and in the γ ray-irradiated microcell-transferred drug resistant clones E14/#22-14 and E14/#22-25 was confirmed by the methods described in (1)–(3) below.

(1) PCR Analysis (FIG. 2)

The presence of the gene on human chromosome #22 (Genetic Maps, supra) and polymorphic markers (Polymorphic STS Primer Pairs: D22S315, D22S275, D22S278, D22S272 and D22S274, BIOS Laboratories, Inc.; Nature 359:794, 1992) was detected by a PCR method using the genomic DNA of the drug resistant clone as a template. The sequences of oligonucleotide primers for the genes prepared on the basis of nucleotide sequences obtained from data bases such as GenBank, EMBL and the like are described below.

PVALB (parvalbumin): 5'-TGGTGGCTGAAAGCTAA-GAA (SEQ ID NO:9), 5'-CCAGAAGAATGGTGT-CATTA (SEQ ID NO:10)

MB (myoglobin): 5'-TCCAGGTTCTGCAGAGCAAG (SEQ ID NO:11), 5'-TGTAGTTGGAGGCCATGTCC (SEQ ID NO:12)

DIA1 (cytochrome b-5 reductase): 5'- CCCCACCCAT-GATCCAGTAC (SEQ ID NO:13), 5'- GCCCTCAGAA-GACGAAGCAG (SEQ ID NO:14)

Igλ (immunoglobulin lambda): 5'-GAGA GTTGCA-GAAGGGGTGACT (SEQ ID NO:15), 5'-GGAGACCACCAAACCCTCCAAA (SEQ ID NO:16)

ARSA (arylsulfatase A): 5'-GGCTATGGGG ACCTGGGCTG (SEQ ID NO:17), 5'- CAGAGACA-CAGGCACGTAGAAG (SEQ ID NO:18)

PCR amplification (Innis et al., supra) was conducted by using about 0.1 μg of the genomic DNA as a template with the above 10 kinds of the primers. As a result, amplification products having expected lengths were detected with all the primers in the case of the two unirradiated clones and with part of the primers in the case of the γ ray-irradiated two clones. The results are shown in FIG. 2. In FIG. 2, a schematic chromosome map based on the G bands of human chrosome #22 and the location of some markers on bands are shown at the left side (O'Brien, GENETIC MAPS, 6th edition, BOOK 5, etc.). The arrangement of the genetic and polymorphic markers shows approximate positional relationships on the basis of the presently available information (Science, HUMAN GENETIC MAP, 1994; Nature Genetics, 7:22, 1994; Nature 359:794, 1992, etc.) and the order is not necessarily correct. With respect to four kinds of the G418.resistant E14 cell clones, the markers for which the expected amplification products were detected by PCR are shown by ■ and the markers for which the expected amplification products were not detected are shown by □. The results of the observation by FISH analysis are shown at the bottom side. A9/#22 is a chromosome donor cell.

(2) Southern Blot Analysis

Southern blot analysis of about 2 μg of the genomic DNA digested with restriction enzyme BglII (TAKARA SHUZO CO., LTD.) was conducted by using human specific repeated sequence L1 ($10^4$–$10^5$ copies were present per haploid genome, obtained from RIKEN DNA Bank; Nucleic acids research, 13;7813, 1985; pUK19A derived EcoRI-BamHI fragment of 1.4 kb) as a probe in accordance with the method described in Ausubel et al., Current Protocols in Molecular Biology, John Wiley & Sons, Inc., 1994. As a result, a large number of bands hybridized with the human L1 sequence were detected in DNA of each drug resistant clone. With respect to the unirradiated 2 clones, their patterns and the quantitative ratio of human chromosomal DNA to mouse genomic DNA which could be presumed from the density of the respective bands were the same as those of A9/#22. The total signal intensity of the bands of the γ-ray irradiated clones correlated with the degree of the deletion confirmed by the PCR analysis, as compared with that of A9/#22.

(3) Fluorescence in Situ Hybridization (FISH)

FISH analysis was conducted with probes specific to human chromosomes #22 (CHROMOSOME PAINTING SYSTEM, Cambio Ltd.) in accordance with the method described in Matsubara et al., "FISH Experiment Protocol", published by Shujunsha, 1994. As a result, in almost all of the observed metaphase spreads, human chromosome #22 was detected in the form of translocation to the mouse chromosome with respect to E14/#22-9 and in the form of an independent chromosome with respect to the three other clones.

The results of the above experiments demonstrate that the obtained G418 resistant clones E14/#22-9 and E14/#22-10 retained all or most part of human chromosome #22 whereas the clones E14/#22-14 and E14/#22-25 retained partial fragments of human chromosome #22.

EXAMPLE 3

Production of Chimeric Mice from the ES Cells Retaining Human Chromosome #22

General procedures for obtaining mouse embryos, cultivation, injection of the ES cells into the embryos, transplantation to the uteri of foster mothers were carried out in accordance with the method described in Aizawa Shinichi, "Biomanual Series 8, Gene Targeting", published by Yodosha, 1995. The cells in a frozen stock of the G418 resistant ES clone E14/#22-9. which was confirmed to retain human chromosome #22 were thawed, started to culture and injected into blastcyst-stage embryos obtained by mating a C57BL/6XC3H F1 female mouse (CREA JAPAN, INC.) with a C3H male mouse (CREA JAPAN, INC.); the injection rate was 10–15 cells per embryo. Two and half days after a foster mother [ICR or MCH(ICR)] mouse (CREA JAPAN, INC) was subjected to a pseudopregnant treatment, about ten of the ES cell-injected embryos were transplanted to each side of the uterus of the foster mother. The results are shown in Table 1.

TABLE 1

Production of chimeric mice from the ES cells retaining human chromosome #22 (fragments)

| ES cell clone/human chromosome | G418 resistant clone No. | Number of ES cell-injected blastocyst stage embryos | Number of offspring mice | Number of chimeric mice | Contribution to coat color | | |
|---|---|---|---|---|---|---|---|
| | | | | | <–10% | 10–30% | 30%< |
| E14/#22 | 9 | 166 | 29 | 16 | 7 | 3 | 6 |

As a result of the transplantation of a total 166 of injected embryos, 29 offspring mice were born. Chimerism in the offsprings can be determined by the extent of E14 cell-derived pale gray coat color in the host embryo-derived agouti coat color (dark brown). Out of the 29 offsprings, 16 mice were recognized to have partial pale gray coat color, indicating the contribution of the E14 cells. The maximum contribution was about 40% in K22-22.

These results show that the mouse ES cell clone E14/#22-9 retaining human chromosome #22 maintains the ability to produce chimera, that is, the ability to differentiate into normal tissues of mouse.

EXAMPLE 4

Confirmation of Retention of Human Chromosomal DNA in Various Tissues of the Chimeric Mice Derived from the ES Cells Retaining Human Chromosome #22

In addition to the determination of coat color in Example 3, the retention of the transferred chromosome was confirmed by PCR analysis using a template genomic DNA prepared from the tail of the chimeric mouse. The tail was obtained from the chimeric mouse at least 3 weeks old in accordance with the method described in Motoya Katsuki, "Development Technology Experiment Manual", published by Kodansha Scientific, 1987. Genomic DNA was extracted from the tail with a Puregene DNA Isolation Kit. Out of the polymorphic primers used in Example 2, PVALB and D22S278 were used, with the extracted genomic DNA as a template, to confirm the amplification products. The analysis was conducted with 10 of the mice in which the contribution to coat color was observed. As a result, the products of amplification with at least either of the primers were detected in all the mice.

Figure 3:
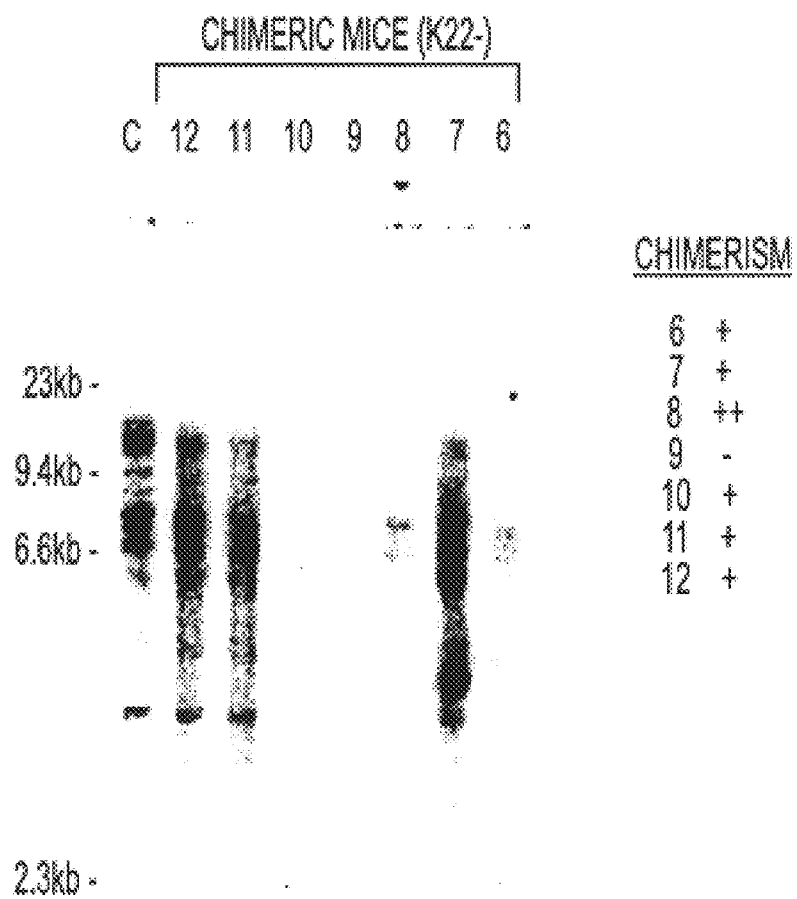
FIG. 3 is a photograph of electrophoresis patterns showing that human L1 sequence is retained in a chimeric mouse produced from a human chromosome #22-transferred ES cell (Southern analysis).

Southern blot analysis was conducted in the same manner as in Example 2 by using human L1 sequence as a probe with 2 μg of the genomic DNA derived from the tails of the 6 chimeric mice and one non-chimeric mouse. As a result, the presence of a large number of human L1 sequence was observed in all the chimeric mice and their patterns were similar to those of E14/#22-9. The quantitative ratio to mouse genome was about 10% at maximum (FIG. 3). In FIG. 3, 2 μg of genomic DNA digested with BglII was used in each lane. Human L1 sequence labeled with $^{32}$P was used as a probe and signals were detected with Image Analyzer BAS2000 (Fuji Photo Film Co., Ltd.). The lanes represent the genomic DNA derived from the tails of the chimeric mice (K22-6, 7, 8, 9, 10, 11 and 12; 9 is the non-chimeric mouse) and control DNA (C which is a mixture of E14/#22-9 genomic DNA and E14 genomic DNA at a weight ratio of 1:9) as counted from the right. The DNA molecular weights are shown at the left side and chimerism in the chimeric mice at the right side (−: 0%, +: <10%, and ++: 10–30%).

Figure 4:
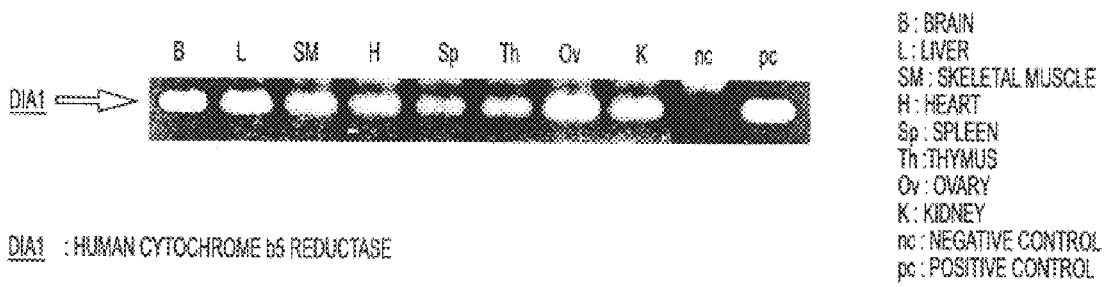
FIG. 4 is a photograph of electrophoresis patterns showing the presence of a human chromosome in organs of a human chromosome #22 transferred chimeric mouse (PCR analysis).

With respect to the chimeric mouse (K22-7) having about 5% contribution to coat color, genomic DNA was obtained from the brain, liver, muscle, heart, spleen, thymus, ovary and kidney with an ISOGEN (Nippon Gene Co.). For each tissue, PCR analysis was conducted with MB and D1A1 selected from the primers for the genes used in Example 2. As a result, both primers gave expected amplification products in all the tissues. The results of PCR analysis using D1A1 primer are shown in FIG. 4. The PCR products were electrophoresed on a 2% agarose gel and stained with ethidium bromide for detection. The lanes in FIG. 4 represent the following from the left: B, brain; L, liver; SM, skeletal muscle; H, heart; Sp, Spleen; Th, thymus; Ov, ovary; K, kidney; nc, non-chimeric mouse tail-derived DNA (negative control); pc, human fibroblast cell (HFL-1) DNA (positive control).

These results show that E14/#22-9 contributed to various normal tissues in the mouse and that it retained human chromosome #22.

EXAMPLE 5

Expression of the Human Genes in the Chimeric Mouse Derived from the ES Cell Retaining Human Chromosome #22

The tail of the mouse (K22-7) having about 5% contribution to coat color was frozen with liquid nitrogen and then disrupted for use as a sample for confirming the expression of the human genes. The sample was a mixture of tissues such as skin, bones, muscles, blood and the like. Total RNA was extracted from the sample with an ISOGEN (Nippon Gene Co.) and used in an RT-PCR method to detect mRNAs of human myoglobin (MB) and human cytochrome b5 reductase (D1A1). The RT-PCR was performed in accordance with the method described in Innis et al., "PCR Experiment Manual", published by HBJ Publication Office, 1991. Randam hexamer oligonucleotides (final concentration: 100 pmol, TAKARA SHUZO CO., LTD.) were used as primers for reverse transcription and Super Script (BRL Co.) as reverse transcriptase. The following primers were used for amplification using cDNA as a template.
MB: 5'-TTAAGGGTCACCCAGAGACT (SEQ ID NO:19), 5'-TGTAGTTGGAGGCCATGTCC (SEQ ID NO:20)
D1A1: 5'-CAAAAAGTCCAACCCTATCA (SEQ ID NO:21), 5'-GCCCTCAGAAGACGAAGCAG (SEQ ID NO:22)

Figure 5:
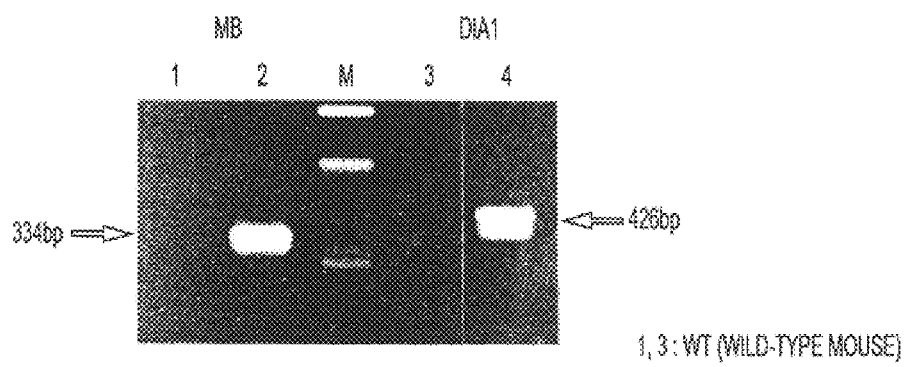
FIG. 5 is a photograph of electrophoresis patterns showing the results of the expression of human genes in a human chromosome #22 transferred chimeric mouse (RT-PCR).

As a result, amplification products specific to mRNAs of both genes were detected (FIG. 5). The RT-PCR products were electrophoresed on a 2% agarose gel and stained with ethidium bromide for detection. In FIG. 5, M is a marker (HindIII digested λ DNA+HaeIII digested φ X174DNA, TAKARA SHUZO CO., LTD.); MB, human myoglobin; D1A1, human cytochrome b5 reductase; and WT, a wild-type C3H mouse.

Figure 6:
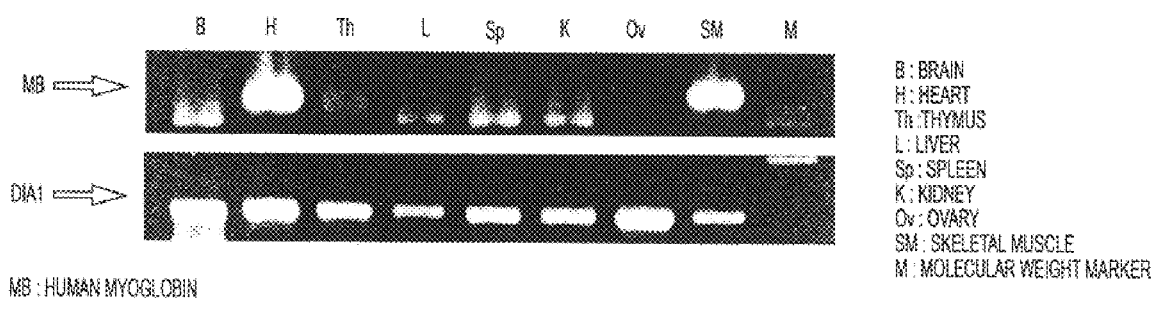
FIG. 6 is a photograph of electrophoresis patterns showing the results of the expression of human genes in organs of a human chromosome #22 transferred chimeric mouse (RT-PCR).

With respect to the same individual (K22-7), total RNA was extracted from the brain, heart, thymus, liver, spleen, kidney, ovary and skeletal muscle with an ISOGEN and RT-PCR was performed on each organ with the above two primers. As a result, expected products of amplification with D1A1 were observed in all the organs and those with MB were observed only in the heart and skeletal muscle (FIG. 6). Myoglobin is known to be expressed specifically in muscle cells (Bassel-Duby et al., MCB, 12:5024, 1992). Hence, the above results show that the gene on the transferred human chromosome can be subjected to the normal tissue-specific regulation in the mouse. The PCR products were electrophoresed on a 2% agarose gel and stained with ethidium bromide for detection. In FIG. 6, the lanes represent the following from the left: B, brain; H, heart; Th, thymus; L, liver; Sp, spleen; K, kidney; Ov, ovary; SM, skeletal muscle; and M, marker (supra). The lower band observed in the results of MB are believed to represent non-specific products.

These results show that the transferred human chromosome #22 can function in normal tissues of the chimeric mice.

EXAMPLE 6

Transfer of Human Chromosome #4 or Fragments Thereof Into ES Cells

Figure 7:
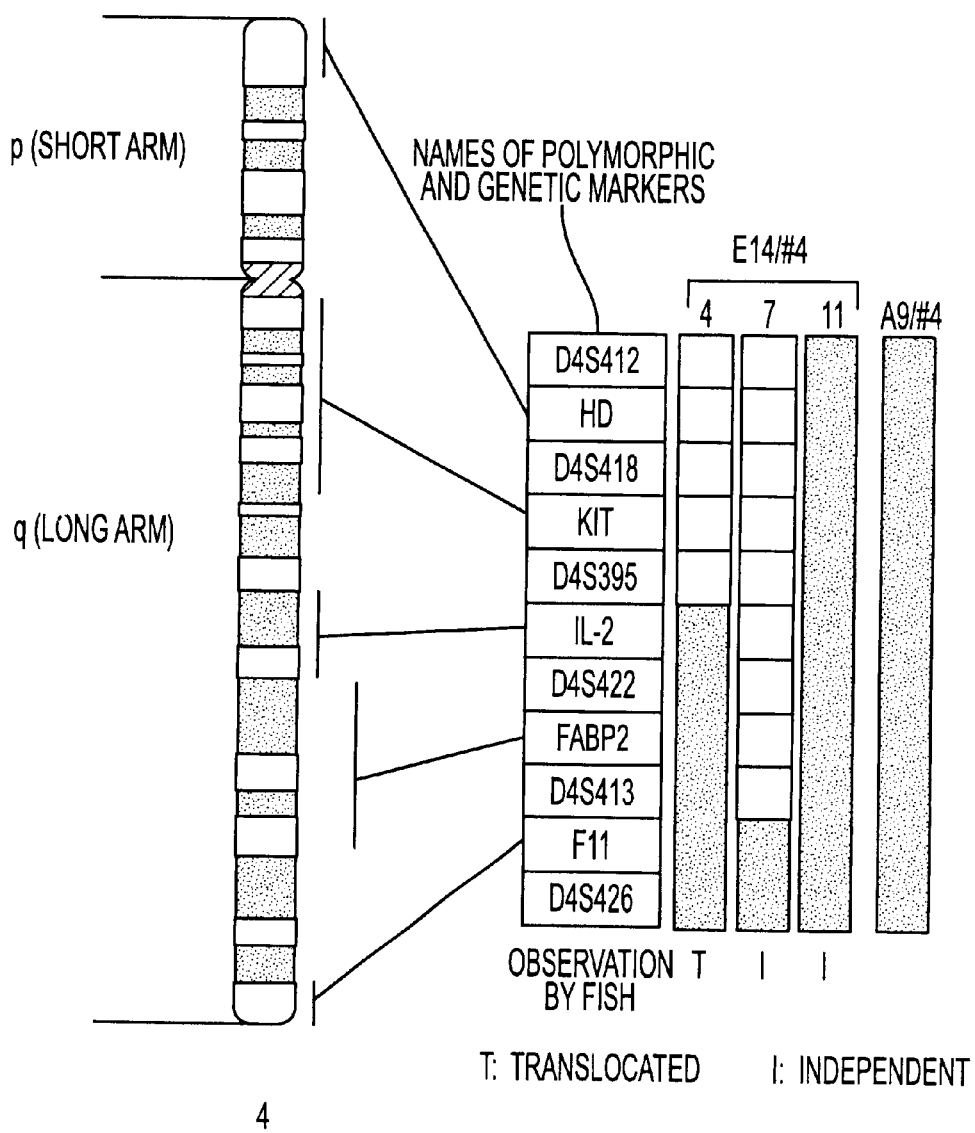
FIG. 7 shows that human chromosome #4 (fragment) is retained in an E14 drug resistant cell (PCR analysis).

The mouse A9 cell clone retaining human chromosome #4 (hereinafter referred to as "A9/#4") from Example 1 was used as a chromosome donor cell. Mouse ES cell line E14 (see Example 2) was used as a chromosome recipient cell. The microcell fusion and the selection of G418 resistant clones were conducted by the same procedures as in Example 2. The frequency of the appearance of the drug resistant clones was 1–2 per $10^7$ of E14 cells. The drug:resistant clones were stored frozen and genomic DNA were prepared by the same procedures as in Example 2. The retention of the transferred human chromosome #4 or fragments thereof in the drug resistant clones E14/#4-4, E14/#4-7 and E14/#4-11 was confirmed by the methods described in (1)–(3) below.
(1) PCR Analysis (FIG. 7)

The presence of the gene on human chromosome #4 (O'Brien, Genetic Maps, 6th edition, Book 5, Cold Spring Harbor Laboratory Press, 1993) and polymorphic markers (Polymorphic STS Primer Pairs: D4S395, D4S412, D4S422, D4S413, D4S418, D4S426 and F11, BIOS Laboratories, Inc.;, Nature 359:794, 1992) was detected by a PCR method. The sequences of oligonucleotide primers for the genes prepared on the basis of nucleotide sequences obtained from data bases such as GenBank, EMBL and the like will be described below.
HD (huntington disease): 5'-TCGTTCCTGTCGAGGATGAA (SEQ ID NO:23), 5'-TCACTCCGAAGCTGCCTTTC (SEQ ID NO:24)
IL-2 (interleukin-2): 5'-ATGTACAGGATGCAACTCCTG (SEQ ID NO:25), 5'-TCATCTGTAAATCCAGCAGT (SEQ ID NO:26)
KIT (c-kit): 5'-GATCCCATCGCAGCTACCGC (SEQ ID NO:27), 5'-TTCGCCGAGTAGTCGCACGG (SEQ ID NO:28)
FABP2 (fatty acid binding protein 2, intestinal), 5'-GATGAACTAGTCCAGGT GAGTT (SEQ ID NO:29), 5'-CCTTTTGGCTTCTACTCCTTCA (SEQ ID NO:30)

PCR amplification was conducted with the above 11 kinds of the primers. As a result, the amplification products having expected lengths were detected with all or part of the primers in all the three clones. In the E14/#4-4 and E14/#4-7 clones, the deletion of partial regions was observed. The results are shown in FIG. 7. In FIG. 7, a schematic chromosome map based on the G bands of human chromosome #4 and the location of some markers on bands are shown at the left side (see Example 2). The arrangement of the genetic and polymorphic markers shows approximate positional relationships on the basis of the presently available information (see Example 2) and the order is not necessarily correct. With respect to the three kinds of the G418 resistant E14 cell clones, the markers for which the expected amplification products were detected are shown by ■ and the markers for which the expected amplification products were not detected are shown by □. The results of the observation by FISH analysis are shown at the lower side. A9/#4 is a chromosome donor cell.

Figure 8:
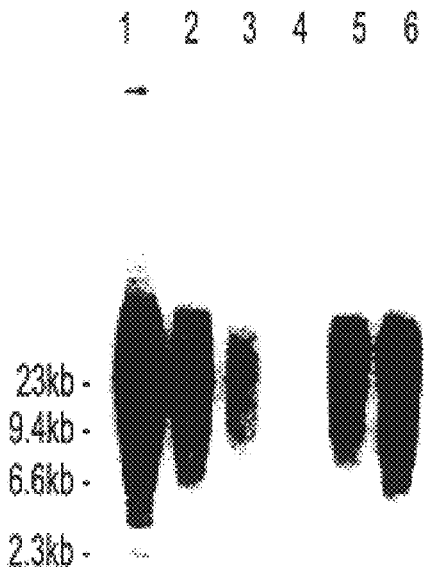
FIG. 8 is a photograph of electrophoresis patterns showing the detection of human L1 sequence in a human chromosome #4-transferred E14 cell clone (Southern analysis).

(2) Southern Blot Analysis (FIG. 8)

Southern blot analysis was conducted by the same procedure as in Example 2 using human L1 sequence as a probe with genomic DNAs obtained from E14/#4-4 and E14/#4-7. As a result, a large number of bands hybridized with the human L1 sequence were detected in DNAs of both drug resistant clones. The total signal intensity correlated with the degree of the deletion confirmed by the PCR analysis, as compared with that of A9/#4. In FIG. 8, 2 μg of genomic DNA digested with BglII was used in each lane. Human L1 sequence labeled with $^{32}$P was used as a probe and the signals were detected with an Image Analyzer (BAS 2000, Fuji Photo Film Co., Ltd.). In FIG. 8, the lanes represent the following as counted from the left: 1, A9/#4 (chromosome donor cell); 2, A9/#4+A9 (1:2); 3, A9/#4+A9 (1:9:); 4, A9; 5, E14/#4-4. Lanes 2 and 3 represent mixtures of two kinds of DNAs at the ratios shown in parentheses. The molecular weights of DNAs are shown at the left side.

(3) Fluorescence in Situ Hybridization (FISH)

FISH analysis was conducted with probes specific to human chromosomes #4 (CHROMOSOME PAINTING SYSTEM, Cambio Ltd.) by the same procedure as in Example 2. As a result, in almost all of the observed metaphase spreads of the three clones used, human chromosome #4 or partial fragments thereof were detected in the form of translocation to the mouse chromosome with respect to E14/#4-4 and in the form of an independent chromosome with respect to the two other clones. The relative sizes of the observed human chromosome were consistent with those presumed from the results of the PCR analysis.

The results of the above experiments demonstrate that the obtained G418 resistant clones retained the whole human chromosome #4 or partial fragments thereof.

EXAMPLE 7

Production of Chimeric Mice from the ES Cells Retaining Human Chromosome #4 Fragments The cells in frozen stocks of the G418 resistant ES cell clones E14/#4-4 and E14/#4-7 which were confirmed to retain partial fragments of human chromosome #4 were thawed, started to culture, and injected into blastcyst stage embryos obtained by the same method as in Example 3; the injection rate was 10–15 cells per embryo. Two and half days after a foster mother [ICR or MCH(ICR)] mouse (CREA JAPAN, INC.) was subjected to a pseudopregnant treatment, about ten of the ES cell-injected embryos were transplanted to each side of the uterus of the foster mother. The results are; shown in Table 2.

TABLE 2

Production of chimeric mice from the E14 cell clones retaining human chromosome #4 (fragments)

| ES cell clone/human chromosome | G418 resistant clone No. | Number of ES cell-injected blastocyst stage embryos | Number of offspring mice | Number of chimeric mice | Contribution to coat color | | |
|---|---|---|---|---|---|---|---|
| | | | | | <10% | 10–30% | 30%< |
| E14/#4 | 4 | 160 | 8 | 5 | 5 | — | — |
| | 7 | 80 | 5 | 2 | 1 | 1 | — |

As a result of the transplantation of a total of 240 injected embryos, 13 offspring mice were born. Chimerism in the offsprings can be determined by the extent of E14 cell-derived pale gray coat color in the host embryo-derived agouti coat color (dark brown). Out of the 13 offsprings, 7 mice were recognized to have partial pale gray coat color, indicating the contribution of the E14 cells. The maximum contribution was about 15% in one individual derived from E14/#4-7.

These results show that the mouse ES cell clones E14/#4-4 and E14/#4-7 which retain fragments of human chromosome #4 maintain the ability to produce chimera, that is, the ability to differentiate into normal tissues of mouse.

EXAMPLE 8

Confirmation of Retention of Human Chromosomal DNA in the Chimeric Mice Derived from the ES Cells Retaining Partial Fragments of Human Chromosome #4 and Expression of the G418 Resistance Gene (1) PCR Analysis Using the chimeric mice produced in Example 7, genomic DNAs were prepared from the tails of one individual derived from E14/#4-7 (K#4-7-1: about 5% chimerism) and one individual derived from E14/#4-4 (K#4-4-41: about 5% chimerism) by the same procedure as in Example 4. These DNAs were used as templates to conduct PCR analysis using polymorphic marker F11 for chromosome #4 analysis (see Example 6) which was detected in E14/#4-7 and E14/#4-4. As a result, expected amplification products were detected in both mice.

Figure 9:
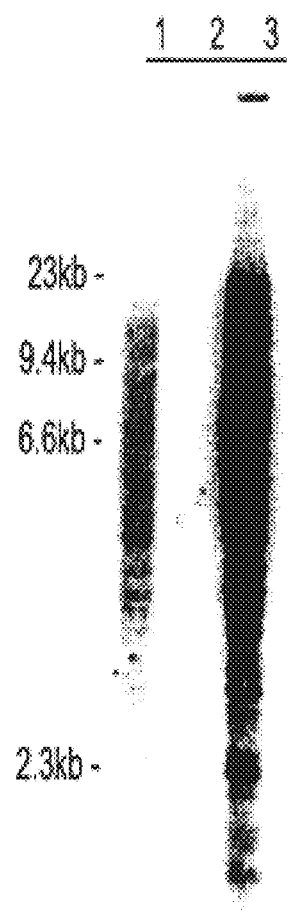
FIG. 9 is a photograph of electrophoresis patterns showing that human L1 sequence is retained in a chimeric mouse produced from a human chromosome #4-transferred ES cell (Southern analysis).

(2) Southern Analysis (FIG. 9)

Southern analysis was conducted in the same manner as in Example 2 by using human L1 sequence as a probe with 2 μg of the genomic DNA derived from the tail of one individual derived from E14/#4-7 (K#4-7-1: about 5% chimerism). As a result, the presence of a large number of human L1 sequence was observed and their patterns were similar to those of E14/#4-7. The quantitative ratio to mouse genome was about 10% of that of E14/#4-7 at maximum. In FIG. 9, 2 μg of genomic DNA digested with BglII was used in each lane. Human L1 sequence labeled with 32P was used as a probe and signals were detected with Image Analyzer BAS2000 (Fuji Photo Film Co.,!, Ltd.). The molecular weights of DNAs are shown at the left side. The lanes represent the following as counted from the left: 1, K#4-7-1; 2, blank; and 3, E14/#4-7.

(3) Test on the Tail-derived Fibroblast Cells for G418 Resistance

Fibroblast cells were prepared from the tails of one individual derived from E14/#4-7 (K#4-7-1: about 5% chimerism) and one individual derived from E14/#4-4 (K#4-4-41: about 5% chimerism). In the same procedure as in Example 4, the tail of each mouse was cut at a length of 5–10 mm and washed several times with PBS/1 mM EDTA, followed by notching of the tail with a knife. The outer skin layer was removed and the inner tissues were cut into fine pieces. The fine pieces of tissues were transferred into a tube containing 5 ml of PBS/1 mM EDTA and left to stand for 30 minutes to 1 hour at room temperature. Subsequently, the supernatant was removed leaving a 1 ml portion of the PBS/EDTA behind, and 1 ml of 0.25% trypsin/PBS was added. The tissues were dispersed thoroughly by tapping or pipetting at room temperature for 5–10 minutes. After centrifugation at 1,000 rpm for 10 minutes, the precipitate was suspended in 2 ml of DMEM (10% FCS) and inoculated into a 35 mm plate. After cultivation for 7–10 days, the cells were treated with trypsin and about $10^4$ cells per plate were inoculated into two 35 mm plates. G418 was added to the medium in one plate at a final concentration of 400 μg/ml. The cells were cultured for 5–7 days and the appearance of viable cells in each plate were examined. Under these conditions, 100% of the wild-type ICR mouse-derived fibroblast cells were killed in the presence of G418. As a result, G418 resistant fibroblast cells was present in both mice.

These results show that E14/#4-7 and E14/#4-4 contributed to various normal tissues in the mouse and that they retained partial fragments of human chromosome #4.

EXAMPLE 9

Transfer of Human Chromosome #14 or Fragments Thereof into Mouse ES Cells

The mouse A9 cell clone retaining human chromosome #14 (hereinafter referred to as "A9/#14") from Example 1 was used as a chromosome donor cell. Mouse ES cell line TT2 (purchased from Lifetech Oriental Co., Yagi et al., Analytical Biochem., 214:70, 1993) was used as a chromosome recipient cell. The TT2 cells were cultured in accordance with the method described in Aizawa Shinichi, "Biomanual Series 8, Gene Targeting", published by Yodosha, 1995 and G418 resistant primary culture cells (purchased from Lifetech Oriental Co.) treated with mitomycin C (Sigma) were used as feeder cells. The microcell fusion and the selection of G418 resistant clones were conducted by the same procedures as in Example 2. The frequency of the appearance of the drug resistant clones was 3–6 per $10^7$ of TT2 cells. The drug resistant clones were stored frozen and genomic DNA was prepared by the same procedures as in Example 2.

Human chromosome #14 was fragmented by irradiating the microcells with γ-rays (Koi et al., Science, 260:361, 1993). The microcells obtained from about $10^8$ cells of A9/#14 were suspended in 5 ml of DMEM and irradiated with γ-rays of 30 Gy on ice with a Gammacell 40 (Canadian Atomic Energy Public Corporation) at 1.2 Gy/min for 25 minutes. The fusion of γ ray-irradiated microcells and the selection of drug resistant clones were conducted by the same procedure as in the case of the unirradiated micorcells. As a result, the frequency of the appearance of the drug resistant clones was 3 per $10^7$ of TT2 cells. The drug resistant clones were frozen stored and DNA was prepared by the same procedure as in Example 2.

The retention of human chromosome #14 or partial fragments thereof in the unirradiated microcell-transferred G418 resistant clones 1-4 and 1-5, and in the G418 resistant clones 3-1 and 3-2 (a total of 4 clones) into which the γ-ray-irradiated microcell was transferred was confirmed by the methods described in (1) and (2) below.

Figure 10:
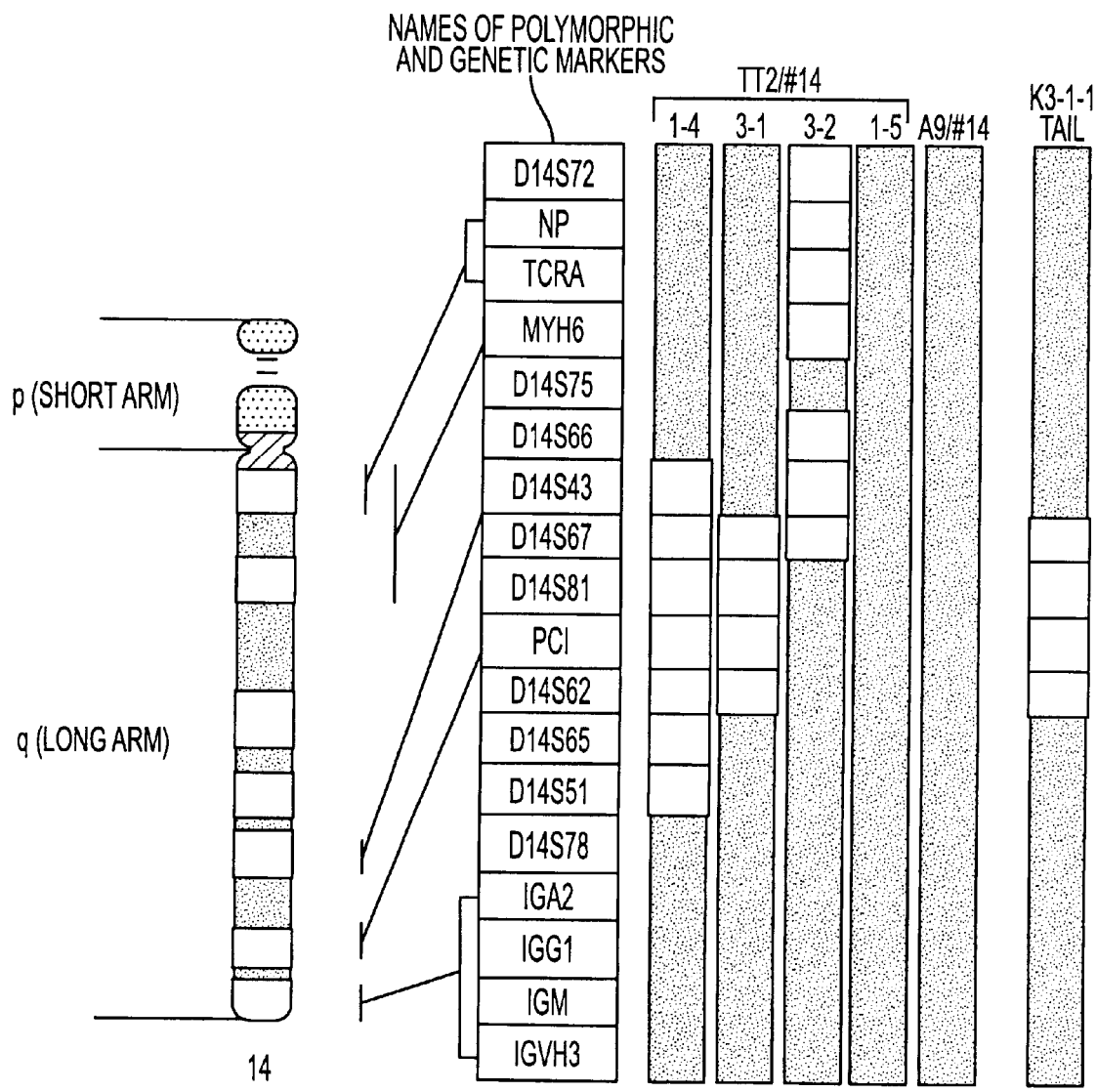
FIG. 10 shows that human chromosome #14 (fragment) is retained in a TT2 drug resistant cell (PCR analysis).

(1) PCR Analysis (FIG. 10)

The presence of the gene on human chromosome #14 (O'Brien, Genetic Maps, 6th edition, Book 5, Cold,Spring Harbor Laboratory Press, 1993) and polymorphic markers (Polymorphic STS Primer Pairs: D14S43, D14S51, D14S62, D14S65, D14S66, D14S67, D14S72, D14S75, D14S78, D14S81 and PCI, BIOS Laboratories, Inc.; Nature 359:794, 1992; Nature Genetics, 7:22, 1994) was detected by a PCR method using genomic DNA of the drug resistant clone as a template. The sequences of oligonucleotide primers for the genes prepared on the basis of nucleotide sequences obtained from data bases such as GenBank, EMBL and the like are described below.

NP (nucleoside phosphorylase):
5'-ATAGAGGGTACCCACTCTGG (SEQ ID NO:31),
5'-AACCAGGTAGGTTGATATGG (SEQ ID NO:32)

TCRA (T-cell receptor alpha):
5'-AAGTTCCTGTGATGTCAAGC (SEQ ID NO:33),
5'-TCATGAGCAGATTAAACCCG (SEQ;ID NO:34)

MYH6 (myosin heavy chain cardiac):
5'-TGTGAAGGAGGACCAGGTGT (SEQ ID NO:35),
5'-TGTAGGGGTTGACAGTGACA (SEQ ID NO:36)

IGA2 (immunoglobulin alpha-2 constant):
5'-CTGAGAGATGCCTCTGGTGC (SEQ ID NO:37),
5'-GGCGGTTAGTGGGGTCTTCA (SEQ ID NO:38)

IGG1 (immunoglobulin gamma-1 constant):
5'-GGTGTCGTGGAACTCAGGCG (SEQ ID NO:39),
5'-CTGGTGCAGGACGGTGAGGA (SEQ ID NO:40)

IGM (immunoglobulin mu constant):
5'-GCATCCTGACCGTGTCCGAA (SEQ ID NO:41),
5'-GGGTCAGTAGCAGGTGCCAG (SEQ ID NO:42)

IGVH3 (immunoglobulin heavy variable-3):
5'-AGTGAGATAAGCAGTGGATG (SEQ ID NO:43),
5'-GTTGTGCTACTCCCATCACT (SEQ ID NO:44)

PCR amplification was conducted using the genomic DNAs of the 4 drug resistant clones as templates with the above 18 kinds of the primers by the same procedure as in Example 2. As a result, expected amplification products were detected with all or part of the primers. In the drug resistant clones 3-1 and 3-2 obtained by using the γ-ray irradiated microcells, a tendency for the deletion of partial regions of chromosome #14 was observed. In the case where the unirradiated microcells were used, deletion was observed as in the case of the 1-4 clone. The results are shown in FIG. 10. In FIG. 10, a schematic chromosome map based on the G bands of human chromosome #14 and the location of some markers on bands are shown at the left side (see Example 2). The arrangement of the genetic and polymorphic markers shows approximate positional relationships on the basis of the presently available information (see Example 2) and the order is not necessarily correct with respect to four kinds of the G418 resistant TT2 cell clones, the markers for which the expected amplification products were detected are shown by ■ and the markers for which the expected amplification products were not detected are shown by □. A9/#14 is a chromosome donor cell. The results of Example 11 (1) are shown at the right side.
(2) Fluorescence in Situ Hybridization (FISH)

FISH analysis was conducted with probes specific to human chromosomes #14 (CHROMOSOME PAINTING SYSTEM, Cambio Ltd.) in accordance with the method described in Matsubara et al., "FISH Experiment Protocol", published by Shujunsha, 1994. As a result, in almost all of the observed metaphase spreads of all the 4 clones, human chromosome #14 or partial fragments thereof were detected in the form of an independent chromosome. The relative sizes of the observed human chromosome were consistent with those presumed from the results of the PCR analysis.

The results of the above experiments demonstrate that the obtained G418 resistant clones 1-4, 1-5, 3-1 and 3-2 retained the whole or partial fragments of human chromosome #14.

EXAMPLE 10

Production of Chimeric Mice from the ES Cells Retaining Human Chromosome #14 or Fragments Thereof The cells in the frozen stocks of four G418 resistant ES cell clones (1-4, 3-1, 3-2 and 1-5) that were prepared in Example 9 and which were confirmed to retain human chromosome #14 or fragments thereof were thawed, started to culture: and injected into 8-cell stage embryos obtained by mating [ICR or MCH(ICR)] male and female mice (CREA JAPAN, INC.); the injection rate was 8–10 cells per embryo. The embryos were cultured in an ES medium overnight to develop to blastocysts. Two and half days after a foster mother ICR mouse (CREA JAPAN, INC.) was subjected to a pseudopregnant treatment, about ten of the injected embryos were transplanted to each side of the uterus of the foster mother. The results are shown in Table 3.

fragments thereof maintain the ability to produce chimera, that is, the ability to differentiate into normal tissues of mouse.

EXAMPLE 11

Confirmation of Retention of Human Chromosome #14 Fragment DNA in the Chimeric Mice Derived from the ES Cells Retaining Human Chromosome #14 Fragments The retention of human chromosome #14 partial fragments in the chimeric mice obtained in Example 10 was confirmed by the methods described in (1)–(3) below.
(1) PCR Analysis Using DNAs Derived from Various Tissues Genomic DNA was extracted from the tail of one individual derived from 3-1 (K3-1-1: about ,25% chimerism) by the same procedure as i Example 4. The DNA was used as a template to conduct PCR analysis using all of the 14 primers for chromosome #14 analysis which were detected in 3-1. As a result, expected amplification products were detected with all the 14 primers. (FIG. 10)

Figure 11:
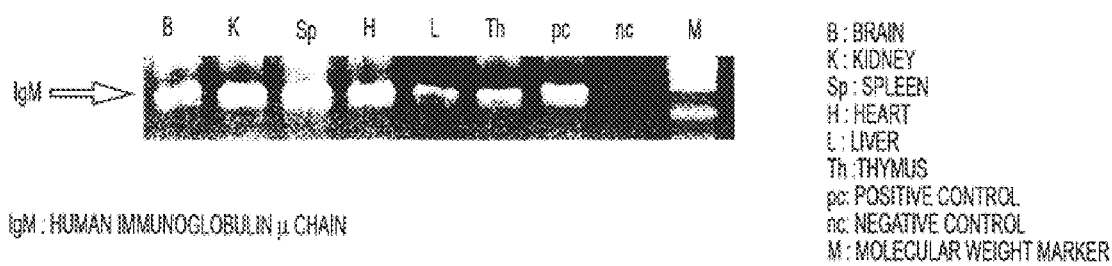
FIG. 11 is a photograph of electrophoresis patterns showing the presence of a human chromosome in organs of a chimeric mouse produced from a human chromosome #14 transferred ES cell (PCR analysis).

With respect to the same individual (K3-1-1), genomic DNA was obtained from the brain, kidney, spleen, heart, liver and thymus with a Puregene DNA Isolation Kit. For each tissue, PCR analysis was conducted with IGM primers (see Example 9). As a result, expected amplification products were detected in all the tissues (FIG. 11). The PCR products were electrophoresed on a 2% agarose gel and stained with ethidium bromide for detection;. In FIG. 11, the lanes represent the following as counted from the left: B, brain; K, kidney; Sp, Spleen; H, heart; L, liver; Th, thymus; pc, human fibroblast cell (HFL-1) DNA (positive control); nc, non-chimeric mouse tail DNA (negative control); and M, marker (HindIII digested γ DNA +HaeIII digested φ X174 DNA, TAKARA SHUZO CO., LTD.).
(2) Test on the Tail-derived Fibroblast Cells for G418 Resistance Fibroblast cells were prepared from the tails of two individuals derived from 3-2 (K3-2-1: about 25%

TABLE 3

Production of chimeric mice from the TT2 cell clones retaining human chromosome #14 (fragments)

| ES cell clone/human chromosome | G418 resistant clone No. | Number of ES cell-injected 8-cell stage embryos | Number of offspring mice | Number of chimeric mice | Contribution to coat color |||
|---|---|---|---|---|---|---|---|
| | | | | | <20% | 20–50% | 50–80% |
| TT2/#14 | 1-4 | 98 | 20 | 1 | — | — | 1 |
| | 1-5 | 110 | 14 | 2 | 1 | — | 1 |
| | 3-1 | 103 | 11 | 2 | 1 | 1 | — |
| | 3-2 | 183 | 19 | 3 | — | 2 | 1 |

As a result of the transplantation of a total of 494 injected embryos, 64 offspring mice were born. Chimerism in the offsprings can be determined by the extent of TT2 cell-derived agouti coat color (dark brown) in the host embryo-derived albino coat color. Out of the 64 produced offsprings, 8 mice were recognized to have partial agouti coat color, indicating the contribution of the ES cells. The maximum contribution was about 80% in:one individual derived from 1-4.

These results show that the G418 resistant ES cell clones (1-4, 1-5, 3-1 and 3-2) retaining human chromosome #14 or chimerism, and K3-2-3: about 50% chimerism) and one individual derived from 1-4 (K1-4-1: about 80% chimerism). In the same procedure as in Example 4, the tail of each chimeric mouse of 3–6 weeks was cut at a length of 5–10 mm and washed several times with PBS/1 mM EDTA, followed by notching of the tail with a knife. The outer layer was removed and the inner tissues were cut into fine pieces. The fine pieces of tissues were transferred into a tube containing 5 ml of PBS/1 mM EDTA and left to stand for 30 minutes to 1 hour at room temperature. Subsequently, the supernatant was removed leaving a 1 ml portion of the PBS/EDTA behind, and 1 ml of 0.25 trypsin/PBS was added.

Figure 12:
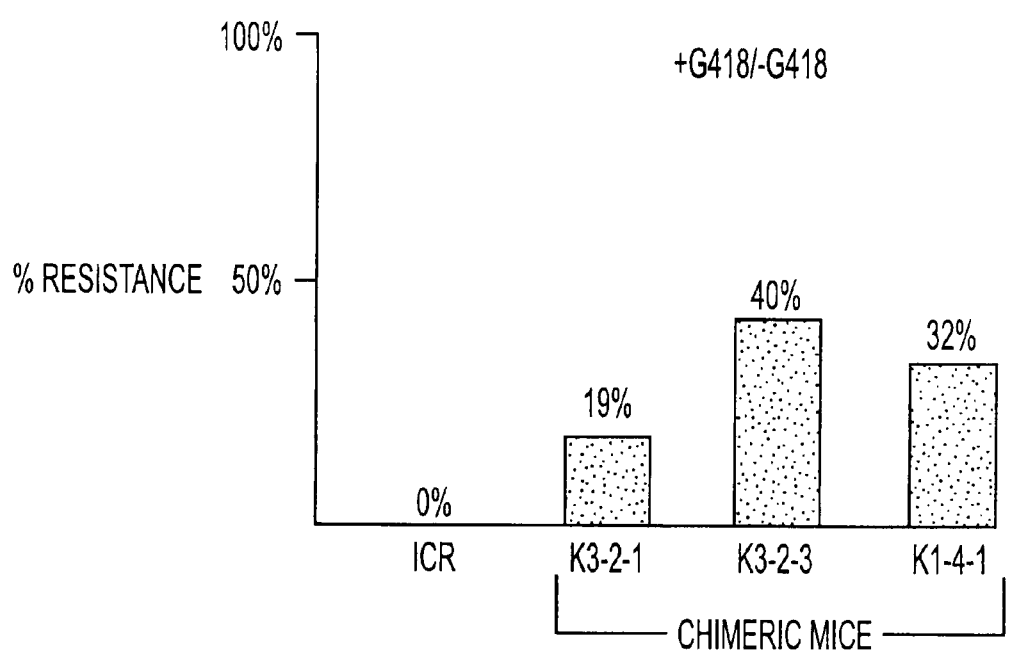
FIG. 12 shows the results of a test on a tail-derived fibroblast cell for resistance to G418.

The tissues were dispersed thoroughly by tapping or pipetting at room temperature for 5–10 minutes. After centrifugation at 1,000 rpm for 10 minutes, the precipitate was suspended in 2 ml of DMEM (10% FCS) and inoculated into a 35 mm plate. After cultivation for 7–10 days, the cells were treated with trypsin and about $10^4$ cells per plate were inoculated into four 35 mm plates. G418 was added to the medium in two of the plates at a final concentration of 400 μg/ml. The cells were cultured for 5–7 days and the viable cells in each plate were counted. Under these conditions, 100% of the wild-type ICR mouse-derived fibroblast cells were killed in the presence of G418. Assuming the same growth rate of the G418 resistant fibroblast in the non-selective and selective media, the ratio of the viable cells in the selective medium to those in the non-selective medium is believed to reflect the contribution in the fibroblast cell populations of the G418 resistant ES cell-drived fiblablast. As a result, the presence of G418 resistant fibroblast cells was observed in all the three individuals as shown in FIG. 12. In FIG. 12, % resistance is an average of 2 pairs of the selective/non-selective 35 mm plates for each mouse. ICR refers to the wild-type ICR mice.

(3) FISH Analysis of the Tail-derived G418 Resistant Fibroblast Cells

FISH analysis of the K3-2-3 and K1-4-1 derived G418 resistant fibroblast cells obtained in (2) was conducted by the same procedure as in Example 2. Total human DNA extracted from the HFL-1 cells (Example 1) was labeled with FITC so that is could be used as a probe (Matsubara et al., "FISH Experimental Protocol", published by Shujunsha, 1994). As a result, in almost all of the observed metaphase spreads of the both individuals, partial fragments of the human chromosome in independent forms were observed.

These results show that the TT2 cell clones retaining fragments c human chromosome #14 contributed to various normal tissues in the mouse individuals and that they retained, partial fragments of human chromosome #14.

EXAMPLE 12

Transfer of Partial Fragments of Human Chromosome #2 into ES Cells

The mouse A9 cell W23 retaining a human chromosome #2 fragment (hereinafter referred to as "A9/#2 W23") from Example 1 was used as a chromosome donor cell. Mouse ES cell line TT2 (see Example 9) was used as a chromosome recipient cell. The microcell fusion and the selection of G418 resistant clones were,conducted by the same procedures as in Example 2. The frequency of the appearance of the drug resistant clones was 1-3 per $10^7$ of TT2, cells. The drug resistant clones were stored frozen and genomic DNA was prepared by the same procedures as in Example 2. The retention of partial fragments of human chromosome #2 in drug resistant clones 5-1, 5-2 and 5-3 was confirmed by the methods described in (1) and (2) below.

(1) PCR Analysis

The presence of $C_K$ and FABP1 that are the genes on human chromosome #2 (Genetic Maps, supra) and which were detected in the chromosome donor cell A9/#2 W23 was detected by a PCR method.

As a result of PCR amplification using each primer, expected amplification products were detected with both primers in all of the 3 clones.

(2) Fluorescence in Situ Hybridization (FISH)

FISH analysis was conducted with probes specific to human chromosome #2 (CHROMOSOME PAINTING SYSTEM, Cambio Ltd.) by the same method as in Example 2. As a result, in almost all of the observed metaphase spreads of the 3 clones, partial fragments of human chromosome #2 in the form of independent chromosomes were detected. The sizes of the observed human chromosome were the same as those observed in A9/#2 W23.

The results of the above experiments demonstrate that the obtained G418 resistant clones retained partial fragments of human chromosome #2.

EXAMPLE 13

Production of Chimeric Mice from the ES Cells Retaining Human Chromosome #2

The cells in a frozen stock of the G418 resistant ES cell clone 5-1 that was obtained in Example 12 and which was confirmed to retain human chromosome #2 was thawed, started to culture and injected into 8-cell stage embryos obtained by mating ICR or MCH(ICR) male and female mice (CREA JAPAN, INC.); the injection rate was 10–12 cells per embryo. The embryos were cultured in an ES, medium (Example 9) overnight to develop to blastocysts. Two and half days after a foster mother ICR mouse (CREA JAPAN, INC.) was subjected to a pseudopregnant treatment, about ten of the injected embryos were transplanted to each side of the uterus of the foster mother. The results are shown in Table 4.

TABLE 4

Production of chimeric mice from the TT2 cell clone retaining human chromosome #2 (fragments)

| ES cell clone/human chromosome | G418 resistant clone No. | Number of ES cell-injected 8-cell stage embryos | Number of offspring mice | Number of chimeric mice | Contribution to coat color | | |
|---|---|---|---|---|---|---|---|
| | | | | | <20% | 20–50% | 50–80% |
| TT2/#2 (W23) | 5-1 | 264 | 51 | 18 | 7 | 5 | 6 |

As a result of the transplantation of a total of 264 injected embryos, 51 offspring mice were born. Chimerism in the offsprings can be determined by the extent of TT2 cell-derived agouti coat color (dark brown) in the host embryo-derived albino coat color. Out of the 51 produced offsprings, 18 mice were recognized to have partial agouti coat color, indicating the contribution of the ES cells. The maximum contribution was about 80%.

EXAMPLE 14

Detection of Human Antibody Heavy Chain in Sera of the Human Chromosome #14 Transferred Chimeric Mice The concentrations of human antibody in the sera were determined by enzyme-linked immunosorbent assay (ELISA). The ELISA for human antibody was performed in accordance with the method described in Toyama and Ando, "Monoclonal Antibody Experiment Manual", published by Kodansha, 1987; Andou and Chiba, "Monoclonal Antibody Experiment Procedure Manual", published by Kodansha Scientific, 1991; Ishikawa, "Super High Sensitivity Enzyme Immuno Assay", published by Gakkai-syuppan center, 1993; Ed Harlow and David Lane, "Antibodies A Laboratory Manual", published by Cold Spring Harbor Laboratory, 1988 and A. Doyle and J. B. Griffiths, "Cell & Tissue Culture: Laboratory Procedures", published by John Wiley & Sons Ltd., 1996. In some assays, the condition of reaction were modified, for example, the reaction was performed at 4° C. over night. Antibodies to human-immunogloblin or antigen were diluted to about 0.5–10 μg/ml (100–5000 fold) and ELISA plates were coated with these solutions. PBS supplemented with 5% mouse serum (Sigma, M5905) was used for blocking and dilution of the samples and labeled antibodies. PBS was used for 20-fold dilution of the chimeric mouse sera. After washed, the coated plate was blocked over 1 hour. After plate was washed, sample was added and incubated over a half hour. After washed, Enzyme labeled anti-human immunogloblin antibodies diluted 100–5000 folds were added to the plates and incubated over 1 hour, the plate was washed and then substrate was added. In some assays, the same procedure was applied except that a biotin-labeled antibody was used. After plate was washed, avidin-enzyme complex was added. After plate was washed, substrate was added. Absorbances were measured with a microplate reader (Bio-tek instrument, EL312e). The chimeric mice (Example 10, K3-1-2, K3-2-2 and K3-2-3) which were 29–35 days old were bled and assayed by ELISA. Anti-human IgM mouse monoclonal antibody (Sigma, I6385) was diluted with 50 mm carbonate-bicartonate buffer (pH 9.6) and absorbed to the 96-well microtiter plates. The serum samples diluted with mouse serum (Sigma, M5905) supplemented PBS were added to the plates. Subsequently, peroxidase-labeled anti-human IgM goat antibody (Tago, 2392) was added and the plates were incubated. After ABTS substrate (Kirkegaard & Perry Laboratories Inc., 506200) was added, enzyme activity was determined by absorbance measurement at 405 nm. Purified human IgM antibody (CAPEL, 6001-1590) and IgG (Sigma, I4506) were used as standards. The standards were diluted stepwise with mouse serum-supplemented PBS. In the determination of human IgG concentration anti-human IgG goat antibody (Sigma, I3382) was absorbed to the plate and the human IgG was detected with peroxidase-labeled anti-human IgG goat antibody (Sigma, A0170). The results are shown in Table 5. Both human IgM and IgG were detected.

TABLE 5

Concentrations of Human Antibodies in Chimeric Mouse Sera (ELISA)

| Chimeric Mouse | IgG (mg/l) | IgM (mg/l) |
|---|---|---|
| K3-1-2 | 0.37 | 3.7 |
| K3-2-2 | 0.33 | 5.9 |
| K3-2-3 | 0.51 | 3.4 |

Figure 13:
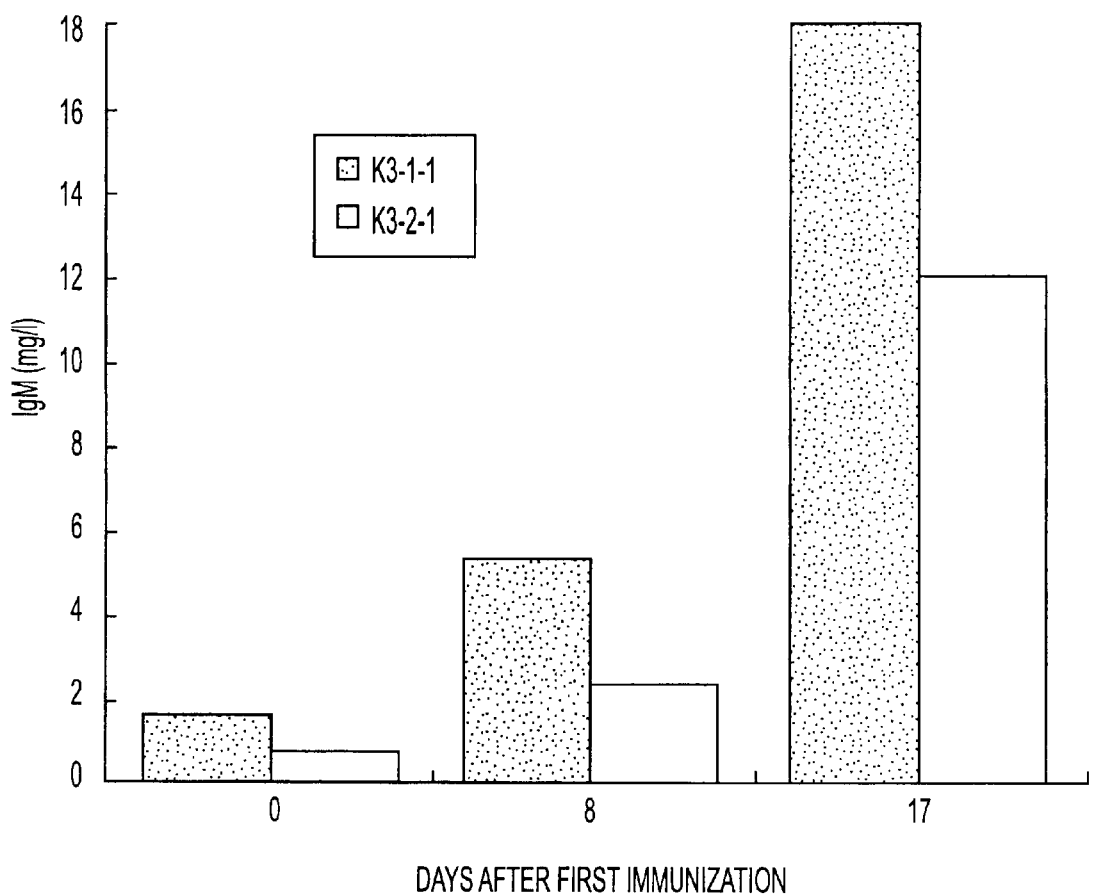
FIG. 13 shows the concentration of human antibody IgM in a serum of a human serum albumin (hereinafter referred to as "HSA")-immunized chimeric mouse (ELISA).
Figure 14:
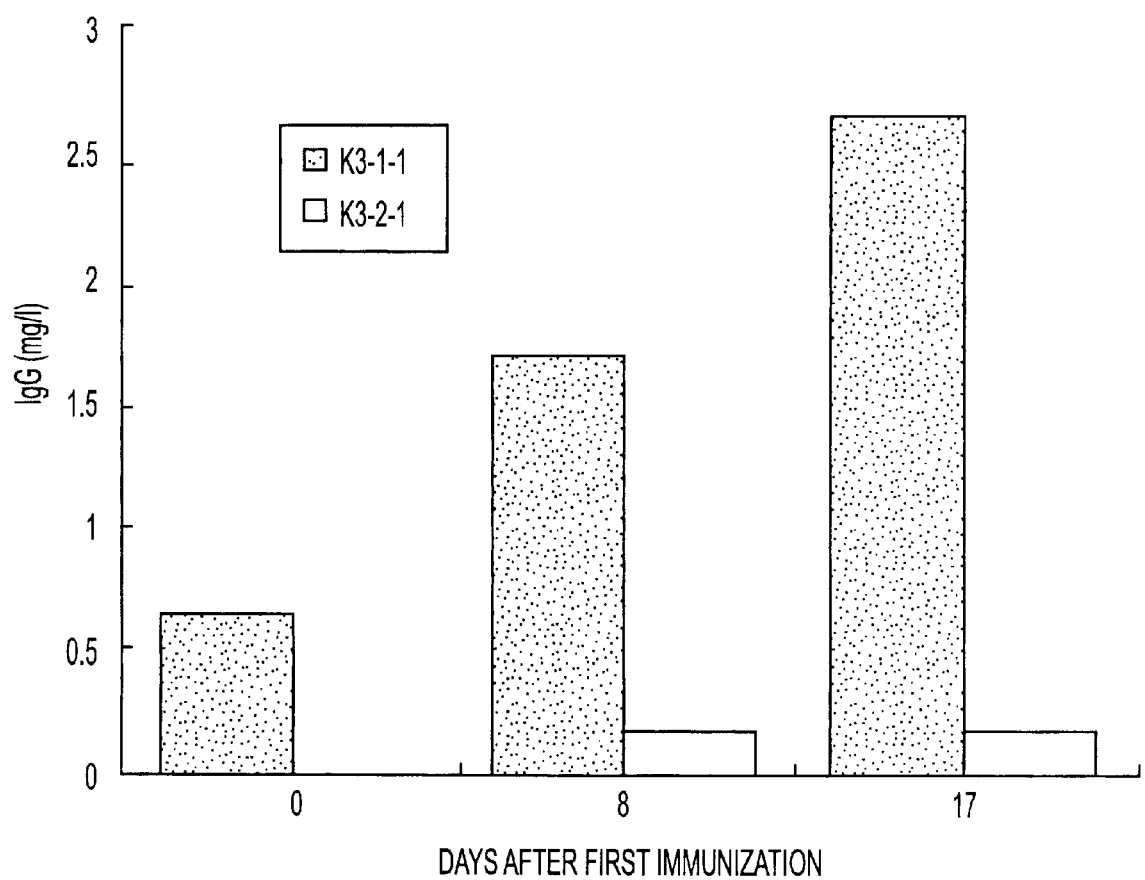
FIG. 14 shows the concentration of human antibody IgG in a serum of an HSA-immunized chimeric mouse (ELISA).

Two milliliters of human serum albumin (HSA, Sigma, A3782) dissolved in PBS was mixed with adjuvant (MPL+ TDM Emulsion, RIBI Immunochem Research Inc.) to prepare an antigen solution at a concentration of 0.25 mg/ml. The chimeric mice retaining human chromosome #14 fragment (Example 10, K3-1-1 and K3-2-1) were immunized with 0.2 ml of the antigen solution 3 times at days 27, 34 and 41 after birth. The chimeric mouse sera were assayed by ELISA. The results are shown in FIGS. 13 and 14. The human antibody concentration in the sera of the HSA-immunized chimeric mice was increased after the immunization. In the K3-1-1 mouse, 18 μg/ml of human IgM and 2.6 μg/ml of IgG were detected in the serum at day 17 after the immunization. In the serum of the control ICR mouse, the human antibody titer was not significant.

EXAMPLE 15

Figure 15:
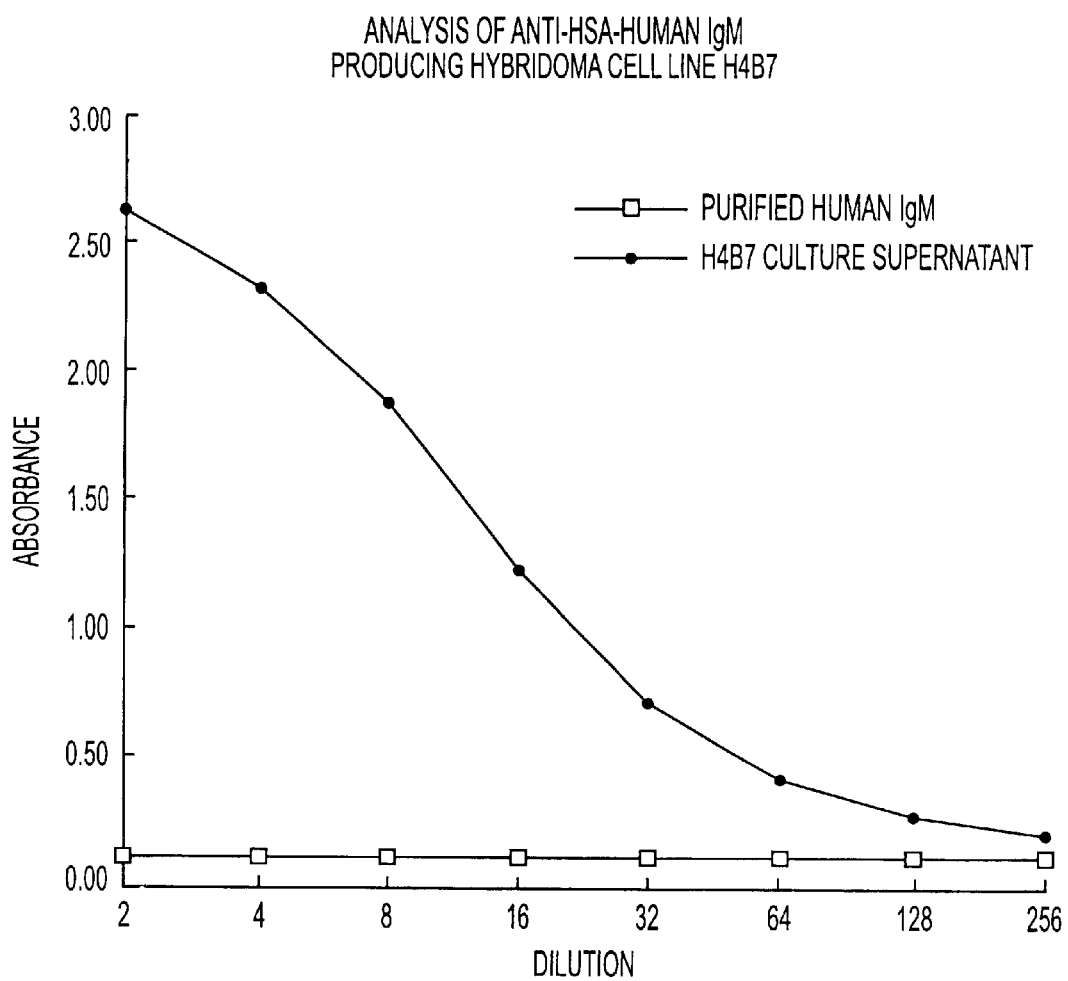
FIG. 15 shows the results of ELISA of hybridoma clone H4B7 capable of producing human IgM.

Production of Human Antibody Heavy Chain-producing Hybridomas from the Human Chromosome #14 Transferred Chimeric Mouse The spleen was removed from the human albumin-immunized chimeri mouse (K3-1-1, Example 141 at day 44 after birth. The spleen cell was fused with a myeloma cell to produce a hybridoma. The hybridoma was produced using a myeloma cell P3X63Ag8.653 (DAINIPPON PHARMACEUTICAL CO., LTD., 05-565) by the method described in Ando and Chiba, "Monoclonal Antibody Experimental Procedure Manual", published by Kodansha Scientific, 1991. The hybridomas were inoculated into ten 96-well plates and cultured for 1 week. The culture supernatant was analyzed by ELISA. The ELISA procedure was conducted by using anti-human IgM mouse monoclonal antibody (Sigma, I6385) immobilized on ELISA plate in the same manner as in Example 14 to give 6 positive clones. HSA (antigen) was dissolved in 50 mM carbonate-bicarbonate buffer (pH 9.6) at a concentration of 5 μg/ml and the antigen solution was dispensed in 100 μl portions into all the wells of the ELISA plates. After the addition of the supernatant, peroxidase-labeled anti-human IgA+IgG+IgM goat antibodies (Kierkegaard & Perry Laboratories Inc., 04-10-17) were used for detection of HSA-specific human antibody. One positive clone was confirmed in the ten plates. This clone was one of the 6 human IgM positive clones. The clone (H4B7) was further cultured and the culture supernatant was diluted, followed by ELISA analysis using HSA as an antigen with peroxidase-labeled anti-human IgM goat antibody (Tago, 2392) in the same manner as described above. As a result, the absorbance decreased with the increase in the dilution of the culture solution. Serial twofold dilutions of 2 μg/ml human IgM (CAPEL, 6001-1590) showed low absorbance regardless of dilution ratios. This suggests that the antibody produced by hybridoma H4B7 had a specificity to HSA (FIG. 15). In FIG. 15, the dilution of the culture supernatant samples is plotted on the horizontal axis and the absorbance at 405 nm is plotted on the vertical axis.

EXAMPLE 16

Re-marking of the G418 Resistance-marked Human Chromosome #2 Fragment with Puromycin Resistance The A9 cells retaining the G418 resistance-marked human chromosome #2 fragment (W23) (see Example 1, FIG. 1) were cultured in a G418 (800 µg/ml) containing selective medium (10% FBS, DMEM) in a 100 mm plate. Plasmid pPGKPuro (provided by Dr., Peter W. Laird (WHITEHEAD INSTITUTE)) containing puromycin resistance gene was linearized with restriction enzyme SalI (TAKARA SHUZO CO., LTD.) before transfection. The cells were treated with trypsin and suspended in Dulbecco's phosphate buffered saline (PBS) at a concentration of $5 \times 10^6$ cells/ml, followed by electroporation using a Gene Puiser (Bio-Rad Laboratories, Inc.) in the presence of 10 µg of DNA in the same manner as in Example 1. A voltage of 1000 V was applied at a capacitance of 25 µF with an Electroporation Cell of 4 mm in length (Example 1) at room temperature. The electroporated cells were inoculated into media in 3–6 plates of 100 mm φ. After one day, the medium was replaced with a double-selective medium containing 10 µg/ml of puromycin (Sigma, P-7255) and 800 µg/ml of G418. The colonies formed after 2–3 weeks were collected in groups each consisting of about 200 colonies. The cells of each of the three groups were cultured in two or three 25 cm² flasks to form microcells. The mouse A9 cells were cultured in a 25 cm² flask and fused with the microcells by the same procedure as in Example 1. The fused cells were transferred into two 100 mm plates and cultured in the double-selective medium containing G418 and puromycin. One of the three groups gave two double-drug resistant clones. In these clones, it was most likely that puromycin resistance marker had been introduced into human chromosome #2 fragment.

EXAMPLE 17

Duplication of Transferred Human Chromosome in the Human Chromosome Transferred ES Cells The ES cell clone retaining the G418 resistance marked human chromosome #14 fragment (E14/#14-36) was cultured in a medium containing G418 at a high concentration to give ES cell clones in which the human chromosome was duplicated ("Biomanual Series 8, Gene Targeting", published by Yodosha, 1995). G418 resistant mouse primary cells (purchased from Lifetech Oriental) were inoculated into a 100 mm plate without treating with mitomycin C and used as feeder cells. The E14/#14-36 cells were inoculated into the 100 mm plate and after half a day, the medium was replaced with a medium containing G418 at a concentration of 16 mg/ml. The medium was replaced every 1–2 days. The G418 concentration was changed to 10 mg/ml one week later and the cultivation was continued. Among the colonies formed, 15 were picked up and cultured, followed by FISH analysis of chromosome using human chromosome #14 specific probes (see Example 9). As a result, human chromosome #14 fragment was found to have duplicated in the 8 clones.

EXAMPLE 18

Preparation of Mouse ES Cells Retaining Both Human Chromosome #2 Partial Fragments and Human Chromosome #14 Partial Fragments In a microcell transfer experiment using the double-drug resistant clone PG-1 from Example 16 as a microcell donor cell and a wild-type A9 cell as a recipient cell, it was confirmed that the human chromosome #2 partial fragment retained in PG-1 was marked with a puromycin resistance gene. The preparation of microcells and the fusion with the A9 cells was carried out by the same methods as in Example 1. As a result, 10 days after the microcell fusion, a total of fifty nine G418 resistant colonies appeared. After the medium for these colonies was changed to one containing 8 µg/ml puromycin, the colonies were cultured for 3 days to give 45 viable colonies (76%). In many cases of microcell fusion, only one or few chromosomes are transferred into a recipient cell. Hence, cotransfer of both the resistance genes at a high frequency shows that the G418 resistance-labeled chromosome #2 partial fragment retained in the PG1 clone was also marked with the puromycin resistance gene. In addition, for the detection of the respective marker genes on the human chromosome #2 partial fragment, FISH analysis was conducted by using pSTneoB (see Example 1) as a probe in the case of the A9/#2 W23 clone having only G418 resistance (see Example 16) and by using pPGKPuro (see Example 16) as a probe in the case of the PG1 clone in accordance with the method described in Matsubara et al., "FISH Experiment Protocol", published by Shujunsha, 1994. As a result, in the case of the A9/#2 W23 clone, one signal was observed in each of the sister chromatids of the human chromosome #2 partial fragment observed in Example 12 (2 signals in total). This indicated the insertion of pSTneoB into the human chromosome #2 partial fragment at one site. In the case of the PG1 clone, a total of 4 signals were observed on a chromosome fragment of the same size as in A9/#2 W23. Since pSTneoB and pPGKPuro had identical sequences in their vector portions, the pSTneoB could be detected by the pPGKPuro probe. Hence, it is believed that out of the four signals observed in the PG1 clone, two were from the pSTneoB and the other two were from the pPGKPuro. These results show that the human chromosome #2 partial fragment retained in the PG1 was marked with both the G418 and puromycin resistances.

The PG1 cell clone was used as a chromosome donor cell to prepare a mouse ES cell retaining both a human chromosome #2 partial fragment and a human chromosome #14 partial fragment. The G418 resistant TT2 cell clone 1–4 already retaining the human chromosome #14 partial fragment (see Example 9) was used as a chromosome recipient cell. The microcell fusion and the selection of puromycin resistant cells were carried out by the same methods as in the selection of the G418 resistant clones in Example 9 except that the concentration of puromycin was 0.75 µg/ml. The frequency of the appearance of the resulting puromycin resistant clones was 3–7 per $10^7$ of 1–4 cells. The presence of G418 resistance in these puromycin resistant clones was confirmed from the fact that they were grown in the presence of 300 µg/ml of G418. The double-drug resistant clones were stored frozen and genomic DNA was prepared by the same methods as in Example 2. The retention of the human chromosome #2 partial fragment and human chromosome #14 partial fragment was confirmed by the method described in (1) in the case of double-drug resistant clones PG5, PG15 and PG16 and by the method described in (2) in the case of the clone PG15.

(1) PCR Analysis

Genomic DNAs of the double-drug resistant clones were used as templates in the PCR amplifications. Among the markers on human chromosomes #2 and #14 (Genetic Maps, supra), the primers whose presence in the A9/#2 W23 clone was confirmed in Example 12 and those whose presence in the TT2/#14 1-4 clone was confirmed in Example 9 were used. All the primers gave expected amplification products in all the three clones.

(2) Fluorescence in Situ Hybridization (FISH)

Figure 16:
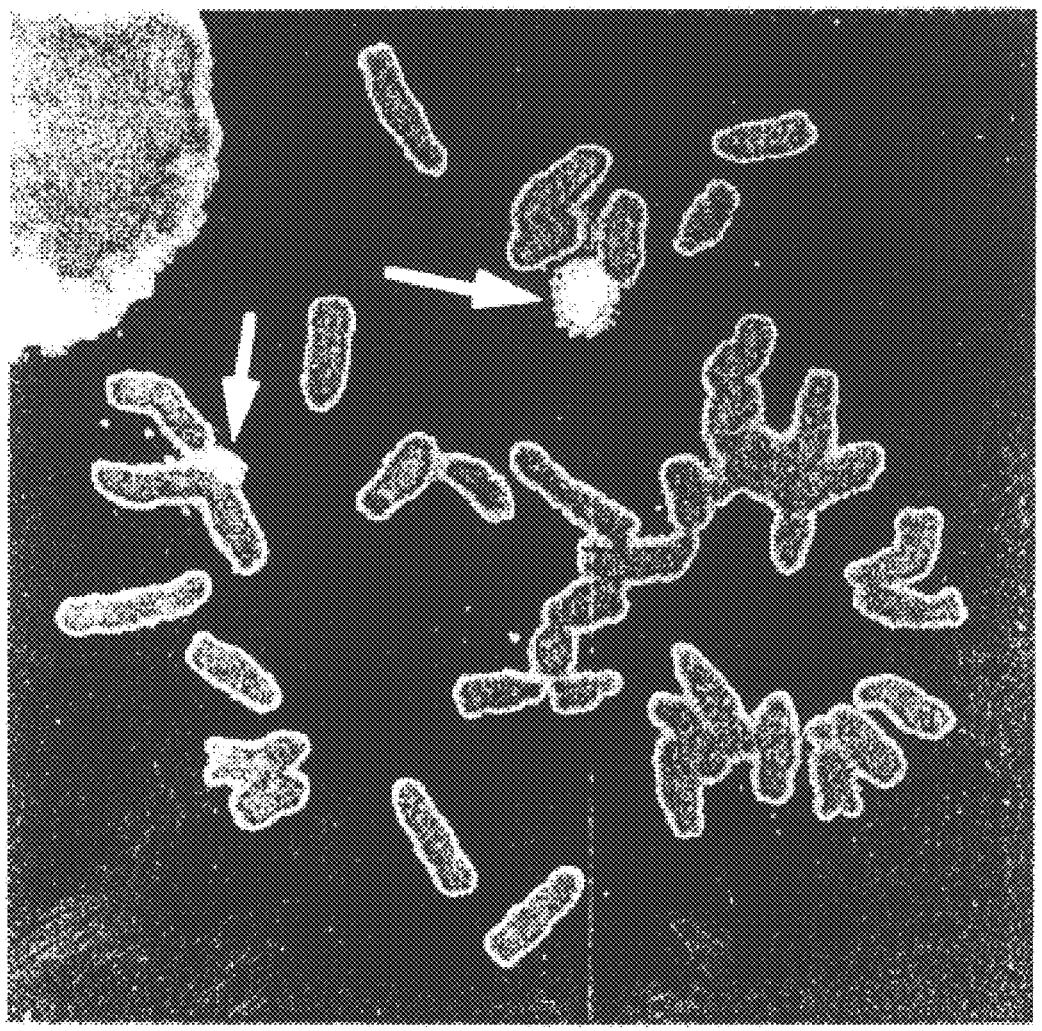
FIG. 16 is a photograph of the results of FISH analysis of a mouse ES cell clone (TT2 cell clone PG15) retaining partial fragments of human chromosomes #2 and 14.

FISH analysis was conducted by using FITC-labeled human total DNA as a probe in the same manner as in Example 11. As a result, in almost all of the metaphase spreads, two (large and small) human chromosome fragments were detected. The large fragment had the same size as that of the partial fragment detected by using the human chromosome #14 specific probes in the case of the TT2/#14 1-4 clone in Example 9 and the small fragment had the same size as that of the partial fragment detected by using the human chromosome #2 specific probes in the case of the TT2/#2 5-1 in Example 12. The results are shown in FIG. 16. In FIG. 16, the less bright chromosome was derived from the mouse. The two (large and small) chromosome fragments of high brightness due to FITC fluorescence as shown by arrows were derived from the human, which are believed to correspond to the human chromosome #14 and #2 partial fragments.

These results show that the obtained double-drug resistant ES clones retained both the human chromosome #2 partial fragment and the human chromosome #14 partial fragment.

EXAMPLE 19

Production of Chimeric Mice from the Mouse ES Cell Clones Retaining Both Human Chromosome #2 Partial Fragments and Human Chromosome #14 Partial Fragments The cells in frozen stocks of the G418 and puromycin double-resistant TT2 cell clones PG5, PG15 and PG16 from Example 18 which were confirmed to retain human chromosome #2 partial fragments and human chromosome #14 partial fragments were thawed, started to culture and injected into 8-cell stage embryos obtained by mating ICR or MCH(ICR) male and female mice (CREA JAPAN, INC.); the injection rate was 10–12 cells per embryo. The embryos were cultured in a medium for ES cells (see Example 9) overnight to develop to blastocysts. Two and a half day after a foster mother ICR mouse was subjected to a pseudopregnant treatment, about ten of the injected embryos were transplanted to each side of the uterus of the foster mother. The results are shown in Table 6.

As a result of the transplantation of a total of 551 injected embryos, 73 offspring mice were born. Chimerism in the offsprings can be determined by the extent of TT2 cell-derived agouti coat color (dark brown) in the host embryo-derived albino coat color. Out of the 73 produced offsprings, 23 mice were recognized to have a partial agouti coat color, indicating the contribution of the ES cells.

These results show that the ES cell clones PG5, PG15 and PG16 retaining human chromosome #2 partial fragments and human chromosome #14 partial fragments maintain the ability to produce chimera, that is, the ability to differentiate into normal tissues of mouse.

EXAMPLE 20

Detection of Human Antibody in Sera of the Chimeric Mice Derived from the ES Cells Retaining Both Human Chromosome #2 Partial Fragments and Human Chromosome #14 Partial Fragments The two KPG-15 (9 weeks old; derived from the PG-5 clone, 10% chimerism) and KPG-18 (5 weeks old; derived from the PG-5 clone, 10% chimerism) chimeric mice from Example 19 were immunized with 0.2 ml of a solution of human serum albumin (HSA, Sigma, A3782) and adjuvant (MPL+TDM Emulsion, RIBI Immunochem Research Inc.) at a HSA concentration of 0.25 mg/ml. The chimeric mice were bled just before the immunization and 8 days after that and the concentrations of human antibody $\mu$ and $\kappa$ chains in the sera were determined by ELISA (see Example 14). Ninety six-well microtiter plates were coated with anti-human antibody $\kappa$ chain goat antibody (VECTOR LABORATORIES INC., AI-3060) diluted with 50 mM carbonate-bicarbonate buffer (pH 9.6) and then a serum sample diluted with mouse serum (Sigma, M5905)-containing PBS was added. Subsequently, biotin-labeled anti-human antibody $\kappa$ chain goat antibody (VECTOR LABORATORIES INC., BA-3060) was added to the plates and incubated. A complex of biotinylated horseradish peroxidase and avidin DH (VECTOR LABORATORIES, INC., Vectastain ABC Kit, PK4000) was added and incubated. After 3,3',5,5'-tetramethylbenzidine (TMBZ, Sumitomo Bakelite, ML-1120T) was added as a peroxidase substrate, enzyme activity was determined by absorbance measurement at 450 nm. Purified human IgG antibody having $\kappa$ chain (Sigma, I-3889) was used as standard. The standard was diluted stepwise with mouse serum-supplemented PBS. In the case of $\mu$ chain, 96-well microtiter plates were coated with anti-human antibody $\mu$ chain mouse monoclonal antibody (Sigma, I-6385) diluted with 50 mM carbonate-bicarbonate

TABLE 6

Production of chimeric mice from the mouse ES cell clones retaining both human chromosome #2 partial fragments and human chromosome #14 partial fragments

| ES cell clone/human chromosome | Double-drug resistant clone No. | Number of ES cell-injected 8-cell stage embryos | Number of offspring mice | Number of chimeric mice | Contribution to coat color | | |
|---|---|---|---|---|---|---|---|
| | | | | | <10% | 10–50% | 50%< |
| TT2/#14 + #2 | PG5 | 160 | 26 | 8 | 7 | 1 | — |
| | PG15 | 168 | 15 | 3 | 1 | 2 | — |
| | PG16 | 223 | 32 | 12 | 3 | 6 | 3 | buffer (pH 9.6) and then a serum sample was added. Subsequently, peroxidase-labeled anti-human antibody $\mu$ chain mouse antibody (The Binding Site Limited, MP008) was added to the plates and incubated. After TMBZ (Sumitomo Bakelite, ML-1120T) was added, enzyme activity was determined by absorbance measurement at 450 nm.

Purified human IgM antibody having μ chain (CAPPEL, 6001-1590) was used as standard. The standard was diluted stepwise with mouse serum-supplemented PBS. As a result, both the human antibody μ and κ chain s were detected in both individuals. The concentrations of these human antibodies in the sera increased after the immunization (Tables 7 and 8).

TABLE 7

Concentrations of Human Antibodies in Chimeric Mouse KPG15 (ELISA)

|  | IgM (mg/l) | Igκ (mg/l) |
|---|---|---|
| Before Immunization | 0.19 |  |
| 8 Days After Immunization | 0.75 |  |

TABLE 8

Concentrations of Human Antibodies in Chimeric Mouse KPG18 (ELISA)

|  | IgM (mg/l) | Igκ (mg/l) |
|---|---|---|
| Before Immunization | 0.29 | 0.57 |
| 8 Days After Immunization | 3.4 | 0.87 |

These results show that human antibody heavy and light chain genes can function in the chimeric mice derived from the ES cells retaining both human chromosome #2 partial fragments and human chromosome #14 partial fragments.

EXAMPLE 21

Figure 17:
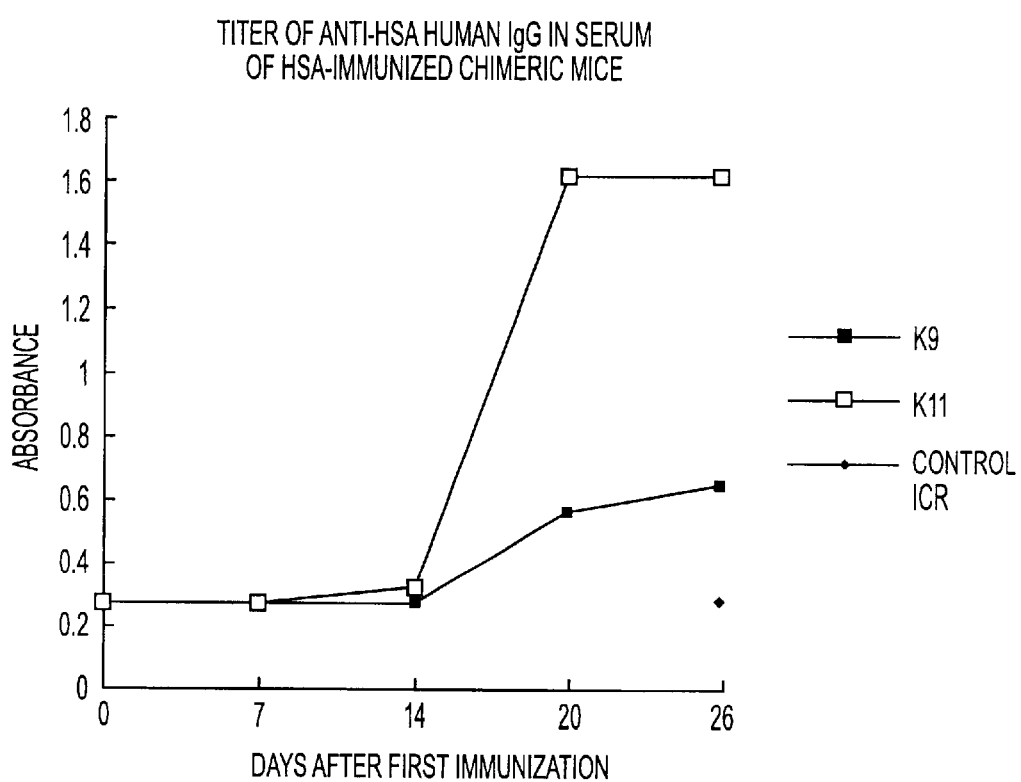
FIG. 17 shows that the antibody titer of anti-HSA human IgG is increased in a serum of an HSA-immunized chimeric mouse.

Detection of Anti-HSA Human Antibody γ Chain in Sera of the Human Chromosome #14 Fragments Transferred Chimeric Mice The chimeric mice retaining human chromosome #14 fragments which were produced by the same method as in Example 10 (K9 and K11: both were derived from the TT2 cell clone 3-2, with chimerisms of 50% and 30%, respectively) were immunized with HSA either 4 times at days 79, 93, 107 and 133 after birth (K9) or 3 times at days 74, 88 and 111 after birth (K11) by the same method as in Example 20. Antibodies including human γ chain against human serum albumin in the sera of the chimeric mice were detected by ELISA. Ninety six-well microtiter plates were coated with HSA (Sigma, A 3782) diluted with 50 mM carbonate-bicarbonate buffer (pH 9.6) and then a sample diluted with PBS was added. Subsequently, peroxidase-labeled anti-human IgG mouse antibody (Pharmingen, 08007E) was added to the plates and incubated. After O-phenylenediamine (OPD, Sumitomo Bakelite, ML-1130O) was added as a peroxidase substrate, enzyme activity was determined by absorbance measurement at 490 nm. The titer of the anti-HSA human IgG in the sera of the chimeric mice immunized with HSA increased after the immunization On the other hand, control ICR mouse gave a background level of the anti-HSA human IgG titer after the immunization with HSA. The result is shown in FIG. 17. In FIG. 17, the number of days after the first immunization of the chimeric mice with HSA is plotted on the horizontal axis and the absorbance at 490 nm is plotted on the vertical axis. These results show that the antibody titer of the antigen specific human IgG was increased by stimulation with the HSA antigen in the chimeric mice retaining human chromosome #14 fragments.

EXAMPLE 22

Detection of Human Antibody λ Chain in a Serum of the Human Chromosome #22 Fragment Transferred Chimeric Mouse The chimeric mouse K22-7 from Example 3 (9 weeks old; 10% chimerism) was bled and human antibody λ chain in the serum was detected by ELISA (see Example 14). Ninety six-well microtiter plates were coated with anti-human antibody λ chain goat antibody (VECTOR LABORATORIES INC., AI-3070) diluted with 50 mM carbonate-bicarbonate buffer (pH 9.6) and then a serum sample was added. Subsequently, biotin-labeled anti-human antibody λ chain goat antibody (VECTOR LABORATORIES INC., BA-3070) was added to the plates and incubated. A complex of biotinylated horseradish peroxidase and avidin DH (VECTOR LABORATORIES, INC., Vectastain ABC Kit) was added and incubated. After TMBZ (Sumitomo Bakelite, ML-1120T) was added as a peroxidase substrate, enzyme activity was determined by absorbance measurement at 450 nm. Purified human IgG antibody having λ chain (Sigma, I4014) was used as standard. The standard was diluted stepwise with mouse serum-supplemented PBS. As a result, human antibody λ chain was detected in the chimeric mouse at a concentration corresponding to 180 ng/ml of human IgG. These results show that human antibody λ chain gene can function in the chimeric mouse retaining a human chromosome #22 fragment.

EXAMPLE 23

Detection of Human Antibody κ Chain in Sera of the Human Chromosome #2 Fragment Transferred Chimeric Mice The chimeric mouse K2-8 from Example 13 (5 weeks old; 70% chimerism) and the chimeric mice K2-3, K2-4 and K2-12 from Example 13 (9 weeks old; chimerisms was 50%, 20% and 80%, respectively) were bled and human antibody κ chain in the sera was detected by ELISA (see Example 14). Ninety six-well microtiter plates were coated with anti-human antibody κ chain goat antibody (VECTOR LABORATORIES INC., AI-3060) diluted with 50 mM carbonate-bicarbonate buffer (pH 9.6) and then a serum sample was added. Subsequently, biotin-labeled anti-human antibody κ chain goat antibody (VECTOR LABORATORIES INC., BA-3060) was added to the plates and incubated. A complex of biotinylated horseradish peroxidase and avidin DH (VECTOR LABORATORIES, INC., Vectastain ABC Kit) was added and incubated. After TMBZ (Sumitomo Bakelite, ML-1120T) was added, enzyme activity was determined by absorbance measurement at 450 nm. Purified human IgG antibody having κ chain (Sigma, I-3889) was used as standard. The standard was diluted stepwise with mouse serum-supplemented PBS. The results are shown in Table 9.

TABLE 9

Concentration of Human Antibody κ Chain in Chimeric Mouse (ELISA)

| Chimeric Mouse | Igκ (mg/l) |
|---|---|
| K2-3 | 124 |
| K2-4 | 85 |
| K2-8 | 25 |
| K2-12 | 56 |

Figure 18:
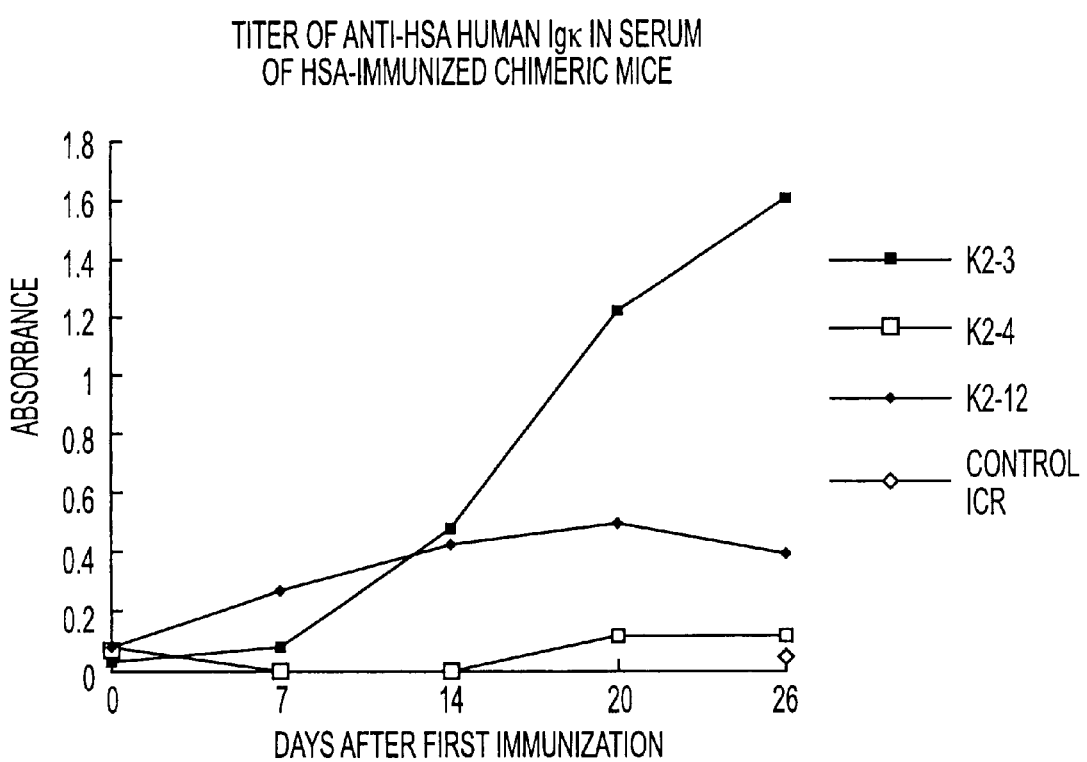
FIG. 18 shows that the antibody titer of anti-HSA human Igκ is increased in a serum of an HSA-immunized chimeric mouse.

The chimeric mice K2-3 and K2-4 retaining human chromosome #2 fragments from Example 13 were immunized with HSA, 3 times at days 66, 80 and 102 after birth by the same method as in Example 20. The chimeric mouse K2-12 was immunized with HSA, 4 times at days 63, 77, 91 and 116 after birth by the same method as in Example 20. Human antibody λ chain against HSA in the sera of the chimeric mice was detected by ELISA (see Example 14). Ninety six-well microtiter plates were coated with HSA (Sigma, A 3782) diluted with 50 mM carbonate-bicarbonate buffer (pH 9.6) and then a sample was added. Subsequently, biotin-labeled anti-human antibody κ chain goat antibody (VECTOR LABORATORIES, INC., BA-3060) was added to the plates and incubated. A complex of biotinylated horseradish peroxidase and avidin DH (VECTOR LABORATORIES, INC., Vectastain ABC Kit) was added and incubated. After OPD (Sumitomo Bakelite, ML-1130O) was added as a peroxidase substrate, enzyme activity was determined by absorbance measurement at 490 nm. The titer of the anti-HSA human κ chain in the sera of the chimeric mice immunized with HSA increased after the immunization. On the other hand, control ICR mouse gave a background level of the anti-HSA human κ chain titer after the immunization. The results are shown in FIG. 18. In FIG. 18, the number of days after the first immunization of the chimeric mice with HSA is plotted on the horizontal axis and the absorbance at 490 nm is plotted on the vertical axis. These results show that human antibody κ chain gene can function in the chimeric mice retaining human chromosome #2 fragments and that the antibody titer of the antigen specific human Ig κ was increased by stimulation with the HSA antigen in the chimeric mice.

EXAMPLE 24

Preparation of Human Antibody Heavy Chain (μ Chain or γ Chain)-producing Hybridomas from the Human Chromosome #14 Transferred Chimeric Mouse The spleen was removed from the HSA-immunized chimeric mouse K9 (see Example 21) at day 136 after birth. A spleen cell was fused with a myeloma cell to produce a hybridoma. The hybridoma was produced using a myeloma cell Sp-2/0-Ag14 (Dainippon Pharmaceutical Co., Ltd., 05-554) by the method described in Toyama and Ando, "Monoclonal Antibody Experiment Procedure Manual", published by Kodansha Scientific, 1991. The cells were inoculated into a medium containing 10% ORIGEN Hybridoma Cloning Factor (HCF, Bokusui Brown) in eight 96-well plates and G418 was added after 3 days at a concentration of 1 mg/ml, followed by cultivation for 1–3 weeks. The culture supernatant was analyzed by ELISA. Ninety six-well microtiter plates were coated with anti-human μ chain mouse monoclonal antibody (Sigma, I-6385) diluted with 50 mM carbonate-bicarbonate buffer (pH 9.6) and a sample diluted with PBS was added. Subsequently, peroxidase-labeled anti-human μ chain mouse antibody (The Binding Site LIMITED, MP008) was added to the plates and incubated. 2,2'-Azino-di-(3-ethyl-benzothiazoline-6-sulfonate)diammonium salt (ABTS, Kirkegaard & Perry Laboratories Inc., 04-10-17) was used as a substrate to detect seven positive clones. In the detection of γ chain-producing clones, 96-well microtiter plates were coated with anti-human γ chain mouse monoclonal antibody (Sigma, I-6260) and a sample diluted with PBS was added. Subsequently, peroxidase-labeled anti-human γ chain mouse antibody (Pharmingen, 08007E) was added to the plates and incubated. ABTS (Kirkegaard & Perry Laboratories Inc., 04-10-17) was used as a substrate and two human antibody γ chain-positive clones were obtained.

EXAMPLE 25

Preparation of Human Antibody Light Chain-producing Hybridomas from the Human Chromosome #2 Transferred Chimeric Mouse The spleen was removed from the HSA-immunized chimeric mouse K2-3 (see Example 23) at day 105 after birth. A spleen cell was fused with a myeloma cell to produce a hybridoma. The hybridoma was produced using a myeloma cell P3X63Ag8.653 (Dainippon Pharmaceutical Co., Ltd., 05-565) by the method described in Toyama and Ando, "Monoclonal Antibody Experiment Procedure Manual", published by Kodansha Scientific, 1991. The cells were inoculated into a medium containing 10% HCF (Bokusui Brown) in ten 96-well plates and G418 was added after 3 days at a concentration of 1 mg/ml, followed by cultivation for 1–3 weeks. The culture supernatant was assayed by ELISA. The ELISA analysis was conducted by the same method as in Example 23 and two human antibody κ chain-positive clones were obtained.

EXAMPLE 26

Re-marking of the G418 Resistance-marked Human Chromosome #22 with Puromycin Resistance The A9 cells retaining the G418 resistance-marked human chromosome #22 (A9/#22 γ 2) from Example 1 were re-marked with puromycin resistance by the same method as in Example 16. About 200 colonies of double-drug resistant clones obtained by electroporation of the γ 2 cells with pPGKPuro were collected as one group and three such groups (P1, P2 and P3) were used as donor cells to perform microcell transfer into wild-type mouse A9 cells. As a result, 6, 1 and 3 of double-drug resistant clones were obtained from the groups P1, P2 and P3, respectively. The clone 6-1 from group P3 was used as a microcell donor cell and a wild-type A9 cell as a recipient cell to perform a microcell transfer experiment (see Example 18). As a result, the human chromosome #22 was confirmed to have been further marked with a puromycin resistance gene. The preparation of microcells and the fusion with A9 cells were conducted by the same methods as in Example 1. As a result, twenty eight G418 resistant colonies appeared 11 days after the microcell transfer. After the medium for these colonies was changed to one containing 8 μg/ml puromycin, these colonies were cultured for 3 days to give 21 (75%) viable colonies. In many cases of microcell fusion, only one or few chromosomes are transferred into a recipient cell. Hence, cotransfer of both the resistance genes at a high frequency shows that the G418 resistance-labeled chromosome #22 retained in the 6-1 clone was marked with the puromycin resistance gene.

EXAMPLE 27

Preparation and Sequencing of cDNA of a Human Antibody Heavy Chain Variable Region from the Human Antibody Heavy Chain-producing Hybridoma Among the human antibody heavy chain (IgM)-producing hybridomas obtained in Example 15, H4B7 (HSA-specific) and H8F9 (non-specific) hybridomas were selected. Total RNAs were obtained from these hybridomas using ISOGEN (Nippon Gene). The synthesis of cDNA from 5 μg each of the total RNAs was conducted with a Ready-To-Go T-primed 1st strand Kit (Pharmacia Co.). Using the resulting cDNA and the following primers prepared with reference to Larrick et al., BIO/TECHNOLOGY, 7, 934-, 1989; Word et al., Int. Immunol., 1, 296-, 1989, PCR was performed to amplify a human antibody heavy chain variable region.

CM1 (human IgM constant region): 5'-TTGTATTTCCAGGAGAAAGTG (SEQ ID NO: 45)

CM2 (ditto): 5'-GGAGACGAGGGGGAAAAGGG (SEQ ID NO:46)

HS1 (human heavy chain variable region): 5'-ATGGACTGGACCTGGAGG(AG)TC(CT)TCT(GT)C (SEQ ID NO:47) (a mixture of 8 sequences)

HS2 (ditto): 5'-ATGGAG(CT)TTGGGCTGA(GC)CTGG(GC)TTT(CT)T (SEQ ID NO:48) (a mixture of 16 sequences)

HS3 (ditto): 5'-ATG(AG)A(AC)(AC)(AT)ACT(GT)TG(GT)(AT)(GCT)C(AT)(CT)(GC)CT(CT)CTG (SEQ ID NO:49) (a mixture of 6144 sequences)

* ( ) means that any one of the bases therein should be selected.

In both cases of the H4B7 and H8F9 hybridomas, the first run of PCR was performed by using three kinds of primer combinations of HS1×CM1, HS2×CM1 and HS3×CM1 in 40 cycles at 94° C. for 1 minute, 50° C. for 2 minutes and 72° C. for 3 minutes with a Thermal Cycler 140 (Perkin-Elmer Corp.). The PCR products were amplified again under the same temperature conditions in 30 cycles using HS1×CM2, HS2×CM2 and HS3×CM2 primers, respectively. The amplification products were electrophoresed on a 1.5% agarose gel and detected by staining with ethidium bromide. As a result, an amplification product of about 490 bp was detected with the HS3×CM2 primer in the case of the H4B7 hybridoma. In the case of the H8F9 hybridoma, a slight band was detected at the same site with the HS3×CM2 primer. The band in the case of H8F9 was amplified again with the HS3×CM2 primer in 30 cycles under the same temperature conditions as above. As a result, the amplification product was detected as a very intensive signal. These PCR products were cloned into a pBlueScriptII SK+ (Stratagene Ltd.) at a SmaI site in accordance with the method described in Ishida et al., "Gene Expression Experiment Manual", published by Kodansha Scientific, 1995. Among the amplification product-inserted plasmids, plasmids #2, #3, #4(H4B7), #11, #13 and #14 (H8F9) were selected and the nucleotide sequences of the amplification products were determined with a Fluorescence Autosequencer (Applied Biosystems Inc.). As a result of the comparison of the obtained nucleotide sequences or deduced amino acid sequences with those of known human antibody VH region (Marks et al., Eur. J. Immunol. 21, 985-, 1991) and JH region (Ravetch et al., Cell, 27, 583-, 1981), it was revealed that both the H4B7 and H8F9 hybridomas contained a combination of genes for VH4 family and JH2. These results show that the chimeric mouse retaining human chromosome #14 partial fragment produced a complete functional human antibody heavy chain protein.

EXAMPLE 28

Preparation and Sequencing of cDNA of Human Antibody κ Chain from the Spleen of the Human Antibody κ Chain-expressing Chimeric Mouse In the same manner as in Example 5, cDNA was prepared from the spleen of the chimeric mouse K2-8 from Example 13 which was confirmed to express human antibody κ chain in Example 23. Using the resulting cDNA and the following primers prepared with reference to Larrick et al., BIO/TECHNOLOGY, 7, 934-, 1989; Whitehurst et al., Nucleic Acids Res., 20, 4929-, 1992, PCR was performed to amplify human antibody κ chain variable region. cDNA from the liver of the chimeric mouse K2-8 and cDNA from the spleen of the chimeric mouse K3-2-2 derived from the TT2/#14 3-2 clone (see Example 10) were used as negative controls.

KC2 (human Ig κ chain constant region): 5'-CAGAGGCAGTTCCAGATTTC (SEQ ID NO:50)

KC3 (ditto): 5'-TGGGATAGAAGTTATTCAGC (SEQ ID NO:51)

KVMIX (human Ig κ chain variable region): 5'-ATGGACATG(AG)(AG)(AG)(AGT)(CT)CC(ACT)(ACG)G(CT)(GT)CA(CG)CTT (SEQ ID NO:52) (a mixture of 3456 sequences)

* ( ) means that any one of the bases therein should be selected.

PCR was performed by using primer combinations of KVMIX×KC2 and KVMIX×KC3 in 40 cycles at 94° C. for 15 seconds, 55° C. for 15 seconds and 72° C. for 20 seconds with a Thermal Cycler 9600 (Perkin-Elmer Corp.). The amplification products were electrophoresed on a 1.5% agarose gel and detected by staining with ethidium bromide. As a result, expected amplification products of about 420 bp (KC2) and about 450 bp (KC3) were detected. In the case of the two negative controls, no specific amplification product was detected. These amplification products were cloned into a pBlueScriptII SK+ (Stratagene Ltd.) at a SmaI or EcoRI site in accordance with the method described in Ishida et al., "Gene Expression Experiment Manual", published by Kodansha Scientific, 1995. Among the amplification product-inserted plasmids, VK-#1 clone derived from the KVMIX×KC2 primers was selected and the nucleotide sequence of the amplification product was determined with a Fluorescence Autosequencer (Applied Biosystems Inc.). Since the obtained nucleotide sequence did not contain a termination codon at any site between an initiation codon and a constant region of human Igκ chain, the cloned amplification products are believed to encode a variable region of functional human Ig κ chain. As a result of the comparison of the obtained nucleotide sequences with those of known human antibody Vκ region (Klein et al., Eur. J. Immundl. 23, 3248-, 1993) and Jκ region (Whitehurst et al., supra), it was revealed that the VK-#1 clone contained a combination of genes for Vκ 3 family and Jκ 4. These results show that the chimeric mouse retaining human chromosome #2 partial fragment produced a complete functional human antibody κ chain protein.

EXAMPLE 29

Detection and Quantitation of Human Antibody γ Chain Subclasses and μ Chain in Sera of the Chimeric Mice Retaining Human Chromosome #14 Fragment The chimeric mice K15A and K16A from Example 10 (derived from the 1-4 clone, with chimerism of 70% and 50%, respectively) of 11 weeks after birth were bled and human antibody γ chain subclasses and μ chain in the sera were detected by the same ELISA method as in Example 14.

Quantative Determination of Human IgG1

Ninety six-well microtiter plates were coated with anti-human IgG antibody (Sigma, I-6260) diluted with PBS. A serum sample was added. Subsequently, peroxidase-labeled anti-human IgG1 antibody (Pharmingen, 08027E) was added to the plates and incubated. After TMBZ (Sumitomo Bakelite, ML-1120T) was added, enzyme activity was determined by absorbance measurement at 450 nm. Purified human IgG1 antibody (Sigma, I-3889) was used as standard. The standard was diluted stepwise with mouse serum-supplemented PBS.

Quantative Determination of Human IgG2

Ninety six-well microtiter plates, were coated with anti-human IgG2 antibody (Sigma, I-9513) diluted with PBS. A serum sample was added. Subsequently, peroxidase-labeled anti-human IgG antibody (Sigma, A-0170) was added to the plates and incubated. After TMBZ (Sumitomo Bakelite, ML-1120T) was added, enzyme activity was determined by absorbance measurement at 450 nm. Purified human IgG2 antibody (Sigma, I-4139) was used as standard. The standard was diluted stepwise with mouse serum-supplemented PBS.

Quantative Determination of Human IgG3

Anti-human IgG3 antibody (Sigma, I-7260) was diluted with 100 mM glycine-HCl buffer (pH 2.5) and incubated for 5 minutes at room temperature, followed by 10-fold dilution with 100 mM phosphate buffer (pH 7.0). Ninety six-well microtiter plates were coated with the anti-human IgG3 antibody solution. A serum sample was added. Subsequently, peroxidase-labeled anti-human IgG antibody (Pharmingen, 08007E) was added to the plates and incubated. After TMBZ (Sumitomo Bakelite, ML-1120T) was added, enzyme activity was determined by absorbance measurement at 450 nm. Purified human IgG3 antibody (Sigma, I-4389) was used as standard. The standard,was diluted stepwise with mouse serum-supplemented PBS.

Quantative Determination of Human IgG4

Anti-human IgG4 antibody (Sigma, I-7635) was diluted with 100 mM glycine-HCl buffer (pH 2.5) and incubated for 5 minutes at room temperature, followed by 10-fold dilution with 100 mM phosphate buffer (pH 7.0). Ninety six-well microtiter plates were coated with the anti-human IgG3 antibody solution. A serum sample was added. Subsequently, peroxidase-labeled anti-human IgG antibody (Pharmingen, 08007E) was added to the plates and incubated. After TMBZ (Sumitomo Bakelite, ML-1120T) was added, enzyme activity was determined by absorbance measurement at 450 nm. Purified human IgG4 antibody (Sigma, I-4639) was used as standard. The standard was diluted stepwise with mouse serum-supplemented PBS.

Quantative Determination of Human IgM

Ninety six-well microtiter plates were coated with anti-human $\mu$ chain mouse monoclonal antibody (Sigma, I-6385) diluted with PBS. A serum sample was added. Subsequently, peroxidase-labeled anti-human $\mu$ chain mouse antibody (The Binding Site Limited, MP008) diluted with mouse serum (Sigma, M5905)-supplemented PBS was added to the plates and incubated. After TMBZ (Sumitomo Bakelite, ML-1120T) was added as a peroxidase substrate, enzyme activity was determined by absorbance measurement at 450 nm. Purified human IgM having $\mu$ chain (CAPPEL, 6001-1590) was used as standard. The standard was diluted stepwise with mouse serum (Sigma, M5905)-supplemented PBS.

The results are shown in Table 10. All the subclasses IgG1, IgG2, IgG3 and IgG4, and IgM were detected in the two chimeric mice K15A and K16A.

TABLE 10

Concentrations of Human antibody IgG Subclasses and IgM in the Chimeric Mice (ELISA)

| Chimeric mouse | IgG1 | IgG2 | IgG3 | IgG4 | IgM (mg/l) |
|---|---|---|---|---|---|
| K15A | 2.25 | 1.96 | 0.17 | 0.43 | 7.09 |
| K16A | 0.30 | 0.69 | 0.10 | 0.07 | 0.87 |

EXAMPLE 30

Preparation of Mouse ES Cell Clones (TT2) Retaining Human Chromosome #22

The cell clone 6-1 (A9/#22, G418 and puromycin resistant) from Example 26 was used as a chromosome donor cell for the preparation of mouse ES cell (TT2) retaining human chromosome #22. A wild-type TT2 cell line (see Example 9) was used as a chromosome recipient cell. The microcell fusion and the selection of puromycin resistant clones were conducted by the same procedures as in the selection of G418 resistant clones in Example 9 except that the concentration of puromycin was 0.75 $\mu$g/ml. The frequency of the appearance of the puromycin resistant clones was 1–2 per $10^7$ of TT2 cells. The puromycin resistant clones were stored frozen and genomic DNA was prepared by the same methods as in Example 2. The retention of human chromosome #22 in the puromycin resistant clone PG22-1 was confirmed by the methods described in (1) and (2) below.

(1) PCR Analysis

Genomic DNA of the puromycin resistant clone was used as a template in PCR amplification. Among the genes on human chromosome #22 (Genetic Maps, supra), ten primers whose presence in the A9/#22 clone was confirmed in Example 2 were used in the PCR amplification. All the markers which existed in the A9/#22 clone (see Example 2) were detected.

(2) Southern Blot Analysis

Figure 19:
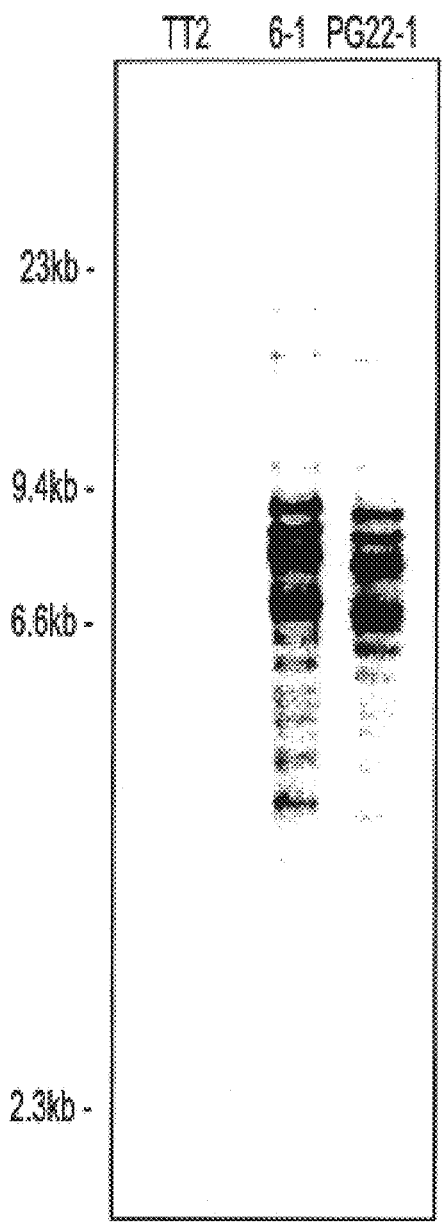
FIG. 19 is a photograph of electrophoresis patterns showing the detection of human L1 sequence in a human chromosome #22-transferred TT2 cell clone (Southern analysis).

In accordance with the same method as described in Example 2 using human L1 sequence as a probe, Southern blot analysis was conducted with genomic DNAs obtained from wild-type TT2 (negative control), the chromosome donor cell 6-1 and the puromycin resistant TT2 cell clone PG22-1. The results are shown in FIG. 19. In FIG. 19, the molecular weights of DNAs are shown at the left side. The band pattern of the PG22-1 clone was equivalent to that of the 6-1 cell and the signal intensities were the same. Hence, it was confirmed that chromosome #22 in the 6-1 cell had been transferred certainly into the PG22-1 clone.

These experiments demonstrate that the puromycin resistant TT2 cell clone PG22-1 retained the whole or the most part of human chromosome #22.

EXAMPLE 31

Production of Chimeric Mice from the Mouse ES Cells (TT2) Retaining Human Chromosome #22

The cells in a frozen stock of the puromycin resistant TT2 cell clone PG22-1 from Example 30 which was confirmed to retain human chromosome #22 were thawed, started to culture and injected into 8-cell stage embryos obtained by mating ICR or MCH(ICR) male and female mice (CREA JAPAN, INC.); the injection rate was 10–12 cells per embryo. The embryos were cultured in a medium for ES cells (see Example 9) overnight to develop to blastocysts. Two and a half day after a foster mother ICR mouse was subjected to a pseudopregnant treatment, about ten of the injected embryos were transplanted to each side of the uterus of the foster mother. The results are shown in Table 11.

TABLE 11

Production of chimeric mice from the TT2 cell clone retaining human chromosome #22

| ES cell clone/human chromosome | Puromycin resistant clone No. | Number of ES cell-injected 8-cell stage embryos | Number of offspring mice | Number chimeric mice | Contribution to coat color | | |
|---|---|---|---|---|---|---|---|
| | | | | | <20% | 20–50% | 50–80% |
| TT2/#22 | PG22-1 | 266 | 36 | 8 | 4 | 1 | 3 |

As a result of the transplantation of a total of 266 injected embryos, 36 offspring mice were born. Chimerism in the offsprings can be determined by the extent of TT2 cell-derived agouti coat color (dark brown) in the host embryo-derived albino coat color. Out of the 36 produced offsprings, 8 mice were recognized to have a partial agouti coat color, indicating the contribution of the ES cells.

These results show that the ES cell clone (derived from TT2, PG22-1) retaining human chromosome #22 maintain the ability to produce chimera, that is, the ability to differentiate into normal tissues of mouse.

EXAMPLE 32

Detection and Quantitation of Human Antibody λ Chain in Sera of the Chimeric Mice Retaining Human Chromosome #22

The concentration of human antibody λ in the sera of the chimeric mice KPG22-1, 2 and 3 from Example 31 was determined by ELISA in accordance with the same procedure as in Example 14. The chimeric mice of 2 months after birth were bled and human antibody λ chain in the sera was detected by ELISA. Ninety six-well microtiter plates were coated with anti-human immunoglobulin λ chain antibody (VECTOR LABORATORIES INC., IA-3070) diluted with PBS and then a serum sample was added. Subsequently, biotin-labeled anti-human immunoglobulin λ chain antibody (VECTOR LABORATORIES INC., BA-3070) was added to the plates and incubated. A complex of biotinylated horseradish peroxidase and avidin DH (VECTOR LABORATORIES, INC., Vectastain ABC Kit) was added and incubated. After TMBZ (Sumitomo Bakelite, ML-1120T) was added, enzyme activity was determined by absorbance measurement at 450 nm. Purified human IgM antibody having λ chain (Dainippon Pharmaceutical Co., Ltd., U13200) was used as standard. The standard was diluted stepwise with mouse serum-supplemented PBS. The results are shown in Table 12. These results show that human antibody λ chain gene can function in the chimeric mice retaining human chromosome #22.

TABLE 12

Concentration of Human Antibody λ Chain in Chimeric Mice (ELISA)

| Chimeric Mouse | % Chimerism | Igλ (mg/l) |
|---|---|---|
| KPG22-1 | 50 | 12 |
| KPG22-2 | 50 | 18 |
| KPG22-3 | 20 | 24 |

EXAMPLE 33

Figure 20:
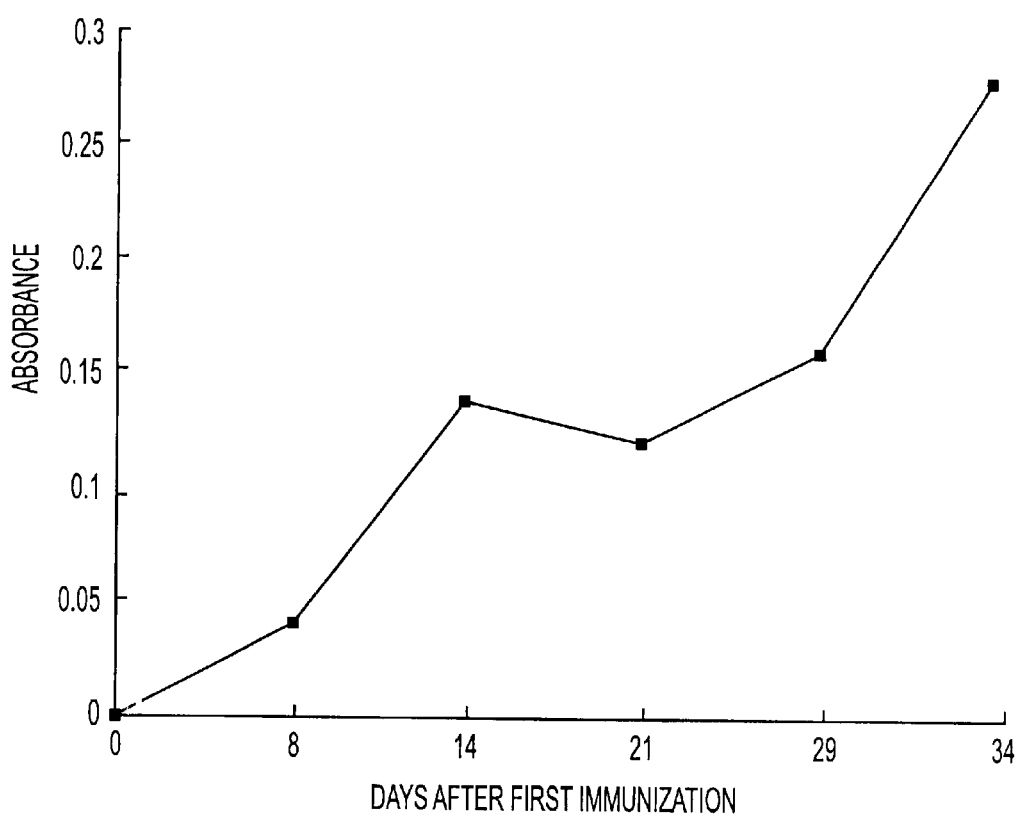
FIG. 20 shows that the antibody titer of anti-HSA human Igλ is increased in a serum of an HSA-immunized chimeric mouse.

Detection of Anti-human HSA Human Antibody λ Chain in a Serum of the Human Chromosome #22 Transferred Chimeric Mouse The chimeric mouse KPG22-3 from Example 31 was immunized with HSA, 3 times at days 79, 94 and 110 after birth by the same method as in Example 20. Human antibody λ chain in the serum of the chimeric mouse was detected by ELISA in accordance with the same procedure as in Example 14. Ninety six-well microtiter plates were coated with HSA (Sigma, A 3782) diluted with 50 mM carbonate-bicarbonate buffer (pH 9.6) to a concentration of 5 µg/ml and a serum sample was added. Biotinylated anti-human Ig λ antibody (VECTOR LABORATORIES INC., BA-3070) was added. Subsequently, a complex of biotinylated-horseradish peroxidase and avidin DH (VECTOR LABORATORIES, INC., Vectastain ABC Kit) was added to the plates and incubated. After TMBZ (Sumitomo Bakelite, ML-1120T) was added, enzyme activity was determined by absorbance measurement at 450 nm. The titer of the anti-HSA human λ chain in the serum of the chimeric mouse increased after the immunization. On the other hand, control ICR mouse gave a background level of the anti-HSA human λ chain titer after the immunization with HSA. The results are shown in FIG. 20. In FIG. 20, the number of days after the first immunization of the chimeric mouse with HSA is plotted on the horizontal axis and the absorbance at 450 nm is plotted on the vertical axis. These results show that human antibody λ chain gene can function in the chimeric mouse retaining human chromosome #22 and that the antibody titer of the antigen specific human Igλ was increased by stimulation with the HSA antigen.

EXAMPLE 34

Preparation of Human Antibody Light chain-producing Hybridomas from the Human Chromosome #22 Transferred Chimeric Mouse The spleen was removed from the mouse KPG22-3 (see Example 33) at day 113 after birth by the same method as in Example 25. A spleen cell was fused with a myeloma cell to produce a hybridoma. The hybridoma was produced using a myeloma cell SP-2/0-Ag14 (Dainippon Pharmaceutical Co., Ltd., 05-554) by the method described in Toyama and Ando, "Monoclonal Antibody Experiment Manual", published by Kodansha Scientific, 1991. The cells were inoculated into a medium containing 10% HCF (Air Brown) in five 96-well plates and cultured for 1–3 weeks. The supernatant of the culture solution in colony-positive wells was analyzed by ELISA. The ELISA analysis was conducted by the same method as in Example 33 and four human antibody λ chain-positive clones were obtained.

EXAMPLE 35

Preparation of Mouse ES Cell Clones Retaining both a Human Chromosome #22 Partial Fragment and a Human Chromosome #14 Partial Fragment The 6-1 cell clone from Example 26 (A9/#22, G418 and puromycin resistant) was used as a chromosome donor cell for the preparation of mouse ES cells retaining both a human chromosome #22 partial fragment and a human chromosome #14 partial fragment. The G418 resistant TT2 cell clone 1-4 retaining a human chromosome #14 partial fragment from Example 9 was used as a chromosome recipient cell. The experiment of microcell fusion and the selection of puromycin resistant cells were carried out by the same methods as in the selection of the G418 resistant clones in Example 9 except that the concentration of puromycin was 0.75 μg/ml. As a result, the frequency of the appearance of the puromycin resistant clones was 1–2 per $10^7$ of 1–4 cells. The retention of G418 resistance in the puromycin resistant clones was confirmed from the fact that these clones were grown in the presence of 300 μg/ml G418. The double-drug resistant clones were stored frozen and genomic DNAs were prepared by the same methods as in Example 2. The retention of human chromosome #22 and a human chromosome #14 partial fragment in the double-drug resistant clone PG22-5 was confirmed by PCR analysis. With genomic DNA of the double-drug resistant clone used as a template, PCR amplification was conducted using primers whose presence on chromosome #22 was confirmed in Example 2 (A9/#22) and primers whose presence on chromosome #14 was confirmed in Example 9 (TT2/#14 1-4); as a result, three markers (D22S275, D22S315 and Igλ) of the ten markers on chromosome #22 and all of the markers on chromosome #14 in the TT2/#14 1-4 clone were detected.

These experiments demonstrate that the obtained double-drug resistant TT2 cell clone retained both a human chromosome #22 partial fragment and a human chromosome #14 partial fragment.

EXAMPLE 36

Production of the Chimeric Mouse from the Mouse ES Cell Clone Retaining both a Human Chromosome #22 Partial Fragment and a Human Chromosome #14 Partial Fragment The cells in a frozen stock of the G418 and puromycin double-resistant TT2 cell clone PG22-5 from Example 35 which was confirmed to retain a human chromosome #22 partial fragment and a human chromosome #14 partial fragment were thawed, started to culture and injected into 8-cell stage embryos obtained by mating ICR or MCH(ICR) male and female mice (CREA JAPAN, INC.); the injection rate was 10–12 cells per embryo. The embryos were cultured in a medium for ES cells (see Example 9) overnight to develop to blastocysts. Two and a half day after a foster mother ICR mouse was subjected to a pseudopregnant treatment, about ten of the injected embryos were transplanted to each side of the uterus of the foster mother. The results are shown in Table 13.

TABLE 13

Production of the chimeric mouse from the mouse ES cell clone retaining both a human chromosome #22 partial fragment and a human chromosome #14 partial fragment

| ES cell clone/human chromosome | Double-drug resistant clone No. | Number of ES cell-injected 8-cell stage embryos | Number of offspring mice | Number of chimeric mice | Contribution to coat color | | |
|---|---|---|---|---|---|---|---|
| | | | | | <20% | 20–50% | 50–80% |
| TT2/#22 + #14 | PG22-5 | 302 | 16 | 5 | 3 | 2 | 0 |

As a result of the transplantation of a total of 302 injected embryos, 16 offspring mice were born. Chimerism in the offsprings can be determined by the extent of TT2 cell-derived agouti coat color (dark brown) in the host embryo-derived albino coat color. Out of the 16 produced offsprings, 5 mice were recognized to have a partial agouti coat color, indicating the contribution of the ES cell.

These results show that the ES cell clone PG22-5 retaining a human chromosome #22 partial fragment and a human chromosome #14 partial fragment maintains the ability to produce chimera, that is, the ability to differentiate into normal tissues of mouse.

EXAMPLE 37

Detection of Human Antibody λ Chain and μ Chain in Sera of the Chimeric Mice Derived from the ES Cells Retaining both a Human Chromosome #22 Partial Fragment and a Human Chromosome #14 Partial Fragment The chimeric mice KPG22-9, 10 and 12 from Example 36 were immunized with HSA. The chimeric mice KPG22-9 and 10 were immunized 11 weeks after birth and bled 2 weeks after the immunization. The chimeric mouse KPG22-12 was immunized twice at 7 and 11 weeks after birth and bled 2 weeks after the second immunization.

A serum human antibody λ chain μ a serum human antibody λ chain, and a serum antibody having both human antibody λ and μ chains were detected by ELISA in accordance with Example 14.

For the detection of complete human antibody molecules, 96-well microtiter plates were coated with anti-human immunoglobulin λ chain antibody (Kirkegaard & Perry Laboratories Inc., 01-10-11) diluted with PBS and a serum sample was added. Subsequently, peroxidase-labeled anti-human immunoglobulin μ chain antibody (The Binding Site Limited, MP008) was added to the plates and incubated. After TMBZ (Sumitomo Bakelite, ML-1120T) was added as a peroxidase substrate, enzyme activity was determined by absorbance measurement at 450 nm. Purified human IgM antibody having λ chain (Dainippon Pharmaceutical Co., Ltd., U13200) was used as standard. The standard was diluted stepwise with mouse serum-supplemented PBS. Human antibody λ and μ chains were detected and determined quantitatively by ELISA in the same manner as in Examples 29 and 32. The results are shown in Table 14.

months after birth 3 times with 0.2 ml of a solution of human serum albumin (HSA, Sigma, A3782) and adjuvant (MPL+ TDM Emulsion, RIBI Immunochem Research Inc.) in PBS at a HSA concentration of 0.25 mg/ml and bled (see Example 15). The chimeric mouse KPG-26 (derived from the TT2ES clone PG6, 40% chimerism) of 6 weeks after birth was bled. The concentration of a complete human antibody molecule in the sera was determined by ELISA in accordance with Example 14. Ninety six-well microtiter plates were coated with anti-human immunoglobulin κ chain antibody (Kirkegaard & Perry Laboratories Inc., 01-10-10) diluted with PBS, and a serum sample was added. Subsequently, peroxidase-labeled anti-human immunoglob-

TABLE 14

Concentrations of Human Antibodies in Chimeric Mice (ELISA)

| ES clone | Chimeric mouse | Chimerism (%) | IgM (mg/l) | Igλ (mg/l) | IgM, λ (mg/l) |
|---|---|---|---|---|---|
| PG22-5 | KPG22-9 | 30 | 2.54 | 9.9 | 0.043 |
| PG22-5 | KPG22-10 | 5 | 4.96 | 21.5 | 0.333 |
| PG22-5 | KPG22-12 | 40 | 3.71 | 7.0 | 0.048 |
| 3-2 | K9 | 50 | 6.66 | — | <0.003 |
| PG22-1 | KPG22-2 | 50 | — | 17.6 | <0.003 |

Both λ and μ chains were detected in the chimeric mice. An antibody molecule having both human antibody μ and λ chains was detected. These results show: the human antibody λ chain gene and human antibody μ chain gene can function at the same time in the chimeric mice derived from the ES cells retaining human chromosome #22 partial fragments and human chromosome #14 partial fragments; and a complete antibody containing both human heavy and light chains was produced in part of the B cells.

The control mice, that is, the chimeric mouse K9 retaining only human chromosome #14 from Example 10 and the chimeric mouse KG22-2 retaining only human chromosome #22 from Example 31, gave background levels of an antibody having both human antibody λ and μ chains in the sera. It was confirmed that in these detection systems, only a complete antibody molecule having human λ and μ chains was detected.

uling chain antibody (The Binding Site Limited, MP008) was added to the plates and incubated. After TMBZ (Sumitomo Bakelite, ML-1120T) was added as a peroxidase substrate, enzyme activity was determined by absorbance measurement at 450 nm. Purified human IgM antibody having κ chain (CAPPEL, 6001-1590) was used as standard. The standard was diluted stepwise with mouse serum-supplemented PBS. The concentrations of κ chain and μ chain were determined by the same method as in Example 20. The results are shown in Table 15.

TABLE 15

Concentrations of Human Antibodies in Chimeric Mice (ELISA)

| ES clone | Chimeric mouse | Chimerism (%) | IgM (mg/l) | Igκ (mg/l) | IgM, κ (mg/l) |
|---|---|---|---|---|---|
| PG-5 | KPG15 | 10 | 0.18 | 1.01 | 0.075 |
| PG-6 | KPG26 | 40 | 1.52 | 1.26 | 0.018 |
| 3-2 | K9 | 50 | 6.66 | — | <0.002 |
| 5-1 | K2-9 | 40 | — | 135 | <0.002 |

EXAMPLE 38

Detection of Human Antibody Having Human λ and μ Chains in Sera of the Chimeric Mice Derived from the ES Cells Retaining both Human Chromosome #2 Partial Fragments and Human Chromosome #14 Partial Fragments The chimeric mouse KPG-15 (derived from the TT2ES clone PG5, 10% chimerism) was immunized during 2–3

A antibody molecule having both human antibody μ and κ chains was detected. The control mice, that is, the chimeric mouse K9 retaining only human chromosome #14 from Example 10 and the chimeric mouse K2-9 retaining only human chromosome #2 from Example 13, gave background levels (<0.002 mg/ml) of an antibody having human antibody κ and μ chains in the sera. These results show: the human antibody κ chain gene and human antibody μ chain gene can function at the same time in the chimeric mice derived from the ES cells retaining both human chromosome #2 partial fragments and human chromosome #14 partial fragments; and a complete antibody molecule containing both human heavy and light chains was produced in part of the B cells.

EXAMPLE 39

Preparation of Mouse ES Cell Clone (TT2F, XO) Retaining a Human Chromosome #2 Partial Fragment The cell clone PG1 from Example 16 was used as a chromosome donor cell for the preparation of a mouse ES cell (XO) retaining a human chromosome #2 partial fragment. A TT2F cell (purchased from Lifetec Oriental Co.) having a karyotype of (39, XO), which was reported to differentiate efficiently into an oocyte in chimeric mice (Shinichi Aizawa, "Biomanual Series 8, Gene Targeting" published by Yodosha, 1995), was used as a chromosome recipient cell. The experiment of microcell fusion and the selection of puromycin resistant cells were carried out by the same methods as in the selection of the G418 resistant clones in Example 9 exclept that the concentration of puromycin was 0.75 μg/ml. The frequency of the appearance of the puromycin resistant clones was 5 per $10^7$ of TT2F cells. The puromycin resistant clones were stored frozen and genomic DNAs were prepared from the clones by the same methods as in Example 2. The retention of human chromosome #2 partial fragments in the drug resistant clones P-20 and P-21 was confirmed by PCR analysis. As a result of PCR amplification using genomic DNAs of the drug resistant clones as templates and three kinds of primers Cκ, FABP1 and Vκ 1-2 whose presence in the A9/#2 W23 clone was confirmed in Example 1, all of the three primers gave expected amplification products in both of the two clones.

These experiments demonstrate that the obtained puromycin resistant ES cell clone (TT2F, XO) retained a human chromosome #2 partial fragment.

EXAMPLE 40

Production of the Chimeric Mice from the Mouse ES Cell Clone (TT2F, XO) Retaining a Human Chromosome #2 Partial Fragment The cells in a frozen stock of the puromycin resistant TT2F cell clone P-21 from Example 39 which was confirmed to retain a human chromosome #2 partial fragment were thawed, started to culture and injected into 8-cell stage embryos obtained by mating ICR or MCH(ICR) male and female mice (CREA JAPAN, INC.); the injection rate was 10–12 cells per embryo. The embryos were cultured in a medium for ES cells (see Example 9) overnight to develop to blastocysts. Two and a half day after a foster mother ICR mouse was subjected to a pseudopregnant treatment, about ten of the injected embryos were transplanted to each side of the uterus of the foster mother. The results are shown in Table 16.

As a result of the transplantation of a total of 141 injected embryos, 20 offspring mice were born. Chimerism in the offsprings can be determined by the extent of TT2F cell-derived agouti coat color (dark brown) in the host embryo-derived albino coat color. Out of the 20 produced offsprings, 9 mice were recognized to have a partial agouti coat color, indicating the contribution of the ES cell. Four of the 9 mice were chimeric mice having a full agouti coat color from the ES cells.

These results show that the ES cell clone P-21 retaining a human chromosome #2 partial fragment maintains the ability to produce chimera, that is, the ability to differentiate into normal tissues of mouse.

EXAMPLE 41

Detection and Quantitative Determination of Human Antibody κ Chain in Sera of the Chimeric Mice Derived from the TT2F Clone Retaining a Human Chromosome #2 Partial Fragment The chimeric mice K2-1F, 2F, 3F and 4F (derived from the P-21 clone, 100% chimerism) from Example 40 of about 1 month after birth were bled and the concentration of human antibody κ chain in the sera was determined quantitatively by ELISA in the same manner as in Example 20.

The results are shown in Table 17. It was confirmed that the human antibody κ chain gene could function in the chimeric mice when the TT2F was used as an ES cell.

TABLE 17

Concentration of Human Antibody κ Chain in Chimeric Mice (ELISA)

| Chimeric mouse | % Chimerism | Ig κ (mg/l) |
| --- | --- | --- |
| K2-1F | 100 | 66 |
| K2-2F | 100 | 156 |
| K2-3F | 100 | 99 |
| K2-4F | 100 | 20 |

EXAMPLE 42

Confirmation of the Retention of Human Chromosome in Progenies of the Chimeric Mice Derived from the Mouse ES Cell (TT2F, XO) Retaining a Human Chromosome #2 Partial Fragment Examination was made as to whether ES cell-derived progenies would be reproduced by mating the female chimeric mice K2-1F and K2-4F (both were of 100% chimerism in coat color) from Example 40 with ICR male mice. In

TABLE 16

Production of the chimeric mice from the TT2F cell clone retaining a human chromosome #2 partial fragment

Figure 21:
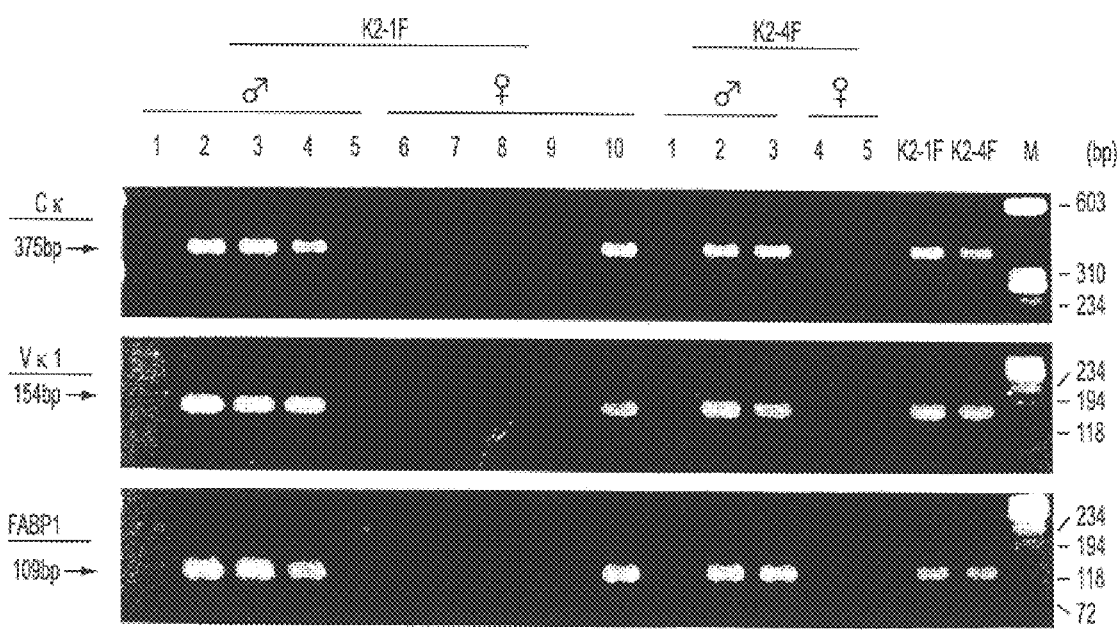
FIG. 21 shows that a partial fragment of human chromosome #2 is retained in a progeny of a chimeric mouse into which a partial fragment of a human chromosome #2 was transferred (PCR analysis).

| ES cell clone/human chromosome | Puromycin resistant clone No. | Number of ES cell-injected 8-cell stage embryos | Number of offspring mice | Number of chimeric mice | Contribution to coat color | | | |
| --- | --- | --- | --- | --- | --- | --- | --- | --- |
| | | | | | <20% | 20–50% | 50–90% | 100% |
| TT2F/#2fg. | P-21 | 141 | 20 | 9 | 0 | 2 | 3 | 4 | such a mating, offspring mice of an agouti coat color should be reproduced from the oocytes derived from the TT2F cell (agouti coat color, dominant) in the chimeric mice and offspring mice of an albino coat color should be reproduced from oocytes derived from ICR if the oocytes are fertilized with the sperms from ICR male mice (albino, recessive). All the viable offspring mice (K2-1F, 10 mice and K2-4F, 5 mice) obtained by one mating of the respective combinations had an agouti coat color which derived from the ES cells. The retention of human chromosome fragments in genomic DNAs prepared from the tails of the offspring mice was examined by a PCR method. As a result of the PCR amplification using three kinds of primers whose presence in the P-21 clone (see Example 39) was confirmed, the presence of these three markers was confirmed in 4 out of the ten mice from K2-1F and in 2 out of the five mice from K2-4F. The results of the PCR of these 15 offspring mice are shown in FIG. 21. In FIG. 21, markers (φ X174/HaeIII fragment, Nippongene) and the DNA molecular weights of main bands are shown at the right side and the lengths of expected products of amplification with the respective primers are shown by arrows at the left side. At the right side, the results with tail-derived DNA of the mother chimeric mice K2-1F and K2-4F (positive controls) are shown. These results show that the TT2 cell clone P-21 differentiated into functional oocyte in the chimeric mice and that a human chromosome #2 partial fragment was transmitted to offsprings through oocyte.

EXAMPLE 43

Confirmation of the Retention of Human Chromosome in Progenies of the Chimeric Mice Derived from the Mouse ES Cell (TT2, XY) Retaining a Human Chromosome #2 Partial Fragment Examination was made as to whether ES cell-contributed offspring mice would be produced by mating K2-18 (70% chimeric male mouse from Example 13) with K2-19 (60% chimeric female mouse of Example 13) or non-chimeric female littermates. Since TT2 cell has the karyotype of (40, XY), it may differentiate into a functional sperm in the male chimeric mouse K2-18. If this is the case, offspring mice of an agouti coat color should be reproduced from ICR (albino, recessive)-derived oocytes fertilized with sperms from TT2 cell (agouti color, dominant) in the chimeric mice. While a total of 110 viable offspring mice were obtained by the mating, ten had an agouti coat color which derived from the ES cells. The retention of human chromosome fragments in genomic DNAs prepared from the tails of 7 out of the ten offspring mice of an agouti coat color was examined by a PCR method. As a result of PCR amplification using two kinds of primers Cκ and FABP1 whose presence in the 5-1 clone (TT2/#2fg . . . Example 12) was confirmed and primer Vκ 1-2 which was shown in Example 1, the presence of all of the three markers was confirmed in 2 out of the seven mice. These results show that the TT2 cell clone 5-1 retaining a human chromosome #2 partial fragment differentiated into functional sperms in the chimeric mice and that the human chromosome #2 partial fragment was transmitted to offsprings through the sperms.

EXAMPLE 44

Detection and Quantitative Determination of Human Antibody κ Chain in Sera of Offspring Mice of the Chimeric Mice The concentration of human antibody κ chain in the sera of the offspring mice K2-1F-1~10 and K2-4F-1~5 from Example 42 was determined quantitatively by ELISA. The mice of about 4–6 months after birth were bled and the concentration of human antibody κ chain in the sera was determined by ELISA in the same manner as in Example 20.

The results are shown in Table 18 together with the data obtained in Example 42 on the retention of chromosome. It was confirmed that the human antibody κ chain gene can function in the offspring mice reproduced from the chimeric mice.

TABLE 18

Concentration of Human Antibody κ Chain in Offspring Mice (ELISA)

| Mother mouse | Number of mouse | Presence of human chromosome #2 fragments | Ig κ (mg/l) |
|---|---|---|---|
| K2-1F | #1 | – | 0.58 |
| K2-1F | #2 | + | 84.1 |
| K2-1F | #3 | + | 12.8 |
| K2-1F | #4 | + | 15.1 |
| K2-1F | #5 | – | 0.52 |
| K2-1F | #6 | – | 0.58 |
| K2-1F | #7 | – | 1.30 |
| K2-1F | #8 | – | 0.90 |
| K2-1F | #9 | – | 0.56 |
| K2-1F | #10 | + | 28.8 |
| K2-4F | #1 | – | <0.04 |
| K2-4F | #2 | + | 23.3 |
| K2-4F | #3 | + | 11.8 |
| K2-4F | #4 | – | 0.08 |
| K2-4F | #5 | – | 0.06 |

EXAMPLE 45

Figure 22:
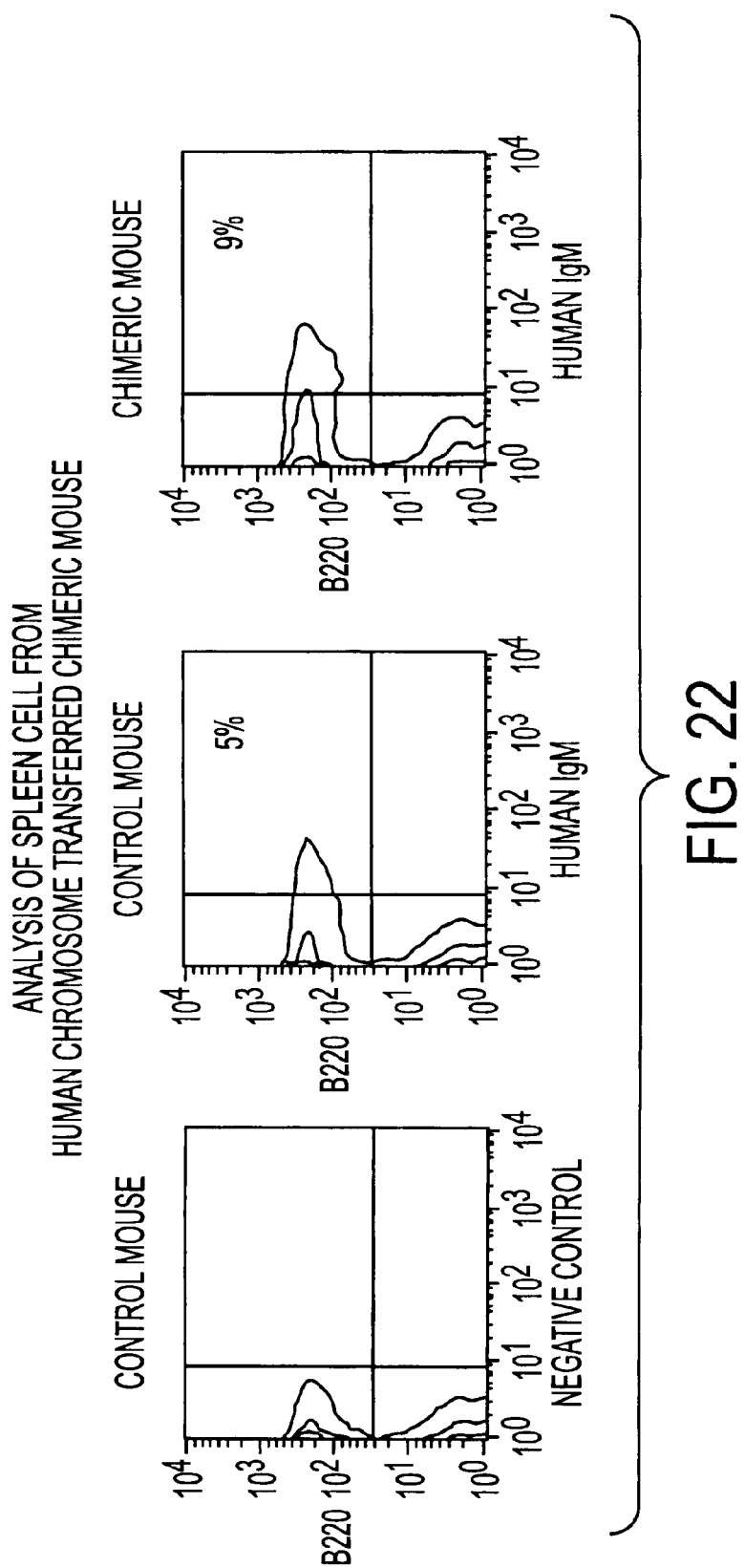
FIG. 22 shows the presence of a cell expressing human μ chain on the cell surface in a spleen of a human chromosome #14-transferred chimeric mouse (flow cytometry analysis).

Analysis of Spleen Cells from the Human Chromosome #14 Partial Fragment Transferred Chimeric Mice Flow cytometry analysis was accordance with the method described in "New Biochemical Experiment Lecture 12, molecular immunology I-Immunocells.Cytokines-", edited by the Japanese Biochemical Society, 1989, published by Tokyo Kagaku Dojin; "Cell Technology Separated Volume 8, New Cell Technology Experiment Protocol", edited by the University of Tokyo, Medical Science Institute, Anti-cancer Laboratory, 1991, published by Shujunsha; and A.Doyle and J. B.Griffiths, "Cell & Tissue Culture: Laboratory Procedures", published by John Wiley & Sons Ltd., 1996. The spleen was removed from the chimeric mouse KPGO6 (derived from the PG16 clone, 30% chimerism) from Example 19 of six months after birth and treated with an aqueous solution of ammonium chloride. The spleen cells were stained with fluorescein isothiocyanate (FITC)-labeled anti-mouse CD45R (B220) antibody (Pharmingen, 01124A) in PBS containing 1% rat serum. After being washed, the cells were reacted with 0.1 μg of biotin-labeled anti-human IgM antibody (Pharmingen, 08072D) or a control biotin-labeled anti-human λ chain antibody (Pharmingen, 08152D) in PBS containing 5% mouse serum and stained with 0.1 μg of streptoavidin-phycoerythrin (Pharmingen, 13025D), followed by analysis with a flowcytometer (Becton Dickinson Immunocytometry Systems, FACSort). An ICR mouse retaining no human chromosome was used as a control for analysis by the same method. The results are shown in FIG. 22. In FIG. 22, the human IgM is plotted on the horizontal axis and the CD45R (B220) is plotted on the vertical axis. A population of cells positive to both B cell marker CD45R (FITC) and human IgM (PE) increased by 4%, indicating that cells expressing human antibody μ chain on the cell surfaces were present in the chimeric mice.

EXAMPLE 46

Cloning and Sequencing of Variable Regions of Human Antibody Genes from cDNA Derived from the Spleen of the Chimeric Mice Expressing Human Antibody Heavy Chain, κ and λ Chains, Respectively In the same manner as in Example 5, cDNAs were synthesized from RNAs extracted from the spleens of the chimeric mice K15A (derived from the 1-4 clone, prepared by the method described in Example 10), K2-8 prepared in Example 13 and KPG22-2 prepared in Example 31, all of which were confirmed to express human antibody heavy chain, κ and λ chains in Examples 29, 23 and 32, respectively. PCR was performed using the respective cDNAs and the following primers to amplify the variable regions of respective human antibody. cDNA derived from the spleen of a non-chimeric mouse ICR was used as a negative control. Those primers set forth below without indication of reference literature were designed on the basis of the nucleotide sequences obtained from data bases such as Genebank and the like.

K15A (heavy chain)
For constant region:
  HIGMEX1-2:
    5'-CCAAGCTTCAGGAGAAAGTGATGGAGTC (SEQ ID NO:53)
  HIGMEX1-1:
    5'-CCAAGCTTAGGCAGCCAACGGCCACGCT (used in 2nd PCR of VH3BACK) (SEQ ID NO:54)
For variable region:
  VH1/5BACK (59° C., 35 cycles, Marks et al., Eur. J. Immnol., 21, 985-, 1991),
  VH4BACK (59° C., 35 cycles, Marks et al., supra), and
  VH3BACK (1st PCR:59° C., 35 cycles; 2nd PCR:59° C., 35 cycles, Marks et al., supra)
K2-8 (light chain κ)
For constant region:
  KC2H:
    5'-CCAAGCTTCAGAGGCAGTTCCAGATTTC (SEQ ID NO:55)
For variable region:
  Vk1/4BACK (55° C., 40 cycles, Marks et al., Eur. J. Immnol., 21, 985-, 1991),
  Vk2BACK (55° C., 40 cycles, Marks et al., supra), and
  Vk3BACK (55° C., 40 cycles, Marks et al., supra)
KPG22-2 (light chain λ)
For constant region:
  Cλ MIX (a mixture of the following three kinds of primers at an equal molar ratio)
  IGL1-CR:
    5'-GGGAATTCGGGTAGAAGTCACTGATCAG (SEQ ID NO:56)
  IGL2-CR:
    5'-GGGAATTCGGGTAGAAGTCACTTATGAG (SEQ ID NO:57)
  IGL7-CR:
    5'-GGGAATTCGGGTAGAAGTCACTTACGAG (SEQ ID NO:58)
For variable region:
  Vλ 1LEA1 (55° C., 40 cycles, Williams et al., Eur. J. Immunol., 23, 1456-, 1993),
  Vλ 2MIX (55° C., 40 cycles, a mixture of Vλ 2 LEA1 and Vλ 2 JLEAD (Williams et al. (supra)) at an equal molar ratio)
  Vλ 3MIX (55° C., 40 cycles, a mixture of Vλ 3LEA1, Vλ 3JLEAD and Vλ 3BACK4, which were reported in Williams et al. (supra) at an equal molar ratio.

The PCR was performed with combinations of the primers for constant regions with those for variable regions (3 primer pairs each for heavy chain, κ and λ chains) at 94° C. for 15 seconds, at the annealing temperatures shown with respect to the respective primers for variable region for 15 seconds, at 72° C. for 20 seconds in the cycle numbers shown with respect to the respective primers for variable region using a Thermal Cycler 9600 (Perkin-Elmer Corp.). In the second run of PCR using VH3BACK, the amplification products of the first run of PCR were amplified again with a combination of the two primers H1GMEX1-1 and VH3BACK. All of the amplification products were electrophoresed on a 1.5% agarose gel and stained with ethiduim bromide for detection. As a result, the amplification products having expected lengths (heavy chain, about 470 bp; light chain κ, about 400 bp; and light chain λ, about 510 bp) were detected in all of the combinations. In the negative control, specific amplification product was not detected at the same position in any of the combinations. The obtained amplification products were extracted from the agarose gel using prep.A.gene (Bio-Rad Laboratories, Inc.), treated with restriction enzymes (heavy chain, HindIII and PstI; light chain κ, HindIII and PvuII; and light chain λ, HindIII and EcoRI), and cloned into pUC119 (TAKARA SHUZO CO., LTD.) at the sites of HindIII/PstI (heavy chain), HindIII/HincII (κ chain) and HindIII/EcoRI (λ chain). The nucleotide sequences of the products that were amplified with the following primers and which were cloned into the plasmids were determined with a Fluorescence Autosequencer (Applied Biosystems Inc.).

HIGMEX1-2×VH1/5BACK: 10 clones
  HIGMEX1-2×VH4BACK: 8 clones
  HIGMEX1-2 (2nd PCR, HIGMEX1-1)×VH3BACK: 5 clones
  KC2H×Vκ 1/4BACK: 6 clones
  KC2H×Vκ 2BACK: 7 clones
  KC2H×Vκ 3BACK: 4 clones
  Cλ MIX×Vλ 1LEA1: 5 clones
  Cλ MIX×Vλ 2MIX: 6 clones
  Cλ MIX×Vλ 3MIX: 5 clones The obtained nucleotide sequences were analyzed with DNASIS (Hitachi Software Engineering Co., Ltd.). The results show that all of the sequences were derived from human and that they were functional sequences which did not contain a termination codon at any site between an initiation codon and a constant region: this was true with all of the κ and λ chains and with 21 out of a total of 23 heavy chains. When the same sequences were removed from the determined sequences, unique variable region sequences were identified. as follows: 17 heavy chains, 11κ, chains, and 12λ chains.

EXAMPLE 47

Analysis of the Nucleotide Sequences of Variable Region of Human Antibody Genes from cDNA Derived from the Spleen of the Chimeric Mouse Expressing Human Antibody Heavy chain, κ and λ Chains, Respectively The nucleotide sequences determined in Example 46 (heavy chain, 17 clones; κ chain, 11 clones; and λ chain, 12 clones) were analyzed in the following points.

1. Identification of known germ line V gene segments used in the respective variable regions
2. Identification of known germ line J gene segments used in the respective variable regions
3. Identification of known germ line D gene segments used in the heavy chain variable regions
4. Identification of the addition of N region in the heavy chain variable regions on the basis of the results of 1, 2 and 3
5. Determination of the amino acid sequences deduced from the nucleotide sequences of the respective variable regions The results are shown in Table 19. For the identification in points of 1 and 2, search for homology with germ line V and J segments registered in Genbank and the like was conducted with DNASIS. The VH segments, Vκ segments and Vλ segments are shown in Table 19 together with the family names of the respective V fragments in accordance with the conventions described in Cook et al., Nature genetics, 7, 162-, 1994 (VH fragments), Klein et al., Eur. J. Immunol, 23, 3248-, 1993 (Vκ fragments) and Williams et al. (supra): (Vλ fragments), respectively. For the identification in point 3, search for homology with germ line D fragments reported in Ichihara et al.,: The EMBO J., 7, 13, 4141-, 1988 was conducted with DNASIS. Assignment was based on at least 8 bp identity and the results are shown in Table 19. DN1* is believed to be the new DN family segment reported in Green et al., Nature Genetics, 7, 13-, 1994. For the identification in point 4, the nucleotide sequences which did not appear in any germline sequences were determined to be N regions on the basis of the results for 1(V), 2(J) and 3 (D). As a result, N region was observed in 11 of the 13 sequences in which D segment was identified and its average length was 8.7 bp. For the determination in point 5, the respective sequences were converted by DNASIS to amino acid sequences which were expressed with one letter symbols. In Table 19, only CDR3 region is shown. At the right side of Table 19, the names of the primers used in cloning of the respective variable regions and the names of clones are shown.

TABLE 19

| V family | V segment | CDR3 | J (D) | V primer | Clone |
|---|---|---|---|---|---|
| K15A | | | | | |
| VH1 | VH1-8 | VRSSSWYEYYYYGMDV | J6 (DN1) | VH4BACK | H4-10 |
| | VH1-18 | GGITMVRGLIITDWYFDL | J2 (DXP'1) | VH1/5BACK | H1-7 |
| | VH1-24 | APYSGRFDY | J4 (DK1) | VH1/5BACK | H1-6 |
| | VH1-46 | ERYYGSGSYQDYYYYYGMDV | J6 (DXP'1) | VH1/5BACK | H1-2 |
| | VH1-46 | GGYSGYEDYYYYGMDV | J6 (DK1) | VH1/5BACK | H1-10 |
| VH2 | VH2-5 | SYFDWPDFDY | J4 (DXP1) | VH4BACK | H4-14 |
| VH3 | VH3-21 | EGCSGGSCLPGYYYYGMDV | J6 (DLR2) | VH1/5BACK | H1-4 |
| | VH3-23 | AHGDPYFDY | J4 | VH1/5BACK | H1-3 |
| | VH3-23 | DADAFDI | J3 | VH1/5BACK | H1-8 |
| | VH3-23 | SGWDY | J4 (DN1*) | VH3BACK | H3-3 |
| | VH3-23 | TGFDL | J2 | VH4BACK | H4-4 |
| | VH3-33 | EGGYGSVGDYYYYGMDV | J6 (DXP'1) | VH1/5BACK | H1-9 |
| | VH3-33 | GGYSYGYDYYYYGMDV | J6 (DXP'1) | VH3BACK | H3-5 |
| | VH3-33 | GYSSGWYDY | J4 (DN1*) | VH4BACK | H4-9 |
| VH4 | VH4-34 | RYSSGWYYFDY | J4 (DN1*) | VH4BACK | H4-15 |
| | VH4-59 | GRIAVASFDY | J4 (DN1*) | VH4BACK | H4-2 |
| | VH4-59 | GSGSYFHFDY | J4 | VH4BACK | H4-6 |
| K2-8 | | | | | |
| Vκ1 | O18-8 | QQHDNLPFT | J3 | Vκ1BACK | K1-1 |
| | O18-8 | QQYDNLPIT | J5 | Vκ1BACK | K1-3 |
| | O18-8 | QQHDNLPFA | J3 | Vκ2BACK | K2-2 |
| | L1 | QQYNSYPLT | J4 | Vκ1BACK | K1-6 |
| Vκ2 | A17 | MQGTHLLT | J4 | Vκ2BACK | K2-1 |
| | A17 | MQGTHWIT | J5 | Vκ2BACK | K2-5 |
| Vκ3 | A27 | QQYGSSPTWT | J1 | Vκ3BACK | K3-1 |
| | A27 | QQYGSSPFT | J3 | Vκ3BACK | K3-4 |
| | A27 | QQYGSSPLWT | J1 | Vκ3BACK | K3-5 |
| | A27 | QQYGSSPPWT | J1 | Vκ3BACK | K3-6 |
| Vκ6 | A26-10 | HQSSSLPQT | J1 | Vκ2BACK | K2-4 |
| KPG22-2 | | | | | |
| Vλ1 | DPL3 | AAWDDSLDVV | JC3 | Vλ1LEA1 | L1-3 |
| | DPL5 | GTWDSSLSAGV | JC2 | Vλ1LEA1 | L1-4 |
| | DPL5 | GTWDSSLSAGVV | JC3 | Vλ1LEA1 | L1-6 |
| | DPL5 | GTWDSSLSAVV | JC2 | Vλ1LEA1 | L1-9 |
| | DPL8 | QSYDSSLSGVV | JC3 | Vλ1LEA1 | L1-8 |
| Vλ2 | DPL10 | CSYAGSSTLV | JC2 | Vλ2MIX | L2-4 |
| | DPL11 | SSYTSSSTVV | JC2 | Vλ2MIX | L2-1 |
| | DPL11 | SSYTSSSTLV | JC2 | Vλ2MIX | L2-3 |
| | DPL11 | CSYTSSSTFV | JC2 | Vλ2MIX | L2-7 |
| | DPL12 | SSYAGSNNLV | JC3 | Vλ2MIX | L2-5 |
| | DPL12 | SSYAGSNNFVV | JC3 | Vλ2MIX | L2-6 |
| Vλ3 | DPL16 | NSRDSSGNLV | JC2 | Vλ3MIX | L3-1 |

EXAMPLE 48

Preparation of a Targeting Vector for Knocking Out Antibody Genes

Figure 23:
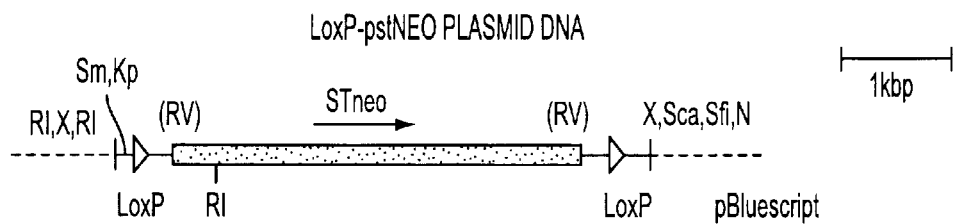
FIG. 23 shows the structure of LoxP-pstNEO plasmid DNA.

It becomes possible to transfer a human chromosome #14 fragment marked with a G418 resistance gene (Example 9)

and human chromosome #2 (Example 18) or #22 (Example 35) marked with a puromycin resistance gene into TT2 (or TT2F) cells in which mouse antibody genes (heavy-chain, light-chain κ) are disrupted. Those chimeric mice which are produced form these human chromosomes #14+#2 or #14+ #22-transferred, mouse antibody genes (heavy-chain, light-chain κ)-disrupted TT2 (or TT2F) ES cells according to the method of Example 19 (heavy-chain+κ chain) or Example 36 (heavy-chain+λ chain) are expected to produce antibodies both heavy- and light-chains of which are mainly derived from humans. The abbreviations of the restriction enzymes, etc. appearing in FIGS. 23–27 are as follows:

Restriction enzymes: Kp: KpnI, B: Ng2:NglII, RI: EcoRI, RV: EcoRV, N: NotI, S1: SalI Sca: ScaI, Sfi: SfiI, Sm: SmaI, X: XhoI, (X): XhoI restriction site from λ vector dK: deletion of KpnI restriction site, dX: deleteion of XhoI restriction site, (Sm/S1): The SalI restriction site was changed to a blunt end and subsequent ligation to a SmaI restriction site, (S1/RV): The SalI restriction site was changed to a blunt end and subsequent ligation to an EcoRV restriction site, Dotted portion: pBluescript SKII(+) or pUC18 plasmid DNA ◁ ▷:LoxP sequence 1Preparation of Plasmid pLoxP-STneo in which LoxP Sequence is inserted at Both the Ends of a G418 Resistance Gene For the deletion of a G418 resistance gene after knocking out an antibody gene of TT2F cells, it is necessary to insert LoxP sequence (Sauer et al., Proc. Natl. Acad. Sci. USA, 85, 5166-, 1988) which is the recognition sequence of Cre recombinase (Sauer et al., supra) at both the ends of the G418 resistance gene (Example 1) in the same direction. Briefly, a G418 resistance cassette (Stneo) was cut out from pSTneoB plasmid DNA (Example 1, Katoh et al., Cell Struct. Funct., 12:575, 1987: Japanese Collection of Research Biologicals (JCRB), Deposit Number: VE039) with restriction enzyme XhoI. The DNA fragment was purified by agarose gel electrophoresis and then blunted with T4-DNA polymerase (Blunting End Kit from Takara Shuzo). LoxP sequence-containing plasmid DNA pBS246 (Plasmid pBS246, loxP2 Cassette Vector, U.S. Pat. No. 4,959,317) was purchased from GIBCO BRL. XhoI linker DNAs were inserted into the EcoRI and SpeI restriction sites of this plasmid to change the sequences of these sites to a XhoI recognition sequence. The STneo DNA fragment described above was inserted into the EcoRV restriction site of the thus modified pBS246 to give plasmid pLoxP-STneo (FIG. 23).

2. Isolation of Genomic DNA Clones Containing C57BL/6-derived Antibody Heavy-chain Cμ (IgM Constant Region) or Light-chain Jκ-Cκ (Igκ Joint Region and Constant Region)

Since TT2 (or TT2F) cells were derived from F1 mice between C56BL/6 mice and CBA mice, the inventors have decided to prepare vectors for antibody gene knockout using genomic DNA clones derived from a C57BL/6 mouse. As a genomic DNA library, an adult C57BL/6N male liver-derived λ DNA library from Clontech was used. As a probe for screening, the following synthetic DNA sequences (60 mers) were used.

Heavy-chain Cλ probe: 5'-ACC TTC ATC GTC CTC TTC CTC CTG AGC CTC TTC TAC AGC ACC ACC GTC ACC CTG TTC AAG-3' (SEQ ID NO: 59)

Light-chain κ probe: 5'-TGA TGC TGC ACC AAC TGT ATC CAT CTT CCC ACC ATC CAG TGA GCA GTT AAC ATC TGG AGG-3' (SEQ ID NO: 60)

Figure 24:
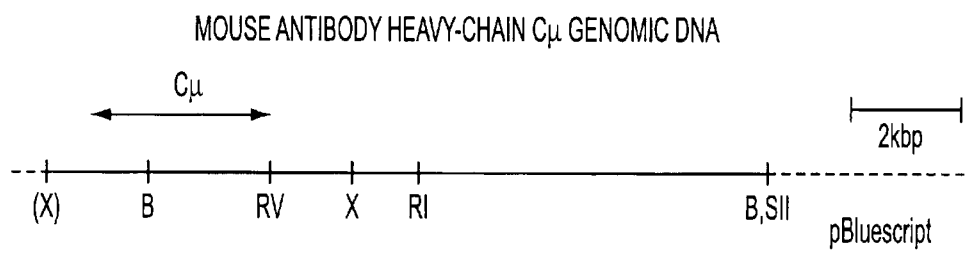
FIG. 24 shows the structure of genomic DNA carrying a mouse antibody heavy chain Cμ gene.
Figure 25:
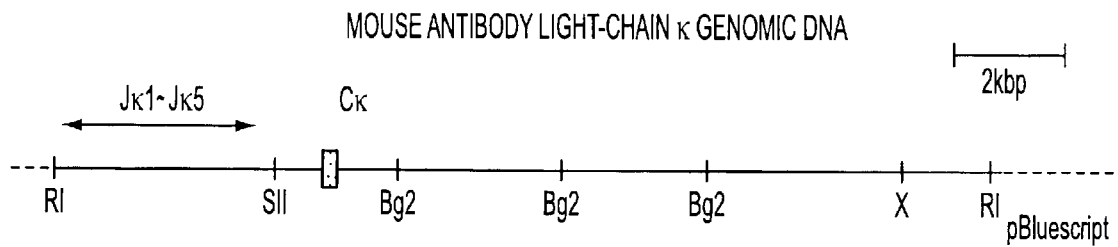
FIG. 25 shows the structure of genomic DNA carrying a mouse antibody light-chain κ gene.

The λ clones were isolated and analyzed to subclone those DNA fragments containing heavy-chain Cμ or light-chain Jκ-Cκ into plasmid pBluescript SKII(+) (Stratagene) (heavy-chain Cμ: FIG. 24; light-chain Jκ-Cκ: FIG. 25). These DNA fragments were used to prepare targeting vectors for disrupting mouse antibody genes in TT2 (or TT2F) cells as described below.

Figure 26:
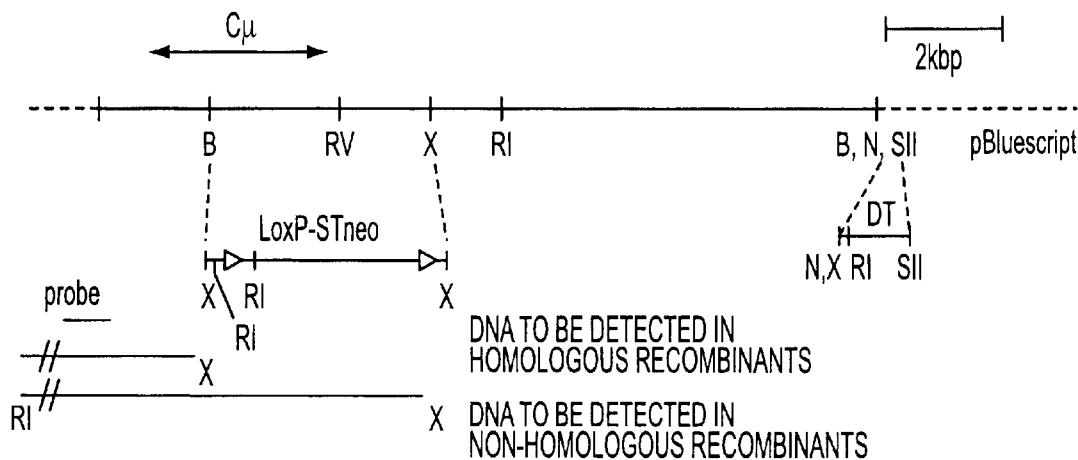
FIG. 26 shows the structures of a mouse antibody heavy-chain targeting vector and a probe for Southern blotting, as well as a DNA fragment to be detected in homologous recombinants.

3. Preparation of a Vector Plasmid for Disrupting a Mouse Antibody Heavy-chain Gene In the Cμ-encoding region in the genomic DNA fragment containing a mouse antibody heavy-chain constant region which was prepared in 2 above, a DNA fragment containing the $2^{nd}$ to $4^{th}$ exons (BamHI-XhoI) was replaced with the LoxP-STneo gene prepared in 1 above (FIG. 26). The direction of transcription of STneo was the same as that of the antibody heavy-chain gene. Further, a DT-A cassette A (Proc. Natl. Acad. Sci. USA, 87, 9918–9922, 1990, made by Oriental Yeast Co.)(hereinafter referred to as "DT") modified by changing the ApaI and SalI sites to NotI sites was inserted into the NotI site of this plasmid. A plasmid DNA containing a DT gene having the samedirection of transcription as that of the heavy-chain gene was selected. This plasmid DNA was amplified using *E. coli* DH5 and purified by cesium chloride equilibrium centrifugation ("Introduction to Cell Technology Experimental Operations", published by Kodansha, 1992). The purified plasmid DNA was cleaved at one site with restriction enzyme SacII and used for transfection of TT2F ES cells. As a probe for Southern blot analysis of transformant genomic DNA to detect from transformant TT2F ES cells those clones in which homologous recombination has taken place in the antibody heavy-chain portion with the targeting vector, a DNA fragment (about 500 bp) of the switch region located upstream of C μ-encoding region. This DNA fragment was obtained by amplifying 129 mouse genomic DNAs by PCR under the following conditions.

Sense primer: 5'-CTG GGG TGA GCC GGA TGT TTT G-3' (SEQ ID NO: 61)

Antisense primer: 5'-CCA ACC CAG CTC AGC CCA GTT C-3' (SEQ ID NO: 62)

Template DNA: 1 μg of EcoRI-digested 129 mouse genomic DNAs

The reaction buffer, deoxynucleotide mix and Taq DNA polymerase used were from Takara Shuzo.

Reaction conditions: 94° C., 3 min, 1 cycle→94° C., 1 min; 55° C., 2 min; 72° C., 2 min; 3 cycles→94° C., 45 sec; 55° C., 1 min; 72° C., 1 min; 36 cycles After it was confirmed that amplified DNA fragment can be cleaved at one site with restriction enzyme HindIII as indicated in the Genbank database, this DNA fragment was subcloned into the EcoRV restriction site of plasmid pbluescript. This plasmid DNA (S8) was cleaved with restriction enzymes BamHI and XhoI. A PCR fragment (about 550 bp) was purified by agarose gel electrophoresis to give a probe. Genomic DNA from those TT2F ES cells transformed with the targeting vector was digested with restriction enzymes EcoRI and XhoI, and separated by agarose gel electrophoresis. Then, Southern blotting was performed using the above probe.

4. Preparation of a Vector for Disrupting the Mouse Antibody Light-chain κ Gene

Figure 27:
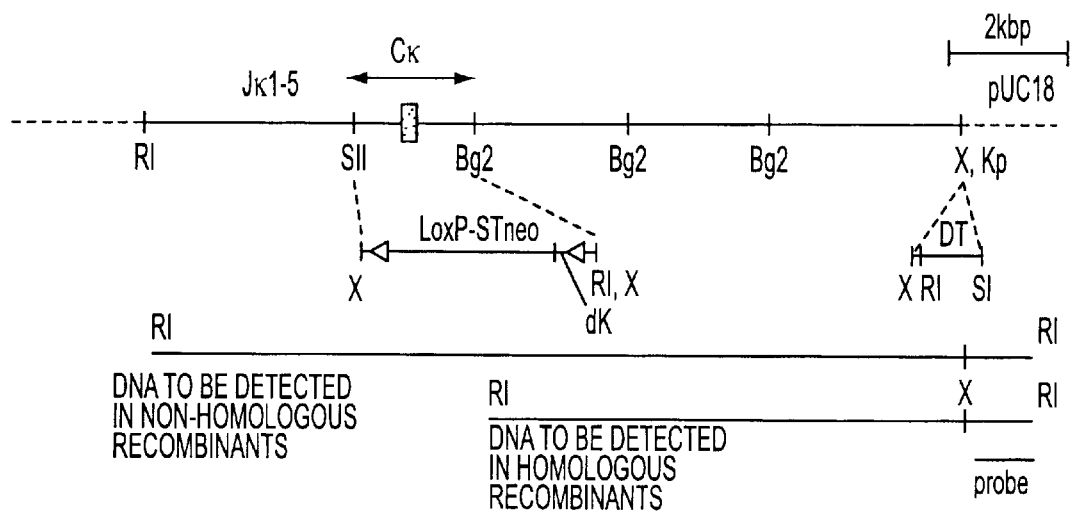
FIG. 27 shows the structures of a mouse antibody light-chain κ targeting vector and a probe for Southern blotting, as well as a DNA fragment to be detected in homologous recombinants.

The genomic DNA fragment prepared in 2 above contains the J region and constant region of mouse antibody light-chain κ. A DNA fragment (SacII-BglII) containing the C region was replaced with the LOXP-Stneo gene having the disrupted KpnI site (FIG. 27). The LoxP-STneo gene was prepared in 1 above. The direction of transcription of STneo was opposite to that of the antibody gene. This plasmid DNA was constructed as follows: the sequence of a multi-cloning site (EcoRI-HindIII) in plasmid pUC18 was changed to the following sequences prepared by DNA chemical synthesis.

5'-AATTCCCGCGGGTCGACGGATCCCTCGAGGGTACCA-3' (SEQ ID NO: 63)
3'-GGGCGCCCAGCTGCCTAGGGAGCTCCCATGGTTCGA-5' (SEQ ID NO: 64)
EcoRI SacII SalI BamHI XhoI KpnI HindIII The EcoRI-SacII DNA fragment containing Jκ (FIG. 25) was inserted into the EcoRI and SacII sites of this plasmid. Then, a 3'-end BglII-BglII-BglII-XhoI DNA fragment (FIG. 25) was inserted into the BamHI and XhoI sites of the resulting plasmid. A XhoI-SalI DNA fragment containing DT and a XhoI DNA fragment containing LoxP-STneo having the disrupted KpnI fragment were inserted sequentially into the XhoI and SalI sites of this plasmid. The direction of transcription of the DT gene is the same as that of the light-chain κ gene. This plasmid DNA was amplified using E. coli DH5 and purified by cesium chloride equilibrium centrifugation. The purified plasmid DNA was cleaved at one site with restriction enzyme KpnI and used for transfection of TT2F ES cells. As a probe for Southern blot analysis of transformant genomic DNA to detect from tranformant TT2F Es cells those clones in which homologous recombination has taken place in the antibody light-chain portion with the targeting vector, a DNA fragment at the 3' end of the light-chain J κ-Cκ genomic DNA fragment (see FIG. 25) (XhoI-EcoRI; about 1.4 kbp) was used. Genomic DNA from those TT2F ES cells transformed with the targeting vector was digested with restriction enzymes EcoRI, and separated by agarose gel electrophoresis. Then, Southern blotting was performed using the above probe.

EXAMPLE 49

Production of a Mouse ES Cell Antibody Heavy-chain Gene-disrupted Clone

In order to obtain a recombinant in which an antibody heavy-chain gene has been disrupted by homologous recombination (hereinafter, referred to as an "antibody heavy-chain homologous recombinant"), the antibody heavy-chain targeting vector prepared in Section 3, Example 48 was linearized with restriction enzyme SacII (Takara Shuzo), and transferred into mouse TT2F ES cells according to the method described by Shinichi Aizawa, "Biomanual Series 8, Gene Targeting", published by Yodosha, 1995. The TT2F cells were treated with trypsin and suspended in HBS at a concentration of $2.5 \times 10^7$ cells/ml. To the cell suspension, 5 μg of DNA was added. Then, electroporation was performed with a gene pulser (Bio-Rad Laboratories, Inc.; resistor unit not connected). A voltage of 250 V was applied at a capacitance of 960 μF using an electroporation cell of 4 mm in length at room temperature. The electroporated cells were suspended in 20 ml of an ES medium and inoculated into two tissue culture plastic plates (Corning) of 100 mm into which feeder cells were seeded preliminarily. Similarly, experiments using 10 and 15 μg of DNA were also conducted. After one day, the medium was replaced with a medium containing 300 μg/ml of G418 (GENETICIN; Sigma). Seven to nine days thereafter, a total of 176 colonies formed were picked up. Each colony was grown up to confluence in a 12-well plate, and then four fifths of the culture was suspended in 0.2 ml of a preservation medium [ES medium+10% DMSO (Sigma)] and stored frozen at −80° C. The remaining one fifth was inoculated into a 12-well gelatin coated plate and cultured for 2 days. Then, genomic DNA was obtained by the method described in Example 2. These genomic DNAs from G418 resistant TT2F cells were digested with restriction enzymes EcoRI and XhoI (Takara Shuzo) and separated by agarose gel electrophoresis. Then, Southern blotting was performed to detect homologous recombinants with the probe described in Section 3, Example 48. As a result, 3 clones out of the 176 clones were homologous recombinants. The results of Southern blot analysis of wild-type TT2F cells and homologous recombinants #131 and #141 are shown in the left-side three lanes in FIG. 28. In wild-type TT2F cells, two bands (a and b) are detected which were obtained by the EcoRI and XhoI digestion. In the homologous recombinants, it is expected that one of these bands disappears and that a new band (c) will appear at the lower part of the lane. Actually, band (a) has disappeared in #131 and #141 in FIG. 28 and a new band (c) has appeared. The size of DNA is shown at the left side of the Figure. These results show that one allele of an antibody heavy-chain gene in these recombinant clones has been disrupted by homologous recombination.

EXAMPLE 50

Production of Chimeric Mice from Antibody Heavy-chain Homologous Recombinant ES Cells The cells in a frozen stock of the antibody heavy-chain homologous recombinant TT2F cell clone #131 from Example 49 were thawed, started to culture and injected into 8-cell stage embryos obtained by mating a male and a female mouse of ICR or MCH(ICR) (CREA JAPAN, INC.); the injection rate was 10–12 cells per embryo. After the embryos were cultured overnight in the medium for ES cells (see Example 9) to develop into blastocysts, about ten of the TT2F cell-injected embryos were transplanted to each side of the uterus of a foster mother ICR mouse (CREA JAPAN, INC.; 2.5 days after pseudopregnant treatment). As a result of transplantation of a total of 94 injected embryos, 22 offspring mice were born. Chimerism in the offsprings can be determined by the extent of TT2F cell-derived agouti coat color (dark brown) in the host embryo (ICR)-derived albino coat color (white). Out of the 22 offsprings, 18 mice were recognized to have partial agouti coat color, indicating the contribution of the ES cells. Out of the 18 mice, 16 mice were female chimeric mice in which more than 80% of their coat color was agouti (i.e. ES cell-derived). From these results, it was confirmed that the antibody heavy-chain homologous recombinant ES cell clone #131 retains the ability to produce chimera. Since a large number of the resultant chimeric mice are :female mice exhibiting extremely high contribution, it is very likely that the ES cells have differentiated into functional germ cells (oocytes). Two female chimeric mice exhibiting 100% contribution were mated with MCH(ICR) male mice. As a result, all of the offspring mice exhibited agouti coat color. These offsprings are derived from #131 (see Example 42), and thus it is considered that a disrupted antibody heavy-chain allele was transmitted to them at a rate of 50%.

EXAMPLE 51

Figure 28:
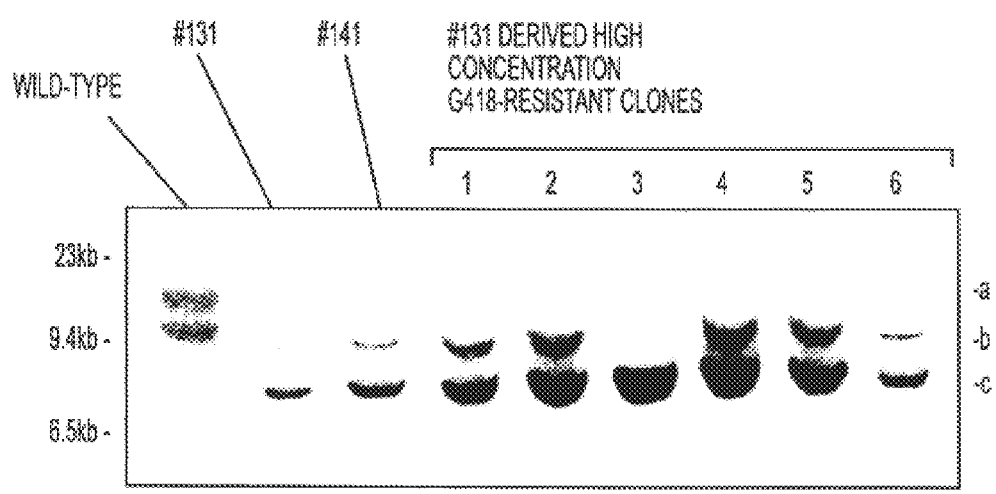
FIG. 28 is a photograph of electrophoresis patterns showing the results of Southern blot analysis of mouse antibody heavy-chain homologous recombinants and high concentration G418 resistant clones derived therefrom.
Figure 29:
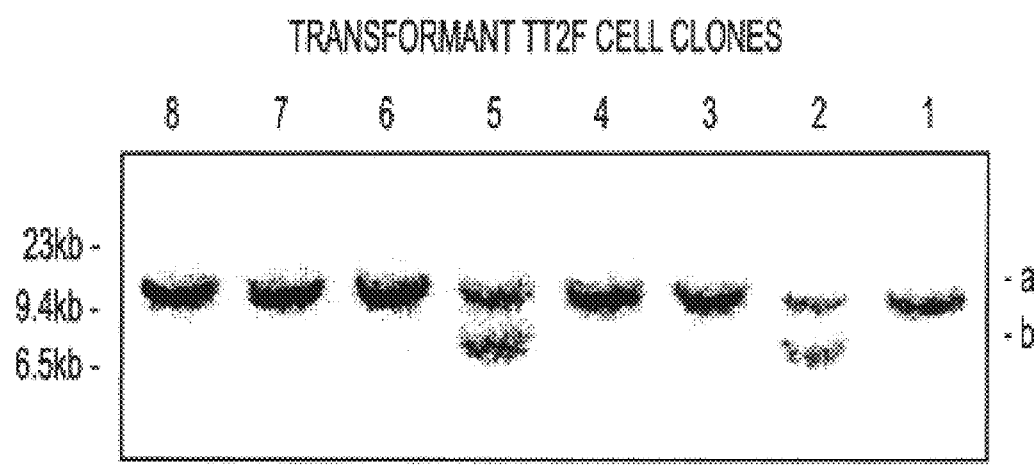
FIG. 29 shows a photograph of electrophoresis patterns showing the results of Southern blot analysis of mouse antibody light-chain homologous recombinants.

Production of a Double Knockout Clone from the Antibody Heavy-chain Homologous Recombinant It has been reported that a clone in which both alleles are disrupted can be obtained by disrupting one allele by insertion of a G418 resistance gene, culturing an ES:cell clone in a medium with an increased G418 concentration and screening the resultant high concentration G418 resistant clones (Shinichi Aizawa, "Biomanual Series 8, Gene Targeting", published by Yodosha, 1995). Based on this technique, the inventors have conducted the following experiments in order to obtain both alleles-disrupted clones from the TT2F antibody heavy-chain homologous recombinants #131 and #141. First, in order to determine the lethal concentration of G4 18 f or both #131 and #141 clones, each clone was inoculated into ten 35 mm plates at a rate of about 100 cells per plate (in this Example, G418 resistant primary culture cells which were not treated with mitomycin were used as feeder cells)(see Example 9). The cells were cultured in an ES medium containing 0, 0.5, 1, 2, 3, 5, 8, 10, 15 and 20 mg/ml of G418 (GENETICIN, Sigma) for 10 days. As a result, definite colonies were observed at a concentration of up to 3 mg/ml, but no colony formation was observed at 5 mg/ml. Based on these results, the minimum lethal concentration was decided to be 5 mg/ml. Then, high concentration G418 resistant clones were selected at concentrations of 4, 5, 6, 7 and 8 mg/ml. For each of #131 and #141, cells were inoculated into ten 100 mm plates at a rate of about $10^6$ cells per plate and cultured in an ES medium containing G418 at each of the concentrations described above (5 grades; two plates for each concentration). Twelve days after the start of culture, definite colonies (#131: 12 clones; #141: 10 clones) were picked up from plates of 7 mg/ml and 8 mg/ml in G418 concentration. These clones were stored frozen and genomic DNA was prepared by the same procedures as in Example 49. The genomic DNAs from these high concentration G418 resistant clones were digested with restriction enzymes EcoRI and XhoI (Takara Shuzo) and separated by agarose gel electrophoresis. Then, Southern blotting was performed to detect with the probe from Section 3, Example 48 those clones in which both alleles have been disrupted. As a result, one clone derived from #131 (#131-3) was found to be both alleles-distrupted clone. The results of Southern blot analysis of 6 clones derived from #131 are shown in FIG. 28. In wild-type TT2F cells, two wild-type bands (a, b) are detected after the EcoRI and XhoI digestion. In one allele homologous: recombinants (#131, #141), the upper band (a) has disappeared and a new band (c) has appeared (Example 49). Furthermore, it is expected that due to the disruption of both alleles, another wild-type band (b) disappears and that the disruption-type band (c) remains alone. In FIG. 28, this band pattern is observed in clone No. 3 (#131-3). This demonstrates that both alleles of an antibody heavy-chain gene have been disrupted in this clone.

EXAMPLE 52

Removal of a G418 Resistance Marker Gene from the Antibody Heavy-chain-deficient Homozygote TT2F Clone The G418 resistance marker gene in the antibody heavy-chain both alleles-disrupted clone (high concentration G418 resistant clone #131-3) from Example 51 was removed by the following procedures. An expression vector, pBS185 (BRL), containing Cre recombinase gene which causes a site-specific recombination between the two LoxP sequences inserted at both the ends of the G418 resistance gene was transferred into #131-3 clone according to the methods described in Shinichi Aizawa, "Biomanual Series 8, Gene Targeting", published by Yodosha, 1995 and Seiji Takatsu et al., "Experimental Medicine (extra number): Basic Technologies in Immunological Researches", p. 255-, published by Yodosha, 1995). Briefly, #131-3 cells were treated with trypsin and suspended in HBS to give a concentration of $2.5 \times 10^7$ cells/ml. To the cell suspension, 30 μg of pBS185 DNA was added. Then, electroporation was performed with a gene pulser (Bio-Rad Laboratories, Inc.; resistor unit not connected). A voltage of 250 V was applied at a capacitance of 960 μF using an electroporation cell of 4 mm in length (see Example 1). The electroporated cells were suspended in 5 ml of an ES medium and inoculated into a tissue culture plastic plate (Corning) of 60 mm in which feeder cells were seeded preliminarily. After two days, the cells were treated with trypsin and reinoculated into three 100 mm plates (preliminarily seeded with feeder cells) such that the three plates have 100, 200 and 300 cells, respectively. A similar experiment was also conducted under the same conditions except that the setting of the gene pulser was changed (resistor: unit connected; resistance value infinite). After seven days, a total of 96 colonies formed were picked up and treated with trypsin. Then, the colonies were divided into two groups; one was inoculated into a 48-well plate preliminarily seeded with feeder cells and the other was inoculated into a 48-well plate coated with gelatin alone. The latter was cultured in a medium containing 300 μg/ml of G418 (GENETICIN, Sigma) for three days. Then, G418 resistance was judged from the survival ratio. As a result, 6 clones died in the presence of G418. These G418 sensitive clones were grown to confluence in 35 mm plates, and four fifths of the resultant culture was suspended in 0.5 ml of a preservation medium [ES medium+10% DMSO (Sigma)] and stored frozen at −80° C. The remaining one fifth was inoculated into a 12-well gelatin coated plate and cultured for two days. Thereafter, genomic DNA was prepared by the same procedures as in Example 2. These genomic DNAs from G418 sensitive TT2F clones were digested with restriction enzyme EcoRI (Takara Shuzo) and separated by agarose gel electrophoresis. Then, Southern blotting was performed to confirm the removal of the G418 resistance gene using a 3.2 kb XhoI fragment (Probe A) from G418 resistance gene-containing pSTneoB. As a result, bands observed in #131-3 clone which hybridize with Probe A were not detected at all in the sensitive clones. From these results, it was confirmed that the G418 resistance marker gene had been surely removed in the G418 sensitive clones obtained. Additionally, as a result of Southern blot analysis performed in the same manner using Probe B obtained by digesting pBS185 DNA with EcoRI, no specific band which hybridizes with Probe B was detected in these G418 sensitive clones. Thus, it is believed that Cre recombinase-containing pBS185 is not inserted into the chromosomes of the sensitive clones. In other words, these sensitive clones can be transformed with the vector for knocking out an antibody light-chain (vector having a loxP sequence at both the ends of a G418 resistance gene) described in Section 4, Example 48.

EXAMPLE 53

Transfer of Human Chromosome #14 (Containing Antibody Heavy-chain Gene) into the Antibody Heavy-chain-deficient ES Cell Clone Human chromosome #14 (containing an antibody heavy-chain gene) marked with a G418 resistance gene is transferred by microcell fusion as described in Example 9 into the mouse ES cell clone (from TT2F, G418 sensitive) obtained in Example 52 which is deficient in an endogenous antibody heavy-chain. In the resultant G418 resistant clone, the retention of human chromosome #14 (fragment) containing a human antibody heavy-chain gene is confirmed by PCR analysis or the like (see Example 9).

EXAMPLE 54

Transfer of Human Chromosome #2 Fragment or Human Chromosome #22 into the Antibody Heavy-chain-deficient ES Cell Clone Retaining Human Chromosome #14 (Fragment)

A human chromosome #2 fragment (containing the antibody heavy-chain κ gene) or human chromosome #22

(containing the antibody heavy-chain λ gene) marked with a puromycin resistance gene is transferred into the antibody heavy-chain-deficient mouse ES cell clone retaining a human chromosome #14 partial fragment (G418 resistant) from Example 53 by microcell fusion as described in Examples 18 and 35. In the resultant puromycin and G418 double drug-resistant clone, the retention of the human chromosome #14 (fragment) and human chromosome #2 fragment or #22 (fragment) is confirmed by PCR analysis or the like (see Examples 18 and 35).

EXAMPLE 55

Production of Chimeric Mice from the Endogenous Antibody Heavy-chain-deficient Mouse ES Cells Retaining Human Chromosome #14 (Fragment) Containing a Human Antibody Heavy-chain Gene Chimeric mice from the endogenous antibody heavy-chain gene-deficient mouse ES cell clone obtained in Example 53 retaining human chromosome #14 (fragment) containing a human antibody heavy-chain gene are produced by the same procedures as in Example 10. In the resultant chimeric mice, a human antibody heavy-chain produced in the ES cell clone-derived B cells is detected by the method described in Example 14. Since antibody heavy-chain genes functional in the ES cell clone-derived B cells are only the human-derived gene on the transferred chromosome, many of the ES cell clone-derived B cells produce human antibody heavy-chain.

EXAMPLE 56

Production of Chimeric Mice from the Endogenous Antibody Heavy-chain-deficient Mouse ES Cells Retaining Human Chromosomes #14+#2 (Fragments) or #14+#22 (Fragments)

Chimeric mice are produced by the same procedures as in Examples 19, 36, etc from the endogenous antibody heavy-chain gene-deficient mouse ES cell clone retaining human chromosomes #14+#2 (fragments) or #14+#22 (fragments) obtained in Example 54. In the resultant chimeric mice, human antibody heavy-chain and light-chain κ or λ are detected in the ES cell clone-derived B cells according to the method described in Examples 14, 23 and 32. As in Example 55, antibody heavy-chain genes functional in the ES cell clone-derived B cells are only the human-derived gene on the transferred chromosome. Thus, many of the ES cell clone-derived B cells produce human heavy-chains. Furthermore, complete human antibody molecules both heavy and light-chains which are derived from humans are also detected by the method described in Examples 37 and 38.

EXAMPLE 57

Production of Human Antibody-producing Hybridomas from the Chimeric Mice Derived from the Endogenous Antibody Heavy-chain-deficient Mouse ES Cells Retaining Human Chromosomes #14+#2 (Fragments) or #14+#22 (Fragments)

The chimeric mice from Example 56 are immunized with an antigen of interest in the same manner as in Examples 15, 25 and 34. The spleen is isolated from each mice and the spleen cells are fused with myeloma cells to produce hybridomas. After cultivation for 1–3 weeks, the culture supernatant is analyzed by ELISA. The ELISA is performed by the method described in Examples 14, 15, 21, 24, 25, 33, 34, 37 and 38. As a result, human antibody positive clones and clones which are human antibody positive and specific to the antigen used in the immunization are obtained.

EXAMPLE 58

Production of an Antibody Light-chain Gene-disrupted Clone from the Antibody Heavy-chain-deficient Homozygote Mouse ES Cells A homologous recombinant, which has further disruption in an antibody light-chain gene in the antibody heavy-chain-deficient homozygote TT2F cell clone (G418 sensitive) obtained in Example 52 is produced by the following procedures. Briefly, the antibody light-chain targeting vector prepared in Section 4, Example 48 is linearized with restriction enzyme KpnI (Takara Shuzo), and transferred into the above TT2F cell clone (G418 sensitive) according to the method described in Shinichi Aizawa, "Biomanual Series 8: Gene Targeting", published by Yodosha, 1995. After 7–9 days, colonies formed are picked up. They are stored frozen and genomic DNA is prepared in the same manner as in Example 49. Genomic DNAs from G418 resistant clones are digested with restriction enzymes EcoRI and NotI (Takara Shuzo) and separated by agarose gel electrophoresis. Then, Southern blot analysis is performed to detect homologous recombinants with the probe described in Section 4, Example 48.

EXAMPLE 59

Production of an Double Knockout Clone from the Antibody Light-chain Homologous Recombinant A clone in which both alleles of a light-chain gene are disrupted is prepared from the TT2F antibody light-chain homologous recombinant (and antibody heavy-chain-deficient homozygote) clone from Example 58 by the procedures described below. Briefly, a high concentration G418 resistant clone is prepared and stored frozen, and DNA is prepared in the same manner as in Example 51. Genomic DNA from the high concentration G418 resistant clone is digested with restriction enzymes EcoRI and NotI (Takara Shuzo) and separated by agarose gel electrophoresis. Then, Southern blot analysis is performed to detect those clones in which both alleles have been disrupted, with the probe from Section 4, Example 48.

EXAMPLE 60

Removal of the G418 Resistance Gene from the Antibody Light-chain-deficient Homozygote (Antibody Heavy-chain-deficient Homozygote) TT2F Cell Clone The G418 resistance marker gene in the antibody light-chain both alleles-disrupted clone (high concentration G418 resistant clone) obtained in Example 59 is removed by the same procedures as in Example 52. Briefly, an expression vector, pBS185 (BRL), containing cre recombinase gene which causes a site-specific recombination between the two loxP sequences inserted at both the ends of the G418 resistance gene (Section 1, Example 48) was transferred into the above clone according to the method described in Example 52. The resultant G418 sensitive clones are grown to confluence in 35 mm plates, and ⅕ of the resultant culture was suspended in 0.5 ml of a preservation medium [ES medium+10% DMSO (Sigma)] and stored frozen at −80° C.

by the same procedures as in Example 52. The remaining ⅕ was inoculated into a 12-well gelatin coated plate. After cultivation for two days, genomic DNA is prepared by the method described in Example 2. These genomic DNAs from G418 sensitive TT2F clones are digested with restriction enzyme EcoRI (Takara Shuzo) and separated by agarose gel electrophoresis. Then, Southern blotting is performed to confirm the removal of the G418 resistance gene using a 3.2 kb XhoI fragment from G418 resistance gene-containing pSTneoB as a probe.

EXAMPLE 61

(1) Transfer of a Human Chromosome #114 Fragment (Containing Antibody Heavy-chain Gene) into the Endogenous Antibody Heavy-chain and κ Chain-deficient ES Cell Clone A human chromosome #14 fragment SC20 (containing a human antibody heavy-chain gene) was transferred by microcell fusion as described in Section 2 of Example 68 into the mouse ES cell clone HKD31 (from TT2F, G418 sensitive, puromycin sensitive) obtained in Example 78 which is deficient in both endogenous antibody heavy-chain and κ chain. The microcell fusion and the selection of G418 resistant clones were performed in the same manner as in Example 2. Eight of the resultant G418 resistant clones were subjected to PCR analysis using IgM and D14S543 primers (see Example 68). As a result, both markers were detected in 8 out of the 7 clones analyzed. Hence, it was confirmed that the antibody heavy-chain and κ chain-deficient ES cell clone retains the human chromosome #14 fragment SC20.

(2) Production of Chimeric Mice from the Endogenous Antibody Heavy-chain and κ Chain Genes-disrupted Mouse ES Cells Retaining a Human Chromosome #14 Fragment (Containing Antibody Heavy-chain Gene)

Chimeric mice were produced by the same procedures as in Example 10, etc. from the endogenous antibody: heavy-chain and κ chain genes-disrupted mouse ES cell clone HKD31-8 which was obtained in Section 1 of Example 61 and which retains a human chromosome #14 fragment (containing a human antibody heavy-chain gene). As a result of transplantation of a total of 188 injected embryos, 25 offspring mice were born. Chimerism in the offsprings can be determined by the extent of TT2 cell-derived agouti coat color (dark brown) in the host embryo (ICR)-derived albino coat color (white). Out of the 25 offsprings, 17 mice were recognized to have partial agouti coat color, indicating the contribution of the ES cells. Out of the 17 mice, three were chimeric mice in which more than 95% of their coat color was (ES cell-derived) agouti.

From these results, it was confirmed that the endogenous antibody heavy-chain and κ chain genes-disrupted mouse ES cell clone retaining the human chromosome #14 fragment (containing a human antibody heavy-chain gene) maintains the ability to produce chimera, that is, the ability to differentiate into normal tissues of mice.

(3) Detection of Human Antibody (Having Human $\mu$, $\gamma$ or $\alpha$ Chain) in Sera of the Chimeric Mice Derived from the Endogenous Antibody Heavy-chain and κ Chain Genes-disrupted Mouse ES Cells Retaining a Human Chromosome #14 Fragment (Containing Antibody Heavy-chain Gene)

The chimeric mice produced in Section 2 of Example 61 (derived from HKD31-8) were bled 12 weeks (#1) or 7 weeks (#2-4) after birth. The human antibody concentration in the sera was determined by ELISA in the same manner as in Example 14. Ninety six-well microtiter plates were coated with PBS-diluted anti-human immunoglobulin $\mu$ chain antibody (Sigma, I6385) or anti-human immunoglobulin $\gamma$ chain antibody (Sigma, I3382) or anti-human immunoglobulin $\alpha$ chain antibody (Pharmingen, 08091D) and then a serum sample diluted with mouse serum (Sigma, M5905)-containing PBS was added. Subsequently, peroxidase-labeled anti-human immunoglobulin $\mu$ chain antibody (The Binding Site Limited, MP008) or peroxidase-labeled anti-human immunoglobulin $\gamma$ chain antibody (Sigma, A0170) was added to the plates and incubated. Alternatively, biotin-labeled anti-human immunoglobulin $\alpha$ chain antibody (Pharmingen, 08092D) was added to the plates and incubated. After the plates were washed, an avidin-peroxidase complex (Vector, ABC Kit PK4000) was added thereto and incubated. TMBZ (Sumitomo Bakelite, ML-1120T) was added as a peroxidase substrate and then enzyme activity was determined by absorbance measurement at 450 nm. Purified human immunoglobulins IgM (CAPPEL, 6001-1590), IgG (Sigma, I4506) and IgA (Sigma, I2636) of known concentrations having $\mu$ chain, $\gamma$ chain and $\alpha$ chain, respectively, were used as standards for determining human antibody concentrations in the sera. These standards were diluted stepwise with mouse serum-supplemented PBS. The results are shown in Table 20. Chimeric mice having concentrations of human antibody $\mu$ and $\lambda$ chains almost as high as in normal mouse sera were confirmed. Also, chimeric mice expressing human$\alpha$ chain were confirmed. Further, human immunoglobulin $\gamma$ chain sub-classes were detected in the same manner as in Example 29. As a result, all of the four subclasses ($\gamma$1, $\gamma$2, $\gamma$3 and $\gamma$4) were detected.

These results show that a human antibody heavy-chain gene is expressed efficiently in the chimeric mice derived from the endogenous antibody heavy-chain and κ chain genes-disrupted mouse ES cells retaining the human chromosome #14 fragment (containing an antibody heavy-chain gene); it was also shown that not only $\mu$ chain but also all of the $\gamma$ chain subclasses and a chain were expressed therein as a result of class switching.

TABLE 20

Human Antibody Concentrations in Chimeric Mice (ELISA)

| Chimeric Mouse | Chimerism % | Human Antibody (mg/l) | | |
|---|---|---|---|---|
| | | IgM | IgG | IgA |
| #1 | 90 | 270 | 1250 | 0.46 |
| #2 | 99 | 370 | 820 | 0.23 |
| #3 | 99 | 550 | 1460 | 0.32 |
| #4 | 95 | 340 | 2300 | 0.06 |

(4) Acquisition of Hybridomas Producing Anti-HSA Antibody Comprising Human $\gamma$ Chain from the Chimeric Mice Derived from the Endogenous Antibody Heavy-chain and κ Chain Genes-disrupted Mouse ES Cells Retaining a Human Chromosome #14 Fragment (Containing Antibody Heavy-chain Gene)

Figure 33:
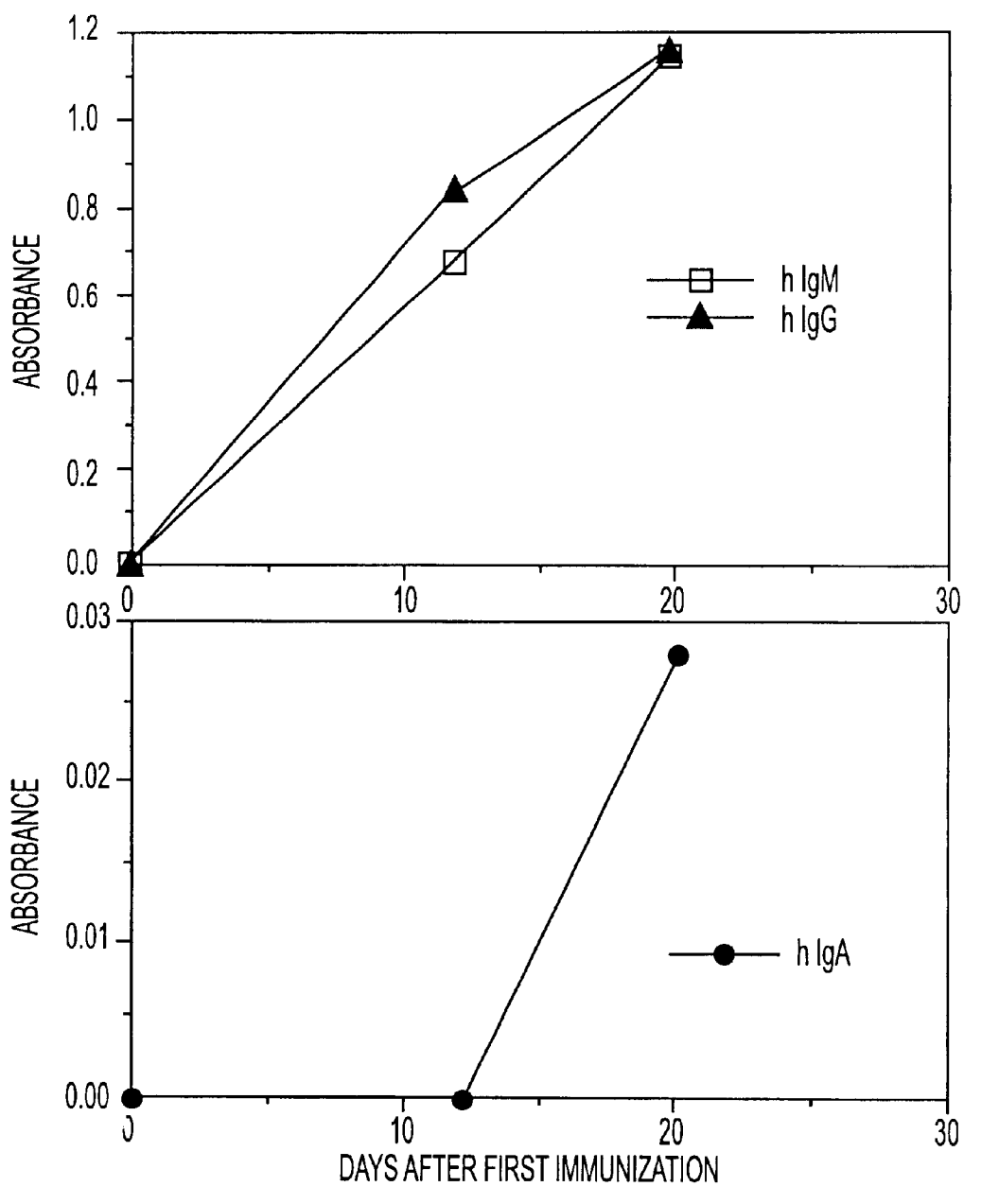
FIG. 33 shows that the antibody titers of anti-HSA human IgH antibodies are increased in a serum of an HSA-immunized chimeric mouse.

Chimeric mice #3 (derived from HKD31-8; chimerism 99%) and #4 (chimerism 95%) which had exhibited a high human antibody 7 concentration in the serum in Section 3 of Example 61 were immunized as described below. Human serum albumin (HSA, Sigma, A3782) dissolved in PBS was mixed with an adjuvant (MPL+TDM Emulsion, RIBI Immunochem Research Inc.) to prepare an HSA solution with a concentration of 0.25 mg/ml. When the above-described chimeric mice became 16-week old, 0.2 ml of this HSA solution was administered intraperitoneally twice at an interval of 2 weeks. Two weeks thereafter, the mice were immunized with human serum albumin dissolved in PBS and then bled. The concentration of anti-HSA human antibody in the sera was determined by ELISA in the same manner as in Example 14. Briefly, ELISA plates were coated with HSA and then peroxidase-labeled anti-human Igμ antibody (The Binding Site, MP008), anti-human Igγ antibody (Sigma, A1070) and anti-human Igα antibody (Kirkegaard &;Perry Laboratories Inc., 14-10-01) were used for detection. The results are shown FIG. 33. Hybridomas were produced using a myeloma cell SP-2/0-Ag14 (Dainippon Pharmaceutical Co., Ltd.) by the method described in Ando, "Monoclonal Antibody Experiment Procedure Manual", published by Kodansha Scientific in 1991. Three days after the final immunization, the spleen was removed from the chimeric mice and then cell fusion was performed using PEG in the same manner as in Example 29 to prepare hybridomas. At the same time, blood samples were collected from the mice to quantitate human Igγ subclasses in the sera. As a result, 920 mg/l of γ1, 520 mg/l of γ2, 11 mg/l of γ3 and 140 mg/l of γ4 were detected in the serum of chimeric mouse #3.

The fused cells were diluted with a medium (Sanko Pure Chemical, S Cloning Medium CM-B) containing 5% HCF (Air Brown) and HAT (Dainippon Pharmaceutical Co., Ltd., No. 16-808-49) or 1 mg/ml of G418 to give a concentration of $10^6$ spleen cells/ml and then dispensed into 96-well plates (100 μl/well), followed by cultivation. At day 8 of the cultivation, the culture supernatant was collected and screened for human antibody-producing hybridomas by ELISA in the same manner as in Example 14. Briefly, ELISA plates were coated with a HSA solution dissolved in CBB buffer to give a concentration of 5 μg/ml. Peroxidase-labeled anti-human immunoglobulin γ chain antibody (Sigma, A0170) and TMBZ (Sumitomo Bakelite, ML-1120T) were used for detection. An absorbance about 3 times higher than the absorbance in the negative control was used as a criterion for judgement. As a result, 74 positive wells were obtained from chimeric mouse #3 and 29 positive wells from chimeric mouse #4. Also, anti-HSA antibody having human μ chain was screened in HSA-solution-coated plates using peroxidase-labeled anti-human immunoglobulin μ chain antibody (Tago, #2392). Briefly, fused cells from chimeric mouse #3 were inoculated into fifteen 96-well plates, from which 4 plates were selected by G418 resistance. The culture supernatants of these 4 plates were screened to obtain 5 positive wells. Wells which exhibited colony formation after selection with HAT or 1 mg/ml of G418 were 74 wells/plate for HAT and 29 wells/plate for G418. The cells of those wells which were positive for human γ chain-containing anti-HSA antibody and which had a relatively large number of cells were transferred into 46-well plates and cultured for another 4 days. The isotype of the antibody in the culture supernatant was determined by ELISA. ELISA was performed in HSA-coated plates using alkali phosphatase-labeled anti-human IgG1 antibody (Zymed Labolatories, Inc., 05-3322), anti-human IgG2 antibody (Zymed Labolatories, Inc., 05-3522), anti-human IgG3 antibody (Zymed Labolatories, Inc., 05-3622) and anti-human IgG4 antibody (Zymed Labolatories, Inc., 05-3822) in the same manner as in Example 14. As a result, 27 human IgG1 positive clones, 11 human IgG2 positive clones, 2 human IgG3 positive clones and 13 human IgG4 positive clones were obtained. Fused cells from chimeric mouse #4 were treated in the same manner to obtain 4 positive clones with a large number of cells as human IgG1 producing clones.

These results show that the immunization by human protein (HSA) of the chimeric mice derived from the endogenous antibody heavy-chain & light-chain-deficient mouse ES cells retaining the human chromosome #14 partial fragment containing a human antibody heavy-chain gene increases the antibody titers of antigen specific human Igμ, γ and α to thereby enable the acquisition of hybridomas producing anti-HSA antibody containing μ chain and all of the human γ chain subclasses.

EXAMPLE 62

Transfer of Human Chromosome #2 (Containing Light-chain κ Gene) into the Endogenous Antibody Heavy-chain and κ Chain-deficient ES Cells Retaining a Human Chromosome #14 Fragment (Containing Antibody Heavy-chain Gene)

Figure 34:
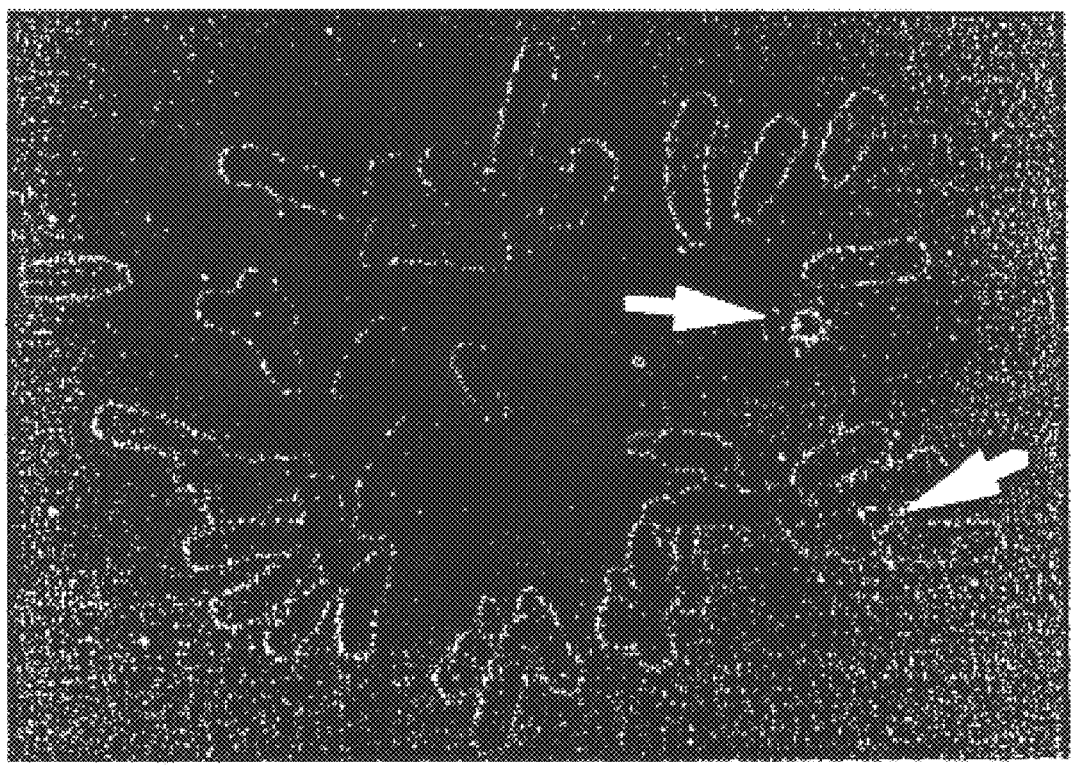
FIG. 34 is a photograph of the result of FISH analysis of an antibody heavy- and light-chains deficient mouse ES cell clone retaining partial fragments of human chromosomes #2 and #14.

A human chromosome #2 fragment (containing antibody light-chain κ gene) marked with a puromycin resistance gene was transferred into the endogenous antibody heavy-chain and κ chain-deficient mouse ES cell clone HKD31-8 obtained in Section 1 of Example 61 and which retained a human chromosome #14 fragment (containing an antibody heavy-chain gene). The method of transfer was by microcell fusion as described in Example 18. As a result, 13 puromycin and G418 double-resistant clones were obtained. These clones were subjected;to PCR analysis (see Example 18) using IgM and D14S543 primers (see Example 68) for the chromosome #14 fragment and Vκ 1 and FABP1 primers (see Example 12) for the chromosome #2 fragment. As a result, the presence of all the 4 markers was confirmed in 8 clones. Of these clones, KH13 clone was subjected to FISH analysis using human chromosome-specific probes (see Examples 9 and 12). The results are shown in FIG. 34. Two independent, small chromosome fragments hybridizing to the probes were observed in KH13. These results show that KH13 retains both the chromosome #14 fragment and the chromosome #2 fragment.

EXAMPLE 63

Transfer of Human Chromosome #22 (Containing Light-chain λ Gene) into the Endogenous Antibody Heavy-chain and κ Chain-deficient ES Cells Retaining a Human Chromosome #14 Fragment (Containing Antibody Heavy-chain Gene)

Human chromosome #22 (containing antibody light-chain λ gene) marked with a puromycin resistance gene was transferred into mouse ES cell clone HKD31-8 obtained in Section 1 of Example 61 which was deficient in the endogenous antibody heavy-chain & K chain and which retained a human chromosome #14 fragment (containing an antibody heavy-chain gene). The method of transfer was by microcell fusion as described in Example 35. As a result, 12 puromycin and G418 double drug-resistant clones were obtained. These clones were subjected to PCR analysis (see Example 35) using IgM and D14S543 primers for the chromosome #14 fragment and Ig λ, D22S315, D22S275, D22S278, D22S272 and D22S274 primers (see Example 2) for the chromosome #22 fragment. As a result, the presence of all of the 8 markers was confirmed in 10 clones. Of the remaining 2 clones, LH13 clone exhibited the presence of 5 markers, IgM, D14S543, IgI, D22S275 and D22S274. Thus, it is believed that this clone contains a fragment of human chromosome #22. LH13 was further subjected to FISH analysis using a human chromosome #22-specific probe and a human chromosome #14-specific probe separately. As a result, independent chromosome fragments hybridizing to the respective probes were observed. This indicates that this clone retains both a chromosome #14 fragment and a chromosome #2 fragment.

EXAMPLE 64

Production of Endogenous Antibody Heavy-chain & Light-chain-deficient Mouse ES Cells Retaining Three Human Chromosomes, #2 (Containing Antibody Light-chain κ Gene), #14 (Containing Antibody Heavy-chain Gene) and #22 (Containing Antibody λ Chain Gene), or Partial Fragments Thereof In order to obtain mouse ES cells retaining three kinds of human chromosomes, human chromosome #2 or #22 is marked by inserting a marker gene such as blasticidin resistance (Izumi et al., Exp. Cell. Res., 197: 229, 1991), hygromycin resistance (Wind et al., Cell, 82:321-, 1995), etc. This marking is performed according to the method described in Examples 16 and 26. Human chromosome #22 (containing human antibody light-chain λ gene) marked with blasticidin resistance, hygromycin resistance, etc. is transferred into the mouse ES cell clone (from TT2F, G418 resistant, puromycin resistant) obtained in Example 62 which is deficient in endogenous antibody heavy-chain & light-chain and which retains both human chromosome #14 (fragment) and human chromosome #2 (partial fragment). The method of transfer is by the method described in Example 9. As feeder cells for culturing ES cells, appropriate cells are selected depending on the selection marker used. When a hygromycin resistance marker is used, primary culture fibroblasts obtained from a transgenic mouse strain which retains and expresses the marker (Johnson et al., Nucleic Acids Research, vol. 23, No. 7, 1273-, 1995) are used. It is confirmed by PCR analysis, etc. (see Examples 9, 18 and 35) that the resultant G418, puromycin and hygromycin (or blasticidin) triple drug-resistant clones retain the three kinds of human chromosomes (fragments) described above. In the same manner, a human chromosome #2 fragment marked with a hygromycin or blasticidin resistance gene is transferred into the mouse ES cell clone (from TT2F, G418 resistant, puromycin resistant) obtained in Example 63 which is deficient in endogenous antibody heavy-chain & light-chain and which retains both human chromosome #14 (fragment) and human chromosome #22 (fragment).

EXAMPLE 65

Production of Chimeric Mice from the Endogenous Antibody Heavy-chain & Light-chain Genes-disrupted Mouse ES Cells Retaining a Plurality of Human Chromosomes (Fragments) Containing Human Antibody Heavy-chain Gene and Light-chain Gene, Respectively Chimeric mice are produded by the same procedures as in Example 10, etc. from the endogenous antibody heavy-chain & light-chain genes-disrupted mouse ES cell clones that retain human chromosomes (fragments) containing human antibody genes and which were obtained in Examples 61, 62, 63 and 64. In the resultant chimeric mice, mouse antibodies produced in host embryo-derived B cells and human antibodies produced mainly in ES cell clone-derived B cells are detected by the method described in Examples 14, 23 and 32. Since the antibody heavy-chain gene and the light-chain κ gene which are both functional in the ES cell clone-derived B cells are only human-derived genes on the transferred chromosomes, many of the ES cell clone-derived B cells produce human antibody heavy-chain and light-chain κ (Lonberg et al., Nature, 368:856-, 1994). Furthermore, complete human antibody molecules in which both heavy- and light-chains are derived from human are also detected by the method described in Examples 37 and 38.

(1) Production of Chimeric Mice from the Endogenous Antibody Heavy-chain and κ Chain Genes-disrupted Mouse ES Cells Retaining both a Human Chromosome #14 Fragment (Containing Antibody Heavy-chain Gene) and a Human Chromosome #2 Fragment (Containing Antibody Light-chain κ Gene)

Chimeric mice were produced by the same procedures as in Example 10, etc. from mouse ES cell clone KH13 obtained in Example 62 which is deficient in the endogenous antibody heavy-chain and κ chain genes and which retains both a human chromosome #14 fragment (containing an antibody heavy-chain gene) and a human chromosome #2 fragment (containing light-chain κ gene). As a result of transplantation of a total of 176 injected embryos, 20 offspring mice were born. Chimerism in the offsprings can be determined by the extent of TT2 cell-derived agouti coat color (dark brown) in the host embryo (ICR)-derived albino coat color (white). Out of the 20 offsprings, 7 mice were recognized to have partial agouti coat color, indicating the contribution of the ES cells.

From these results, it was confirmed that the endogenous antibody heavy-chain and κ chain genes-disrupted mouse ES cell clone retaining both a human chromosome #14 fragment (containing an antibody heavy-chain gene) and a human chromosome #2 fragment (containing light-chain κ gene) maintains the ability to produce chimera, that is, the ability to differentiate into normal tissues of mice.

(2) Production of Chimeric Mice from the Endogenous Antibody Heavy-chain and κ Chain Genes-disrupted Mouse ES Cells Retaining both a Human Chromosome #14 Fragment (Containing Antibody Heavy-chain Gene) and a Human Chromosome #22 Fragment (Containing Light-chain λ Gene)

Chimeric mice were produced by the same procedures as in Example 10, etc. from mouse ES cell clone LH13 obtained in Example 63 which is deficient in the endogenous antibody heavy-chain and κ chain genes and which retains both a human chromosome #14 fragment (containing an antibody heavy-chain gene) and a human chromosome #22 fragment (containing light-chain λ gene). As a result of transplantation of a total of 114 injected embryos, 22 offspring mice were born. Chimerism in the offsprings can be determined by the extent of TT2 cell-derived agouti coat color (dark brown) in the host embryo (ICR)-derived albino coat color (white). Out of the 22 offsprings, 5 mice were recognized to have partial agouti coat color, indicating the contribution of the ES cells.

From these results, it was confirmed that the endogenous antibody heavy-chain and κ chain genes-disrupted mouse ES cell clone retaining both a human chromosome #14 fragment (containing an antibody heavy-chain gene) and a human chromosome #22 fragment (containing light-chain λ gene) maintains the ability to produce chimera, that is, the ability to differentiate into normal tissues of mice.

(3) Detection and Quantitative Determination of Complete Human Antibody in Sera of the Chimeric Mice Derived from the Endogenous Antibody Heavy-chain and κ Chain-deficient Mouse ES Cells Retaining both a Human Chromosome #2 Partial Fragment and a Human Chromosome #14 Partial Fragment The chimeric mice (derived from KH13) produced in Section 1 of Example 65 were bled at day 40 after birth. The concentrations of human antibody in the sera were determined by ELISA in the same manner as in Example 14. Briefly, ELISA plates were coated with PBS-diluted anti-human immunoglobulin κ chain antibody (Kirkegaard & Perry Labolatories Inc., 01-10-10) or anti-human immunoglobulin κ chain antibody (Vector, AI-3060) and then serum samples diluted with mouse serum (Sigma, M5905) supplemented PBS were added. Subsequently, peroxidase-labeled anti-human immunoglobulin μ chain antibody (The Binding Site Limited, MP008) or peroxidase-labeled anti-human immunoglobulin γ chain antibody (Sigma, A0170) was added and incubated. TMBZ (Sumitomo Bakelite, ML-1120T) was added as a peroxidase substrate and then enzyme activity was determined by absorbance measurement at 450 nm. Purified human immunoglobulins IgM (Caltag, 13000) and IgG (Sigma, I4506) of known concentrations having μ chain and κ chain were used as standards for determining human antibody concentrations in the sera by comparison. These standards were diluted stepwise with mouse serum-supplemented PBS. The results are shown in Table 21. Chimeric mice were confirmed that had concentrations,of complete human antibody more than 10 times higher than in chimeric mice derived from ES cells whose endogenous antibody genes were not knocked out. Also, complete human antibody containing humanγ chain was confirmed in the sera of the chimeric mice.

From these results, it was confirmed that the concentration of complete human antibody in which both heavy- and light-chains were derived from human increasesed in the chimeric mice derived from the endogenous antibody heavy-chain and κ chain-deficient mouse ES cells retaining both a human chromosome #14 partial fragment and a human chromosome #22 partial fragment.

TABLE 21

Concentrations of Human Antibodies in Chimeric Mice (ELISA)

| ES clone | Chimeric mouse | Chimerism (%) | IgM, κ (mg/l) | IgG, κ (mg/l) |
|---|---|---|---|---|
| KH13 | CKH13-1 | 95 | 0.1 | 0.07 |
| KH13 | CKH13-2 | 85 | 0.9 | 0.13 |

(4) Detection and Quantitative Determination of Complete Human Antibody in Sera of the Chimeric Mice Derived from the Endogenous Antibody Heavy-chain and κ Chain-deficient Mouse ES Cells Retaining both a Human Chromosome #14 Partial Fragment and a Human Chromosome #22 Partial Fragment The chimeric mice (derived from KH13) produced in Section 2 of Example 65 were bled at day 49 after birth. The concentrations of human antibody in the sera were determined by ELISA in the same manner as in Example 14. Briefly, ELISA plates were coated with PBS-diluted anti-human immunoglobulin A chain antibody (Kirkegaard & Perry Labolatories Inc., 01-10-11) or anti-human immunoglobulin λ chain antibody (Vector, AI-3070) and then serum samples diluted with mouse serum (Sigma, M5905) supplemented PBS were added. Subsequently, peroxidase-labeled anti-human immunoglobulin μ chain antibody (The Binding Site Limited, MP008) or peroxidase-labeled anti-human immunoglobulin γ chain antibody (Sigma, A0170) was added and incubated. TMBZ (Sumitomo Bakelite, ML-1120T) was added as a peroxidase substrate and then enzyme activity was determined by absorbance measurement at 450 nm. Purified human immunoglobulins IgM (Caltag, 13000) and IgG (Sigma, I4506) of known concentrations having μ chain and κ chain were used as standards for determining human antibody concentrations in the sera by comparison. These standards were diluted stepwise with mouse serum-supplemented PBS. The results are shown in Table 22. Chimeric mice individuals were confirmed that had concentrations of complete human antibody about 40 times higher than in chimeric mice derived from ES cells whose endogenous antibody genes were not knocked out. Also, complete human antibody containing human γ chain was confirmed in the sera of the chimeric mice.

From these results, it was confirmed that the concentration of complete human antibody in which both heavy- and light-chains were derived from human increasesed in the chimeric mice derived from the endogenous antibody heavy-chain and κ chain-deficient mouse ES cells retaining both a human chromosome #14 partial fragment and a human chromosome #22 partial fragment.

TABLE 22

Concentrations of Human Antibodies in Chimeric Mice (ELISA)

| ES clone | Chimeric mouse | Chimerism (%) | IgM, λ (mg/l) | IgG, λ (mg/l) |
|---|---|---|---|---|
| LH13 | CLH13-1 | 95 | 13 | 2.6 |
| LH13 | CLH13-2 | 90 | 2.8 | 0.36 |

EXAMPLE 66

Figure 35:
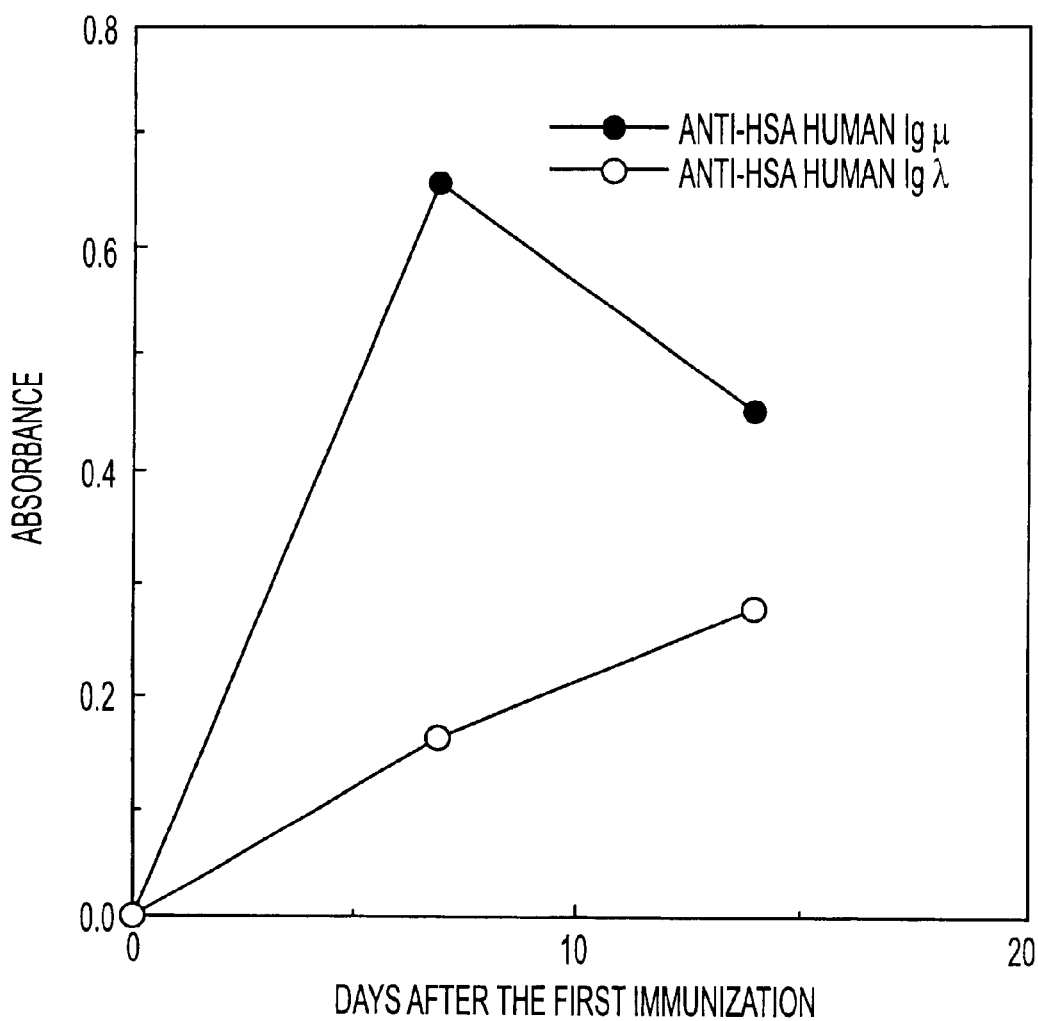
FIG. 35 shows that the antibody titers of anti-HSA human Ig antibodies are increased in a serum of: an HSA-immunized chimeric mouse.

Production of Complete Human Antibody-producing Hybridomas from Chimeric Mice Prepared by Transferring the Endogenous Antibody Heavy-chain and Light-chain-deficient Mouse ES Cells Retaining Both a Human Chromosome #14 Partial Fragment and a Human Chromosome #22 Partial Fragment into Immunodeficient Mouse Host Embryos A chimeric mouse CLH13-3 (derived from TT2FES clone LH13; chimerism 35%) obtained in Section 3 of Example 67 was immunized with HSA from day 43 after birth. Briefly, human serum albumin (HSA, Sigma, A3782) dissolved in PBS was mixed with an adjuvant (MPL+TDM Emulsion, RIBI Immunochem Research Inc.) to prepare a HSA solution with a concentration of 0.25 mg/ml, 0.2 ml of which was administered intraperitoneally twice at an interval of 1 week. One week thereafter, the mouse was immunized with human serum albumin dissolved in PBS. The mouse was bled every 1 week to determine the concentrations of anti-HSA human antibodies in the serum by ELISA in the same manner as in Example 14. The results are shown in FIG. 35. The spleen was removed from the chimeric mouse at day 3 after the final immunization and then cell fusion was performed using PEG in the same manner as in Example 24 to prepare hybridomas. Briefly, the fused cells were diluted with a medium (Sanko Pure Chemical, S Cloning Medium CM-B) containing HAT (Dainippon Pharmaceutical Co., Ltd., No. 16-808-49) or 1 mg/ml of G418 to give a concentration of $10^6$ spleen cells/ml and then dispensed into 96-well plates (100 μl/well), followed by cultivation. Both of the selection media contained 5% HCF (Air Brown). At day 6 of the cultivation, colonies were formed in almost all wells in both the G418 selection and HAT selection plates. A total of about 770 hybridoma-positive wells were obtained. The culture supernatants were collected and subjected to screening for human antibody-producing hybridomas by ELISA in the same manner as in Example 14. Briefly, ELISA plates were coated with anti-human immunoglobulin λ chain antibody (Vector, AI-3070). Biotin-labeled anti-human immunoglobulin λ chain antibody (Vector, BA-3070) and an avidin-peroxidase complex (Vector ABC Kit PK4000) were used for detection with TMBZ (Sumitomo Bakelite, ML-1120T) used as a substrate. An absorbance about 2 times higher than the absorbance in the negative control was used as a criterion for judgement. As a result, 17 positive wells were obtained. The cells of the positive wells were transferred into 24-well plates and cultured in IMDM medium containing 10% FBS. The culture supernatants were analyzed by ELISA in the same manner as in Section 4 of Example 65. As a result, the presence of 0.09–11 mg/ml of complete human antibody having both human Igµ & Igλ was confirmed in 16 wells. The antibody titer of anti-HSA human λ chain was determined in the same manner as in Example 33 to obtain one positive well. The cells of the well which was complete human antibody-positive and anti-HSA human λ chain-positive were cloned by limiting dilution according to the method described in Ando, "Monoclonal Antibody Experiment Procedure Manual", published by Kodansha Scientific in 1991. As a result, 2 clones of anti-HSA human λ chain-positive hybridomas were obtained.

From these results, it was confirmed that complete human antibody-producing hybridomas could be obtained from chimeric mice prepared by transferring the endogenous antibody heavy-chain and light-chain-deficient mouse ES cells retaining both a human chromosome #14 partial fragment and a human chromosome #22 partial fragment into immunodeficient mouse host embryos. Furthermore, it was confirmed that the antibody titers of antigen-specific, human Igµ and Igλ increased in response to the stimulation with the HSA antigen. It was further confirmed that hybridomas producing a HAS-specific antibody consisting of human Igµ and Igλ could be obtained from this chimeric mouse.

Since the fused cells had a drug resistance marker on their chromosome, it was possible to select hybridomas using G418 without adding HAT. After G418 selection, only those cells having a human chromosome grow and, thus, hybridomas can be obtained selectively. Also, it is expected that a human chromosome can be prevented from falling off fused cells. Furthermore, it is expected that even myeloma cells unsuitable for HAT selection such as those having HGPRT (hypoxanthine-guanine-phosphoribosyltransferase) enzyme may become available for cell fusion.

EXAMPLE 67

Production of Chimeric Mice with Heavy-chain Gene-disrupted Host Embryos

From those mice exhibiting agouti coat color among the progeny of the endogenous antibody heavy-chain one allele-disrupted TT2F cell clone-derived chimeric mice produced in Example 49, mice retaining the disrupted allele are selected by Southern blot analysis (Example 49) or the like (the expected possibility is ½). Offsprings born by the mating of those antibody heavy-chain-deficient heterozygous male and female mice are subjected to Southern blot analysis (see Example 49), analysis of the production of antibody, heavy-chains in sera (Kitamura et al., Nature, 350:423-, 1991), etc. Thus, antibody heavy-chain-deficient homozygotes can be obtained which are deficient in both alleles and which can hardly produce functional antibodies of their own (the expected possibility is ¼; for the results in membrane-type µ chain-deficient mice, see Kitamura et al., Nature, 350:423-, 1991).

(1) Establishment of an Antibody Heavy-chain Knockout Mouse Strain

Those mice that exhibited agouti coat color among the progeny of the endogenous antibody heavy-chain one allele-disrupted TT2F cell clone-derived chimeric mice produced in Example 49 were subjected to Southern blot analysis (Example 49) to select those mice that retained the disrupted allele. Offsprings born by the mating of these antibody heavy-chain-deficient heterozygous male and female mice were subjected to Southern blot analysis (see Example 49) and analysis of the production of antibody µ chain in sera (Kitamura et al., Nature, 350:423–, 1991), etc. As a result, antibody heavy-chain-deficient homozygotes could be obtained which were deficient in both alleles and which could hardly produce functional antibodies of their own (for the results in membrane-type µ chain-deficient mice, see Kitamura et al., Nature, 350:423-, 1991).

Thus, an antibody heavy-chain knockout mouse strain could be established from the antibody heavy-chain one allele-disrupted TT2F cell clone.

Embryos obtained by mating the homozygous male and female mice bred in a clean environment may be used as hosts for producing chimeric mice. In this case, most of the B cells functional in the resultant chimeric mice are derived from the injected ES cells. Other mouse strains which cannot produce their own functional B cells, such as RAG-2-deficient mouse (Sinkai et al., Cell, 68:855-, 1992), may also be used for this purpose. In this system, chimeric mice are produced by the same procedures as in Example 10, etc. using the mouse ES cell clone from Examples 62, 63 or 64 which is deficient in endogenous antibody heavy-chain & light-chain and which retains human chromosomes #14+#2, #14+#22 or #14+#2+#22 (fragments). The resultant chimeric mice mainly produce human antibodies by the expression of human antibody heavy-chain (on chromosome #14), light-chain κ (on chromosome #2) and light-chain λ (on chromosome #22) genes that are functional in ES cell-derived B cells.

(2) Detection and Quantitative Determination of Complete Human Antibody in Sera of the Chimeric Mice Produced by Injecting the Endogenous Antibody Heavy-chain and κ Chain-deficient Mouse ES Cells Retaining Both a Human Chromosome #2 Partial Fragment and a Human Chromosome #14 Partial Fragment into Immunodeficient Mouse Host Embryos Chimeric mice were produced in the same manner as in Section 1 of Example 65 by injecting the ES cell clone KH10 from Example 62 into the embryos obtained by mating male and female mice of the antibody heavy-chain knockout mouse strain established in Section 1 of Example 67. Seven-week old resultant chimeric mice were bled to determine the concentrations of human antibodies in the sera by ELISA in the same manner as in Example 14 and Section 3 of Example 65. The results are shown in Table 23. Complete human antibodies having human µ chain+κ chain and human γ chain+κ chain, respectively, were confirmed in the sera of the chimeric mice. It was also confirmed that by transferring ES cells into immunodeficient host embryos, complete antibodies could be obtained even in the resultant chimeric mice of low chimerism since B cells are differentiated only from ES cells.

TABLE 23

Concentrations of Human Antibodies in Chimeric Mice (ELISA)

| ES clone | Chimeric mouse | Chimerism (%) | IgM, κ (mg/l) | IgG, κ (mg/l) |
|---|---|---|---|---|
| KH13 | CKH10-1 | 6 | 6.1 | 0.17 |
| KH13 | CKH10-2 | 3 | 1.9 | 0.4 |

(3) Detection and Quantitative Determination of Complete Human Antibody in Sera of the Chimeric Mice Produced by Injecting the Endogenous Antibody Heavy-chain and κ Chain-deficient Mouse ES Cells Retaining Both a Human Chromosome #14 Partial Fragment and a Human Chromosome #22 Partial Fragment into Immunodeficient Mouse Host Embryos Chimeric mice were produced in the same manner as in Section 2 of Example 65 by injecting the ES cell clone LH13 from Example 62 into the embryos obtained by mating male and female mice of the antibody heavy-chain knockout mouse strain established in Section 1 of Example 67. Five-week old resultant chimeric mice were bled to determine the concentrations of human antibodies in the sera by ELISA in the same manner as in Example 14 and Section 4 of Example 65. The results are shown in Table 24. Complete human antibodies having human μ chain+λ chain and human γ chain+λ chain, respectively, were confirmed in the sera of the chimeric mice.

TABLE 24

Concentrations of Human Antibodies in Chimeric Mice (ELISA)

| ES clone | Chimeric mouse | Chimerism (%) | IgM, λ (mg/l) |
|---|---|---|---|
| LH13 | CLH13-3 | 35 | 51 |
| LH13 | CLH13-4 | 85 | 32 |
| LH13 | CLH13-4 | 30 | 27 |

EXAMPLE 68

Retention of the Human Chromosome in Offsprings of Human Chromosome #14 Fragment (Containing Antibody Heavy-chain Gene)-transferred ES Cell-derived Chimeric Mice (1) Isolation of Human-mouse Hybrid Cells Retaining a Human Chromosome #14 Fragment Containing an Antibody Heavy Chain Gene It was observed in Example 42 that a human chromosome #2 fragment transferred into mice was transmitted to their progeny. Thus, it is expected that the possibility of transmission of human chromosome #14 to progeny will be increased if a fragment of this chromosome is used. A9/#14 clone (Example 9; corresponding to A9/14-C11 clone described in Tomizuka et al., Nature Genet. vol 16, 133–143 (1997)) retaining an intact human chromosome #14 marked with a G418 resistance gene was subjected to a more detailed FISH analysis (Example 9). As a result, it was observed that about 10% of the cell population contained only a very small, fragmented human chromosome #14. This chromosome fragment is almost of the same size as the chromosome #2 fragment (Example 12) and believed to contain the G418 resistance marker.

In order to isolate the cell clones containing the fragmented human chromosome #14, (about 300) A9/#14 cells were seeded on 10 cm plates and cultured. At day 10 of the cultivation, 31 colonies were picked up. Genomic DNAs were prepared from these clones and subjected to PCR analysis in the same manner as in Example 9 using chromosome #14 specific primers (the 18 primers shown in Example 9 were used except PCI and NP). Out of the 16 primers, only IgM, IGG1, IGA2 and IGVH3 were found in one clone (A9/SC20). Since D14S543 (Science, HUMAN GENETIC MAP (1994); the base sequence was obtained from databases of GenBank, etc.) which is a marker located near the human chromosome #14 long arm telomere was also detected in the clone, the fragment of interest (hereinafter referred to as "SC20 fragment") retained in the clone is believed to contain a region adjacent to the chromosome #14 telomere and which contained an antibody heavy-chain gene.

SC20 fragment was subjected to FISH analysis (Tomizuka et al., Nature Genet. vol 16, 133–143 (1997)) using a human chromosome-specific probe. As a result, it was observed that the size of the chromosome in the clone that hybridized to the probe was smaller than in the control clone (containing an intact chromosome #14). Thus, it was confirmed that A9/SC20 contained a fragment of human chromosome #14.

Figure 36:
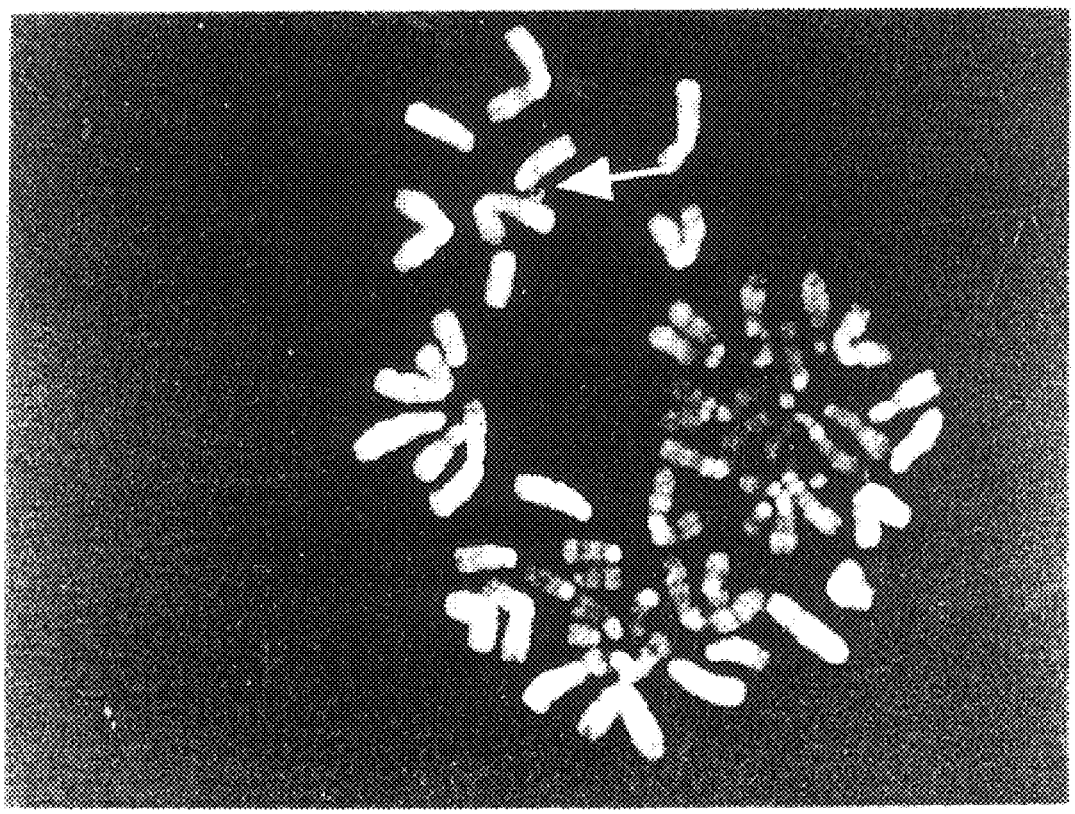
FIG. 36 shows a photograph of the result of FISH analysis of a mouse A9 cell containing human chromosome #14 (human centromere sequence probe).

Further, in order to examine whether SC20 fragment contained a human chromosome #14-derived centromere sequence, chromosome samples from A9/SC20 cells were hybridized to digoxigenin-11-dUTP-labeled human chromosome #14 or #22-specific α satelite DNA (purchased from COSMOBIO) which was used as a probe, followed by FISH analysis according to the method described in a reference (Tomizuka et al., Nature Genet. vol 16, 133–143 (1997)). As a result, a signal hybridizing to the above probe was confirmed. Thus, it has become clear that SC20 fragment contains a human-derived centromere sequence (FIG. 36).

Figure 37:
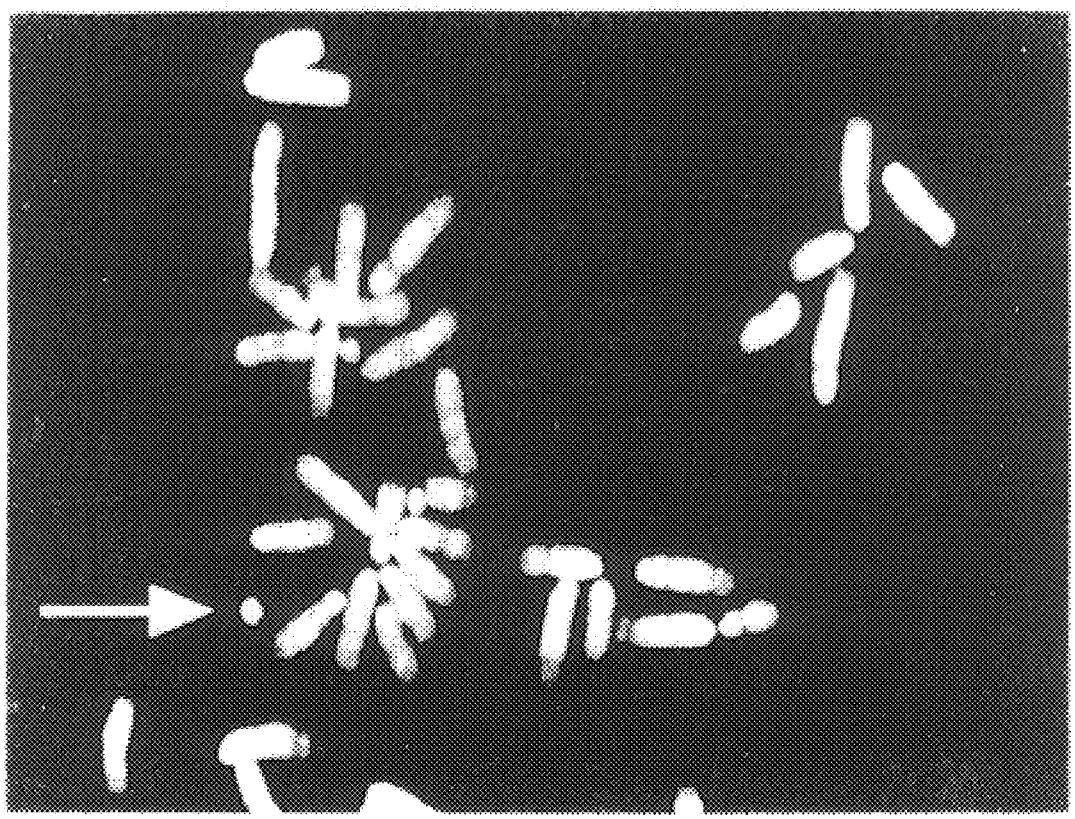
FIG. 37 shows a photograph of the result of FISH analysis of a mouse A9 cell containing human chromosome #14 (human chromosome-specific probe).

(2) Transfer of Human Chromosome #14 (Fragment) into TT2F Cells and Stable Retention of the Chromosome Therein A human chromosome #14 fragment was microcell-transferred into TT2F cells using A9/SC20 as a chromosome donor cell in the same manner as in Example 9. As a result of G418 (300 μg/ml) selection, 5 resistant clones were obtained. These ES cell clones were subjected to PCR analysis (Example 68, Section 1) and FISH analysis (using human chromosome-specific probes; Tomizuka et al., supra) to confirm the retention of a human chromosome #14 fragment. The results of the FISH analysis are shown in FIG. 37.

Stable retention of transferred human chromosomes in mice is important for efficient expression of the transferred genes and efficient transmission of the transferred chromosomes to their progeny. Since selection by addition of drugs is impossible after an ES cell clone has been injected into host embryos, it is desired that transferred human chromosomes be retained stably even under non-selective conditions.

TT2F(SC20)-21 clone containing SC20 fragment was cultured in a medium not containing G418 for a long period to examine the retention of SC20 fragment under this condition.

Figure 38:
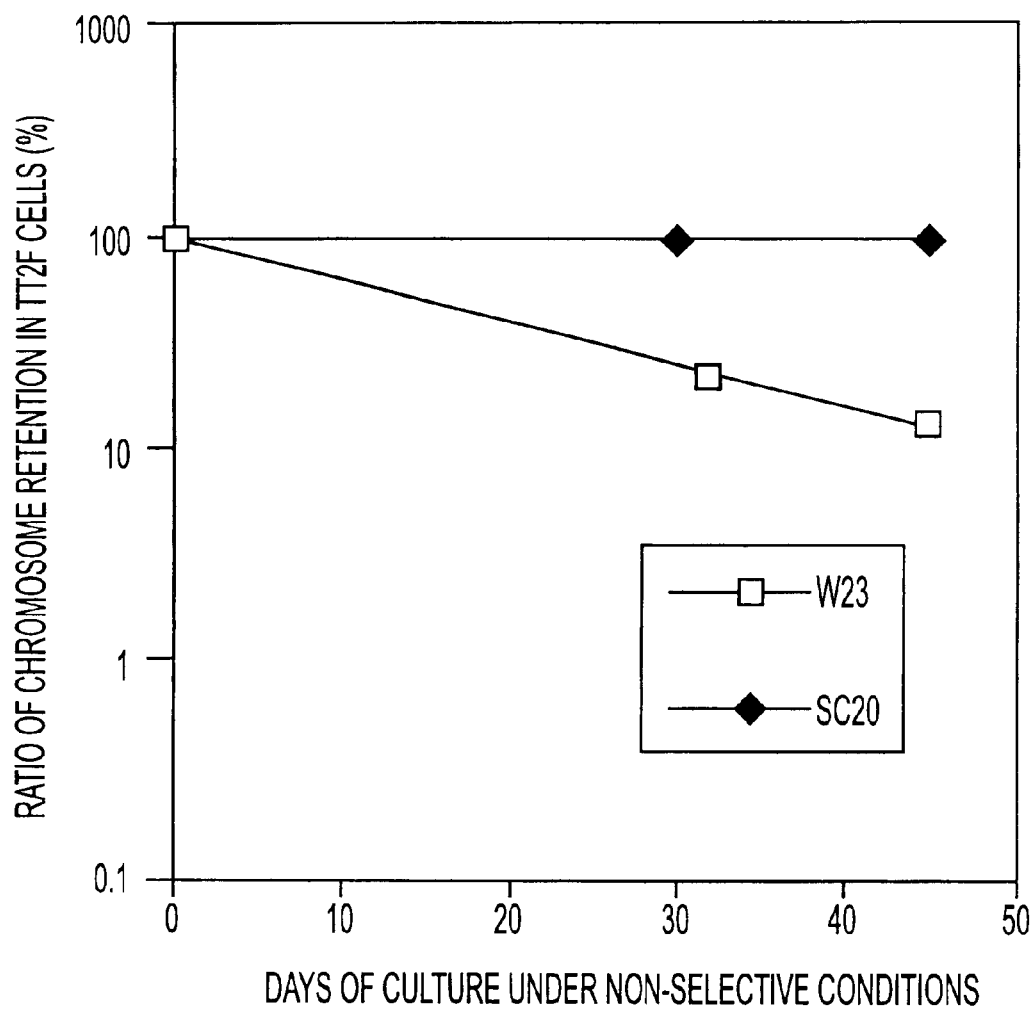
FIG. 38 shows the results of a test for stability of human chromosome fragments (#14: SC20, #2:W23) in a mouse ES cell.

Briefly, TT2F(SC20)-21 clone was cultured in a selective medium (G418: 300 μg/ml) for 1 week and then subcultured in a non-selective medium for 45 days (subcultured every other day with 8-fold dilution). At day 0, 15, 30 and 45 of the subculture, 300–1000 cells were seeded in six 35 mm plates, three of which contained the selective medium and the other three non-selective medium. The cells were cultured in these plates for about 1 week and then the colonies were counted. Chromosome retention ratio (A/B) was calculated by dividing the total number of colonies in the 3 plates under selective conditions (A) by the total number of colonies in the 3 plates under non-selective conditions (B). For the purpose of comparison, an experiment was conducted using P-21 clone (Example 40) containing W23 fragment derived from human chromosome #2 in the same manner as described above (the selective medium contained 0.75 μg/ml of puromycin). The results are shown in FIG. 38. The values shown in FIG. 38 are average values from 3 independent experiments. SC20 fragment exhibited a high retention ratio of 95% or above even after the 45 day cultivation under non-selective conditions. On the other hand, W23 fragment exhibited a retention ratio of 14% under identical conditions.

There have been reports of the transfer of a human Y chromosome-derived artificial chromosome (containing human Y-derived centromere) into CHO (hamster fibroblasts), DT40 (chicken B lymphocytes) and mouse ES cell (Shen et al., Hum. Mol. Genet. 6, 1375–1382). Under non-selective cultivation, the artificial chromosome was retained stably in CHO and DT40. In mouse ES cells, however, only the chromosome which accidentally acquired the mouse centromere as a result of rearrangement was retained stably. From these results, an opinion was proposed that a human-derived centromere is unstable in mouse ES cells (Shen et al., supra).

The results described above show that SC20, though it contains a human-derived centromere (Example 68, Section 1), is very stable in mouse ES cells. Since the retention of W23 fragment (which is also suggested to contain a human-derived centromere) (Tomizuka et al., supra) in mouse ES cells appeared to be unstable, it is considered that the stability of human-derived chromosomes in mouse ES cells varies depending on the type of the chromosome.

From these results, it was demonstrated that SC20 fragment is very useful as a vector for transferring a gene into mice.

(3) Production of Chimeric Mice from the ES Cell Clone Retaining Human Chromosome #14 (Fragment)

Cells in the frozen stock of G418 resistant ES cell clone TT2F(SC20)-21 which was obtained in Example 68, Section 2 and which was confirmed to retain a human chromosome #14 fragment were thawed, started up for culture and injected into 8-cell stage embryos obtained by mating male and female mice of ICR (CREA JAPAN, INC.); the injection rate was 10–12 cells per embryo. After the embryos were cultured overnight in the medium for ES cells (see Example 9) to develop into blastocysts, about 10 of the injected embryos were transplanted to each side of the uterus of foster mother ICR mice (CREA JAPAN, INC.; 2.5 days after pseudopregnant treatment).

As a result of transplantation of a total of 188 injected embryos, 22 offspring mice were born. Chimerism in the offsprings can be determined by the extent of TT2 cell-derived agouti coat color (dark brown) in the host embryo (ICR)-derived albino coat color (white). Out of the 22 offsprings, 20 mice were recognized to have partial agouti coat color, indicating the contribution of the ES cells. Out of the 20 mice, two were chimeric mice in which their coat color was complete agouti (i.e. ES cell-derived).

From these results, it was confirmed that ES cell clone TT2F(SC20)-21 retaining a human chromosome #2 fragment maintains the ability to produce chimera, that is, the ability to differentiate into normal tissues of mice.

Two 5-week old chimeric mice [derived from TT2F (SC20)-21, chimerism 100%, C14m-16 and -17] were bled to determine the concentrations of human antibody IgM and IgG in the sera by ELISA in the same manner as in Example 14. The results are shown in Table 25.

TABLE 25

Concentrations of Human Antibody Heavy-Chains in Chimeric Mice (ELISA)

| Chimeric mouse | Chimerism (%) | IgM (mg/l) | IgG (mg/l) |
|---|---|---|---|
| C14m-16 | 100 | 7.9 | 1.0 |
| C14m-17 | 100 | 6.0 | 1.3 |

Human antibodies IgM and IgG were detected in the sera of both chimeric mice. The concentrations of these human antibodies were comparable to the concentrations in the chimeric mice retaining the larger human chromosome #14 fragment (see Example 14). Thus, it was demonstrated that the human antibody gene contained in SC20 fragment is functional.

(4) Confirmation of the Retention of Human Chromosome in the Progeny of Chimeric Mice Derived from the Mouse ES Cells (TT2F, XO) Retaining a Human Chromosome #14 Fragment, and Detection and Quantitative Determination of Human Antibody $\mu$ Chain and $\gamma$ Chain in Sera of the Progeny Examination was made as to whether ES cell-derived offsprings would be produced by mating the female chimeric mice C14m-16 and C14m-17 (both having 100% chimerism in coat color) from Example 68, Section 3 with male ICR mice. By this mating, offsprings with agouti coat color should be produced from TT2F cell (agouti: dominant)-derived oocytes in the chimeric mice fertilized by male ICR mouse (albino: recessive)-derived sperms, and offsprings with albino coat color should be produced from ICR-derived oocytes in the chimeric mice. Actually, all of the viable offspring mice obtained by this mating (30 in total) exhibited ES cell-derived agouti coat color, indicating efficient transmission of ES cells to the germ cell lineage. Genomic DNAs were prepared from the tails of these offspring mice to examine the retention of a human chromosome fragment by PCR. PCR amplification was performed using the three primers (IGVH3, IgM and D14S543) of which the presence in TT2F(SC20)-21 was confirmed. As a result, the presence of the three markers detected in TT2F(SC20)-21 was confirmed in 10 out of the 30 offspring mice (33%). These results show that TT2F cell clone TT2F(SC20)-21 retaining a human chromosome #14 fragment differentiated into functional oocytes in the chimeric mice and that the human chromosome #14 fragment was transmitted to the $F_1$ progeny derived from the oocytes.

Detection and quantitative determination of human antibodies IgM and IgG in sera were performed on 9 out of the 10 offspring mice which were confirmed to retain a human chromosome #14 fragment, as described below. About 4–8 week-old mice were bled to detect human antibody $\mu$ chain and $\gamma$ chain by ELISA in the same manner as in Example 14. As a result, human antibody $\mu$ chain and $\gamma$ chain were detected in the sera of all of the mice tested (see Table 26). Thus, It was confirmed that the human antibody heavy chain gene also functions in the $F_1$ progeny born by the chimeric mice.

TABLE 26

Concentrations of Human Antibodies IgM and IgG in Chimeric Mice (ELISA)

| Mother Chimeric Mouse | Mouse Individual No. | IgM (mg/l) | IgG (mg/l) |
|---|---|---|---|
| c14m-16 | 16-5 | 12.9 | 2.2 |
| C14m-16 | 16-14 | 3.5 | 2.2 |
| C14m-16 | 16-16 | 4.1 | 2.0 |
| C14m-16 | 16-17 | 5.5 | 3.9 |
| C14m-17 | 17-7 | 5.7 | 1.0 |
| C14m-17 | 17-8 | 3.6 | 1.2 |
| C14m-17 | 17-19 | 3.5 | 0.75 |
| C14m-17 | 17-22 | 2.4 | 1.4 |
| C14m-17 | 17-23 | 5.3 | 1.9 |

Further, 3 male mice and 4 female mice in the $F_1$ progeny were mated with MCH(ICR) mice (purchased from CREA JAPAN, INC.) to obtain $F_2$ progenies, which were subjected to PCR analysis of tail DNA and analysis for human antibody $\mu$ chain expression as described above. As a result, it was confirmed that SC20 fragment was transmitted to 30% of the F₂ progeny through F₁ male mice (43 out of the 142 offsprings were positive) and to 33% of the F₂ progeny through F₁ female mice (20 out of the 60 offsprings were positive).

These results show that a mouse strain was established which retains the human chromosome #14 fragment (containing a human antibody heavy chain gene), which expresses human antibody heavy-chains and which can transmit the human chromosome to the subsequent generation.

(5) Stable Retention of a Human Chromosome #14 Fragment in Mice

Three F₁ mice (16-5, 17-8 and 17-23 shown in Table 26) which were obtained in Example 68, Section 4 and which retained SC20 fragment were used in analysis for the ratio of retention of SC20 fragment in mice. The mice were injected intraperitoneally with 0.3 ml of CORCEMID (100 μg/ml) and then killed by dislocation of the cervical vertebrae in an euthanasic manner, followed by removal of the brain, liver, spleen, testis and bone marrow. All of these tissues except the bone marrow were washed with PBS(-), cut into pieces with scissors for anatomy, given hypotonic treatment with KCl (0.075 M) for 15 minutes, and fixed in Carnoy's fixative. Specimens were prepared using the supernatant of the Carnoy fixation by conventional methods. FISH analysis was performed using a human chromosome-specific probe (Human COT-1 DNA) according to the method described in a reference (Tomizuka et al., Nature Genetics, 16, 133–143). As to the brain, spleen, liver and bone marrow, 30 or more nuclei in interphase were selected randomly for each of these tissues. Then, the number of nuclei in which a signal was detected (mark "+" in FIG. 39) and the number of nuclei in which a signal was not detected (mark "−" in FIG. 39) were counted to calculate the retention ratio. The testis were classified into the 1st meiosis phase spreads, the 2nd meiosis phase spreads and sperms. Ten or more spreads or sperms were selected for each group and then counting was performed in the same manner as described above to calculate the retention ratio. As a result, all of the 3 mice exhibited a retention ratio of almost 100% in the brain and liver. A decrease in the retention ratio was observed in the bone marrow and spleen. In the testis, a retention ratio of 80–100% was obtained for the 1st meiosis phase spreads, and a retention ratio of 30–50% for sperms. Assuming that SC20 fragment is retained stably, the theoretical retention ratio should be 100% for the 1st meiosis phase spreads and 50% for the 2nd meiosis phase spreads and sperms. Thus, it is believed that SC20 fragment is retained stably in the testis.

At the same time, fibroblasts were prepared from the tail and then the ratio of retention of SC20 fragment was examined in the same manner as in Example 79. As a result, the retention ratios in mice 16-5, 17-8 and 17-23 were 98%, 96% and 98%, respectively (50 nuclear plate were tested for each mouse).

(6) Hereditary Relief of Antibody Production Ability-deficient Mice by the Transfer of a Human Chromosome #14 Fragment (Containing Antibody Heavy-chain Gene)

The knockout mouse whose antibody μ chain gene essential for the generation of B lymphocytes is disrupted (Section 1, Example 67) cannot produce antibody because the mouse is deficient in mature B lymphocytes responsible for humoral immunity. The following experiment was conducted to examine as to whether this deficiency could be relieved by transferring SC20 fragment (containing a human antibody heavy-chain gene) by mating.

Those mice exhibiting agouti coat color among the progeny obtained by mating the endogenous antibody heavy-chain one allele-disrupted TT2F cell clone-derived chimeric mice from Example 49 with MCH(ICR) mice were subjected to Southern blot analysis to select mice retaining the disrupted allele. A female antibody heavy-chain-deficient heterozygote thus selected was mated with a male F₁ offspring (17-7) which was obtained in Example 68, Section 4 and which retains SC20 fragment. The resultant 5 offspring mice were subjected to both PCR analysis for confirming the retention of SC20 fragment and determination of human antibody μ chain and γ chain in the sera (see Example 68, Section 4). As a result, it was confirmed that three mice #2, #3 and #5 retained SC20 fragment (Table 27). Furthermore, as a result of the analysis for mouse antibody μ chain expression (Example 75), it was demonstrated that mice #2 and #3 are mouse μ chain-negative, that is, endogenous antibody heavy-chain-deficient homozygotes (Table 27). These results were consistent with the results of Southern blot analysis (see Example 49) using the DNAs prepared from the tails of the 5 mice. Compared to mouse #1 in which neither mouse nor human antibody heavy chain was detected, very high concentrations of human antibody μ chain (310 mg/l) and γ chain (860 mg/l) were detected in mouse #3 which is antibody heavy-chain-deficient homozygote and which retains the human chromosome #14 fragment. Further, quantitative determination of human γ subclasses was performed on mouse #3 in the same manner as in Example 29 to detect all of the 4 subclasses (γ1, γ2, γ3 and γ4). In particular, the concentration of human μ chain in this mouse is comparable to the concentration of mouse μ chain in wild-type mice (Mendez et al., Nature Genet. 15, 146–156 (1977)). These results show that the symptom of inability for antibody production because of disruption of endogenous heavy-chain gene (deficiency of B lymphocytes: see Kitamura et al., Nature, 350, 423-, 1991) in this mouse was cured by the transfer of human chromosome #14 fragment SC20 (containing an antibody heavy-chain gene), and that the mouse has recovered the ability to produce antibody and the ability to produce B lymphocytes.

TABLE 27

| Mouse No. | Retention of SC20 Fragment | Mouse μ Chain | Human IgM (mg/l) | Human IgG (mg/l) |
|---|---|---|---|---|
| 1 | − | − | Below detection limit | 0.33 |
| 2 | + | + | 8.4 | 5.3 |
| 3 | + | − | 310 | 860 |
| 4 | − | + | Not measured | Not measured |
| 5 | + | + | 4.8 | 0.86 |

EXAMPLE 69

Retention of the Human Chromosome in Offsprings of Human Chromosome #22 (Fragment)-transferred ES Cell-derived Chimeric Mice (1) Fragmentation of Human Chromosome #22 Using Microcell Fusion Since it was observed that both a human chromosome #2 fragment (Example 42) and a human chromosome #14 fragment (Example 68, Section 4) once transferred into mice were transmitted to their offsprings, it is expected that fragmentation of human chromosome #22 would increase the possibility of transmission of this chromosome to offspring mice. When a human chromosome is transferred into a recipient cell by microcell fusion, it is observed that 40–80% of the transferred clones retain the human chromosome which has been fragmented at the time of fusion (Oshimura et al., Protein, Nucleic Acid, Enzyme, vol. 35, No. 14, 1990). The present inventors tried to fragment human chromosome #22 utilizing this phenomenon.

Figure 40:
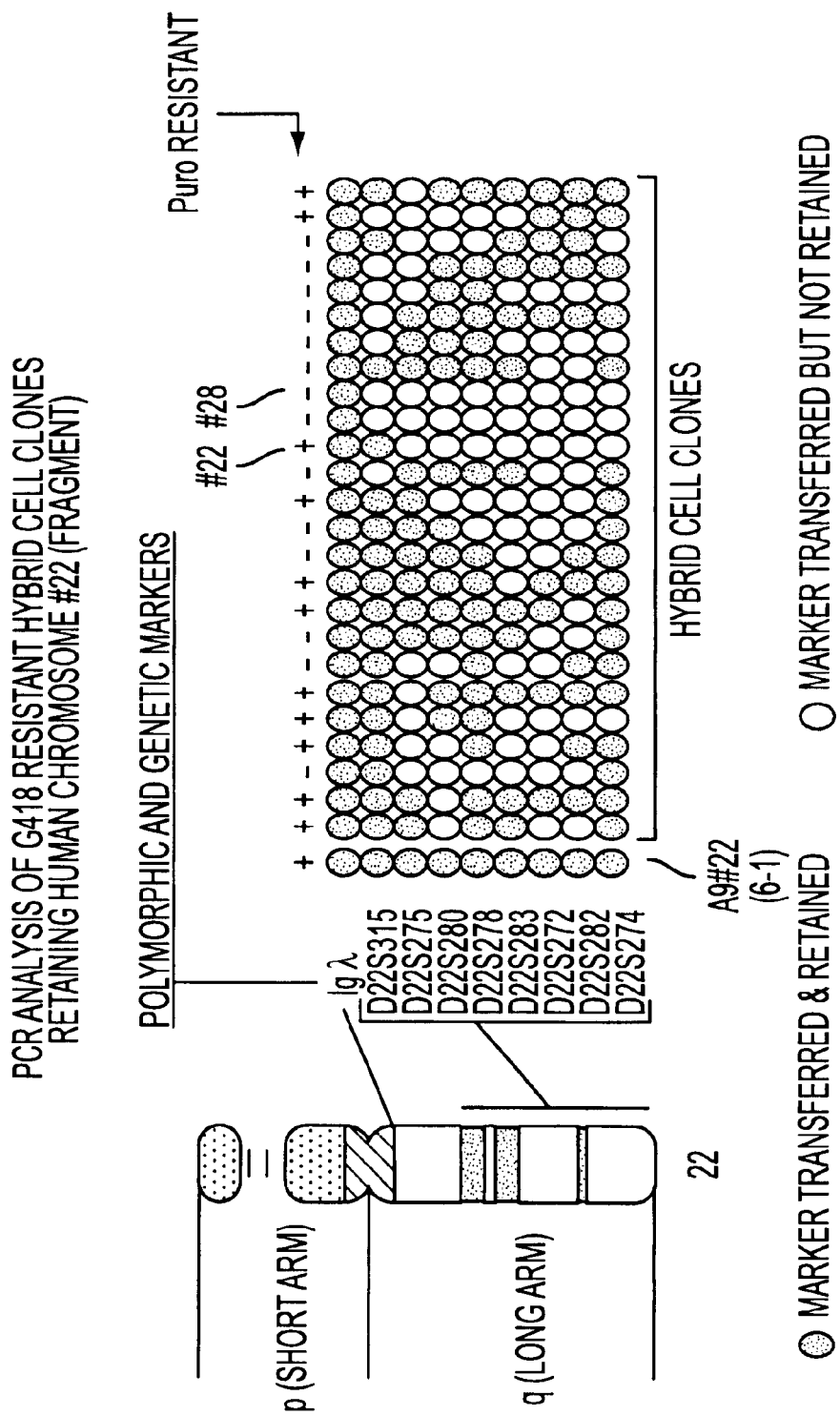
FIG. 40 shows the results of PCR analysis of a G418 resistant hybrid cells retaining human chromosome #22 (fragment).

A microcell fusion experiment (see Example 1) was conducted using clone 6-1 from Example 35 as a chromosome donor cell and wild-type mouse A9 cells as a recipient cell, thereby producing seventy-three G418 resistant clones. Genomic DNAs were prepared from the resultant clones and then screened by PCR using Ig λ primers (Example 2). Sixty-seven clones which retained human Igλ gene were subjected to PCR analysis using primers specific to 8 markers located on human chromosome #22 (D22S315, D22S275, D22S280, D22S278, D22S283, D22S272, D22S282 and D22S274; for the order of location on human chromosome #22, see Nature, vol. 377, 367–379 (1995); base sequences for these primers were obtained from databases of such as GenBank). As a result, it was found that a part of the markers disappeared in 25 clones. Thus, it was suggested that chromosome #22 was fragmented in these clones (FIG. 40). Among them, clone #22 and clone #28 are considered to have a fairly small fragment, because markers other than Igλ and D22S315 disappeared in the former and markers other than Igλ disappeared in the latter (FIG. 40). Clone #28 was subjected to FISH analysis (see Example 18) using a human chromosome-specific probe. The results are shown in FIG. 41. It is observed that the size of the chromosome hybridizing to the probe is smaller in this clone than in the control clone (containing an intact chromosome #22). Thus, a human chromosome #22 fragment containing antibody λ gene could be obtained as a result of fragmentation which occurred at the time of microcell fusion.

(2) Transfer of Chromosome #22 (Fragment) into TT2F Cells

Chromosome #22 (fragment) was microcell-transferred into TT2F cells by the method described in Example 2, using clones #22, #28 and 6-1 as chromosome donor cells. Clones #22 and A9/#22(6-1) were subjected to puromycin (0.75 μg/ml) selection, and clone #28 was subjected to G418 (225 μg/ml) selection. As a result, drug resistant clones were obtained as follows: 13 from clone #22, 5 from clone 6-1 and 3 from clone #28. These ES cell clones are subjected to PCR analysis and FISH analysis to confirm the retention of human chromosome #22 (fragment) in the same manner as in Example 69, Section 1.

(3) Production of Chimeric Mice from ES Cell Clones Retaining Human Chromosome #22 (Fragment)

In the same manner as in Example 3, chimeric mice are produced from the drug resistant ES cell clones which were obtained in Example 69, Section 2 and which were confirmed to retain human chromosome #22. Confirmation of the retention of human chromosome #22 (fragment) in the resultant chimeric mice is performed by the method described in Example 4.

(4) Transmission of Human Chromosome #22 (Fragment) to Offsprings

The chimeric mice retaining human chromosome #22 (fragment) are mixed and mated with ICR mice. Retention of a human chromosome #22 fragment in the offsprings is examined by PCR using genomic DNAs prepared from the tails of the offspring mice having agouti coat color (see Examples 30, 42 and 43). As shown in Examples 42 and 43, mouse ES cell clones retaining human chromosome #22 or a fragment thereof can differentiate into oocytes or sperms functional in chimeric mice, thereby allowing to the human chromosome #22 (fragment) to be transmitted their progenies. Thus, it is possible to establish a mouse strain which retains human chromosome #22 (fragment) containing human antibody light-chain λ gene and which can transmit it to the subsequent generation.

EXAMPLE 70

Production of Mice Retaining Both Human Chromosome #2 (Fragment) and #14 (Fragment) by Mating The human chromosome #2 (fragment)-retaining mouse strain from Example 42 or 43 is mated with the human chromosome #14 (fragment)-retaining mouse strain from Example 68 to produce offsprings. Genomic DNAs are prepared from the tails of the offspring mice. The DNA is analyzed by PCR, etc. (Examples 9, 42 and 43) to produce those mice which retain both human chromosome #2 partial fragment and human chromosome #14 (fragment).

EXAMPLE 71

Production of Mice Retaining Both Human Chromosome #22 (Fragment) and #14 (Fragment) by Mating The human chromosome #22 (fragment)-retaining mouse strain from Example 69 is mated with the human chromosome #14 (fragment)-retaining mouse strain from Example 68 to produce offsprings. Genomic DNAs are prepared from the tails of the offspring mice. The DNA is analyzed by PCR, etc. (Examples 30, 42 and 43) to produce those mice which retain both human chromosome #22 (fragment) and #14 (fragment).

EXAMPLE 72

Production of Mice Retaining the Three Human Chromosomes #2 (Fragment), #14 (Fragment) and #22 (Fragment) by Mating The mouse strain retaining both human chromosome #2 (fragment) and #14 (fragment) obtained in Example 71 is mated with the mouse strain retaining a human chromosome #2 fragment obtained in Example 42 or 43 to produce offsprings. Genomic DNAs are prepared from the tails of the offspring mice. The DNA is analyzed by PCR, etc. (Examples 9, 30, 42 and 43) to produce those mice which retain all of the three human chromosomes, #22 (fragment), #14 (fragment) and #2 (fragment). Alternatively, mice retaining all of the above three human chromosomes may also be obtained by mating the mouse strain retaining both human chromosome #2 (fragment) and #14 (fragment) from Example 70, with the mouse strain retaining a human chromosome #22 fragment from Example 69.

EXAMPLE 73

Production of a Complete Human Antibody-producing Mouse Strain by Mating

The mouse strains retaining human chromosomes #2+#14 (Example 70), #14+#22 (Example 71) and #2+#14+#22 (Example 72), respectively, are repeatedly mated with a mouse strain deficient in endogenous antibody heavy-chain and light-chain κ genes. From the resultant offsprings, those mouse strains which retain human chromosomes #2+#14, #14+#22 or #2+#14+#22 and which are homozygotes in the deficiency of endogenous antibody heavy-chain and light-chain κ genes, are selected by PCR analysis, etc. (Examples 9, 30, 42 and 43). In these strains, complete human antibodies are mainly produced (Green et al., Nature Genetics, 7:13-, 1994; Lonberg et al., Nature, 368:856-, 1994).

Hereinbelow, the establishment of a mouse strain which retains both a human chromosome #2 fragment and a human chromosome #14 fragment and which is homozygote in the deficiency of endogenous antibody heavy-chain and light-chain κ genes will be described. The 4 strains used for the mating and the method for assaying the genotypes of each strain are as follows.

(1) The mouse strain from Example 42 retaining a human chromosome #2 fragment: the retention of the human chromosome #2 fragment is assayed by PCR analysis of the tail-derived DNA as described in Example 42 and by the expression of human antibody κ chain in the sera.

(2) The mouse strain from Example 68, Section 4 retaining a human chromosome #14 fragment: the retention of the human chromosome #14 fragment is assayed by PCR analysis of the tail-derived DNA as described in Example 68, Section 4 and by the expression of human antibody μ chain in the sera.

(3) The antibody heavy-chain knockout mouse strain from Example 67, Section 1: heavy-chain deficiency-homozygotes or heterozygotes were assayed by Southern blot analysis of the tail-derived DNA as described in Example 67, Section 1 and by the presence or absence of the expression of mouse antibody μ chain in the sera (see Example 75).

(4) The antibody κ chain knockout mouse strain from Example 80: κ chain deficiency-homozygotes or heterozygotes were assayed by Southern blot analysis of the tail-derived DNA as described in Example 80.

A mouse strain which retains all of the 4 genotypes (i.e., retaining a human chromosome #2 fragment, retaining a human chromosome #14 fragment, antibody heavy-chain-deficiency homozygote or heterozygote, and antibody κ chain-deficiency homozygote or heterozygote) was established by mating the above 4 strains with each other. Specifically, after the above 4 strains used as starting materials were mated several times, a male mouse having the genotypes of "retaining the human chromosome #14 fragment, antibody heavy-chain-deficiency homozygote and antibody κ chain-deficiency heterozygote" was mated with a female mouse having the genotypes of "retaining the human chromosome #2 fragment, antibody heavy-chain-deficiency homozygote and antibody κ chain-deficiency homozygote" or "retaining the human chromosome #2 fragment, antibody heavy-chain-deficiency homozygote and antibody κ chain-deficiency heterozygote" or "retaining the human chromosome #2 fragment, antibody heavy-chain-deficiency heterozygote and antibody κ chain-deficiency homozygote". As a result, mouse HK23 "retaining the human chromosome #2 fragment, retaining the human chromosome #14 fragment, antibody heavy-chain-deficiency homozygote and antibody κ chain-deficiency heterozygote" and mouse HK29 "retaining the human chromosome #2 fragment, retaining the human chromosome #14 fragment, antibody heavy-chain-deficiency heterozygote or wild-type, and antibody κ chain-deficiency heterozygote" were obtained. FIG. 42 shows the concentration of each antibody in the sera and the genotypes of these mice, together with the data on mouse HK28 which was also produced by the above-described mating and which has the genotypes of "retaining the human chromosome #2 fragment, retaining the human chromosome #14 fragment, antibody heavy-chain-deficiency heterozygote or wild-type, and antibody κ chain-deficiency wild-type". A complete human antibody consisting of human μ chain and human κ chain was detected at a concentration of 18 mg/l in the serum of mouse HK23 (Example 38).

It is possible to produce those mice having the genotypes of "retaining the human chromosome #2 fragment, retaining the human chromosome #14 fragment, antibody heavy-chain-deficiency homozygote and antibody κ chain-deficiency homozygote" by mating the mice obtained by the above mating with each other. In this mouse strain, it is expected that human antibody κ chain will be expressed at a higher concentration than in mouse HK23 because the deficiency of the endogenous κ chain gene is substituted by the human antibody κ chain gene contained in the human chromosome #2 fragment (Lonberg et al., Nature, 368, 856-, 1994). It is also expected that the concentration of a complete human antibody consisting of human heavy-chain and human κ chain will increase further.

EXAMPLE 74

Production of a Human Antibody-producing Hybridoma from a Mouse Strain Which is Obtained by Mating and Which Retains a Human Chromosome(s) Containing a Human Antibody Gene(s)

The mice retaining a human chromosome(s) containing a human antibody gene(s) which were obtained in Example 42, 43, 68, 69, 70, 71, 72 or 73 are immunized with an antigen of interest in the same manner as in Example 25. The spleen is removed from each mice and the spleen cells are fused with myeloma cells to produce hybridomas. After cultivation for 1–3 weeks, the culture supernatant is analyzed by ELISA. The ELISA is performed by the method described in Examples 14, 15, 21, 22, 25, 33, 34, 37 and 38. As a result, human antibody positive clones and clones which are human antibody positive and specific to the antigen used in the immunization are obtained.

EXAMPLE 75

Detection and Determination of Mouse IgM in Sera of Chimeric Mice Derived from the Mouse Antibody Heavy-chain Both Alleles-disrupted TT2F Cell Clone Offspring mice were born in the same manner as in Example 40 from the mouse antibody heavy-chain both alleles-disrupted TT2F cell clone (#131-3) from Example 51. Three mice having chimerisms of 0%, 50% and 99%, respectively, were selected from the offspring mice. Mouse IgM in their sera was detected and determined. Briefly, the chimeric mice of about 2 weeks after birth were bled and mouse IgM concentration in the sera was determined by ELIZA by the same procedures as in Example 14. A PBS-diluted anti-mouse IgM antibody (Kirkegaard & Perry Laboratories Inc., 01-18-03) was fixed, and then a PBS-diluted serum sample supplemented with 5% FBS was added. Peroxidase-labeled anti-mouse IgM antibody (Kirkegaard & Perry Laboratories Inc., 074-1803) was added and the absorbance at 450 nm was determined using TMBZ as a substrate. Purified mouse IgM (Pharmingen, 0308ID) was used as a standard. This standard was diluted stepwise with FBS-supplemented PBS. The results are shown in Table 28. Of the chimeric mice derived from the mouse antibody heavy-chain both alleles-disrupted TT2F cells, the mouse having a chimerism of 99% exhibited a low mouse IgM concentration. Thus, it was confirmed that the mouse heavy-chain gene from the ES cells hardly functions in this mouse.

TABLE 28

Concentration of Mouse IgM in Chimeric Mice (ELISA)

| Chimerism % | IgM (mg/l) |
|---|---|
| 0 | 12 |
| 50 | 11 |
| 99 | 1.5 |

EXAMPLE 76

Figure 30:
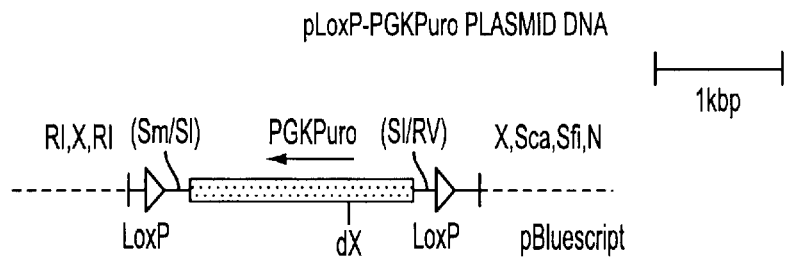
FIG. 30 shows the structure of pLoxP-PGKPuro plasmid DNA.
Figure 31:
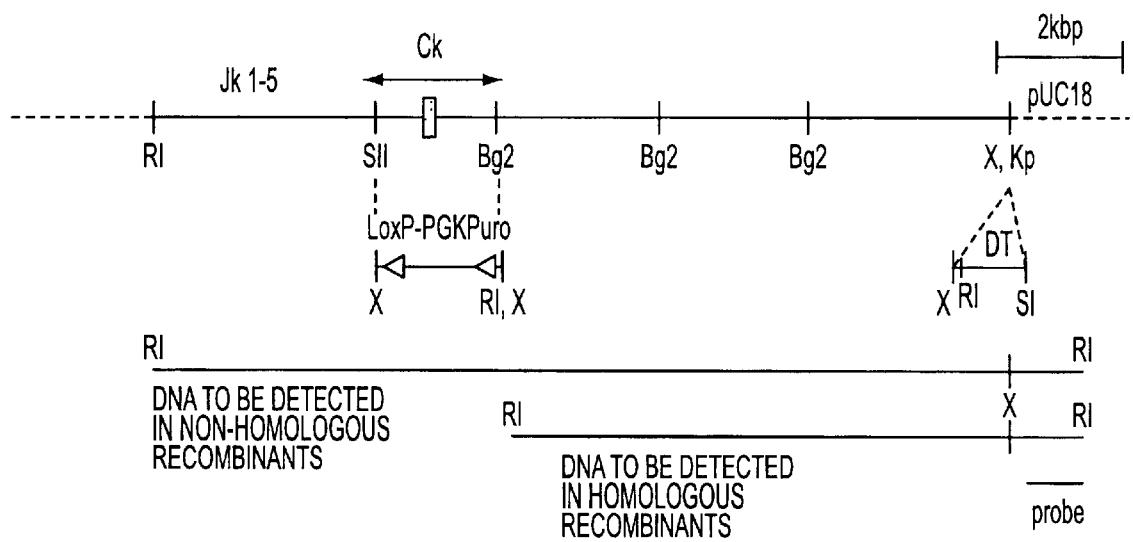
FIG. 31 shows a mouse antibody light-chain κ targeting vector, a probe for use in the southern blot analysis of genomic DNA from transformant TT2F cells, and DNA fragments to be detected in homologous recombinants.
Figure 32:
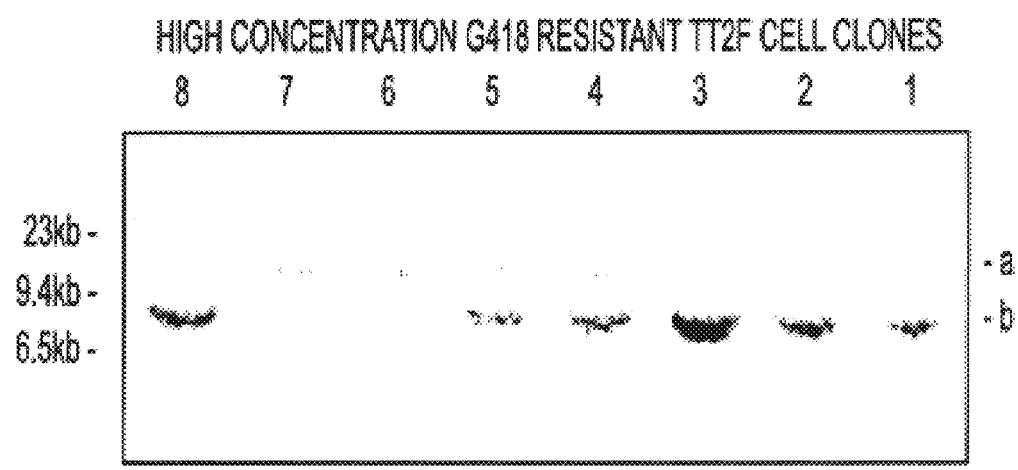
FIG. 32 shows a photograph of electrophoresis patterns showing the results of Southern blot analysis of high concentration G418 resistant cell clones derived from mouse antibody light-chain homologous recombinants.

Preparation of a Targeting Vector for Knocking Out Antibody Light-chain κ Gene in ES Cells Plasmid LoxP-PGKPuro in which LoxP sequence was inserted at both ends of a puromycin resistance gene was prepared in the same manner as in Example 48, Section 1. Briefly, a puromycin resistance cassette PGKPuro was cut out from PGKPuro plasmid DNA (Watanabe et al., Biochem. Biophys. Res. Commun. 213:130–137 (1995); released from Peter W. Laird, Whitehead Institute for Biochemical Research and Massachusetts Institute of Technology, Dept. of Biology, Cambridge, Mass.) using restriction enzyme SalI and then blunted. PGKPuro was inserted into the SmaI and EcoRV restriction sites of a LoxP-sequence containing plasmid to produce plasmid pLoxP-PGKPuro (FIG. 30). Further, a DNA fragment comprising a genomic DNA constant region containing the mouse antibody light-chain κ J region and constant region was replaced with the LoxP-PGKPuro gene in the same manner as in Example 48 (FIG. 31).

EXAMPLE 77

Production of an Antibody Light-chain Gene Both Alleles-disrupted Strain from Antibody Light-chain-deficient-heterozygote (and Antibody Heavy-chain-deficient-homozygote) Mouse ES Cells (1) A Puromycin Resistance Gene was Inserted into the Antibody Light-chain Deficient-heterozygote TT2F Clone (HD43) Obtained in Example 58 to Give a Strain in Which Both Alleles of a Light-chain Gene Were Disrupted The antibody light-chain targeting vector prepared in Example 76 was linearized with restriction enzyme KpnI to transform HD43 clone in the same manner as in Example 58. The resultant transformants were subjected to selective culture at a puromycin concentration of 0.75 µg/ml. At day 7–9 of the cultivation, colonies formed were picked up. A part of these colonies was stored frozen, and the remaining part was used to prepare genomic DNA in the same manner as in Example 49. Genomic DNAs from the puromycin resistant strains were digested with restriction enzyme EcoRI (Takara Shuzo), separated by agarose gel electrophoresis and subjected to Southern blot analysis to detect homologous recombinants using the probe described in Example 48, Section 4 (see Examples 58 and 59). As a result, 4 clones in which both alleles of an antibody light-chain were disrupted were obtained from the 74 clones analyzed. Under usual culture conditions, no changes in growth rate and morphology were observed in these clones, as compared to the TT2F clone before gene disruption. This suggests that the clones under consideration retain the ability to produce chimera.

(2) Production of Chimeric Mice from the Antibody Heavy-chain-deficient-homozygote and Antibody Light-chain Gene Both Alleles-disrupted Clone Cells in the frozen stock of antibody light-chain gene both alleles-disrupted TT2F cell clone HD43P-10 from Example 77, Section 1 were thawed, started up for culture and injected into 8-cell stage embryos obtained by mating male and female mice of ICR (CREA JAPAN, INC.); the injection rate was 10–12 cells per embryo. After the embryos were cultured overnight in the medium for ES cells (see Example 9) to develop into blastocysts, about 10 of the injected embryos were transplanted to each side of the uterus of foster mother ICR mice (CREA JAPAN, INC.; 2.5 days after pseudopregnant treatment).

As a result of transplantation of a total of 161 injected embryos, 37 offspring mice were born. Chimerism in the offsprings can be determined by the extent of TT2 cell derived agouti coat color (dark brown) in the host embryo (ICR)-derived albino coat color (white). Out of the 37 offsprings, 9 mice were recognized to have partial agouti coat color, indicating the contribution of the ES cells. Out of the 9 mice, four were chimeric mice in which more than 80% of their coat color was agouti (i.e. ES cell-derived).

From these results, it was confirmed that antibody light-chain both alleles-disrupted ES cell clone HD43P-10 maintains a high ability to produce chimera.

EXAMPLE 78

Removal of the G418 Resistance and Puromycin Resistance Marker Genes from the Antibody Light-chain Deficient-homozygote (and Antibody Heavy-chain Deficient-homozygote) TT2F Cell Clone From the antibody light-chain both alleles-disrupted HD43P-10 clone (puromycin resistant, G418 resistant) which was obtained and confirmed to have a high chimera-forming ability in Example 77, the puromycin resistance and G418 resistance marker genes were removed by the procedures described in Example 52. Briefly, an expression vector pBS185 (BRL) containing a Cre recombinase gene which causes a site-specific recombination between the LoxP sequences inserted at both ends of the G418 resistance marker gene was transferred into the clone described above in the same manner as in Example 52. The resultant puromycin (0.75 µg/ml) sensitive clones (6 clones) were grown to confluence in 35 mm plates in the same manner as in Example 52. Three fifths (3/5) of the resultant culture were suspended in 0.5 ml of a preservation medium [ES medium+ 10% DMSO (Sigma)] and stored frozen at −80° C. The remaining two fifth (2/5) were divided into two portions and inoculated into two 12-well gelatin-coated plates. Cells in one plate were cultured in non-selective medium for 2 days. Cells in other plate were cultured in the presence of 300 µg/ml of G418 for 2 days. As a result, 5 puromycin sensitive and G418 sensitive clones which would be killed in the presence of G418 were obtained.

EXAMPLE 79

Increase in the Expression of Human Antibody κ Chain in Sera as a Result of Mating a Human Chromosome #2 Fragment-retaining Mouse Strain with c57BL/6 Strain The hereditary background of the progenies of the chimeric mice [hereinafter referred to as "F₁(chimera×MCH)"] which were described in Examples 43 and 44 and which retain a human chromosome #2 fragment (hereinafter referred to as "W23 fragment") is that they are a mixture of TT2F cell (Example 39)-derived CBA mouse strain and C57BL/6 mouse strain, and MCH(ICR) mouse strain mated with the chimeric mice. In order to observe the behavior of W23 fragment under a hereditary background as homogeneous as possible, first, $F_1$(chimera×MCH) were back-crossed with MCH(ICR). The offspring mice obtained by the mating of $F_1$(chimera×MCH) (randomly selected 8 male and 6 female mice)×MCH(ICR) were examined as to whether they would retain W23 fragment in the same manner as in Example 43. As a result, it was confirmed that W23 fragment was transmitted through male to 8% of the offsprings (25 out of the 324 offsprings were positive) and through female to 22% of the offsprings (32 out of the 148 offsprings were positive). When the resultant $F_2(F_1 \times MCH)$(randomly selected 8 male and 8 female mice) were further mated with MCH(ICR), the transmission ratio was 9% through male (30 out of the 346 offsprings were positive) and 24% through female (48 out of the 202 offsprings were positive). Thus, the results was similar to that obtained by the mating of $F_1$(chimera×MCH)×MCH(ICR). $F_3(F_2 \times MCH)$ were obtained by the latter mating.

Figure 43:
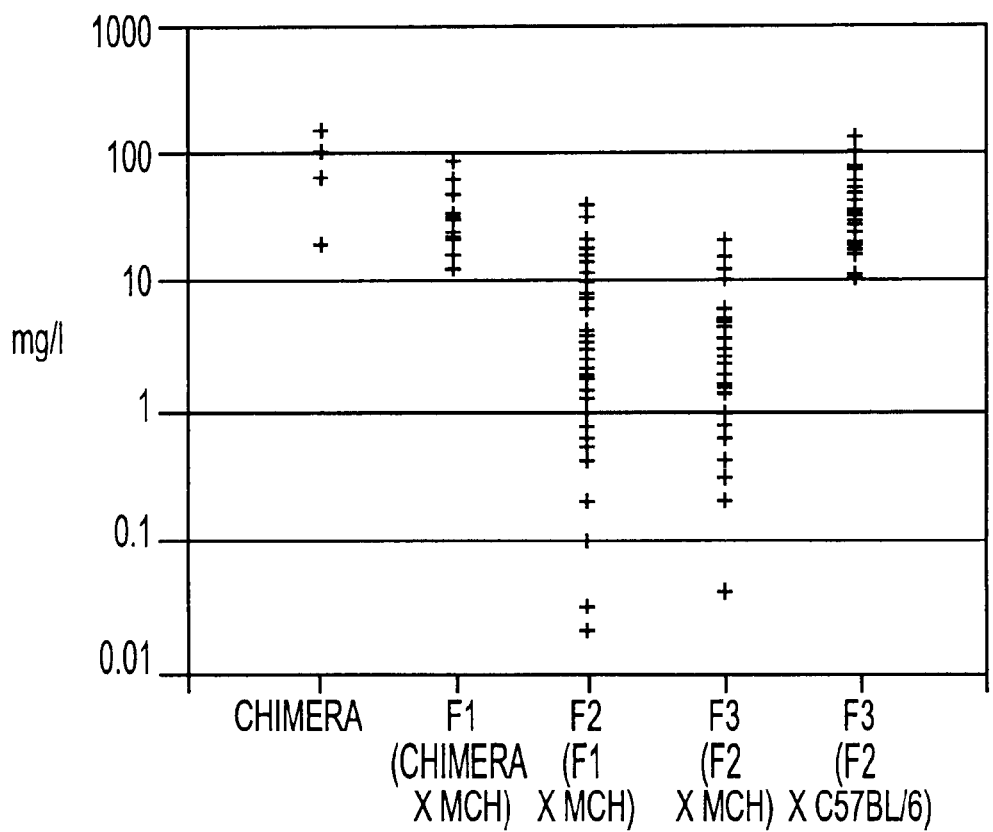
FIG. 43 shows the results of the determination of the concentration of human antibody κ chain in a serum of a mouse retaining a human chromosome #2 fragment, W23.

The concentrations of human antibody κ chain in the sera of 4–12-week old chimeric mice (FIG. 43, indicated as "Chimera", 4 mice), $F_1$(chimera×MCH) (19 mice), $F_2(F_1 \times MCH)$ (39 mice) and $F_3(F_2 \times MCH)$ (33 mice) were determined in the same manner as in Example 44. The results are shown in FIG. 43. Human antibody κ chain was detected in all of the mice retaining W23 fragment. On the other hand, the κ chain concentrations varied greatly in $F_2(F_1 \times MCH)$ and $F_3(F_2 \times MCH)$; the averaged values in these groups were lower than those in the chimeric mice and $F_1$(chimera×MCH).

In order to examine the influence which would be caused by the mating with a strain other than MCH(ICR), the same $F_2(F_1 \times MCH)$ mice as used in the experiment of mating with MCH(ICR) were mated with C57BL/6N (purchased from CREA JAPAN, INC.). Concentrations of κ chain were determined in the same manner on the resultant 26 mice retaining W23 fragment [$F_3(F_2 \times C57BL/6)$]. As a result, these mice exhibited κ chain concentrations as high as those in the chimeric mice and $F_1$(chimera×MCH) (FIG. 43). As described above, $F_3(F_2 \times MCH)$ and $F_3(F_2 \times C57BL/6)$ are derived from the same $F_2(F_1 \times MCH)$ mice as one of the parents. Therefore, it is believed that the difference between $F_3(F_2 \times MCH)$ and $F_3(F_2 \times C57BL/6)$ is in their hereditary background alone. Thus, it is indicated that difference in hereditary background influences the amount of expression of human antibody κ chain. Further, it has become clear that the hereditary background of C57BL/6 is more desirable than that of MCH(ICR) for efficient expression of human antibody κ chain. From similar experiments, it has been demonstrated that the hereditary background of C3H HeN (purchased from CREA JAPAN, INC.) is comparable to or better than that of C57BL/6 for efficient expression of human antibody κ chain.

The following experiment was conducted to examine as to whether the influence of hereditary background on antibody κ chain concentrations observed above is related to the ratio of chromosome retention (stability) at the level of individual mice. Briefly, metaphase chromosome samples were prepared from tail-derived fibroblasts and bone marrow cells of 2F-1 mouse (serum κ chain concentration: 84 mg/l) and 1F-3 mouse (serum κ chain concentration: 13 mg/l) in $F_1$(chimera×MCH) and subjected to FISH analysis (Tomizuka et al., Nature Genetics, vol 16, 133–143). The ratio of those metaphase spreads containing W23 fragment hybridizing to a human chromosome-specific probe to all of the spreads observed was determined. It is believed that the resultant values represent the W23 fragment retention ratios in fibroblasts and bone marrow cells, respectively. As a result, with respect to 2F-1, the retention ratio was 51% in fibroblasts and 34% in bone marrow cells; and with respect to 1F-3, the retention ratio was 23% in fibroblasts and 18% in bone marrow cells (more than 50 nuclear plate were measured for each case). These results suggest that the κ chain concentrations in sera correlated to the ratios of retentions of W23 fragment in fibroblasts and bone marrow cells. In other words, it is very likely that hereditary background influences the stability of the transferred human chromosome fragment itself. Thus, it is believed that the hereditary background of C57BL/6 or C3H strain is desirable for efficient expression of a gene not only on the chromosome #2 fragment described herein but also on other chromosome fragments (e.g. chromosome #14 fragment).

In order to verify the above conjecture, a male mouse #17-7 in $F_1$(chimera×MCH) which retains the human chromosome #14 fragment obtained in Example 68 (hereinafter referred to as "SC20 fragment") and which expresses a human antibody heavy-chain in the serum was mated with MCH(ICR) and C57BL/6. Of the resultant offsprings, two $F_2$ ($F_1 \times MCH$) mice and two $F_2$ ($F_1 \times C57BL/6$) mice, each retaining SC20 fragment, were subjected to determination of human antibody heavy-chain concentrations in the sera (see Example 68). Furthermore, metaphase chromosome samples were prepared from the tails of these mice and then the ratio of SC20 fragment retention was determined in the same manner as for W23 fragment. As a result, the human μ chain concentration was 11.0 mg/l and 1.1 mg/l and the chromosome retention ratio 74% and 54% in $F_2(F_1 \times MCH)$, whereas the human μ chain concentration was 47 mg/l and 54 mg/l and the chromosome retention ratio 84% and 88% in $F_2(F_1 \times C57BL/6)$. $F_2(F_1 \times C57BL/6)$ mice exhibited higher values in both the human μ chain concentration and the chromosome retention ratio. Thus, it has become clear that the hereditary background of C57BL/6 is desirable for stable retention of a transferred human chromosome and for efficient expression of a gene located thereon, as presumed from the results obtained on W23 fragment-retaining mice.

EXAMPLE 80

Production of Chimeric Mice from an Antibody Heavy-chain-deficient and Antibody κ Chain-homologous Recombinant ES Cell Clone Cells in the frozen stock of antibody heavy-chain-deficient and antibody κ chain-homologous recombinant ES cell clone HD43 from Example 58 were thawed, started up for culture and injected into 8-cell stage embryos obtained by mating male and female mice of ICR (CREA JAPAN, INC.); the injection rate was 10–12 cells per embryo. After the embryos were cultured overnight in the medium for ES cells (see Example 9) to develop into blastocysts, about 10 of the injected embryos were transplanted to each side of the uterus of foster mother ICR mice (CREA JAPAN, INC.; 2.5 days after pseudopregnant treatment).

As a result of transplantation of a total of 314 injected embryos, 51 offspring mice were born. Chimerism in the offsprings can be determined by the extent of TT2 cell-derived agouti coat color (dark brown) in the host embryo (ICR)-derived albino coat color (white). Out of the 51 offsprings, 26 mice were recognized to have partial agouti coat color, indicating the contribution of the ES cells. Out of the 26 mice, two were chimeric female mice in which 100% of their coat color was agouti (i.e. ES cell-derived).

From these results, it was confirmed that antibody heavy-chain-deficient and antibody light-chain-homologous recombinant ES cell clone HD43 maintains the ability to produce chimera. In the female mice exhibiting 100% contribution, it is highly possible that the ES cells have been differentiated into functional germ cells (oocytes).

Examination was made as to whether ES cell-derived offsprings would be produced by mating the above female chimeric mice (both having 100% chimerism in coat color) with male ICR mice. By this mating, offsprings with agouti coat color should be produced from TT2F cell (agouti: dominant)-derived oocytes in the chimeric mice fertilized by male ICR mouse (albino: recessive)-derived sperms, and offsprings with albino coat color should be produced from ICR-derived oocytes. Actually, all of the viable offspring mice obtained by one mating for each female mouse exhibited ES cell-derived agouti coat color. Genomic DNAs were prepared from the tails of these offspring mice to examine the presence of an antibody κ chain disrupted allele by Southern blot analysis (Example 58). As a result, mice having an antibody κ chain disrupted allele were obtained.

Figure 44:
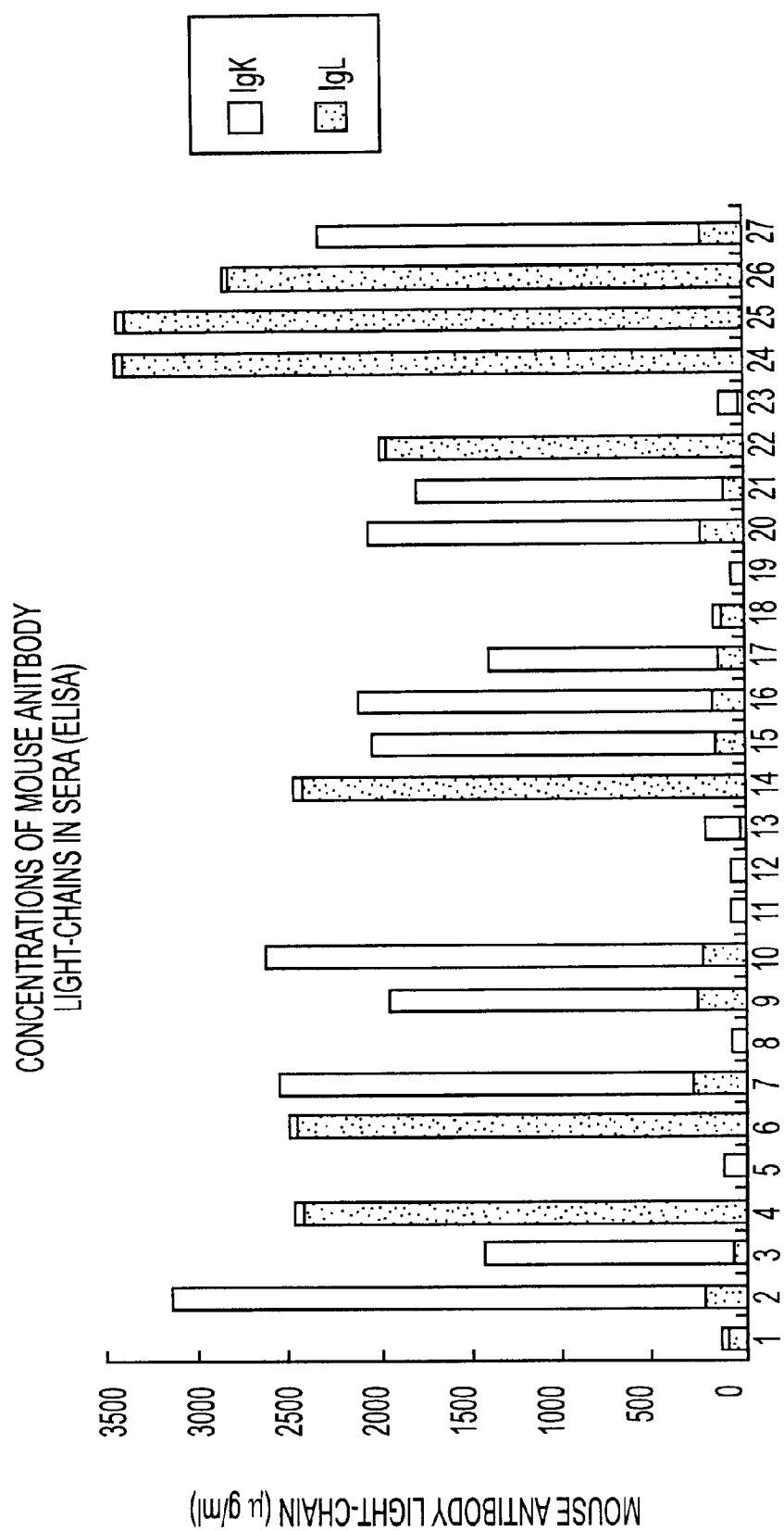
FIG. 44 shows the results of the determination of the concentration of human antibody κ and λ chains in a serum of a mouse.

Twenty-seven offspring mice produced by the mating of the antibody light-chain deficient-heterozygote male and female mice were subjected to Southern blot analysis (Example 58). As a result, antibody light-chain wild-type alleles disappeared and only disrupted alleles were observed in 7 offspring mice. Hence, these mice were believed to be antibody light-chain-deficient homozygotes. FIG. 44 shows the results of detection and quantitative determination of mouse antibody κ chain and λ chain in the sera.

In those mice which were judged to be antibody light-chain-deficient homozygotes by the Southern blot analysis (Nos. 4, 6, 14, 22, 24, 25 and 26 in FIG. 44), the concentrations of κ chain are greatly reduced (the remaining κ chain appears to be derived from their mother mice). Instead, the concentrations of λ chain are greatly increased in these mice. These results are consistent with the reported results of analysis of the antibody κ chain knockout mouse (Yong-Rui Zou et al., EMBO J. 12, 811–820 (1993)).

Thus, an antibody κ chain knockout mouse strain could be established from antibody κ chain homologous recombinant ES cell clone HD43.

EXAMPLE 81

Preparation of a Targeting Vector for Inserting Human Telomere Sequence into Human Chromosome #22

Fragmentation of human chromosome #22 on which human antibody λ chain gene (hereinafter referred to as "Igλ gene") was located was attempted by inserting human telomere sequence by homologous recombination (J. E. Itzhaki et al., Nature Genet., 2, 283–287, 1992). Specifically, a targeting vector for inserting human telomere sequence into the LIF locus located very close to Ig λ gene (on the telomere side) was prepared.

Human telomere sequence was synthesized by PCR according to the method of J. J. Harrington et al. (Nature Genet., 15, 345–355, 1997). The PCR product was purified by agarose gel electrophoresis and then blunted with DNA Blunting Kit (Takara Shuzo). The blunted PCR product was inserted into the Eco RV site of pBluescript SK II(+) (Toyobo) by ligation using DNA Ligation Kit (Takara Shuzo) (pBS-TEL). This plasmid pBS-TEL was sequenced. As a result, it was found that the telomere sequence had been inserted in the following direction: Hind III-(TTAGGG)n-Eco RI.

Subsequently, the LIF gene region on human chromosome #22 to be used in the homologous recombination was amplified by PCR as described below, and then cloned into plasmid pBS-TEL. The sequences of the primers used in the PCR were as follows.

Sense primer: 5'-TCGAACTAGTAGGAGAAGTG AACTTGAGGAGGC-3' (SEQ ID NO: 65)
Antisense primer: 5'-TCGAACTAGTGATTCAG TGATGCTGTGCAGG-3' (SEQ ID NO: 66)

The PCR reaction mixture was composed of 5 μl of 10×LA PCR buffer II ($Mg^{2+}$ free) (Takara Shuzb); 5 μl of 25 mM $MgCl_2$; 8 μl of dNTP mixture (2.5 mM each) (Takara Shuzo); 10 pmol of sense primer; 10 pmol of antisense primer; 100 ng of template DNA (HFL1, genomic DNA from primary culture human fibroblasts); 0.5 μl of LA Taq (5 U/μl) (Takara Shuzo) and sterile distilled water to make a total volume of 50 μl. All of the operations for preparing the reaction mixture were carried out on ice. Then, reaction tubes were placed in the well of a thermal cycler (PCR System 9600, Perkin-Elmer,) preset at 85° C. After the tubes were heated at 94° C. for 1 minute, 35 cycles of reaction were carried out at 98° C. for 10 seconds and at 65° C. for 5 minutes. The PCR product was purified and then digested with a Spe I (Spe I site was present in the primers), followed by insertion into the Spe I site in PBS-TEL. The plasmid in which the LIF gene had been inserted in a opposite direction of the human telomere sequence (TTAGGG)n was selected (M. Giovannini et al., Cytogenet Cell Genet 64, 240–244, 1993) (pBS-TEL/LIF).

Figure 45:
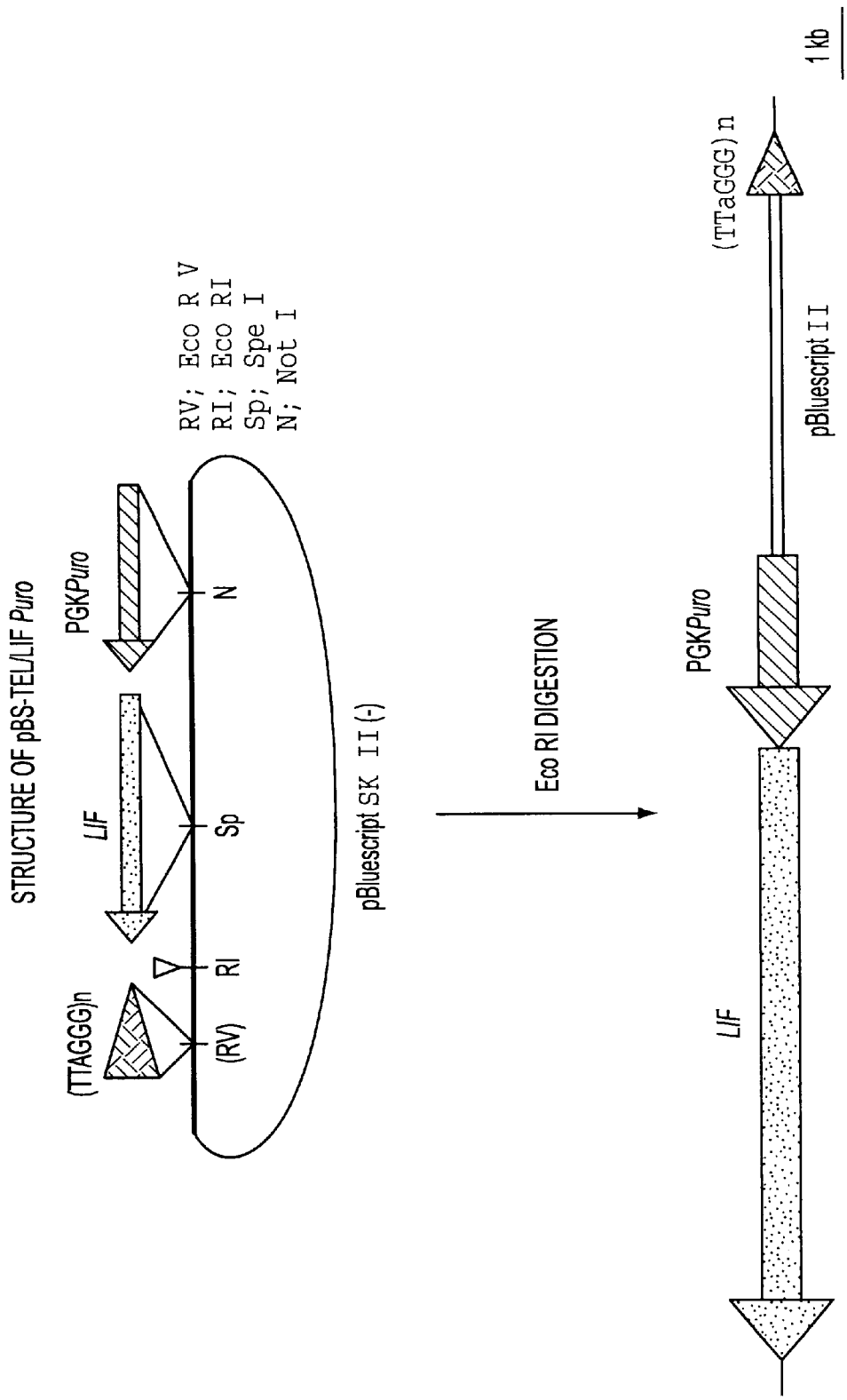
FIG. 45 shows the structure of pBS-TEL/LIFPuro.

Subsequently, plasmid pGKpuro containing a puromycin resistance gene (S. Watanabe et al., Biochem. Biophys. Res. Comm., 213, 130–137, 1995) was digested with ECo RI and blunted, followed by insertion of Not I linker. The puromycin resistance gene was cut out by digesting the resultant plasmid with Not I and then inserted into the Not I site of pBS-TEL/LIF. The plasmid in which the direction of transcription of the puromycin resistance gene was the same as that of the LIF gene was selected (pBS-TEL/LIFPuro, see FIG. 45). The resultant plasmid was amplified in *E. coli* DH5, purified with QUIAGEN column (Funakoshi) and used for transfection (as described later).

EXAMPLE 82

Transfer of Human Chromosome #22 into Chicken DT40 Cells

Mouse A9 cells containing human chromosome #22 marked with a G418 resistance gene (Tomizuka et al., Nature Genet., vol 16, 133–143, 1997; hereinafter referred to as "A9/#22neo") were cultured in Dulbecco's modified Eagle's Minimal Essential Medium (hereinafter referred to as "DMEM") supplemented with 10% fetal bovine serum and G418 (800 μg/m). Chicken DT40 cells were cultured in DMEM supplemented with 10% FBS, 1% chicken serum and $10^{-4}$ M 2-mercaptoethanol.

Microcells were prepared as described below (for details, see Shimizu et al., "Cell Technology Handbook", published by Yodosha, p. 127-). A9/#22neo cells were cultured in twelve 25 $cm^2$ centrifuge flasks (Costar) until the cell concentration reached about 90% saturation. Then, the medium was exchanged with a medium (DMEM+20% FBS) supplemented with COLCEMID (0.07 μg/ml; demecolcine, Wako Pure Chemical Industries, Inc.). The cells were cultured for another 2.5–3 days to form microcells. Thereafter, the culture solution was removed from the centrifuge flasks, into which a solution of cytochalasin B (10 μg/ml, Sigma) prewarmed at 37° C. was filled and centrifuged at 34° C. at 8000 rpm for 1 hour. The microcells were suspended in DMEM and purified by filtration with filters. After the purification, the microcells were centrifuged at 1500 rpm for 10 minutes and then suspended in 5 ml of DMEM. DT40 cells ($2\times10^7$) were centrifuged at 1000 rpm for 5 minutes, washed with DMEM twice and suspended in 5 ml of DMEM. The microcells prepared above were re-centrifuged at 1500 rpm for 10 minutes and then, without removal of the supernatant, 5 ml of the previously prepared DT40 suspension was overlayered gently. After centrifugation at 1300 rpm for 5 minutes, the supernatant was removed. The cell pellet was suspended in 2 ml of PHA-P (100 $\mu$g/ml, DIFCO) and left to stand in an incubator at 37° C. under 5% $CO_2$ for 15 minutes. Then, the suspension was centrifuged at 1700 rpm for 7 minutes. The supernatant was removed and the cell pellet was loosened by tapping. To the cell pellet, 1 ml of PEG1500 (polyethylene glycol, Boehringer) was added gently and the pellet was treated for 1.5–2 minutes under agitation. After this treatment, 1 ml of DMEM was added over approximately 1 minute. Then, 3 ml of DMEM was added over approximately 2 minutes. Thereafter, DMEM was added to make a total volume of 11 ml and the resultant mixture was mixed gently. The mixture was left to stand for 10 minutes at room temperature and then centrifuged at 1300 rpm for 5 minutes. The supernatant was removed. The cells were suspended in 10 ml of the above-described culture medium and cultured in $\phi$100 mm plates for 24 hours. Twenty-four hours later, the medium was exchanged with one supplemented with G418 (1 mg/ml). The resultant culture was dispensed into three 24-well plates (Sumitomo Bakelite), followed by selective culture for about 2 weeks to isolate G418 resistant clones.

(1) PCR Analysis

As a result of the selective culture, about thirty G418 resistant clones were obtained. Genomic DNAs were extracted from these clones using Puregene DNA Isolation Kit (Gentra System). Using the genomic DNA as a template, PCR was performed with human Ig$\lambda$ gene-specific primers to identify clones having human chromosome #22 containing Ig$\lambda$ gene. The Ig$\lambda$ gene-specific primers used were as follows.

5'-GAGAGTTGCAGAAGGGGTGACT-3' (SEQ ID NO: 67)

5'-GGAGACCACCAAACCCTCCAAA-3' (SEQ ID NO: 68)

Figure 46:
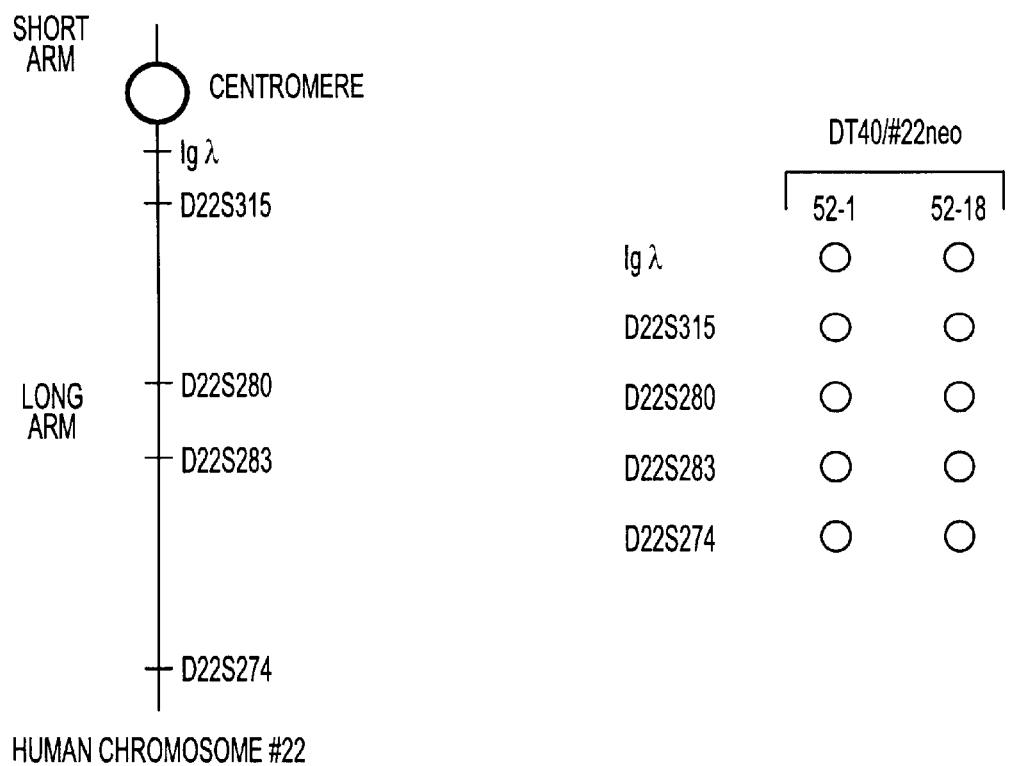
FIG. 46 shows that human chromosome #22 is retained in a DT40 cell clone.

The PCR reaction mixture was composed of 5 $\mu$l of 10×Ex Taq buffer (Takara Shuzo); 8 $\mu$l of dNTP mixture (2.5 mM each) (Takara Shuzo); 10 pmol of each primer; 100 ng of genomic DNA; 0.5 $\mu$l of Ex Taq (5 U/$\mu$l) (Takara Shuzo) and sterile distilled water to make a total volume of 50 $\mu$l. All of the operations for preparing the reaction mixture were carried out on ice. Then, reaction tubes were placed in the well of a thermal cycler (PCR System 9600, Perkin-Elmer) preset at 85° C. After the tubes were heated at 94° C. for 1 minute, 35 cycles of reaction were carried out at 98° C. for 10 seconds, at 56° C. for 30 seconds and at 72° C. for 30 seconds. As a result, 2 clones having human Ig$\lambda$ gene were identified. The presence of polymorphic markers (D22S315, D22S280, D22S283 and D22S274; Polymorphic STS Primer Pair, BIOS; J. E. Collins et al., Nature 377 suppl.: 367, 1995) located on human chromosome #22 were detected in these clones by PCR (FIG. 46). The PCR conditions were the same as used for the detection of human Ig$\lambda$ gene. Mark "○" indicates that the marker was detected. Mark "×" indicates that the marker was not detected. The diagram at the left side shows the location of each marker on chromosome #22 based on a physical map. From these results, it was suggested that these 2 clones have a almost intact human chromosome #22. As to the other clones, although human Ig$\lambda$ gene was not detected, some of the polymorphic markers on chromosome #22 described above were detected.

(2) FISH Analysis

One of the above 2 clones (clone No. 52-18) was subjected to FISH analysis to examine how the human chromosome #22 actually existed in cells. Basic operations such as preparation of chromosome samples, hybridization and detection were performed according to Tomizuka et al. (Nature Genet. 16, 133–143, 1997). As a probe, human COT-1 DNA (labeled with Rhodamine) was used. As a result of observation of 20–30 spreads, it was confirmed that an almost intact human chromosome #22 was present independently (FIG. 50). Those stained in red are human chromosome #22.

From these results of analysis, it was thought that chicken DT40 cell clone 52-18 (hereinafter referred to as "DT40/#22neo") has intact human chromosome #22.

EXAMPLE 83

Targeted Truncation of Human Chromosome #22 in Chicken DT40 Cells

DT40/#22neo from Example 82 was transfected with plasmid pBS-TEL/LIFPuro prepared in Example 81 and an attempt was made to perform targeted truncation of the human chromosome #22 on the LIF locus DT40/#22neo cells were cultured under the same conditions as described in Example 82 in the presence of G418 (1 mg/ml). $10^7$ cells were washed with cold PPS once, suspended in 0.5 ml of PBS and placed on ice. Then, 25–30 $\mu$g of pBS-TEL/LIFPuro linearized with Eco RI was added to the cells, mixed with a pipette, transferred into an electroporation cuvette (Bio-Rad) and left to stand in ice for 10 minutes. The cuvette was set in a gene pulser (Bio-Rad) and then a voltage of 550 V was applied at a capacitance of 25 $\mu$F. After the cuvette was left to stand on ice for 10 minutes, the cells were transferred into 72 $cm^2$ culture flasks containing the above-described medium and cultured for 24 hours. Twenty-four hours later, the medium was exchanged with a medium supplemented with G418 (1 mg/ml) and puromycin (0.3 $\mu$g/ml, Sigma). The resultant culture was dispensed into five to eight 96-well culture plates:, followed by selective culture for about 2 weeks to isolate resistant clones.

(1) PCR Analysis

As a result of the selective culture, about 80 resistant clones were obtained. Genomic DNAs were extracted from these cells as described above and subjected to PCR to identify homologous recombinants in which a human telomere sequence was integrated into the LIF locus. One of the primers was designed such that its sequence was complementary to a part of the LIF gene region which was not contained in the vector (see FIG. 47). The other primer was designed such that its sequence was complementary to a part of the puromycin resistance gene which was contained in the vector. The sequences of the primers are as follows.

Puro.1: 5'-GAGCTGCAAGAACTCTTCCTCACG-3' (SEQ ID NO: 69)

LIF1: 5'-ATGACTCTAAGGCAGGAACATCTGTACC-3' (SEQ ID NO: 70)

Figure 47:
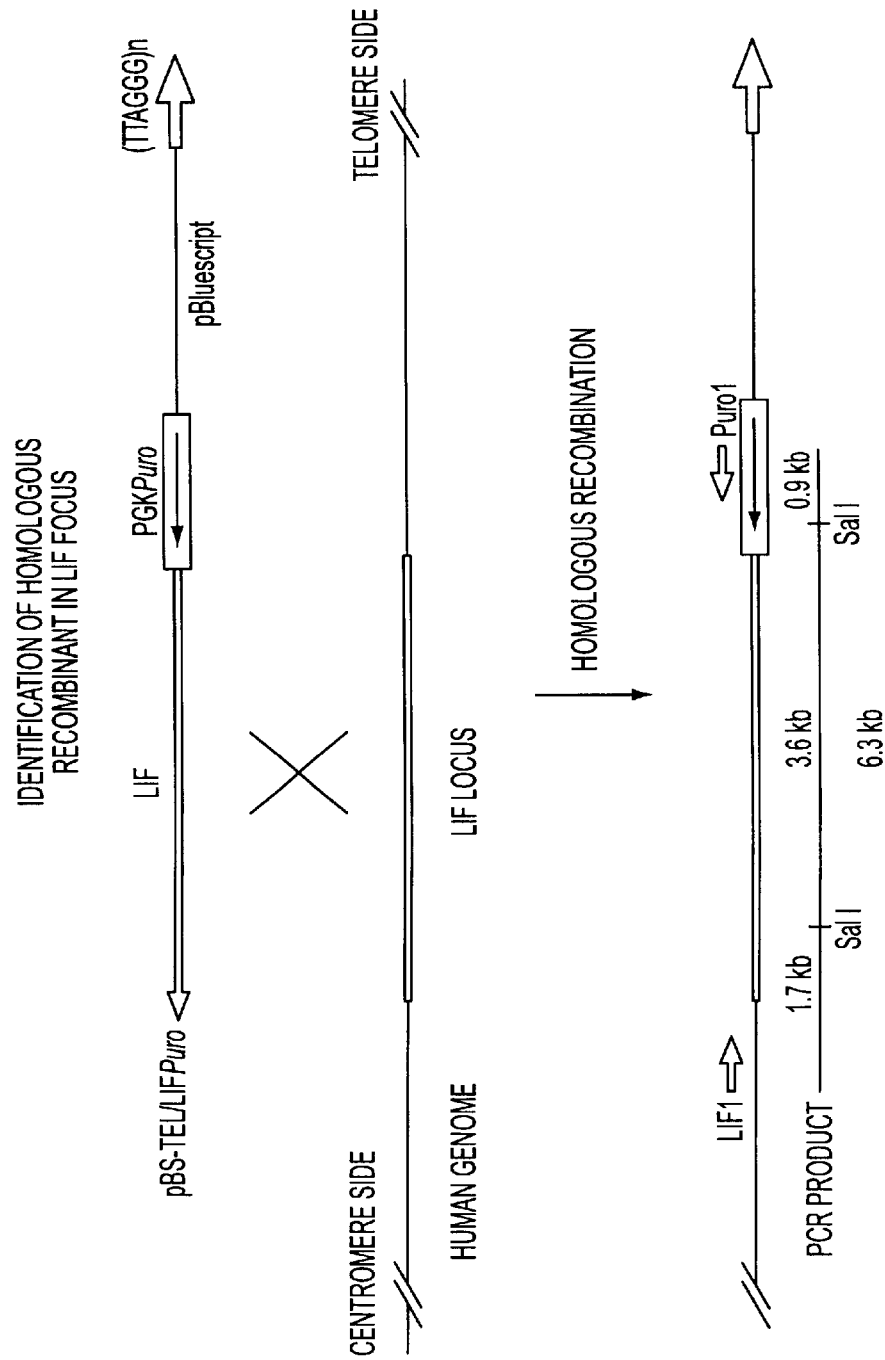
FIG. 47 shows the identification of homologous recombinant in LIF locus.

The PCR reaction mixture was composed of 5 $\mu$l of 10×LA PCR buffer II ($Mg^{2+}$+free) (Takara Shuzo); 5 $\mu$l of 25 mM $MgCl_2$; 8 $\mu$l of dNTP mixture (2.5 mM each) (Takara Shuzo); 10 pmol of each primer; 100 ng of template DNA;

0.5 μl of LA Taq (5 U/μl ) (Takara Shuzo) and sterile distilled water to make a total volume of 50 μl. All of the operations for preparing the reaction mixture were carried out on ice. Then, reaction tubes were placed in the well of a thermal cycler (PCR System 9600, Perkin-Elmer) pre-set at 85° C. After the tubes were heated at 94° C. for 1 minute, 35 cycles of reaction were carried out at 98° C. for 10 seconds and at 65° C. for 10 minutes. A 6.3 kb PCR product as shown in FIG. 47 should be detected only in the homologous recombinants of interest. As a result of the PCR, this 6.3 kb band was detected in 8 clones (homologous recombination ratio: about 10%). When this PCR product was digested with Sal I, a cut pattern was obtained in exactly the same way as expected. Thus, it was confirmed that these 8 clones were homologous recombinants.

Subsequently, whether or not the truncation occurred as expected in these 8 clones was examined by PCR detection of the presence of genes (Igλ, LIF, MB, IL2RB, CYP2D6, DIA1, ECGF$_1$ and ARSA; J. E. Collins et al., Nature 377 suppl:367, 1995) and polymorphic markers (D22S315, D22S275, D22S280, D22S281, D22S277, D22S278, D22S283, D22S272, D22S282 and D22S274; J. E. Collins et al., Nature 377 suppl.:367, 1995) on chromosome #22.

A part of the primer sequences used is as described below. The remaining primer sequences were the same as used by Tomizuka et al. (Nature Genet. 16, 133–143, 1997). The presence of LIF is evident from the experiment described above.

CYP2D6
Sense primer: 5'-CTGCGTGTGTAATCGTGTCC-3' (SEQ ID NO:71)
Antisense primer: 5'-TCTGCTGTGAGTGAACCTGC-3' (SEQ ID NO:72)
ECGF1
Sense primer: 5'-AGGAGGCACCTTGGATAAGC-3' (SEQ ID NO:73)
Antisense primer: 5'-TCACTCTGACCCACGATACAGC-3'(SEQ ID NO:74)

Figure 48:
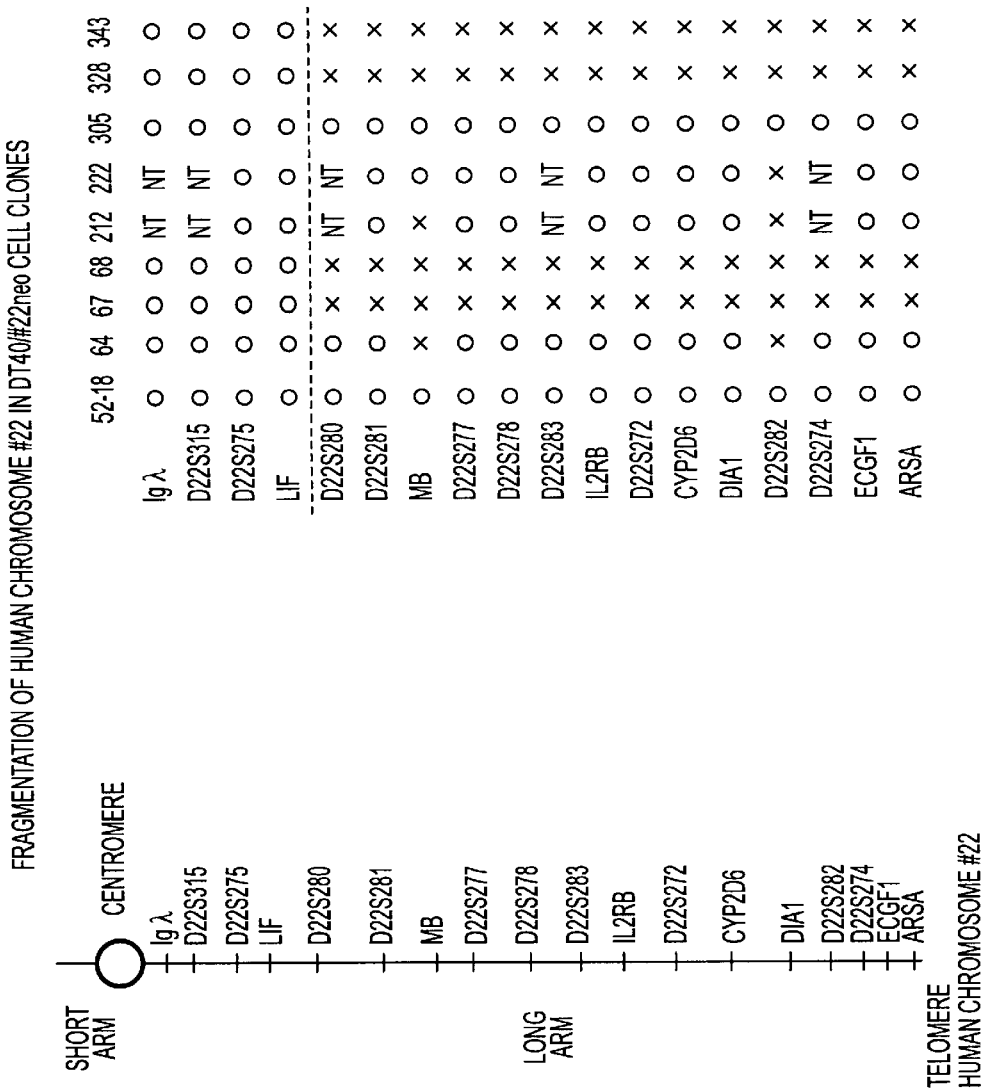
FIG. 48 shows the fragmentation of human chromosome #22 in a DT40/#22neo cell clone.

The PCR reaction mixture was composed of 5 μl of 10×Ex Taq buffer (Takara Shuzo); 8 μl of dNTP mixture (2.5 mM each) (Takara Shuzo); 10 pmol of each primer; 100 ng of genomic DNA; 0.5 μl of Ex Taq (5 U/μl) (Takara Shuzo) and sterile distilled water to make a total volume of 50 μl. All of the operations for preparing the reaction mixture were carried out on ice. Then, reaction tubes were placed in the well of a thermal cycler (PCR System 9600, Perkin-Elmer) pre-set at 85° C. After the tubes were heated at 94° C. for 1 minute, 35 cycles of reaction were carried out at 98° C. for 10 seconds, at 56° C. (65° C. for CYP2D6 and ECGF$_1$) for 30 seconds and at 72° C. for 30 seconds. The results are shown in FIG. 48. Marks "◯" and "×" have the same meanings as described above. As is clear from this Figure, none of the genes and markers located on the telomere side of the LIF locus into which a human telomere sequence had been integrated were detected in clones 67, 68, 328 and 343. It is suggested that truncation by the integration of a telomere sequence did occur as expected in at least those 4 clones.

(2) FISH Analysis

Figure 49:
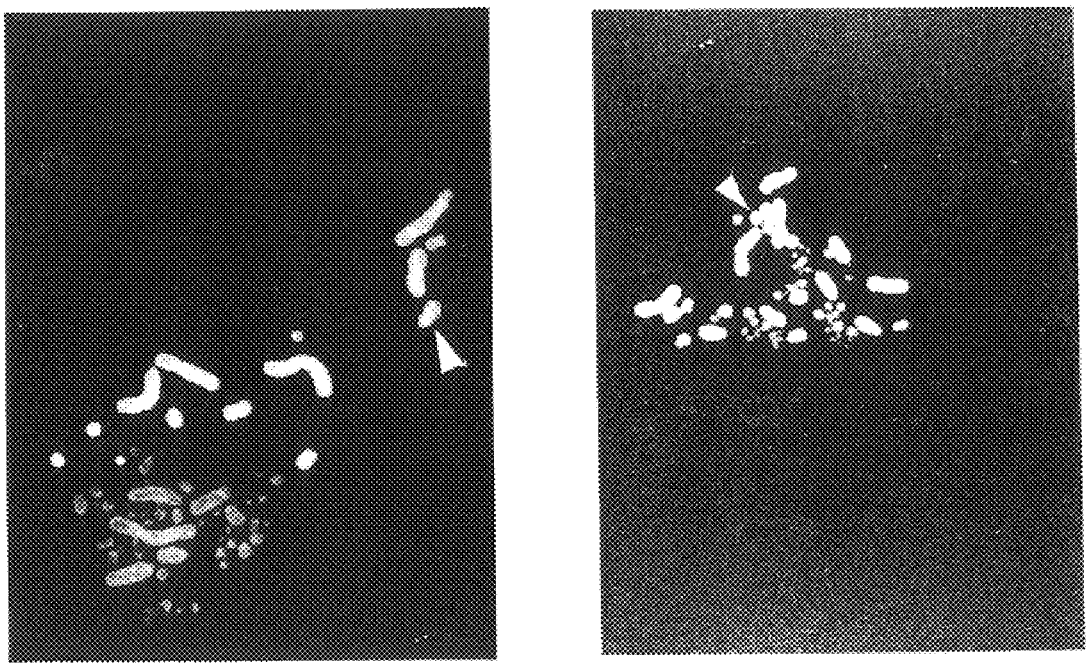
FIG. 49 shows a DT40 cell clone retaining full length or fragmented human #22 chromosome.

Whether the human chromosome #22 had been actually truncated or not was examined by FISH analysis. The experimental method was the same as described above. As probes, human COT1 DNA (labeled with Rhodamine) and plasmid pGKPuro (labeled with FITC) were used. By COT1 staining, the human chromosome #22 can be visually checked for truncation in comparison with DT40/#22neo having intact human chromosome #22. Furthermore, if the chromosome #22 is truncated as expected on the LIF locus into which the vector has been integrated, a signal from the Puro probe should be detected at one end of the telomere of the chromosome #22 fragment. A part of the results;is shown in FIG. 49. As a result of observation of 20–30 spreads for each clone, a small fragment of human chromosome #22 (red) having a Puro probe-derived signal (yellow green) at one end of the telomere was surprisingly observed in all of the 8 homologous recombinant clones. As for clones 64, 212, 222 and 305 which were presumed not to have undergone truncation from the results of the PCR analysis, cells having intact chromosome #22 occupied about 10% of all cells.

These experimental results show that homologous recombinants in which a human telomere sequence has been integrated into the LIF locus can be obtained at an efficiency of about 10% in chicken DT40/#22neo cells and that truncation of the human chromosome #22 has occurred at the integration site in all of the homologous recombinants (efficiency 100%).

What is claimed is:

1. A method for producing a chimeric mouse wherein at least some mouse cells retain a foreign chromosome(s) or a fragment(s) thereof, which method comprises:
   1) preparing a microcell retaining a foreign chromosome (s) or a fragments thereof that comprise a human antibody gene;
   2) transferring the foreign chromosome(s) or fragment(s) thereof into a pluripotent mouse cell by fusion with the microcell;
   3) transferring the pluripotent mouse cell into a mouse embryo;
   4) transferring the mouse embryo into a uterus or oviduct of a pseudo-pregnant female mouse; and
   5) allowing said mouse embryo to develop into said chimeric mouse.

2. A method for producing a pluripotent mouse cell retaining a foreign chromosome(s) or a fragment(s) thereof, which comprises preparing a microcell retaining a foreign chromosome(s) or a fragment(s) thereof and transferring the foreign chromosome(s) or fragment(s) thereof into a pluripotent mouse cell by fusion with the microcell, wherein the foreign chromosome(s) or fragment(s) thereof comprise a human antibody gene.

3. The method of claim 1 or 2, wherein the foreign chromosome(s) or fragment(s) thereof is human-derived and has a base length not less than 1 Mb.

4. The method of claim 1 or 2, wherein the microcell retaining a foreign chromosome(s) or a fragment(s) thereof is induced from a hybrid cell prepared by the fusion of a cell from which the foreign chromosome(s) or fragment(s) thereof is derived, with a cell having a high ability to form a microcell.

5. The method of claim 4, wherein the microcell retaining a foreign chromosome(s) or a fragment(s) thereof is induced from a cell prepared by a further fusion of the microcell induced from the hybrid cell with a cell having a high ability to form a microcell.

6. The method of claim 4, wherein the cell having a high ability to form a microcell is a mouse A9 cell.

7. The method of claim 1 or 2, wherein the foreign chromosome(s) or fragment(s) thereof is derived from a human normal diploid cell.

8. The method of claim 1 or 2, wherein the pluripotent mouse cell is an ES cell.

9. The method of claim 1, wherein the pluripotent mouse cell has a disrupted endogenous antibody gene that is homologous to the human antibody gene.

10. The method of claim 2, wherein the pluripotent mouse cell has a disrupted endogenous antibody gene that is homologous to the human antibody gene.

11. The method of claim 9 or 10, wherein the endogenous antibody gene is disrupted by homologous recombination.

12. The method of claim 9, wherein the mouse embryo for the production of the chimeric mouse is derived from a mouse strain deficient in an endogenous antibody gene that is homologous to the human antibody gene.

13. The method of claim 12, wherein the mouse strain deficient in the endogenous antibody gene is produced by homologous recombination.

14. The method of claim 1, wherein the chimeric mouse expresses the human antibody gene.

15. The method of claim 1, wherein the chimeric mouse can transmit the foreign chromosome(s) or fragment(s) thereof to its progeny.

16. The method of claim 1, wherein the foreign chromosome(s) or a fragment(s) is independently maintained from the mouse chromosomes.

17. The method of claim 1, wherein the foreign chromosome(s) or a fragment(s) has a base length not less than 1 Mb.

18. The method of claim 1, wherein the human antibody gene is selected from the group consisting of human heavy-chain gene, human light-chain κ (kappa) gene, human light-chain λ (lambda) gene and combinations thereof.

19. The method of claim 2, wherein the human antibody gene is selected from the group consisting of human heavy-chain gene, human light-chain κ (kappa) gene, human light-chain λ (lambda) gene and combinations thereof.

20. A pluripotent mouse cell which retains a human-derived chromosome(s) or a fragment(s) thereof having a base length not less than 1 Mb, and which can express the gene(s) on the human-derived chromosome(s) or fragment(s) thereof after the differentiation of the cell, wherein the human-derived chromosome(s) or fragment(s) thereof comprise a human antibody gene.

21. The pluripotent mouse cell of claim 20, wherein the human antibody gene is selected from the group consisting of human heavy-chain gene, human light-chain κ (kappa) gene, human light-chain λ (lambda) gene and combinations thereof.

22. A mouse wherein at least some mouse cells retain a foreign chromosome(s) or a fragment(s) thereof, wherein said foreign chromosome(s) or a fragment(s) thereof is independently maintained from the mouse chromosomes and/or has a base length not less than 1 Mb, and wherein the foreign chromosome(s) or fragment(s) thereof comprise a human antibody gene.

23. The mouse of claim 21, wherein the foreign chromosome(s) or a fragment(s) has a base length not less than 1 Mb.

24. The mouse of claim 21, wherein the foreign chromosome(s) or a fragment(s) is independently maintained from the mouse chromosomes.

25. The mouse of claim 22, wherein the human antibody gene is selected from the group consisting of human heavy-chain gene, human light-chain κ (kappa) gene, human light-chain λ (lambda) gene and combinations thereof.

26. The mouse of claim 22, wherein the foreign chromosome is a human-derived chromosome.

27. A mouse wherein at least some mouse cells retain a human-derived chromosome(s) or a fragment(s) thereof having a base length not less than 1 Mb, and which can express the gene(s) on the human-derived chromosome(s) or fragment(s) thereof, wherein at least one of the genes expressed on the human-derived chromosome(s) or fragment(s) is a human antibody gene.

28. The mouse of claim 27, wherein the human antibody gene is selected from the group consisting of human heavy-chain gene, human light-chain κ (kappa) gene, human light-chain λ (lambda) gene and combinations thereof.

29. A mouse which can be produced by mating the mice of any one of claims 22, 26, or 27, wherein at least some of the cells of the mouse retain a foreign or human-derived chromosome(s) or a fragment(s) thereof, which has a base length not less than 1 Mb and/or is independently maintained from the mouse chromosomes, and wherein the foreign chromosome(s) or fragment(s) thereof comprise a human antibody gene.

30. The mouse of claim 29, wherein the foreign chromosome(s) or a fragment(s) has a base length not less than 1 Mb.

31. The mouse of claim 29, wherein the foreign chromosome(s) or a fragment(s) is independently maintained from the mouse chromosomes.

32. A progeny of the mouse of claim 29, wherein at least some of the cells of the progeny retain a foreign or human-derived chromosome(s) or a fragment(s) thereof, which has a base length not less than 1 Mb and/or is independently maintained from the mouse chromosomes.

33. The progeny of claim 32, wherein the foreign chromosome(s) or a fragment(s) has a base length not less than 1 Mb.

34. The progeny of claim 32, wherein the foreign chromosome(s) or a fragment(s) is independently maintained from the mouse chromosomes.

35. A progeny mouse which can be produced by mating the mouse of any one of claims 22, 26, or 27 with a mouse strain deficient in an endogenous antibody gene that is homologous to the human antibody gene, wherein at least some cells of the progeny mouse retain the foreign or human-derived chromosome(s) or fragment(s) thereof, which has a base length not less than 1 Mb and/or is independently maintained from the mouse chromosomes.

36. A progeny of the mouse of claim 35, wherein the progeny retains a foreign or human-derived chromosome(s) or a fragment(s) thereof, which has a base length not less than 1 Mb and/or is independently maintained from the mouse chromosomes, and wherein the progeny is deficient in the endogenous antibody gene.

37. The progeny mouse of claim 35, wherein the foreign chromosome(s) or a fragment(s) has a base length not less than 1 Mb.

38. The progeny mouse of claim 35, wherein the foreign chromosome(s) or a fragment(s) is independently maintained from the mouse chromosomes.

39. A mouse wherein at least some mouse cells retain a human-derived DNA fragment(s) comprising human antibody gene, having a base length not less than 1 Mb and/or independently maintained from the mouse chromosome, wherein the mouse is capable of expressing the human antibody gene.

40. The mouse of claim 39, wherein the human antibody gene is selected from the group consisting of human heavy-chain gene, human light-chain κ (kappa) gene, human light-chain λ (lambda) gene and combinations thereof.

41. A method for producing an antibody, which comprises expressing a foreign or human-derived gene in the mouse of any one of claims 22, 26, 27 and 39, the tissue thereof, the cell thereof, the B cell thereof or the hybridoma prepared by the fusion of the B cell thereof with a myeloma cell, and collecting the antibody as an expression product.

42. A method for producing an antibody, which comprises expressing a foreign or human-derived gene in the progeny mouse of claim 35, the tissue thereof, the cell thereof, the B cell thereof or the hybridoma prepared by the fusion of the B cell thereof with a myeloma cell, and collecting the antibody as an expression product.

43. A method for producing an antibody, which comprises expressing a foreign or human-derived gene in the progeny of claim 36, the tissue thereof, the cell thereof, the B cell thereof or the hybridoma prepared by the fusion of the B cell thereof with a myeloma cell, and collecting the antibody as an expression product.

44. A mouse wherein at least some mouse cells retain a human-derived chromosome(s) or a fragment(s) thereof containing a human antibody gene and having a base length not less than 1 Mb, and which can express at least one class or subclass of the human antibody.

45. The mouse of claim 44, wherein the foreign chromosome(s) or a fragment(s) is independently maintained from the mouse chromosomes.

46. A mouse wherein at least some mouse cells retain a human antibody gene having a base length not less than 1 Mb, and which can express at least one class or subclass of the human antibody.

47. The mouse of claim 44 or 46, wherein the human antibody gene is selected from the group consisting of human heavy-chain gene, human light-chain κ (kappa) gene, human light-chain λ (lambda) gene and combinations thereof.

48. The mouse of claim 44 or 46, wherein at least some mouse cells retain the entire region of the unrearranged human antibody heavy-chain gene locus.

49. The mouse of claim 44 or 46, wherein at least some mouse cells retain the entire region of the unrearranged human antibody light-chain κ (kappa) gene locus.

50. The mouse of claim 44 or 46, wherein at least some mouse cells retain the entire region of the unrearranged human antibody light-chain λ (lambda) gene locus.

51. The mouse of claim 44 or 46, in the genome of which there is a disrupted, endogenous antibody gene.

52. The mouse of claim 51, wherein the disruption of the endogenous antibody gene is by homologous recombination.

53. A method for preparing a human polyclonal antibody, which comprises immunizing the mouse of claim 44 or 46 with an antigen, and collecting anti-serum from the blood of the mouse.

54. A method for preparing anti-serum containing a human antibody, which comprises immunizing the mouse of claims 44 or 46 with an antigen, and collecting an anti-serum from the blood of the mouse.

* * * * *

UNITED STATES PATENT AND TRADEMARK OFFICE
CERTIFICATE OF CORRECTION

PATENT NO.   : 6,632,976 B1
DATED        : October 14, 2003
INVENTOR(S)  : Tomizuka et al.

It is certified that error appears in the above-identified patent and that said Letters Patent is hereby corrected as shown below:

Column 127,
Line 15, delete "fragments" and insert -- fragment(s) --.

Column 128,
Lines 46-48, delete "is independently maintained from the mouse chromosomes and/or".
Lines 51-53, cancel claim 23 in its entirety.
Line 54, delete "21", and insert -- 22 --.

Column 129,
Lines 15-17, cancel claim 30 in its entirety.
Line 8, delete "22, 26, or 27" and insert -- 22 to 28 --;
Lines 11-12, delete "and/or is independently maintained from the mouse chromosomes,".
Lines 24-25, delete "and/or is independently maintained from the mouse chromosomes".
Lines 26-28, cancel claim 33 in its entirety.
Lines 32-39, delete "A progeny mouse .... is independently maintained from the mouse chromosomes" and insert -- A mouse produced by mating a first mouse of any one of claims 22 to 28 with a second mouse that is deficient in an endogenous antibody gene, wherein the endogenous antibody gene is homologous to a human antibody gene, and wherein at least some cells of the mouse retain the foreign or human-derived chromosome(s) or fragment(s) thereof, which has a base length not less than 1 Mb --.
Lines 43-44, delete the phrase "and/or is independently maintained from the mouse chromosomes".
Line 46-48, cancel claim 37 in its entirety.
Line 49, delete "progeny".
Lines 52-57, delete "A mouse wherein ---- antibody gene" and insert -- A mouse, wherein at least some mouse cells retain a human-derived DNA fragment(s) that comprises a human antibody gene, wherein the DNA fragment(s) has a base length not less than 1Mb, and wherein the mouse is capable of expressing the human antibody gene --.

UNITED STATES PATENT AND TRADEMARK OFFICE
CERTIFICATE OF CORRECTION

PATENT NO. : 6,632,976 B1
DATED : October 14, 2003
INVENTOR(S) : Tomizuka et al.

It is certified that error appears in the above-identified patent and that said Letters Patent is hereby corrected as shown below:

Column 130,
Line 5, delete "22, 26, 27 and 39", and insert -- 22, 24, 25, 26, 27, 28, or 39 --.
Line 10, delete "progeny".
Lines 33, 38, 41, 44, 47, 52 and 57, delete "44 or 46" and insert -- 44 to 46 --.
Lines 59, insert the following:
-- 55. A method for producing an antibody, which comprises expressing a foreign or human-derived gene in the mouse of claim 29, the tissue thereof, the cell thereof, the B cell thereof or the hybridoma prepared by the fusion of the B cell thereof with a myeloma cell, and collecting the antibody as an expression product.
  56. A method for producing an antibody, which comprises expressing a foreign or human-derived gene in the progeny of claim 32, the tissue thereof, the cell thereof, the B cell thereof or the hybridoma prepared by the fusion of the B cell thereof with a myeloma cell, and collecting the antibody as an expression product. --

Signed and Sealed this

Thirteenth Day of April, 2004

JON W. DUDAS
*Acting Director of the United States Patent and Trademark Office*